(12) United States Patent
Perlroth et al.

(10) Patent No.: US 11,066,465 B2
(45) Date of Patent: Jul. 20, 2021

(54) ANTIBODIES AND CONJUGATES THEREOF

(71) Applicant: KODIAK SCIENCES INC., Palo Alto, CA (US)

(72) Inventors: Daniel Victor Perlroth, Palo Alto, CA (US); Wah Yuen To, San Mateo, CA (US); Hong Liang, Hillsborough, CA (US)

(73) Assignee: KODIAK SCIENCES INC., Palo Alto, CA (US)

( * ) Notice: Subject to any disclaimer, the term of this patent is extended or adjusted under 35 U.S.C. 154(b) by 0 days.

(21) Appl. No.: 15/394,500

(22) Filed: Dec. 29, 2016

(65) Prior Publication Data

US 2017/0190766 A1    Jul. 6, 2017

Related U.S. Application Data

(60) Provisional application No. 62/273,177, filed on Dec. 30, 2015.

(51) Int. Cl.
| *A61K 47/68* | (2017.01) |
| *C07K 16/22* | (2006.01) |
| *A61K 39/44* | (2006.01) |
| *A61P 27/02* | (2006.01) |
| *A61K 47/60* | (2017.01) |
| *A61K 47/58* | (2017.01) |

(52) U.S. Cl.
CPC ............ *C07K 16/22* (2013.01); *A61K 47/605* (2017.08); *A61K 47/6845* (2017.08); *C07K 2317/526* (2013.01); *C07K 2317/565* (2013.01); *C07K 2317/73* (2013.01); *C07K 2317/76* (2013.01); *C07K 2317/92* (2013.01)

(58) Field of Classification Search
CPC .. A61K 47/605; A61K 47/6845; A61K 39/44; A61K 2039/6093; A61K 47/6883; A61K 47/48; A61K 47/60; C07K 16/22; C07K 2317/76; C07K 2317/565; C07K 2317/526; C07K 2317/92; C07K 2317/73; A61P 27/02

See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 4,609,707 A | 9/1986 | Nowinski et al. |
| 4,634,664 A | 1/1987 | Oestberg |
| 4,634,666 A | 1/1987 | Engleman et al. |
| 4,777,127 A | 10/1988 | Suni et al. |
| 4,816,567 A | 3/1989 | Cabilly et al. |
| 4,892,538 A | 1/1990 | Aebischer et al. |
| 5,047,335 A | 9/1991 | Paulson et al. |
| 5,219,740 A | 6/1993 | Dusty et al. |
| 5,225,539 A | 7/1993 | Winter |
| 5,252,713 A | 10/1993 | Morgan, Jr. et al. |
| 5,278,299 A | 1/1994 | Wong et al. |
| 5,283,187 A | 2/1994 | Aebischer et al. |
| 5,325,525 A | 6/1994 | Shan et al. |
| 5,336,603 A | 8/1994 | Capon et al. |
| 5,510,261 A | 4/1996 | Goochee et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,663,425 A | 9/1997 | Detroit et al. |
| 5,681,746 A | 10/1997 | Bodner et al. |
| 5,733,743 A | 3/1998 | Johnson et al. |
| 5,741,923 A | 4/1998 | Driver et al. |
| 5,763,548 A | 6/1998 | Matyjaszewski et al. |
| 5,770,429 A | 6/1998 | Lonberg et al. |
| 5,789,487 A | 8/1998 | Matyjaszewski et al. |
| 5,789,650 A | 8/1998 | Lonberg et al. |
| 5,807,937 A | 9/1998 | Matyjaszewski et al. |
| 5,814,318 A | 9/1998 | Lonberg et al. |
| 5,814,482 A | 9/1998 | Dubensky, Jr. et al. |
| 5,834,597 A | 11/1998 | Tso et al. |
| 5,837,242 A | 11/1998 | Holliger et al. |
| 5,858,657 A | 1/1999 | Winter et al. |
| 5,859,205 A | 1/1999 | Adair et al. |
| 5,863,551 A | 1/1999 | Woerly |
| 5,871,907 A | 2/1999 | Winter et al. |
| 5,872,218 A | 2/1999 | Wolf et al. |
| 5,874,299 A | 2/1999 | Lonberg et al. |

(Continued)

FOREIGN PATENT DOCUMENTS

| AU | 2010330727 | 12/2010 |
|---|---|---|
| AU | 2011239434 | 8/2015 |

(Continued)

OTHER PUBLICATIONS

Yu et al (Investigative Ophthalmology & Visual Science 49(2): 522-527, Feb. 2008.*

(Continued)

*Primary Examiner* — Phuong Huynh

(74) *Attorney, Agent, or Firm* — Knobbe, Martens, Olson & Bear, LLP

(57) ABSTRACT

Provided herein are anti-VEGF-A antibodies and antibody conjugates thereof. Some embodiments of the antibodies can be conjugated to a moiety, such as a HEMA-PC polymer. Some embodiments of the antibody conjugates can retain or enhance antibody activity. The antibody and conjugate thereof can be particularly useful for treating diabetic retinopathy. Further provided are methods for conjugation of a polymer to a protein such as an antibody, such as IgG1.

15 Claims, 28 Drawing Sheets

Specification includes a Sequence Listing.

(56) References Cited

U.S. PATENT DOCUMENTS

| | | |
|---|---|---|
| 5,877,218 A | 3/1999 | Herzig et al. |
| 5,877,397 A | 3/1999 | Lonberg et al. |
| 5,882,644 A | 3/1999 | Chang et al. |
| 5,945,491 A | 8/1999 | Matyjaszewski et al. |
| 5,981,786 A | 11/1999 | Kitano et al. |
| 6,111,022 A | 8/2000 | Matyjaszewski et al. |
| 6,121,371 A | 9/2000 | Matyjaszewski et al. |
| 6,124,411 A | 9/2000 | Matyjaszewski et al. |
| 6,162,882 A | 12/2000 | Matyjaszewski et al. |
| 6,270,993 B1 | 8/2001 | Shibuya et al. |
| 6,344,050 B1 | 2/2002 | Chen |
| 6,376,471 B1 | 4/2002 | Lawrence, III et al. |
| 6,383,486 B1 | 5/2002 | Davis-Smyth et al. |
| 6,407,187 B1 | 6/2002 | Matyjaszewski et al. |
| 6,407,213 B1 | 6/2002 | Carter et al. |
| 6,413,942 B1 | 7/2002 | Feigner et al. |
| 6,436,908 B1 | 8/2002 | Koch et al. |
| 6,512,060 B1 | 1/2003 | Matyjaszewski et al. |
| 6,538,091 B1 | 3/2003 | Matyjaszewski et al. |
| 6,541,580 B1 | 4/2003 | Matyjaszewski et al. |
| 6,554,853 B2 | 4/2003 | Chen |
| 6,555,593 B1 | 4/2003 | Hoyle et al. |
| 6,583,272 B1 | 6/2003 | Bailon |
| 6,624,262 B2 | 9/2003 | Matyjaszewski et al. |
| 6,624,821 B1 | 9/2003 | Shin et al. |
| 6,627,314 B2 | 9/2003 | Matyjaszewski et al. |
| 6,632,926 B1 | 10/2003 | Chen et al. |
| 6,759,491 B2 | 7/2004 | Matyjaszewski et al. |
| 6,790,919 B2 | 9/2004 | Matyjaszewski et al. |
| 6,833,349 B2 | 12/2004 | Xia et al. |
| 6,852,816 B2 | 2/2005 | Lewis et al. |
| 6,870,033 B1 | 3/2005 | Hsei et al. |
| 6,881,557 B2 | 4/2005 | Foote |
| 6,884,879 B1 | 4/2005 | Baca et al. |
| 6,887,962 B2 | 5/2005 | Matyjaszewski et al. |
| 6,979,556 B2 * | 12/2005 | Simmons ............... C07K 16/00 435/252.3 |
| 6,992,176 B2 | 1/2006 | Reiter et al. |
| 7,019,082 B2 | 3/2006 | Matyjaszewski et al. |
| 7,049,373 B2 | 5/2006 | Matyjaszewski et al. |
| 7,052,691 B2 | 5/2006 | Sleeman et al. |
| 7,056,455 B2 | 6/2006 | Matyjaszewski et al. |
| 7,056,509 B2 | 6/2006 | Thorpe et al. |
| 7,060,269 B1 | 6/2006 | Baca et al. |
| 7,060,271 B2 | 6/2006 | Ramakrishnan et al. |
| 7,064,166 B2 | 6/2006 | Matyjaszewski et al. |
| 7,071,159 B2 | 7/2006 | Kendall et al. |
| 7,122,636 B1 | 10/2006 | Hsei et al. |
| 7,125,938 B2 | 10/2006 | Matyjaszewski et al. |
| 7,157,530 B2 | 1/2007 | Matyjaszewski et al. |
| 7,169,901 B2 | 1/2007 | Baca et al. |
| 7,297,334 B2 | 1/2007 | Baca et al. |
| 7,214,776 B2 | 5/2007 | Hsei et al. |
| 7,291,721 B2 | 11/2007 | Giles-Komar et al. |
| 7,300,653 B2 | 11/2007 | Wiegand et al. |
| 7,300,990 B2 | 11/2007 | Lewis et al. |
| 7,303,748 B2 | 12/2007 | Wiegand et al. |
| 7,306,799 B2 | 12/2007 | Wiegand et al. |
| 7,345,027 B2 | 3/2008 | Tolentino et al. |
| 7,348,424 B2 | 3/2008 | Miyazawa et al. |
| 7,351,411 B2 | 4/2008 | Holash et al. |
| 7,354,578 B2 | 4/2008 | Kandel et al. |
| 7,354,579 B2 | 4/2008 | Holash et al. |
| 7,354,580 B2 | 4/2008 | Cedarbaum |
| 7,354,581 B2 | 4/2008 | Cedarbaum et al. |
| 7,354,582 B2 | 4/2008 | Yung et al. |
| 7,365,166 B2 | 4/2008 | Baca et al. |
| 7,374,767 B2 | 5/2008 | Papadopoulos et al. |
| 7,375,193 B2 | 5/2008 | Baca et al. |
| 7,378,095 B2 | 5/2008 | Cao et al. |
| 7,507,405 B2 | 3/2009 | Hsei et al. |
| 7,521,541 B2 | 4/2009 | Eigenbrot et al. |
| 7,531,172 B2 | 5/2009 | Stahl et al. |
| 7,560,112 B2 | 7/2009 | Chen et al. |
| 7,569,655 B2 | 8/2009 | Pacetti et al. |
| 7,608,261 B2 | 10/2009 | Furfine et al. |
| 7,612,182 B2 | 11/2009 | Giles-Komar et al. |
| 7,740,844 B2 | 6/2010 | Hong et al. |
| 7,740,850 B2 | 6/2010 | Zhu et al. |
| 7,750,138 B2 | 7/2010 | Fang et al. |
| 7,754,208 B2 | 7/2010 | Ledbetter et al. |
| 7,754,855 B1 | 7/2010 | Cox, III et al. |
| 7,758,859 B2 | 7/2010 | Fuh et al. |
| 7,759,472 B2 | 7/2010 | Shima et al. |
| 7,842,789 B2 | 11/2010 | Hsei et al. |
| 7,855,178 B2 | 12/2010 | Alitalo et al. |
| 7,893,173 B2 | 2/2011 | Matyjaszewski et al. |
| 7,919,099 B2 | 4/2011 | Tahara et al. |
| 7,928,072 B2 | 4/2011 | Scaria et al. |
| 7,955,597 B2 | 6/2011 | Giles-Komar et al. |
| 8,003,097 B2 * | 8/2011 | Schroeter ............... C07K 16/18 424/133.1 |
| 8,007,798 B2 | 8/2011 | Ashkenazi et al. |
| 8,007,799 B2 | 8/2011 | Van Bruggen et al. |
| 8,008,453 B2 | 8/2011 | Gegg et al. |
| 8,034,905 B2 | 10/2011 | Kavlie et al. |
| 8,048,418 B2 | 11/2011 | Noguera-Troise et al. |
| 8,092,797 B2 | 1/2012 | Fuh et al. |
| 8,101,177 B2 | 1/2012 | Fuh et al. |
| 8,110,546 B2 | 2/2012 | Dix et al. |
| 8,124,076 B2 | 2/2012 | Solomon et al. |
| 8,147,830 B2 | 4/2012 | Johnson et al. |
| 8,163,726 B2 | 4/2012 | Wen et al. |
| 8,187,597 B2 | 5/2012 | Shima et al. |
| 8,206,707 B2 | 6/2012 | Shima et al. |
| 8,211,864 B2 | 7/2012 | Ambati et al. |
| 8,216,571 B2 | 7/2012 | Ramachandra et al. |
| 8,216,575 B2 | 7/2012 | Yu |
| 8,231,907 B2 | 7/2012 | Lillard et al. |
| 8,236,312 B2 | 8/2012 | Park et al. |
| RE43,672 E | 9/2012 | Chan et al. |
| 8,268,314 B2 | 9/2012 | Baehner et al. |
| 8,273,353 B2 | 9/2012 | Davis-Smyth et al. |
| 8,309,532 B2 | 11/2012 | Feinstein et al. |
| 8,318,169 B2 | 11/2012 | Trogden et al. |
| 8,324,169 B2 | 12/2012 | Quinn |
| 8,329,866 B2 | 12/2012 | Rosendahl et al. |
| 8,349,325 B2 | 1/2013 | Brophy et al. |
| 8,388,963 B2 | 3/2013 | Vrignaud et al. |
| 8,455,622 B2 | 6/2013 | McDonagh et al. |
| 8,486,397 B2 | 7/2013 | Bagri et al. |
| 8,492,527 B2 | 7/2013 | Fuh et al. |
| 8,506,962 B2 | 8/2013 | Trogden et al. |
| 8,512,699 B2 | 8/2013 | Fuh et al. |
| 8,546,345 B2 | 10/2013 | Tolentino et al. |
| 8,557,246 B2 | 10/2013 | Martinez Escribano et al. |
| 8,571,802 B2 | 10/2013 | Robinson et al. |
| 8,614,235 B2 | 12/2013 | Robinson et al. |
| 8,632,774 B2 | 1/2014 | Misher et al. |
| 8,658,633 B2 | 2/2014 | Poulaki et al. |
| 8,663,639 B2 | 3/2014 | Dor et al. |
| 8,685,397 B2 | 4/2014 | Shima et al. |
| 8,691,226 B2 | 4/2014 | Chiu et al. |
| 8,703,130 B2 | 4/2014 | Baehner et al. |
| 8,703,133 B2 | 4/2014 | Chen et al. |
| 8,765,432 B2 | 7/2014 | Charles et al. |
| 8,785,385 B2 | 7/2014 | Stout et al. |
| 8,790,647 B2 | 7/2014 | Greenwood et al. |
| 8,802,129 B2 | 8/2014 | Whitcup et al. |
| 8,815,236 B2 | 8/2014 | Burke et al. |
| 8,822,645 B2 | 9/2014 | Ghayur et al. |
| 8,834,884 B2 | 9/2014 | Trogden et al. |
| 8,846,021 B2 | 9/2014 | Charles et al. |
| 8,864,869 B2 | 9/2014 | Pakola et al. |
| 8,883,157 B1 | 11/2014 | Clube |
| 8,883,519 B1 | 11/2014 | Perez et al. |
| 8,911,768 B2 | 12/2014 | Whitcup et al. |
| 8,926,972 B2 | 1/2015 | Zhou et al. |
| 8,945,552 B2 | 2/2015 | Baehner et al. |
| 8,986,692 B2 | 3/2015 | Li et al. |
| 9,029,508 B2 | 5/2015 | Ghayur et al. |
| 9,045,551 B2 | 6/2015 | Gu et al. |
| 9,079,953 B2 | 7/2015 | Harding et al. |
| 9,125,940 B2 | 9/2015 | Ma et al. |

(56) References Cited

U.S. PATENT DOCUMENTS

| | | |
|---|---|---|
| 9,149,427 B2 | 10/2015 | Ling et al. |
| 9,163,093 B2 | 10/2015 | Gu et al. |
| 9,214,906 B2 | 12/2015 | Marsan et al. |
| 9,217,039 B2 | 12/2015 | Pedersen et al. |
| 9,220,631 B2 | 12/2015 | Sigg et al. |
| 9,226,917 B2 | 1/2016 | Strong et al. |
| 9,254,338 B2 | 2/2016 | Yancopoulos |
| 9,334,324 B2 | 5/2016 | Choo et al. |
| 9,353,177 B2 | 5/2016 | Fuh et al. |
| 9,388,239 B2 | 7/2016 | Baldi et al. |
| 9,388,180 B2 | 8/2016 | Clube |
| 9,409,990 B2 | 8/2016 | Zhang |
| 9,416,180 B1 | 8/2016 | Clube |
| 9,416,210 B2 | 8/2016 | Emrick et al. |
| 9,421,256 B2 | 8/2016 | Kavlie et al. |
| 9,428,575 B2 | 8/2016 | Lai et al. |
| 9,567,403 B2 | 2/2017 | Wu et al. |
| 9,575,067 B2 | 2/2017 | Kosmeder et al. |
| 9,650,443 B2 | 5/2017 | Song et al. |
| 9,650,444 B2 | 5/2017 | Wiegand et al. |
| 9,682,144 B2 | 6/2017 | Thorin et al. |
| 9,695,233 B2 | 7/2017 | Duerr et al. |
| 9,708,390 B2 | 7/2017 | Sivakumar et al. |
| 9,708,396 B2 | 7/2017 | Baehner et al. |
| 9,708,397 B2 | 7/2017 | Greenwood et al. |
| 9,815,893 B2 | 11/2017 | Akamatsu |
| 9,840,553 B2* | 12/2017 | Perlroth ............ A61K 38/1866 |
| 9,850,514 B2 | 12/2017 | Laird et al. |
| 9,914,770 B2 | 3/2018 | Shandilya et al. |
| 9,931,330 B2 | 4/2018 | Zarnitsyn et al. |
| 9,937,129 B2 | 4/2018 | Freeman et al. |
| 9,943,573 B2 | 4/2018 | Constable et al. |
| 9,944,720 B2 | 4/2018 | Gu et al. |
| 9,962,333 B2 | 5/2018 | Gailard et al. |
| 10,004,788 B2 | 6/2018 | Constable et al. |
| 10,035,850 B2 | 7/2018 | Gekkieva et al. |
| 10,072,075 B2 | 9/2018 | Koenig et al. |
| 10,106,605 B2 | 10/2018 | Ghosh et al. |
| 10,184,010 B2 | 1/2019 | Lee et al. |
| 10,208,124 B2 | 2/2019 | Le Bouteiller et al. |
| 10,208,355 B2 | 2/2019 | Bais et al. |
| 10,240,207 B2 | 3/2019 | Yu et al. |
| 10,259,862 B2 | 4/2019 | Carter et al. |
| 10,363,290 B2 | 7/2019 | Perlroth et al. |
| 10,421,984 B2 | 9/2019 | Laird et al. |
| 10,456,466 B2 | 10/2019 | Fang et al. |
| 10,456,470 B2 | 10/2019 | Bais et al. |
| 10,519,226 B2 | 12/2019 | Rau et al. |
| 10,526,382 B2 | 1/2020 | Bel Aiba et al. |
| 10,568,951 B2 | 2/2020 | Sigl |
| 10,548,998 B2 | 4/2020 | Bradbury et al. |
| 10,702,608 B2 | 7/2020 | Charles et al. |
| 2002/0032315 A1 | 6/2002 | Baca et al. |
| 2002/0091082 A1 | 7/2002 | Aiello |
| 2003/0113335 A1 | 6/2003 | Li et al. |
| 2003/0118592 A1 | 6/2003 | Ledbetter et al. |
| 2003/0143596 A1 | 7/2003 | Bentley et al. |
| 2003/0171320 A1 | 9/2003 | Guyer |
| 2003/0235536 A1 | 12/2003 | Blumberg et al. |
| 2004/0010376 A1 | 1/2004 | Luo et al. |
| 2004/0063881 A1 | 4/2004 | Lewis et al. |
| 2004/0091490 A1 | 5/2004 | Johnson et al. |
| 2004/0247588 A1 | 12/2004 | Johnson et al. |
| 2004/0253596 A1 | 12/2004 | Pawlak et al. |
| 2004/0266688 A1 | 12/2004 | Nayak |
| 2005/0041080 A1 | 2/2005 | Hall et al. |
| 2005/0074497 A1 | 4/2005 | Schultz |
| 2005/0100500 A1 | 5/2005 | Kishita |
| 2005/0100550 A1 | 5/2005 | Trikha et al. |
| 2005/0112061 A1 | 5/2005 | Holash et al. |
| 2005/0112088 A1 | 5/2005 | Zhao et al. |
| 2005/0118651 A1 | 6/2005 | Basi et al. |
| 2005/0123501 A1 | 6/2005 | Lews |
| 2005/0136049 A1 | 6/2005 | Ledbetter et al. |
| 2005/0159556 A1 | 7/2005 | Lewis et al. |
| 2005/0180945 A1 | 8/2005 | Chaikof et al. |
| 2005/0214286 A1 | 9/2005 | Epstein et al. |
| 2005/0220880 A1 | 10/2005 | Lewis et al. |
| 2005/0239088 A1 | 10/2005 | Shepard et al. |
| 2005/0276796 A1 | 12/2005 | Tomatsu et al. |
| 2005/0281822 A1 | 12/2005 | Cedarbaum et al. |
| 2005/0281861 A1 | 12/2005 | Hughes et al. |
| 2005/0282233 A1 | 12/2005 | Eriksson et al. |
| 2006/0058234 A1 | 3/2006 | Daly et al. |
| 2006/0067930 A1 | 3/2006 | Adams et al. |
| 2006/0135714 A1 | 6/2006 | Lewis et al. |
| 2006/0165804 A1 | 7/2006 | Lewis et al. |
| 2006/0167230 A1 | 7/2006 | Koga et al. |
| 2006/0182783 A1 | 8/2006 | Hughes et al. |
| 2006/0193830 A1 | 8/2006 | Hauswirth et al. |
| 2006/0217285 A1 | 9/2006 | Destarac |
| 2006/0231107 A1 | 10/2006 | Glickman et al. |
| 2006/0234347 A1 | 10/2006 | Harding et al. |
| 2006/0234437 A1 | 10/2006 | Harding et al. |
| 2007/0037183 A1 | 2/2007 | Edwards et al. |
| 2007/0037214 A1 | 2/2007 | Luo et al. |
| 2007/0037760 A1 | 2/2007 | Tolentino et al. |
| 2007/0041967 A1 | 2/2007 | Jung et al. |
| 2007/0059302 A1 | 3/2007 | Baca et al. |
| 2007/0059336 A1 | 3/2007 | Hughes et al. |
| 2007/0071756 A1 | 3/2007 | Peyman |
| 2007/0111279 A1 | 5/2007 | Rosenberg |
| 2007/0134244 A1 | 6/2007 | Slakter et al. |
| 2007/0141104 A1 | 6/2007 | Hauenstein |
| 2007/0167526 A1 | 7/2007 | Zhang et al. |
| 2007/0190058 A1 | 8/2007 | Shams |
| 2007/0196374 A1 | 8/2007 | Baca et al. |
| 2007/0258976 A1 | 11/2007 | Ward et al. |
| 2007/0264236 A1 | 11/2007 | Yang |
| 2008/0008736 A1 | 1/2008 | Glauser |
| 2008/0070855 A1 | 3/2008 | Gills |
| 2008/0096923 A1 | 4/2008 | Girach |
| 2008/0124450 A1 | 5/2008 | Pacetti |
| 2008/0147178 A1 | 6/2008 | Pacetti et al. |
| 2008/0152654 A1 | 6/2008 | Reich et al. |
| 2008/0167600 A1 | 7/2008 | Peyman |
| 2008/0187534 A1 | 8/2008 | Baca et al. |
| 2008/0187966 A1 | 8/2008 | Simmons |
| 2008/0199464 A1 | 8/2008 | Plowman et al. |
| 2008/0226629 A1 | 9/2008 | Baca et al. |
| 2008/0242587 A1 | 10/2008 | Kim et al. |
| 2008/0248030 A1 | 10/2008 | Folkman et al. |
| 2008/0268051 A1 | 10/2008 | Hughes et al. |
| 2008/0292628 A1 | 11/2008 | Hui |
| 2009/0053137 A1 | 2/2009 | Moore |
| 2009/0053217 A1 | 2/2009 | Blank et al. |
| 2009/0053786 A1 | 2/2009 | Kao et al. |
| 2009/0060906 A1 | 3/2009 | Barry et al. |
| 2009/0061533 A1 | 3/2009 | Minami |
| 2009/0092664 A1 | 4/2009 | Mumper et al. |
| 2009/0098139 A1 | 4/2009 | Katz et al. |
| 2009/0104259 A1 | 4/2009 | Tolentino et al. |
| 2009/0117103 A1 | 7/2009 | Devalaraja et al. |
| 2009/0220504 A1 | 9/2009 | Chuntharapai et al. |
| 2009/0226441 A1 | 9/2009 | Yan et al. |
| 2009/0249503 A1 | 10/2009 | Rosendahl |
| 2009/0285826 A1 | 11/2009 | Bonnel et al. |
| 2009/0324679 A1 | 12/2009 | Ippoliti et al. |
| 2010/0086551 A1 | 4/2010 | Olwill et al. |
| 2010/0098730 A1 | 4/2010 | Lowman et al. |
| 2010/0059541 A1 | 5/2010 | Downing et al. |
| 2010/0111942 A1 | 5/2010 | Shima et al. |
| 2010/0111963 A1 | 5/2010 | Shams |
| 2010/0129375 A1 | 5/2010 | Junge et al. |
| 2010/0150911 A1 | 6/2010 | Caiado De Castro et al. |
| 2010/0151566 A1 | 6/2010 | Lamdan Ordas et al. |
| 2010/0158850 A1 | 6/2010 | Baker, Jr. et al. |
| 2010/0166700 A1* | 7/2010 | Charles ................ A61K 47/58 424/85.2 |
| 2010/0233079 A1 | 9/2010 | Jakob et al. |
| 2010/0247515 A1 | 9/2010 | Steward et al. |
| 2010/0254995 A1 | 10/2010 | Steward et al. |
| 2010/0260668 A1 | 10/2010 | Ghayur et al. |
| 2010/0260760 A1 | 10/2010 | Blank et al. |

(56) References Cited

U.S. PATENT DOCUMENTS

| | | |
|---|---|---|
| 2010/0278896 A1 | 11/2010 | Khaw et al. |
| 2010/0291065 A1 | 11/2010 | Kabanov et al. |
| 2010/0322931 A1 | 12/2010 | Harding et al. |
| 2011/0033378 A1 | 2/2011 | Dimasi et al. |
| 2011/0047103 A1 | 2/2011 | Swamy et al. |
| 2011/0052575 A1 | 3/2011 | Baca et al. |
| 2011/0054031 A1 | 3/2011 | McNamara et al. |
| 2011/0059080 A1 | 3/2011 | Cornfeld et al. |
| 2011/0064738 A1 | 3/2011 | Blank et al. |
| 2011/0076278 A1 | 3/2011 | Khodadoust |
| 2011/0076279 A1 | 3/2011 | Ramachandra et al. |
| 2011/0081342 A1 | 4/2011 | Baca et al. |
| 2011/0104069 A1 | 5/2011 | Xu et al. |
| 2011/0110932 A1 | 5/2011 | Patel |
| 2011/0117189 A1 | 5/2011 | Mazzone et al. |
| 2011/0159608 A1 | 6/2011 | Graham |
| 2011/0165648 A1 | 7/2011 | Campange et al. |
| 2011/0177074 A1 | 7/2011 | Sivakumar et al. |
| 2011/0189174 A1 | 8/2011 | Shafiee et al. |
| 2011/0200593 A1 | 8/2011 | Shima et al. |
| 2011/0262432 A1 | 10/2011 | Plouet et al. |
| 2011/0263827 A1 | 10/2011 | Ghayur et al. |
| 2012/0003641 A1 | 1/2012 | Graham et al. |
| 2012/0006716 A1 | 1/2012 | Frey et al. |
| 2012/0009185 A1 | 1/2012 | Shams |
| 2012/0070428 A1 | 3/2012 | Chan et al. |
| 2012/0076787 A1 | 3/2012 | Adamson et al. |
| 2012/0100136 A1 | 4/2012 | Patel et al. |
| 2012/0100166 A1 | 4/2012 | Roschke et al. |
| 2012/0128626 A1 | 5/2012 | Smith |
| 2012/0134993 A1 | 5/2012 | Pan et al. |
| 2012/0135070 A1 | 5/2012 | Kros et al. |
| 2012/0156202 A1 | 6/2012 | Shantha et al. |
| 2012/0164079 A1 | 6/2012 | Sharma |
| 2012/0014957 A1 | 7/2012 | Ghayur et al. |
| 2012/0213705 A1 | 8/2012 | Dimasi et al. |
| 2012/0244147 A1 | 9/2012 | Theuer et al. |
| 2012/0258108 A1 | 10/2012 | Ghayur et al. |
| 2012/0263722 A1 | 10/2012 | Ghayur et al. |
| 2012/0276083 A1 | 11/2012 | Junge et al. |
| 2012/0282211 A1 | 11/2012 | Washburn et al. |
| 2012/0301478 A1 | 11/2012 | Ohura et al. |
| 2012/0322738 A1* | 12/2012 | Behrens ............... C07K 14/755 514/14.1 |
| 2013/0004486 A1 | 1/2013 | Chan et al. |
| 2013/0004511 A1 | 1/2013 | Thorin et al. |
| 2013/0034517 A1* | 2/2013 | Charles ............ A61K 47/48176 424/78.29 |
| 2013/0040889 A1 | 2/2013 | Bolt et al. |
| 2013/0045522 A1* | 2/2013 | Charles .............. A61K 38/1816 435/188 |
| 2013/0058927 A1 | 3/2013 | Baca et al. |
| 2013/0071394 A1 | 3/2013 | Troyer et al. |
| 2013/0129733 A1 | 5/2013 | Ye et al. |
| 2013/0129749 A1 | 5/2013 | Ye et al. |
| 2013/0129830 A1 | 5/2013 | Chen et al. |
| 2013/0142796 A1 | 6/2013 | Ray et al. |
| 2013/0195806 A1 | 8/2013 | Gay et al. |
| 2013/0202613 A1 | 8/2013 | Pakola et al. |
| 2013/0259881 A1 | 10/2013 | Fandl et al. |
| 2013/0323242 A1 | 12/2013 | Everett et al. |
| 2013/0323302 A1 | 12/2013 | Constable et al. |
| 2013/0330341 A1 | 12/2013 | Chiron et al. |
| 2013/0337534 A1 | 12/2013 | Charles |
| 2013/0344129 A1 | 12/2013 | Washburn et al. |
| 2014/0010823 A1 | 1/2014 | Robinson et al. |
| 2014/0024776 A1 | 1/2014 | Charles et al. |
| 2014/0051642 A1 | 2/2014 | Castan |
| 2014/0170140 A1 | 2/2014 | Bennett et al. |
| 2014/0065137 A1 | 3/2014 | Huang et al. |
| 2014/0065142 A1 | 3/2014 | Roschke et al. |
| 2014/0079694 A1 | 3/2014 | Robinson et al. |
| 2014/0081003 A1 | 3/2014 | Laird et al. |
| 2014/0086934 A1 | 3/2014 | Shams |
| 2014/0093499 A1 | 4/2014 | Gschwing et al. |
| 2014/0128575 A1 | 5/2014 | Kao et al. |
| 2014/0134169 A1 | 5/2014 | Kuhnert et al. |
| 2014/0154246 A1 | 6/2014 | Robinson et al. |
| 2014/0154255 A1 | 6/2014 | Akamatsu |
| 2014/0161817 A1 | 6/2014 | Siedler et al. |
| 2014/0186350 A1 | 7/2014 | Ghosh et al. |
| 2014/0193486 A1 | 7/2014 | Liu et al. |
| 2014/0213769 A1 | 7/2014 | Hong et al. |
| 2014/0242082 A1 | 8/2014 | Shima et al. |
| 2014/0287025 A1 | 9/2014 | Liu et al. |
| 2014/0294810 A1 | 10/2014 | Lowman et al. |
| 2014/0302009 A1 | 10/2014 | Ogura et al. |
| 2014/0339122 A1 | 11/2014 | Weeks et al. |
| 2014/0341893 A1 | 11/2014 | Andres et al. |
| 2014/0341977 A1 | 11/2014 | Constable et al. |
| 2015/0004128 A1 | 1/2015 | Charles et al. |
| 2015/0017095 A1 | 1/2015 | Ghayur et al. |
| 2015/0017163 A1 | 1/2015 | Patel et al. |
| 2015/0023951 A1 | 1/2015 | Baca et al. |
| 2015/0030598 A1 | 1/2015 | Croasdale et al. |
| 2015/0037422 A1 | 2/2015 | Kaplan et al. |
| 2015/0037627 A1 | 2/2015 | Armacanqui et al. |
| 2015/0044214 A1 | 2/2015 | Imhof-Jung et al. |
| 2015/0050714 A1 | 2/2015 | Charles |
| 2015/0056195 A1 | 2/2015 | Bertolotto-Ballotti |
| 2015/0065781 A1 | 3/2015 | Bais et al. |
| 2015/0071861 A1 | 3/2015 | Kondo et al. |
| 2015/0071924 A1 | 3/2015 | Swamy et al. |
| 2015/0071941 A1 | 3/2015 | Sodhi et al. |
| 2015/0073381 A1 | 3/2015 | Kauper et al. |
| 2015/0079084 A1 | 3/2015 | Her et al. |
| 2015/0079089 A1 | 3/2015 | Wadehra et al. |
| 2015/0093375 A1 | 4/2015 | Junge et al. |
| 2015/0093390 A1 | 4/2015 | Bansal |
| 2015/0098988 A1 | 4/2015 | Bollag et al. |
| 2015/0104452 A1 | 4/2015 | Ghayur et al. |
| 2015/0105734 A1 | 4/2015 | Bryant et al. |
| 2015/0110788 A1 | 4/2015 | Kim et al. |
| 2015/0147317 A1 | 5/2015 | Robblee et al. |
| 2015/0148585 A1 | 5/2015 | Das et al. |
| 2015/0158952 A1 | 6/2015 | Mao et al. |
| 2015/0175689 A1 | 6/2015 | Fuh et al. |
| 2015/0182623 A1 | 7/2015 | Everett et al. |
| 2015/0191535 A1 | 7/2015 | Baehner et al. |
| 2015/0202289 A1 | 7/2015 | Shima et al. |
| 2015/0203591 A1 | 7/2015 | Liang et al. |
| 2015/0210771 A1 | 7/2015 | Crystal et al. |
| 2015/0216795 A1 | 8/2015 | Assadourian et al. |
| 2015/0232548 A1 | 8/2015 | Klien et al. |
| 2015/0246124 A1 | 9/2015 | Fyfe et al. |
| 2015/0250874 A1 | 9/2015 | Yan et al. |
| 2015/0266962 A1 | 9/2015 | Ma et al. |
| 2015/0297675 A1 | 10/2015 | Osborne |
| 2015/0307551 A1 | 10/2015 | Doroski et al. |
| 2015/0315283 A1 | 11/2015 | Ghayur et al. |
| 2015/0368329 A1 | 12/2015 | Hastings et al. |
| 2015/0376271 A1 | 12/2015 | Perlroth et al. |
| 2015/0376272 A1 | 12/2015 | Chung et al. |
| 2016/0008485 A1 | 1/2016 | Marquette et al. |
| 2016/0015770 A1 | 1/2016 | Zacks et al. |
| 2016/0024483 A1 | 1/2016 | Kim et al. |
| 2016/0038589 A1 | 2/2016 | Patel |
| 2016/0046730 A1 | 2/2016 | Ghayur et al. |
| 2016/0068613 A1 | 3/2016 | Regula et al. |
| 2016/0129080 A1 | 5/2016 | Osborne |
| 2016/0130321 A1 | 5/2016 | Burian |
| 2016/0130336 A1 | 5/2016 | Lai et al. |
| 2016/0137717 A1 | 5/2016 | Burian |
| 2016/0144025 A1 | 5/2016 | Vitti et al. |
| 2016/0158320 A1 | 6/2016 | Schultz et al. |
| 2016/0159893 A1 | 6/2016 | Burian |
| 2016/0159894 A1 | 6/2016 | Hartmann et al. |
| 2016/0168240 A1 | 6/2016 | Burian et al. |
| 2016/0184445 A1 | 6/2016 | Perlroth et al. |
| 2016/0194370 A1 | 7/2016 | Quian et al. |
| 2016/0194389 A1 | 7/2016 | Regula et al. |
| 2016/0199501 A1 | 7/2016 | Charles et al. |
| 2016/0243225 A1 | 8/2016 | Ioffe et al. |
| 2016/0243227 A1 | 8/2016 | Fyfe et al. |

(56) References Cited

U.S. PATENT DOCUMENTS

| | | |
|---|---|---|
| 2016/0257738 A1 | 9/2016 | Baca et al. |
| 2016/0279241 A1 | 9/2016 | Dupont et al. |
| 2016/0287715 A1 | 10/2016 | Charles et al. |
| 2016/0289317 A1 | 10/2016 | Bollag et al. |
| 2016/0296550 A1 | 10/2016 | Patel et al. |
| 2016/0297854 A1 | 10/2016 | Ghosh et al. |
| 2016/0340420 A1 | 11/2016 | Zhang et al. |
| 2016/0346400 A1 | 12/2016 | Emrick et al. |
| 2016/0347843 A1 | 12/2016 | Broering et al. |
| 2016/0369005 A1 | 12/2016 | Lippincott et al. |
| 2017/0002056 A1 | 1/2017 | Ke et al. |
| 2017/0002060 A1 | 1/2017 | Bolen et al. |
| 2017/0007581 A1 | 1/2017 | Robinson et al. |
| 2017/0007710 A1 | 1/2017 | Charles et al. |
| 2017/0015755 A1 | 1/2017 | Walsh et al. |
| 2017/0029494 A1 | 2/2017 | Ashman et al. |
| 2017/0035883 A1 | 2/2017 | Gragoudas et al. |
| 2017/0056469 A1 | 3/2017 | Lezzi |
| 2017/0079955 A1 | 3/2017 | Boyd |
| 2017/0100478 A1 | 4/2017 | Fyfe et al. |
| 2017/0114127 A1 | 4/2017 | Trout et al. |
| 2017/0129962 A1 | 5/2017 | Regula |
| 2017/0143826 A1 | 5/2017 | Dupont et al. |
| 2017/0143841 A1 | 5/2017 | Charles et al. |
| 2017/0143848 A1 | 5/2017 | Calias et al. |
| 2017/0159114 A1 | 6/2017 | Graham et al. |
| 2017/0210796 A1 | 7/2017 | Siedler et al. |
| 2017/0224815 A1 | 8/2017 | Tirgan |
| 2017/0232199 A1 | 8/2017 | Fiedler |
| 2017/0233444 A1 | 8/2017 | Stout et al. |
| 2017/0240626 A1 | 8/2017 | Baehner et al. |
| 2017/0240629 A1 | 8/2017 | Bedoucha et al. |
| 2017/0253651 A1 | 9/2017 | Chen et al. |
| 2017/0290876 A1 | 10/2017 | Ghosh et al. |
| 2017/0275353 A1 | 11/2017 | Sheng et al. |
| 2017/0313780 A1 | 11/2017 | Kao et al. |
| 2017/0327569 A1 | 11/2017 | Lu et al. |
| 2017/0349669 A1 | 12/2017 | Imhof-Jung et al. |
| 2017/0362317 A1 | 12/2017 | Lee et al. |
| 2017/0369564 A1 | 12/2017 | Baca et al. |
| 2017/0369566 A1 | 12/2017 | Baehner et al. |
| 2018/0000779 A1 | 1/2018 | Sakamoto et al. |
| 2018/0000933 A1 | 1/2018 | Ingram et al. |
| 2018/0042765 A1 | 2/2018 | Noronha et al. |
| 2018/0057602 A1 | 3/2018 | Theuer et al. |
| 2018/0092897 A1 | 4/2018 | Zarnitsyn et al. |
| 2018/0133288 A1 | 5/2018 | Kim et al. |
| 2018/0134780 A1 | 5/2018 | Klein et al. |
| 2018/0334499 A1 | 5/2018 | Olwill et al. |
| 2018/0155431 A1 | 6/2018 | Herting et al. |
| 2018/0161407 A1 | 6/2018 | Borodic |
| 2018/0186866 A1 | 7/2018 | Falkenstein et al. |
| 2018/0207292 A1 | 7/2018 | Burian et al. |
| 2018/0208642 A1 | 7/2018 | Lim et al. |
| 2018/0221339 A1 | 8/2018 | Boyd et al. |
| 2018/0221483 A1 | 8/2018 | Gaillard et al. |
| 2018/0230540 A1 | 8/2018 | Gosh et al. |
| 2018/0236066 A1 | 8/2018 | Maecher et al. |
| 2018/0237484 A1 | 8/2018 | Kwon et al. |
| 2018/0244762 A1 | 8/2018 | Perlroth et al. |
| 2018/0251545 A1 | 9/2018 | Cao et al. |
| 2018/0276336 A1 | 9/2018 | Perlee et al. |
| 2018/0298092 A1 | 10/2018 | Gekkieva et al. |
| 2018/0326126 A1 | 11/2018 | Fiedler |
| 2018/0334496 A1 | 11/2018 | Perlroth et al. |
| 2018/0344847 A1 | 12/2018 | Dupont et al. |
| 2018/0355030 A1 | 12/2018 | Greene et al. |
| 2018/0369380 A1 | 12/2018 | Gragoudas et al. |
| 2018/0371072 A1 | 12/2018 | Theuer et al. |
| 2019/0000919 A1 | 1/2019 | Brockmeyer et al. |
| 2019/0011455 A1 | 1/2019 | Lebert et al. |
| 2019/0016817 A1 | 1/2019 | Taddei et al. |
| 2019/0031750 A1 | 1/2019 | Koenig et al. |
| 2019/0031783 A1 | 1/2019 | Gu et al. |
| 2019/0062444 A1 | 2/2019 | Walsh et al. |
| 2019/0085056 A1 | 3/2019 | Lebert et al. |
| 2019/0091331 A1 | 3/2019 | Yang et al. |
| 2019/0100581 A1 | 4/2019 | Koenig et al. |
| 2019/0100582 A1 | 4/2019 | Blumenkran et al. |
| 2019/0127454 A1 | 5/2019 | Yang et al. |
| 2019/0127455 A1 | 5/2019 | Simpson et al. |
| 2019/0142975 A1 | 5/2019 | Keravala et al. |
| 2019/0153119 A1 | 5/2019 | Migone et al. |
| 2019/0153471 A1 | 5/2019 | Paul et al. |
| 2019/0161549 A1 | 5/2019 | Choong |
| 2019/0185555 A1 | 6/2019 | Swamy et al. |
| 2019/0194713 A1 | 6/2019 | Mandell et al. |
| 2019/0202904 A1 | 7/2019 | Fellouse et al. |
| 2019/0211091 A1 | 7/2019 | Simpson et al. |
| 2019/0216945 A1 | 7/2019 | Yang et al. |
| 2019/0218263 A1 | 7/2019 | Trese et al. |
| 2019/0224046 A1 | 7/2019 | Heitzmann et al. |
| 2019/0231986 A1 | 8/2019 | Devaraneni |
| 2019/0233517 A1 | 8/2019 | Wu |
| 2019/0255074 A1 | 8/2019 | Song et al. |
| 2019/0255155 A1 | 8/2019 | Perlroth et al. |
| 2019/0256556 A1 | 8/2019 | Giese et al. |
| 2019/0262476 A1 | 8/2019 | Lorenz et al. |
| 2019/0231799 A1 | 9/2019 | Peters et al. |
| 2019/0270806 A1 | 9/2019 | Jacobson et al. |
| 2019/0292239 A1 | 9/2019 | Carter et al. |
| 2019/0300607 A1 | 10/2019 | Isumi |
| 2019/0307691 A1 | 10/2019 | Gaillard et al. |
| 2019/0321467 A1 | 10/2019 | Santos et al. |
| 2019/0322732 A1 | 10/2019 | Murakami et al. |
| 2019/0330335 A1 | 10/2019 | Schwabe et al. |
| 2019/0336482 A1 | 11/2019 | Boyd |
| 2019/0343918 A1 | 11/2019 | Graham et al. |
| 2019/0358335 A1 | 11/2019 | Russell et al. |
| 2019/0360027 A1 | 11/2019 | Perlee et al. |
| 2019/0381008 A1 | 12/2019 | Zeitz et al. |
| 2019/0381194 A1 | 12/2019 | Tretiakova et al. |
| 2019/0388522 A1 | 12/2019 | Burian et al. |
| 2020/0000930 A1 | 1/2020 | Charles |
| 2020/0002411 A1 | 1/2020 | Famili et al. |
| 2020/0002426 A1 | 1/2020 | Sheng et al. |
| 2020/0048341 A1 | 2/2020 | Ghosh et al. |
| 2020/0055923 A1 | 2/2020 | Torella et al. |
| 2020/0055933 A1 | 2/2020 | Hailman et al. |
| 2020/0055958 A1 | 2/2020 | Chen et al. |
| 2020/0057058 A1 | 2/2020 | Olsen et al. |
| 2020/0086139 A1 | 3/2020 | Das et al. |
| 2020/0087389 A1 | 3/2020 | Theuer et al. |
| 2020/0095309 A1 | 3/2020 | Peters |
| 2020/0095310 A1 | 3/2020 | Regula et al. |
| 2020/0171179 A1 | 6/2020 | Charles et al. |
| 2020/0261590 A1 | 8/2020 | Charles et al. |
| 2020/0262905 A1 | 8/2020 | Perlroth et al. |

FOREIGN PATENT DOCUMENTS

| | | |
|---|---|---|
| AU | 2015207898 | 8/2015 |
| AU | 2017201930 | 4/2017 |
| BR | 11 2012 0145568 | 3/2017 |
| BR | 11 2012 0261185 | 8/2017 |
| CA | 2783615 | 6/2011 |
| CA | 2795667 | 10/2011 |
| CL | 02881/2012 | 7/2013 |
| CN | 101389690 | 3/2009 |
| CN | 102250246 A | 11/2011 |
| CN | 102311502 A | 1/2012 |
| CN | 102811713 | 12/2012 |
| CN | 103134874 | 6/2013 |
| CN | 103193819 | 7/2013 |
| CN | 103421039 | 12/2013 |
| CN | 103492489 | 1/2014 |
| CN | 103898101 | 7/2014 |
| CN | 106075466 | 11/2016 |
| CN | 106432557 | 2/2017 |
| CN | 106905431 A | 6/2017 |
| CN | 107208076 | 9/2017 |
| CN | 107428824 | 12/2017 |
| CO | 12119310 | 12/2012 |
| CO | 12203725 | 2/2013 |

(56) References Cited

FOREIGN PATENT DOCUMENTS

| | | |
|---|---|---|
| EP | 0345242 | 12/1989 |
| EP | 0577648 | 6/2001 |
| EP | 0968291 | 1/2004 |
| EP | 1179541 | 6/2004 |
| EP | 0929323 | 12/2004 |
| EP | 1325932 | 4/2005 |
| EP | 0971959 | 12/2005 |
| EP | 0973804 | 12/2006 |
| EP | 1465933 | 8/2007 |
| EP | 1135498 | 1/2008 |
| EP | 1592719 | 3/2008 |
| EP | 198810 | 11/2008 |
| EP | 1605847 | 9/2009 |
| EP | 1732621 | 12/2009 |
| EP | 1968594 | 9/2010 |
| EP | 2260873 | 12/2010 |
| EP | 1802373 | 7/2011 |
| EP | 2301580 | 1/2012 |
| EP | 1660057 | 5/2012 |
| EP | 2029746 | 7/2012 |
| EP | 1802334 | 8/2012 |
| EP | 2329821 | 8/2012 |
| EP | 2512462 | 10/2012 |
| EP | 2203180 | 11/2012 |
| EP | 2558538 | 2/2013 |
| EP | 2199306 | 6/2013 |
| EP | 2155783 B1 | 7/2013 |
| EP | 2446890 | 9/2013 |
| EP | 2344537 | 1/2014 |
| EP | 2274008 | 2/2014 |
| EP | 2042597 | 5/2014 |
| EP | 2524693 | 5/2014 |
| EP | 2540843 | 7/2014 |
| EP | 1991275 | 11/2014 |
| EP | 2443150 | 1/2015 |
| EP | 1802325 | 2/2015 |
| EP | 1989231 | 5/2015 |
| EP | 2217261 | 10/2015 |
| EP | 2596807 | 12/2015 |
| EP | 2200700 | 1/2016 |
| EP | 2307055 | 1/2016 |
| EP | 2259795 | 4/2016 |
| EP | 2516465 | 5/2016 |
| EP | 3041513 | 7/2016 |
| EP | 1763365 B1 | 8/2016 |
| EP | 2411411 | 8/2016 |
| EP | 2575881 | 9/2016 |
| EP | 2473526 | 8/2017 |
| EP | 2491134 | 8/2017 |
| EP | 3222142 | 9/2017 |
| EP | 2327415 | 10/2017 |
| EP | 2785744 | 10/2017 |
| EP | 2188302 | 11/2017 |
| EP | 2467156 | 11/2017 |
| EP | 2894167 | 11/2017 |
| EP | 2925778 | 11/2017 |
| EP | 2784092 | 12/2017 |
| EP | 3254678 | 12/2017 |
| EP | 2792687 | 5/2018 |
| EP | 2319925 | 7/2018 |
| EP | 2662388 | 8/2018 |
| EP | 2872534 | 8/2018 |
| EP | 3122878 | 10/2018 |
| EP | 3401331 | 11/2018 |
| EP | 1861096 | 12/2018 |
| EP | 2726612 | 3/2019 |
| EP | 3038647 | 3/2019 |
| EP | 3020731 | 6/2019 |
| EP | 2924052 | 7/2019 |
| EP | 2846836 | 8/2019 |
| EP | 3327026 | 8/2019 |
| EP | 2951307 | 12/2019 |
| EP | 3450553 | 12/2019 |
| EP | 3600441 | 2/2020 |
| EP | 3038646 | 3/2020 |
| EP | 3104880 | 3/2020 |
| EP | 3216803 | 3/2020 |
| GB | 2200651 | 8/1988 |
| IL | 260323 | 8/2018 |
| IN | 6116/CHENP/2012 | 12/2015 |
| IN | 9473/CHENP/2012 | 12/2015 |
| JP | H04-502850 | 5/1992 |
| JP | H10 139832 | 5/1998 |
| JP | H11 217588 | 8/1999 |
| JP | 2003-064132 | 3/2003 |
| JP | 2005-239989 | 9/2005 |
| JP | 2005-255969 | 9/2005 |
| JP | 2006-503549 | 2/2006 |
| JP | 2007-263935 | 10/2007 |
| JP | 2007-531513 | 11/2007 |
| JP | 2008-133434 | 6/2008 |
| JP | 2008-524247 | 7/2008 |
| JP | 2008-536498 A | 9/2008 |
| JP | 2009-042617 | 2/2009 |
| JP | 2009-532330 | 9/2009 |
| JP | 2009-533519 | 9/2009 |
| JP | 2009-542862 | 12/2009 |
| JP | 2009-543895 | 12/2009 |
| JP | 2010-117189 | 5/2010 |
| JP | 2010-279389 | 12/2010 |
| JP | 2011-50073 | 1/2011 |
| JP | 2011501945 A | 1/2011 |
| JP | 2011-518546 A | 6/2011 |
| JP | 2012-025820 | 2/2012 |
| JP | 2012-521768 A | 9/2012 |
| JP | 2013-515099 | 5/2013 |
| JP | 2013-519699 | 5/2013 |
| JP | 2013-534931 | 9/2013 |
| JP | 2014-043456 | 3/2014 |
| JP | 2014043405 A | 3/2014 |
| JP | 5528710 | 6/2014 |
| JP | 2015502397 A | 1/2015 |
| JP | 5760007 | 6/2015 |
| JP | 5745009 | 7/2015 |
| JP | 2016-14015 | 1/2016 |
| JP | 5846044 | 1/2016 |
| JP | 2016-040371 | 3/2016 |
| JP | 5990629 | 8/2016 |
| JP | 2016-530302 | 9/2016 |
| JP | 2017-31410 | 2/2017 |
| JP | 2018-87330 | 6/2018 |
| KR | 10-0808116 | 3/2008 |
| KR | 20120123340 | 11/2012 |
| KR | 2013-0097636 | 9/2013 |
| KR | 10-1852044 | 4/2018 |
| MX | 2012006970 | 10/2012 |
| MX | 2012011876 | 11/2012 |
| MX | 346423 | 3/2017 |
| MX | 2016017290 | 8/2017 |
| WO | WO 1987/04462 | 7/1987 |
| WO | WO 1990/07936 | 7/1990 |
| WO | WO 1990/11092 | 10/1990 |
| WO | WO 1991/02805 | 3/1991 |
| WO | WO 91/10741 | 7/1991 |
| WO | WO 1991/14445 | 10/1991 |
| WO | WO 91/17271 | 11/1991 |
| WO | WO 92/01047 | 1/1992 |
| WO | WO 1993/03769 | 3/1993 |
| WO | WO 1993/10218 | 5/1993 |
| WO | WO 93/12227 | 6/1993 |
| WO | WO 1993/11230 | 6/1993 |
| WO | WO 1993/19191 | 9/1993 |
| WO | WO 93/25673 | 12/1993 |
| WO | WO 1993/25234 | 12/1993 |
| WO | WO 1993/25698 | 12/1993 |
| WO | WO 1994/03622 | 2/1994 |
| WO | WO 1994/016748 | 8/1994 |
| WO | WO 1994/23697 | 10/1994 |
| WO | WO 1994/12649 | 11/1994 |
| WO | WO 1994/28938 | 12/1994 |
| WO | WO 1995/00655 | 1/1995 |
| WO | WO 1995/07994 | 3/1995 |
| WO | WO 1995/13796 | 5/1995 |
| WO | WO 1995/11984 | 7/1995 |

(56) References Cited

FOREIGN PATENT DOCUMENTS

| | | |
|---|---|---|
| WO | WO 1995/30763 | 11/1995 |
| WO | WO 1996/17072 | 6/1996 |
| WO | WO 97/14702 | 4/1997 |
| WO | WO 97/14703 | 4/1997 |
| WO | WO 1997/37029 | 10/1997 |
| WO | WO 1997/42338 | 11/1997 |
| WO | WO 98/45331 | 10/1998 |
| WO | WO 99/42133 A1 | 8/1999 |
| WO | WO 1999/064065 | 12/1999 |
| WO | WO 2000/09560 | 5/2000 |
| WO | WO 2000/034337 | 6/2000 |
| WO | WO 2000/059968 | 10/2000 |
| WO | WO200100854 A2 | 1/2001 |
| WO | WO 0141827 | 6/2001 |
| WO | WO 2002/028929 | 4/2002 |
| WO | WO2003020906 A2 | 3/2003 |
| WO | WO 2003/062290 | 7/2003 |
| WO | WO 2003/074026 | 9/2003 |
| WO | WO 2003/074090 | 9/2003 |
| WO | WO 2004/003144 A2 | 1/2004 |
| WO | WO 2004/020405 | 3/2004 |
| WO | WO 2004/063237 | 7/2004 |
| WO | WO 2004/065417 | 8/2004 |
| WO | WO 2004/091494 | 10/2004 |
| WO | WO 2004/113394 | 12/2004 |
| WO | WO 2005/028539 | 3/2005 |
| WO | WO 2005/047334 | 5/2005 |
| WO | WO 2005/058367 | 6/2005 |
| WO | WO 2005/120166 A2 | 12/2005 |
| WO | WO 2006/063055 | 6/2006 |
| WO | WO 2006/118547 | 11/2006 |
| WO | WO 2007/005253 | 1/2007 |
| WO | WO 2007/011873 | 1/2007 |
| WO | WO 2007/075534 | 7/2007 |
| WO | WO 2007/100902 | 9/2007 |
| WO | WO 2008/020827 | 2/2008 |
| WO | WO 2008/025856 | 3/2008 |
| WO | WO 2008/055206 A2 | 5/2008 |
| WO | WO 2008/098930 | 8/2008 |
| WO | WO 2008/112257 | 9/2008 |
| WO | WO 2008/112289 | 9/2008 |
| WO | WO 2008/119565 A2 | 10/2008 |
| WO | WO 2008/119567 A2 | 10/2008 |
| WO | WO 2008/144248 | 11/2008 |
| WO | WO 2008/155134 | 12/2008 |
| WO | WO 2009/052249 | 4/2009 |
| WO | WO 2009/052439 | 6/2009 |
| WO | WO 2009/105669 | 8/2009 |
| WO | WO 2009/134711 A1 | 11/2009 |
| WO | WO 2009/138473 | 11/2009 |
| WO | WO09149205 A2 | 12/2009 |
| WO | WO 2010/040508 | 4/2010 |
| WO | WO 2010/068862 | 6/2010 |
| WO | WO 2010/068864 | 6/2010 |
| WO | WO 2010/085542 | 7/2010 |
| WO | WO 2010/111625 | 9/2010 |
| WO | WO2010136492 A2 | 12/2010 |
| WO | WO 01/18080 | 3/2011 |
| WO | WO 2011/057014 A1 | 5/2011 |
| WO | WO 2011/075185 | 6/2011 |
| WO | WO 2011/075736 | 6/2011 |
| WO | WO 2011/116387 | 9/2011 |
| WO | WO 2011/119656 | 9/2011 |
| WO | WO 2011/130694 | 10/2011 |
| WO | WO 2011/153243 | 12/2011 |
| WO | WO 2012/145746 A1 | 10/2012 |
| WO | WO2012146610 A1 | 11/2012 |
| WO | WO 2013/059137 | 4/2013 |
| WO | WO2013071016 A2 | 5/2013 |
| WO | WO2013/093809 * | 6/2013 |
| WO | WO 2013/093809 | 6/2013 |
| WO | WO2013082563 | 6/2013 |
| WO | WO 2013/173129 | 11/2013 |
| WO | WO2014006113 A1 | 1/2014 |
| WO | WO2014033184 A1 | 3/2014 |
| WO | WO 2014/060401 | 4/2014 |
| WO | WO 2014/068443 A1 | 5/2014 |
| WO | WO 2014/072888 A1 | 5/2014 |
| WO | WO2014101287 A1 | 7/2014 |
| WO | WO 2014/160507 | 10/2014 |
| WO | WO 2014/177460 | 11/2014 |
| WO | WO2015004616 A1 | 1/2015 |
| WO | WO 2015/035342 | 3/2015 |
| WO | WO2015058048 A1 | 4/2015 |
| WO | WO2015058369 A1 | 4/2015 |
| WO | WO2015059220 A1 | 4/2015 |
| WO | WO 2015/109898 | 7/2015 |
| WO | WO2015109898 A1 | 7/2015 |
| WO | WO2015110067 A1 | 7/2015 |
| WO | WO 2015/135583 | 9/2015 |
| WO | WO 2015/168468 A1 | 11/2015 |
| WO | WO2015168321 A2 | 11/2015 |
| WO | WO 2015/200905 | 12/2015 |
| WO | WO2015198240 A2 | 12/2015 |
| WO | WO2015198243 A2 | 12/2015 |
| WO | WO2016008975 A1 | 1/2016 |
| WO | WO2016044041 A1 | 3/2016 |
| WO | WO2016045626 A1 | 3/2016 |
| WO | WO 2016/061562 | 4/2016 |
| WO | WO 2016/073157 | 5/2016 |
| WO | WO2016073894 A1 | 5/2016 |
| WO | WO2016085750 A1 | 6/2016 |
| WO | WO2016145189 A1 | 9/2016 |
| WO | WO 2016/160923 A1 | 10/2016 |
| WO | WO 2016/170039 | 10/2016 |
| WO | WO 2017/046140 | 3/2017 |
| WO | WO 2017/075173 A2 | 5/2017 |
| WO | WO 2017/100470 | 6/2017 |
| WO | WO 2017/117464 | 7/2017 |
| WO | WO 2017/120600 | 7/2017 |
| WO | WO 2017/120601 | 7/2017 |
| WO | WO 2017/129064 A1 | 8/2017 |
| WO | WO 2017/204298 | 11/2017 |
| WO | WO 2017/205559 | 11/2017 |
| WO | WO 2018/114728 | 6/2018 |
| WO | WO 2018/122053 | 7/2018 |
| WO | WO 2018/139991 | 8/2018 |
| WO | WO 2018/175319 | 9/2018 |
| WO | WO 2018/175752 | 9/2018 |
| WO | WO 2018/182527 | 10/2018 |
| WO | WO 2018/185110 | 10/2018 |
| WO | WO 2018/191548 | 10/2018 |
| WO | WO 2018/217995 | 11/2018 |
| WO | WO 2018/218215 | 11/2018 |
| WO | WO 2019/020777 | 1/2019 |
| WO | WO 2019/038552 | 2/2019 |
| WO | WO 2019/040397 | 2/2019 |
| WO | WO 2019/043649 | 3/2019 |
| WO | WO 2019/057946 | 3/2019 |
| WO | WO 2019/067540 | 4/2019 |
| WO | WO 2019/091384 | 5/2019 |
| WO | WO 2019/099786 | 5/2019 |
| WO | WO 2019/104279 | 5/2019 |
| WO | WO 2019/113225 | 6/2019 |
| WO | WO2009/092011 | 7/2019 |
| WO | WO 2019/134686 | 7/2019 |
| WO | WO 2019/147944 | 8/2019 |
| WO | WO 2019/154349 | 8/2019 |
| WO | WO 2019/154776 | 8/2019 |
| WO | WO 2019/164219 | 8/2019 |
| WO | WO 2019/020418 A1 | 9/2019 |
| WO | WO 2019/169341 | 9/2019 |
| WO | WO 2019/173482 | 9/2019 |
| WO | WO 2019/175727 | 9/2019 |
| WO | WO 2019/178438 | 9/2019 |
| WO | WO 2019/184909 | 10/2019 |
| WO | WO 2019/195313 | 10/2019 |
| WO | WO 2019/200181 | 10/2019 |
| WO | WO 2019/201866 | 10/2019 |
| WO | WO 2019/204380 | 10/2019 |
| WO | WO 2019/229116 | 12/2019 |
| WO | WO 2020/006486 | 1/2020 |
| WO | WO 2020/043184 | 3/2020 |

(56) References Cited

FOREIGN PATENT DOCUMENTS

OTHER PUBLICATIONS

Alconcel, S.N.S. et al., "FDA-approved poly(ethylene glycol)-protein conjugate drugs," Polymer Chemistry, vol. 2, Issue 7, pp. 1442, 2011.
Alley, S. et al., "Contribution of linker stability to the activities of anticancer immunoconjugates," Bioconjugate Chem., vol. 19, No. 3, pp. 759-765, 2008.
Altamirano, C.V. et al., "Association of tetramers of human butyrylcholinesterase is mediated by conserved aromatic residues of the carboxy terminus," Chemico-Biological Interactions, vols. 119-120, pp. 53-60, May 14, 1999.
Ambati et al., "Mechanisms of age-related macular degeneration," Neuron, vol. 75, No. 1, pp. 26-39, 2012.
Anderson, W.F., "Human gene therapy," Science, vol. 256, No. 5058, pp. 808-813, May 8, 1992.
Andrae et al., "Role of platelet-derived growth factors in physiology and medicine," Genes & Development, vol. 22, pp. 1276-1312, 2008.
Armulik, A. et al., "Endothelial/Pericyte Interactions," Circulation Research, vol. 97, Issue 6, pp. 512-523, Sep. 16, 2005.
Baldwin, A. et al., "Reversible maleimide-thiol adducts yield glutathione-sensitive poly(ethylene glycol)-heparin hydrogels," Polymer Chemistry, vol. 4, Issue 1, pp. 133-143, Jan. 7, 2013.
Baldwin, A. et al., "Tunable degradation of maleimide-thiol adducts in reducing environments," Bioconjug Chem, vol. 22, No. 10, pp. 1946-1953, Oct. 19, 2011.
Baluk, P. et al., "Cellular abnormalities of blood vessels as targets in cancer," Current Opinion in Genetics & Development, vol. 15, Issue 1, pp. 102-111, Feb. 2005.
Bates, D.O. et al., "Vascular endothelial growth factor increases microvascular permeability via a Ca(2+)-dependent pathway," American Journal of Physiology, vol. 273, No. 2, pp. H687-H694, Aug. 1, 1997.
Berthold, W. et al., "Protein Purification: Aspects of Processes for Pharmaceutical Products," Biologicals, vol. 22, Issue 2, pp. 135-150, Jun. 1994.
Blong, M. Renee et al., "Tetramerization domain of human butyrylcholinesterase is at the C-terminus," Biochemical Journal, vol. 327, No. 3, pp. 747-757, Nov. 1, 1997.
Bowen-Pope et al., "History of Discovery: Platelet-derived Growth Factor," Arterioscler Thromb Vasc Biol., vol. 31, No. 11, pp. 2397-2401, Nov. 2011.
Bontempo, et al., "Cysteine-Reactive Polymers Synthesized by Atom Transfer Radical Polymerization for Conjugation to Proteins," J. Am. Chem. Soc. (2004), 126, pp. 15372-15373.
Brown, D. et al., "Ranibizumab versus Verteporfin for Neovascular Age-Related Macular Degeneration," The New England Journal of Medicine, vol. 355, No. 14, pp. 1432-1444, Oct. 5, 2006.
Cannard, K., "The acute treatment of nerve agent exposure," Journal of the Neurological Sciences, vol. 249, Issue 1, pp. 86-94.
Capon, D. et al., "Designing CD4 immunoadhesins for AIDS therapy," Nature, vol. 337, pp. 525-531, 1989.
Carmeliet, P., "Angiogenesis in healt and disease," Nature Medicine, vol. 9, pp. 653-660, (2003).
Carmeliet, P., "Synergism between vascular endothelial growth factor and placental growth factor contributes to angiogenesis and plasma extravasation in pathological conditions," Nature Medicine, vol. 7, No. 5, pp. 575-583, May 2001.
Carmeliet, "Mechanisms of angiogenesis and arteriogenesis," Nature Medicine, vol. 6, No. 3, pp. 389-395, 2000.
Cascio, C. et al., "Use of serum cholinesterases in severe organophosphorus poisoning," Minerva Anestesiologica, vol. 54, pp. 337-345, 1988.
Chen et al., "Factors affecting endotoxin removal from recombinant therapeutic proteins by anion exchange chromatography," Protein Expression and Purification, vol. 64, pp. 76-81, 2009.

Chen, et al., "Lubrication at Physiological Pressures by Polyzwitterionic Brushes," Science, (2009), 323, pp. 1698-1701.
Chen, et al., "Polymeric Phosphorylcholine-Camptothecin Conjugates Prepared by Controlled Free Radical Polymerizationand Click Chemistry," Bioconjugate Chem., (2009), 20:12, pp. 2331-2341.
Chothia, C. et al., "Canonical structures for the hypervariable regions of immunoglobulins," Journal of Molecular Biology, vol. 196, Issue 4, pp. 901-917, Aug. 20, 1989.
Chothia, C. et al., "Conformations of immunoglobulin hypervariable regions," Nature, vol. 342, pp. 877-883, Dec. 1989.
Christy, N.E. et al., "Antibiotic prophylaxis of postoperative endophthalmitis," Annals of Ophthalmology, vol. 11, No. 8, pp. 1261-1265, Aug. 1, 1979.
Cohen, S.Y. et al., "Causes of unsuccessful ranibizumab treatment in exudative age-related macular degeneration in clinical settings," Retina, vol. 32, Issue 8, pp. 1480-1485, Sep. 2012.
Crowe, et al., "Recombinant human respiratory syncytial virus (RSV) monoclonal antibody Fab is effective therapeutically when introduced directly into the lungs of RSV-infected mice," Proc. Natl. Acad. Sci. USA, (1994) 91 pp. 1386-1390.
Da Pieve, et al., "Conjugation of PolyPEG®, Linear PEG and Branched PEG to a Thiol-Modified Aptamer," Poster, Warwick Effect Polymers Ltd, retrieved from <http:www.wep-ltd.co.uk> (2010).
Da Pieve, et al., "Modification of Thiol Functionalized Aptamers by Conjugation of Synthetic Polymers," Bioconjugate Chem., (2010), 21:1, pp. 169-174.
Daneshian, M. et al., "In vitro pyrogen test for toxic or immunomodulatory drugs," Journal of Immunological Methods, vol. 313, Issues 1-2, pp. 169-175, Jun. 30, 2006.
De Pascalis, R. et al., "Grafting of "abbreviated" complementarity-determining regions containing specificity-determining residues essential for ligand contact to engineer a less immunogenic humanized monoclonal antibody," J. Immunol., vol. 169, No. 6, pp. 3076-3084, Sep. 15, 2002.
Declaration of Harvey N. Masonson, M.D., Jul. 6, 2011.
Dillon et al., "Structural and functional characterization of disulfide isoforms of the human IgG2 subclass," The Journal of Biological Chemistry, vol. 283, No. 23, pp. 16206-16215, 2008.
Ding, J.L. et al., "A new era of pyrogen testing," Trends in Biotechnology, vol. 19, Issue 8, pp. 277-281, Aug. 1, 2001.
Dong, et al., "ARGET ATRP of 2-(Dimethylamino)ethyl Methacrylate as an Intrinsic Reducing Agent," Macromolecules, (2008), 41:19 pp. 6868-6870.
Dong, et al., "Well-Defined High-Molecular-Weight Polyacrylonitrile via Activators Regenerated by Electron Transfer ATRP," Macromolecules, (2007), 40:9, pp. 2974-2977.
Du et al. "pH-Sensitive Vesicles based on a Biocompatible Zwitterionic Diblock Copolymer" J. Am. Chem. Soc., Dec. 1, 2005, 127, 17982-17983.
Edelman et al., "The covalent structure of an entire yG immunoglobulin molecule," Proceedings of the National Academy of Sciences, vol. 63, pp. 78-85, May 1, 1969.
Ellman, G. et al., "A new and rapid colorimetric determination of acetylcholinesterase activity," Biochemical Pharmacology, vol. 7, Issue 2, pp. 88-95, Jul. 1961.
Facts About Diabetic Eye Disease, National Eye Institute, National Institute of Health <https://nei.nih.gov/health/diabetic/retinopathy> accessed Mar. 27, 2018; However, as this item is accessible on the world wide web, it may have been available in some form at an earlier point in time.
Fares, F.A. et al., "Design of a long-acting follitropin agonist by fusing the C-terminal sequence of the chorionic gonadotropin beta subunit to the follitropin beta subunit," Proc Natl Acad Sci USA, vol. 89, No. 10, pp. 4304-4308, May 15, 1992.
Ferrara, N. et al., "Discovery and development of bevacizumab, an anti-VEGF antibody for treating cancer," Nature Reviews Drug Discovery, vol. 3, pp. 391-400, May 2004.
Ferrara, N. et al., "The biology of vascular endothelial growth factor," Endocrine Reviews, vol. 18, No. 1, pp. 4-25, (1997).
Ferrara, et al. Development of Ranibizumab, An Anti-Vascular Endothelial Growth, as Therapy for Neovascular Age-Related Macular

(56) References Cited

OTHER PUBLICATIONS

Degeneration, Retina, The Journal of Retinal and Vitreous Diseas, vol. 26, Issue No. 8, pp. 859-870, (2006).
Ferrara, et al The Biology of VEGF and its Receptors, Nature Medicine, vol. 9 No. 6, pp. 669-676, (2003).
Fiske, M. et al., "Method for reducing endotoxin in Moraxella catarrhalis UspA2 protein preparations," Journal of Chromatography B: Biomedical Sciences and Applications, vol. 753, Issue 2, pp. 269-278, Apr. 5, 2001.
Folkman, J., "Angiogenesis: an organizing principle for drug discover?" Nature Reviews, Drug Discovery, vol. 6, pp. 273-286, Apr. 2007.
Fontaine et al., "Long-Term Stabilization of Maleimide-Thiol Conjugates," Bioconjugate Chem., vol. 26, pp. 145-152, 2015.
Foster, Graham R., "Pegylated interferons for the treatment of chronic Hepatitis C," Drugs, vol. 70, Issue 2, pp. 147-165, Jan. 2010.
Friedman, D.S. et al., "Prevalence of age-related macular degeneration in the United States," Arch. Ophthalmol., vol. 122, No. 4, pp. 564-572, Apr. 2004.
Greene et al., "Protective Groups in Organic Synthesis," 3rd Edition, John Wiley and Sons, Inc., New York, (1999).
Gillies, et al., "Dendrimers and Dedritic Polymers in Drug Delivery," Drug Delivery today, Jan. 2005, vol. 10, No. 1, pp. 35-43.
Goodson, R.J. et al., "Site-directed pegylation of recombinant interleukin-2 at its glycosylation site," Nature Biotechnology, vol. 8, pp. 343-346, 1990.
Goel, N. et al., "Certolizumab pegol," mAbs, vol. 2, No. 2, pp. 137-147, Mar./Apr. 2010.
Gordon, M. et al., "Determinatino of the normality of cholinesterase solutions," Analytical Biochemistry, vol. 85, Issue 2, pp. 519-527, Apr. 1978.
Gorun, V. et al., "Modified Ellman procedure for assay of cholinesterases in crude enzymatic preparations," Analytical Biochemistry, vol. 86, Issue 1, pp. 324-326, May 1978.
Greene T.W. et al., "Protective Groups in Organic Synthesis," 3rd Edition, John Wiley and Sons, Inc., New York, 1999.
Gualberto, Antonio, "Brentuximab Vedotin (SGN-35), an antibody-drug conjugate for the treatment of CD30-positive malignancies," Expert Opinion on Investigational Drugs, vol. 21, Issue 2, pp. 205-216, 2012.
Haddleton, et al., "Pheriolic Ester-Based Initiators for Transition Metal Mediated Living Polymerization," Macromolecules, (1999), 32, pp. 8732-8739.
Haishima, Y et al. Estimation of uncertainty in kinetic-calorimetric assay of bacterial endotoxins, J Pharm Biomed Analysis, 32: 1, pp. 495-503, (2003).
Haupt, H. et al., "Isolierung und physikalisch-chemische Charakterisierung der Cholinesterase aus Humanserum," Blut, vol. 14, Issue 2, pp. 65-75, Nov. 1966.
Heise et al., "Starlike Polymeric Architectures by Atom Transfer Radical Polymerization: Templates for the Production of Low Dielectric Constant Thin Films," Macromolecules, Jan. 17, 2000, 33:2346-2354.
Heise, et al., "Investigation of the Initiation Behavior of a Dendritic 12-Arm Initiator in Atom Transfer Radical Polymerization," Macromolecules, (2001), 34:11, pp. 3798-3801.
Heredia, et al., "In Situ Preparation of Protein-'Smart' Polymer Conjugates with Retention of Bioactivity," J. Am. Chem. Soc., (2005), 127, pp. 16955-16960.
Hirayama, C. et al., "Chromatographic removal of endotoxin from protein solutions by polymer particles," Journal of Chromatography B, vol. 781, Issues 1-2, pp. 419-432, Dec. 5, 2002.
Hoffmann, S. et al., "International validation of novel pyrogen tests based on human monocytoid cells," Journal of Immunological Methods, vol. 298, Issues 1-2, pp. 161-173, Mar. 2005.
Holash, J et al. VEGF-Trap: A VEGF Blocker with Potent Antitumor Effects, PNAS, vol. 9, No. 17, pp. 11393-11398, (2002).

Holliger, P. et al., "'Diabodies': small bivalent and bispecific antibody fragments," Proc. Natl. Acad. Sci. USA, vol. 90, No. 14, pp. 6444-6448, Jul. 15, 1993.
Hong, et al., "Preparation of Segmented Copolymers in the Presence of an Immobilized/Soluble 320 Hybrid ATRP Catalyst System," Macromolecules, (2003), 36:1, pp. 27-35.
Huang, Y.J. et al., "Recombinant human butyrylcholinesterase from milk of transgenic animals to protect against organophosphate poisoning," PNAS, vol. 104, No. 34, pp. 13603-13608, Aug. 21, 2007.
Huang, Y-S. et al., "Engineering a pharmacologically superior form of granulocyte-colony-stimulating factor by fusion with gelatin-like-protein polymer," European Journal of Pharmaceutics and Biopharmaceutics, vol. 74, Issue 3, pp. 435-441, Mar. 2010.
Humphreys et al., "Alternative antibody FAB' fragment PEGylation strategies: combination of strong reducing agents, disruption of the interchain disulphide bond and disulphide engineering," Protein Engineering, Design & Selection, vol. 20, No. 5, pp. 227-234, 2007.
Huston, James S., "Protein engineering of single-chain Fv analogs and fusion proteins," Methods of Enzymology, vol. 203, pp. 46-96, 1991.
IMGT Scientifitc Chart, 2011.
Ishikawa, K. et al., "Molecular mechanisms of subretinal fibrosis in age-related macular degeneration," Experimental Eye Research, vol. 142, pp. 19-25, Jan. 2016.
IUPAC Gold Book, Random copolymer, available at https://goldbook.iupac.org/html/R/R05126.html, accessed Nov. 21, 2017; However, as this item is accessible on the world wide web, it may have been available in some form at an earlier point in time.
IUPAC Gold Book, Random Copolymerization, available at https://goldbook.iupac.org/html/R/R05126.html, accessed Nov. 21, 2017; However, as this item is accessible on the world wide web, it may have been available in some form at an earlier point in time.
Iwasaki, et al., "Platelet compatible blood filtration fabrics using a phosphorylcholine polymer having high surface mobility ," Biomaterials, (2003), 24 pp. 3599-3604.
Iwasaki, Yasuhiko et al., "Synthesis and Characterization of Amphiphilic Polyphosphates with hydrophilic graft chains and Cholesteryl Groups as Nanocarriers", Biomacromolecules, 2006, 7, 1433-1438.
Jaffe, G. et al., "Intraocular drug delivery," CRC Press, Mar. 2006.
Jakubowski, et al., "Activators Regenerated by Electron Transfer for Atom Transfer Radical Polymerization of Styrene," Macromolecules, (2006), 39:1, pp. 39-45.
Jankova, et al., "Star Polymers by ATRP of Styrene and Acrylates Employing Multifunctional Initiators," Journal of Polymer Science Part A: Polymer Chemistry, Mar. 30, 2005, vol. 43, pp. 3748-3759.
Jeon, et al., "Synthesis of High Molecular Weight 3-Arm Star PMMA by ARGET ATRP," Macromolecular, 17:4 pp. 240-244, (2009).
Jo, N. et al., "Inhibition of platelet-derived growth factor B signaling enhances the efficacy of anti-vascular endothelial growth factor therapy in multiple models of ocular neovascularization," American Journal of Pathology, vol. 168, No. 6, pp. 2036-2053, Jun. 2006.
Jones, A., Analysis of Polypeptides and Proteins, Adv. Drug Delivery Rev. 10:, pp. 29-90, (1993).
Junghans, R.P., "Anti-Tac-H, a humanized antibody to the interleukin 2 receptor with new features for immunotherapyin malignant and immune disorders," Cancer Research, vol. 50, pp. 1495-1502, Mar. 1, 1990.
Kabat, E.A. et al., "Sequences of proteins of immunological interest," DIANE publishing, 1992.
Kallis, G.B. et al., "Differential reactivity of the functional sulfhydryl groups of cysteine-32 and cysteine-35 present in the reduced form of thioredoxin from *Escherichia coli*.," The Journal of Biological Chemistry, vol. 255, No. 21, pp. 10261-10266, Nov. 10, 1980.
Kempen, J, et al. The Prevalence of Diabetic Retinopathy Among Adults in the United States, Arch Opthalmol., vol. 122, pp. 532-563, (2004).
Kizhakkedathu, et al., "Synthesis of Well-Defined Environmentally Responsive Polymer Brushes by Aqueous ATRP," Macromolecules, (2004), 37:3, pp. 734-743.

(56) References Cited

OTHER PUBLICATIONS

Kostelny, S.A. et al., "Formation of a bispecific antibody by the use of leucine zippers," J. Immunol., vol. 148, No. 5, pp. 1547-1553, Mar. 1, 1992.
Kuhnert, F. et al. "Soluble receptor-mediated selective inhibition of VEGFR and PDGFR_ signaling during physiologic and tumor angiogenesis" PNAS, vol. 105, No. 29, pp. 10185-10190, (2008).
Kumar et al., "PDGF-DD targeting arrests pathological angiogenesis by modulating GSK3β phosphorylation," JBC Papers in Press, published on Mar. 15, 2010 as Manuscript M110.113787, retrieved on Jun. 18, 2015 from http://www.jbc.org; However, as this item is accessible on the world wide web, it may have been available in some form at an earlier point in time.
Kumar, A. et al., "Platelet-derived growth factor-DD targeting arrests pathological angiogenesis by modulating glycogen synthase kinase-3β phosphorylation," The Journal of Biological Chemistry, vol. 285, No. 20, pp. 15500-15510, May 14, 2010.
Kwiatdowski, et al., "High Molecular Weight Polymethacrylates by AGET ATRP under High Pressure," Macromolecules, (2008), 41:4, pp. 1067-1069.
Lacciardi, et al., "Synthesis of Novel Folic Acid-Functionalized Biocompatible Block Copolymers by Atom Transfer Radical Polymerization for Gene Delivery and Encapsulation of Hydrophobic Drugs," Biomacromolecules, (2005), 6:2, pp. 1085-1096.
Lafaut et al., "Clinicopathological correlation in exudative age related macular degeneration: histological differentiation between classic and occult choroidal neovascularisation," Br J Ophthalmol, vol. 84, pp. 239-243, 2000.
Lee, Ernes C., "Clinical manifestations of sarin nerve gas exposure," J. Am. Med. Assoc., vol. 290, No. 5, pp. 659-662, Aug. 6, 2003.
Lee, Vincent H.L., "Peptide and Protein Drug Delivery," CRC Press, 1990.
Lena, et al., "Investigation of metal ligand affinities of atom transfer radical polymerization catalysts with a quadrupole ion trap," Dalton Transactions, (2009), 41, pp. 8884-8889.
Lewis, et al., "Crosslinkable coatings from phosphorylcholine-based polymers," Biomaterials, (2001), 22, pp. 99-111.
Lewis, et al., "Poly(2-methacryloyloxyethyl phosphorylcholine) for Protein Conjugation," Bioconjugate Chem., (2008), 19:11, pp. 2144-2155.
Lin, Weifeng et al., "A novel zwitterionic copolymer with a short poly(methyl acrylic acid) block for improving both conjugation and separation efficiency of a protein without losing its bioactivity". Journal of Materialos Chemistry B. May 21, 2013, vol. 1, No. 19, pp. 2482-2488. See abstract; and p. 2487.
Lindley, H., "A study of the kinetics of the reaction between thiol compounds and chloroacetamide," Biochem J., vol. 74, pp. 577-584, Mar. 1960.
Liu, et al., "Syntheses and Micellar Properties of Well-Defined Amphiphilic $AB_2$ and $A_2B$ Y-Shaped Miltoarm Star Copolymers of ε-Caprolactone and 2-(Dimethylamino) ethyl Methacdrylate," *Journal of Polymer Science: Part A: Polymer Chemistry*, DOI 10.1002/pola, published online in Wiley InterSciences (www.intersience.wiley.com), Sep. 22, 2006; accepted Nov. 23, 2006.
Lockridge, O. et al., "Complete amino acid sequence of human serum cholinesterase," The Journal of Biological Chemistry, vol. 262, pp. 549-557, Jan. 15, 1987.
Lockridge, O. et al., "Large scale purification of butyrylcholinesterase from human plasma suitable for injection into monkeys; A potential new therapeutic for protection against cocaine and nerve agent toxicity, The Journal of Medical, Chemical, Biological, and Radiological Defense," 3:nimhs5095, doi: 10.1901/jaba.2005.3-nihms5095, 2005.
Lucentis ramibizumab (reb) Product Information Sheet most recent amendment Oct. 23, 2013.
Lutz, et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, (2006), 39:2, pp. 893-896.

Luxon, B. et al, "Pegylated interferons for the treatment of chronic hepatitis C infection," Clinical Therapeutics, vol. 24, Issue 9, pp. 1363-1383, Sep. 2002.
Ma, et al., "Synthesis of Biocompatible Polymers. 1. Homopolymerization of 2-Methacryloyloxyethyl Phosphorylcholine via ATRP in Protic Solvents: An Optimization Study," Macromolecules, (2002), 35:25, pp. 9306-9314.
Ma, et al., "Well-Defined Biocompatible Block Copolymers via Atom Transfer Radical Polymerization of 2-Methacryloyloxyethyl Phosphorylcholine in Protic Media," Macromolecules, (2003), 36:10, pp. 3475-3484.
Mabry, R. et al., "A dual-targeting PDGFRβ/VEGF—A molecule assembled from stable antibody fragments demonstrates anti-angiogenic activity in vitro and in vivo", Landes Bioscience, vol. 2, Issue 2, pp. 20-34 (2010).
Magalhaes et al., "Methods of Endotoxin Removal from Biological Preparations: a Review," J. Pharm Pharmaceut Sci., vol. 10, No. 3, pp. 388-404, 2007.
Mantovani, et al., "Design and Synthesis of N-Maleimido-Functionalized Hydrophilic Polymers via Copper-Mediated Living Radical Polymerization: A Suitable Alternative to PEGylation," J. Am. Chem. Soc., (2005), 127, pp. 2966-2973.
Marticorena, J. et al., "Sterile endophthalmitis after intravitreal injections," Mediators of Inflammation, vol. 2012, 6 pages, (2012).
Masson, P. et al., "Multidisciplinary approaches to cholinesterase functions. expression and refoldin of functional human butyrylcholinesterase in." E. coli., pp. 49-52, 1992.
Matyjaszewski, et al., "Diminishing catalyst concentration in atom transfer radical polymerization with reducing agents," PNAS, (Oct. 17, 2006), 103:42, pp. 15309-15314.
Mcpherson, D. et al., "Production and Purification of a Recombinant Elastomeric Polypeptide, G-(VPGVG)19-VPGV, from *Escherichia coli*," Biotechnology Process, vol. 8, Issue 4, pp. 347-352, Jul./Aug. 1992.
McRae, et al. "Pentafluorophenyl Ester-Functionalized Phosphorylcholine Polymers: Preparation of Linear, Two-Arm, and Grafted Polymer-Protein Conjugates," Biomacromolecules, 13, 2099-2109 (2012).
Millard, C.B. et al., "Design and expression of organophosphorus acid anhydride hydrolase activity in human butyrylcholinesterase," Biochemistry, vol. 34, No. 49, pp. 15925-15933, 1995.
Min, et al., "Use of Ascorbic Acid as Reducing Agent for Synthesis of Well-Defined Polymers by ARGET ATRP," Macromolecules, (2007), 40:6, pp. 1789-1791.
Miyamoto, et al., "Effect of water-soluble Phospholipid polymers conjugated with papain on the enzymatic stability," Biomaterials, (2004), 25, pp. 71-76.
Mones, "Inhibiting VEGF and PDGF to Treat AMD," Review of Ophthalmology, retrieved from <http://www.reviewofophthalmology.com/content/d/retinal_insider/c/29979/#>, Sep. 9, 2011; However, as this item is accessible on the world wide web, it may have been available in some form at an earlier point in time.
Morris, G.E., "Epitope mapping protocols in methods in molecular biology," vol. 66, 1996.
Neuberger, M., "Generating high-avidity human Mabs in mice," Nature Biotechnology, vol. 14, pp. 826, 1996.
Ng, et al., "Successful Cu-Mediated Atom Transfer Radical Polymerization in the Absence of Conventional Chelating Nitrogen Ligans," Macromolecules, (2010), 43:2, pp. 592-594.
Ogikubo, Y. et al., "Evaluation of the bacterial endotoxin test for quantification of endotoxin contamination of porcine vaccines," Biologicals, vol. 32, Issue 2, pp. 88-93, Jun. 2004.
Oh, et al., "Preparation of Poly(oligo(ethylene glycol) monomethyl ether methacrylate) by Homogeneous Aqueous AGET ATRP," Macromolecules, (2006), 39:9, pp. 3161-3167.
Ong, K. et al., "A rapid highly-sensitive endotoxin detection system," Biosensors and Bioelectronics, vol. 21, Issue 12, pp. 2270-2274, Jun. 15, 2006.
Ostberg, L. et al., "Human X (mouse X human) hybridomas stably producing human antibodies," Hybridoma, vol. 2, No. 4, pp. 361-367, 1983.
Padlan, Eduardo A., "A possible procedure for reducing the immunogenicity of antibody variable domains while preserving

(56) References Cited

OTHER PUBLICATIONS their ligand-binding properties," Molecular Immunology, vol. 28, Issues 4-5, pp. 489-498, Apr.-May 1991.
Palma, et al., "A new bispphosphonate-containing $^{99}$mTc(I) tricarbonyl complex potentially useful as bone-seeking agent: synthesis and biological evaluation," J Biol Inorg Chem, 12:667-679, (2007).
Papadopoulos et al., "Binding and neutralization of vascular endothelial growth factor (VEGF) and related ligands by VEGF Trap, ranibizumab and bevacizumab," Angiogenesis, vol. 15, pp. 171-185, 2012.
Pasut, et al., "Protein peptide and non-peptide drug PEGylation for therapeutic application," Expert Opin. Ther. Patents, 14(6) 859-894 (2004).
Paul, W., Fundamental Immunology, 2nd ed. Raven Press, N.Y., (1989).
Petsch, D. et al., "Endotoxin removal from protein solutions," Journal of Biotechnology, vol. 76, Issues 2-3, pp. 97-119, Jan. 21, 2000.
Pennock, S. et al Vascular Endothelial Growth Factor A Competitively Inhibits Platelet-Derived Growth Factor (PDGF)-Dependent Activation of PDGF Receptor and Subsequent Signaling Events and Cellar Responses, Molecular and Cell Biology, vol. 32, No. 2, pp. 1955-1966, (2012).
Piedmonte, D. et al., "Formulation of Neulasta® (pegfilgrastim)," Advanced Drug Delivery Reviews, vol. 60, Issue 3, pp. 50-58, Jan. 3, 2008.
Pietrasik, et al., "Synthesis of High Molecular Weight Poly(styrene-co-acrylonitrile) Copolymers with Controlled Architecture," Macromolecules, (2006), 39:19, pp. 6384-6390.
Poljak, R. "Production and structure of diabodies," Structure, vol. 2, Issue 12, pp. 1121-1123, Dec. 1994.
Pratt, et al. End-Functionalized Phosphorycholine Methacrylate and Their Use in Protein Conjugation, Biomacromlecules, vol. 9, pp. 2891-2897, (2008).
Presta et al., "Humanization of an Anti-Vascular Endothelial Growth Factor Monoclonal Antibody for the Therapy of Solid Tumors and Other Disorders," Cancer Research, vol. 57, pp. 4593-4599, 1997.
Raetz, C.R. et al., "Gram-negative endotoxin: an extraordinary lipid with profound effects on eukaryotic signal transduction," The FASEB Journal, vol. 5, No. 12, pp. 2652-2660, Sep. 1991.
Raica, M. et al., "Platelet-derived growth factor (PDGF)/PDGF receptors (PDGFR) axis as target for antitumor and antiangiogenic therapy," Pharmaceuticals, vol. 3, No. 3, pp. 572-599, (2010).
Ranganathan, et al., "Synthesis of Thermoresponsive Mixed Arm Star Polymers by Combination of RAFT and ATRP from a Multifunctional Core and Its Self-Assembly in Water," Macromolecules, (2008), 41:12, pp. 4226-4234.
*Regeneron Pharmaceuticals Inc.* vs. *Bayer Pharma AG* Approved Judgment dated Feb. 21, 2013.
Regillo, C. et al., "Randomized, double-masked, sham-controlled trial of ranibizumab for neovascular age-related macular degeneration: PIER Study Year 1," American Journal of Ophthalmology, vol. 145, Issue 2, pp. 239-248, Feb. 2008.
Roberts et al., "Chemistry for Peptide and Protein PEGylation," Advanced Drug Delivery Reviews 2002 54:459-476.
Roberts, W.G. et al., "Increased microvascular permeability and endothelial fenestration induced by vascular endothelial growth factor," Journal of Cell Science, vol. 108, pp. 2369-2379, (1995).
Rosenfeld, P. et al., "Ranibizumab for neovascular age-related macular degeneration," The New England Journal of Medicine, vol. 355, No. 14, pp. 1419-1431, Oct. 5, 2006.
Ruiz, et al., "Synthesis structure and surface dynamics of phosphorylcholine functional biomimicking polymers," Biomaterials, (1998), 19, pp. 987-998.
Ryan, et al., "Conjugation of salmon calcitonin to a combed-shaped end functionalized poly(poly(ethylene glycol) methyl ether methacrylate) yields a bioactive stable conjugate," Journal of Controlled Release, (2009), 135 pp. 51-59.
Rycroft, B.W., "Penicillin and the control of deep intra-ocular infection," British J. Ophthalmol, vol. 29, No. 2, pp. 57-87, Feb. 1945.

Sakaki, et al., "Stabilization of an antibody conjugated with enzyme by 2-methacryloyloxyethyl phosphorylcholine copolymer in enzyme-linked immunosorbent assay," J Biomed Mater Res, (1999), 47, pp. 523-528.
Samanta, et al., "End-Functionalized Phosphorylcholine Methacrylates and their Use in Protein Conjugation," Biomacromolecules, (2008), 9:(10), pp. 2891-2897.
Sayers, et al., "The Reduced Viscosity of PolyPEG® Compared with Linear PEG," Poster Warwick Effect Polymers Ltd, retrieved from <http:www.wep-ltd.co.uk> on Feb. 11, 2009.
Schellenberger, V. et al., "A recombinant polypeptide extends the in vivo half-life of peptides and proteins in a tunable manner," Nature Biotechnology, vol. 27, pp. 1186-1190, 2009.
Schlapschy, M. et al., "Fusion of a recombinant antibody fragment with a homo-amino-acid polymer; effects on biophysical properties and prolonged plasma half-life," Protein Eng Des Sel, vol. 20, Issue 6, pp. 273-284, Jun. 1, 2007.
Seo et al., "Conformational Recovery and Preservation of Protein Nature from Heat-Induced Debaturation by Water-Soluble Phospholipid Plymer Conjugation," Biomaterials, vol. 30, 2009, pp. 4859-4867.
Shen, B.Q. et al., "Conjugation site modulates the in vivo stability and therapeutic activity of antibody-drug conjugates," Nature Biotechnology, vol. 30, pp. 184-189, 2012.
Shim et al., "Structures of a platelet-derived growth factor/propeptide complex and a platelet-derived growth factor/receptor complex," PNAS, vol. 107, No. 25, pp. 11307-11312, 2010.
Songsilvilai, S. et al., "Bispecific antibody: a tool for diagnosis and treatment of disease," Clin Exp. Immunol., vol. 79, No. 3, pp. 315-321, Mar. 1990.
Stenzel, Martina H., "Bioconjugation using thiols: Old chemistry rediscovered to connect polymers nature's building blocks," ACS Macro letters, vol. 2, No. 1, pp. 14-18, 2013.
Stuttfeld et al., "Structure and function of VEGF receptors," Life, vol. 61, No. 9, pp. 915-922, 2009.
Tamura, M. et al., "Structural correlates of an anticarcinoma antibody: Identification of specificity-determining residues (SDRs) and development of a minimally immunogenic antibody variant by retention of SDRs only," The Journal of Immunology, vol. 164, No. 3, pp. 1432-1441, Feb. 1, 2000.
Tao, et al., "α-Aldehyde Terminally Functional Methacrylic Polymers from Living Radical Polymerization: Application in Protein Conjugation 'Pegylation'," J. Am, Chem. Soc., (2004), 126:41, pp. 13220-13221.
Tao, Lei et al., "Branched polymer-protein conjugates made from mid-chain-functional P (HPMA)", Biomacromolecules, 2009, vol. 10, No. 10, pp. 2487-2851. See abstract; pp. 2847 and 2850; and scheme 2.
Tonkinson, J. et al., "New Drugs: Antisense Oligodeoxynucleotides as Clinical Therapeutic Agents," Cancer Investigation, vol. 14, No. 1, pp. 54-65, 1996.
Ueda, et al., "Preparation of 2-Methacryloyloxyethyl Phosphocrycholine Copolymers with Alkyl Methacrylates and their Blood Campatability," Polymer Journal, vol. 24, No. 11, pp. 1259-1269 (1992).
UniProtKB-G3R0B5, retrieved on Mar. 19, 2016.
Uutela et al., "PDFG-D induces macrophage recruitment, increased intersitial pressure, and blood vessel maturation during angiogenesis," Blood, vol. 104, No. 10, pp. 3198-3204, Nov. 15, 2004.
Vajdos, F. et al., "Comprehensive functional maps of the antigen-binding site of an anti-ErbB2 antibody obtained with shotgun scanning mutagenesis," Journal of Molecular Biology, vol. 320, issue 2, pp. 415-428, Jul. 5, 2002.
Venditto, et al., "Cancer Therapies Utilizing the Camtothecins: A Review of the Vivo Literature," Molecular Pharmaceutics, vol. 7, No. 2, pp. 307-349 (2010).
Veronese, Francesco M., "Peptide and protein PEGylation: a review of problems and solutions," Biomaterials, vol. 22, Issue 5, pp. 405-417, Mar. 1, 2001.
Voynov et al., "Design and application of antibody cysteine variants," Bioconjugate Chemistry, vol. 21, pp. 385-392, Jan. 21, 2010.
Wagner, E. et al., "Transferrin-polycation conjugates as carriers for DNA uptake into cells," Proc. Natl. Acad. Sci. USA, vol. 87, No. 9, pp. 3410-3414, May 1, 1990.

(56) References Cited

OTHER PUBLICATIONS

Wang, X. et al., "Disulfide scrambling in IgG2 monoclonal antibodies: Insights from molecular dynamics simulations," Pharmaceutical Research, vol. 28, Issue 12, pp. 3128-3144, Dec. 2011.
Wang, et al., "Controlled/'Living' Radical Polymerization. Atom Transfer Radical Polymerization in the Presence of Transition-Metal Complexes," J. Am. Chem. Soc., (1995), 117:20, pp. 5614-5615.
Wang, et al., "Synthesis and Evaluation of Water-Soluble Polymers Bone-Targeted Drug Delivery Systems," Bioconjugate Chem., 14, 853-859 (2003).
Warwick Effect Polymers, PowerPoint presentation, "Polymers for the Healthcare and Specialty Materials Industries," Jan. 2009, pp. 1-29.
Wolfe, A. et al., "Use of cholinesterases as pretreatment drugs for the protection of rhesus monkeys against soman toxicity," Toxicology and Applied Pharmacology, vol. 117, Issue 2, pp. 189-193, Dec. 1992.
Wu, G.Y. et al., "Receptor-mediated in vitro gene transformation by a soluble DNA carrier system," Journal of Biological Chemistry, vol. 262, pp. 4429-4432, Apr. 5, 1987.
Yaseen, et al., "The Structure of Zwitterionic Phosphoacholine Surfactant Monolayers," Langmuir, (2006), 22:13, pp. 5825-5832.
Yeh, P. et al., "Design of yeast-secreted albumin derivatives for human therapy: biological and antiviral properties of a serum albumin-CD4 genetic conjugate," Proc Natl Acad Sci USA, vol. 89, No. 5, pp. 1904-1908, Mar. 1, 1992.
Yusa, et al., "Synthesis of Well-Defined Amphiphilic Block Copolymers Having Phospholipid Polymer Sequences as a Novel biocompatible Polymer Micelle Reagents," Biomacromolecules, 6, 663-670 (2005).
Zebrowski, B. et al., "Vascular endothelial growth factor levels and induction of permeability in malignant pleural effusions," Clinical Cancer Research, vol. 5, pp. 3364-3368, Nov. 1999.
Zetter, "Angiogenesis and Tumor Metastasis," Annu. Rev. Med., vol. 49, pp. 407-424, 1998.
Zhang, X et al., Prevalence of Diabetic Retinopathy in the United States, 2005-2008, JAMA. vol. 304, No. 6, pp. 649-656, (2010).
Advisory Action dated Jun. 12, 2014 in U.S. Appl. No. 13/959,563.
Extended European Search Report received in European Patent Application No. 17165316.5 dated Aug. 2, 2017.
Extended European Search Report received in European Patent Application No. 17181272.0 dated Feb. 23, 2018 in.
Extended European Search Report dated Mar. 21, 2016 in EP Application No. 11769715.1, dated Jul. 18, 2016.
Extended Search Report received in European Patent Application No. 14841835.3 dated Mar. 14, 2017.
Extended Search Report received in European Patent Application No. 15851363.0 dated Jan. 30, 2, 2018.
First Examination Report in NZ Application No. 6009449, dated Mar. 14, 2013.
First Examination Report in NZ Application No. 603048, dated Jun. 13, 2013 in 2 pages.
International Preliminary Report on Patentability dated Feb. 11, 2014 in PCT Application Np. PCT/US2011/32768.
International Preliminary Report on Patentability (IPRP) dated Jun. 24, 2014, in International Application No. PCT/IB2012/057491, 10 pages.
International Preliminary Report on Patentability (IPRP) dated Jul. 5, 2016, in International Application No. PCT/US2015/038203.
International Preliminary Report on Patentability dated Apr. 18, 2017 in International Application No. PCT/US2015/056112.
International Search Report and Written Opinion dated Feb. 27, 2013 in Internatnional Application No. PCT/US2012/060301.
International Search Report and Written Opinion dated Mar. 30, 2017 for International Patent Application No. PCT/US2016/069336 filed Dec. 29, 2016.
International Search Report in PCT Application No. PCT/US2007/005372, dated Aug. 8, 2008.
International Search Report and Written Opinion dated Sep. 9, 2010 in PCT Application No. PCT/US2010/034252.
International Search Report and Written Opinion dated May 9, 2011 in PCT Application No. PCT/US2010/61358.
International Search Report and Written Opinion dated Dec. 16, 2011 in PCT Application Np. PCT/US2011/327681.
International Search Report in PCT Application No. PCT/US2014/054622, dated Feb. 27, 2015.
International Search Report and Written Opinion for PCT/US2015/038203, dated Dec. 8, 2015.
International Search Report and Written Opion dated Apr. 1, 2016 in in International Application No. PCT/US2015/056112.
International Search Report dated Jun. 4, 2013, in International Application No. PCT/IB2012/057491.
Notice of Allowance dated Jul. 31, 2014 in U.S. Appl. No. 13/959,563.
Notice of Allowance dated Jan. 28, 2014 in U.S. Appl. No. 13/515,913.
Notice of Allowance dated Aug. 9, 2017 in U.S. Appl. No. 14/753,824.
Notice of Final Rejection received in Korean Patent Application No. 10-2012-7029878 dated Aug. 28, 2017.
Notice of Final Rejection received in Korean Patent Application No. 10-2012-7029878 dated Oct. 27, 2017.
Notice of Rejection received in Japanese Patent Application No. 2016-159104 dated Jun. 27, 2017.
Notice of Rejection received in Japanese Patent Application No. 2016-159104 dated Feb. 26, 2018.
Office Action in U.S. Appl. No. 13/959,563, dated Oct. 10, 2013.
Office Action in U.S. Appl. No. 13/959,563, dated Feb. 20, 2014.
Office Action in U.S. Appl. No. 14/456,875, dated Jun. 9, 2015.
Office Action in U.S. Appl. No. 14/456,875, dated Oct. 5, 2016 in 10 pages.
Office Action in U.S. Appl. No. 14/456,875, dated Apr. 20, 2017.
Office Action in U.S. Appl. No. 14/456,875, dated Dec. 14, 2017.
Office Action dated Feb. 7, 2012 in U.S. Appl. No. 12/281,071.
Office Action in JP Patent Application No. 2008-557399, dated May 25, 2013.
Office Action in CA Application No. 2783615, dated Sep. 16, 2016.
Office Action in CA Application No. 2783615, dated Jan. 9, 2018.
Office Action dated Dec. 14, 2015 in U.S. Appl. No. 14/265,174.
Office Action in EP Application No. 10838353.0, dated Oct. 4, 2016.
Office Action in JP Application No. 2012-544945, dated Jul. 9, 2014.
Office Action in JP Application No. 2016-159104, dated Jun. 27, 2017.
Office Action dated Feb. 8, 2018 in Indian Patent Application No. 6116/CHENP/2012.
Office Action dated Dec. 31, 2013 in U.S. Appl. No. 13/516,173.
Office Action dated Jul. 2, 2014 in U.S. Appl. No. 13/516,173.
Office Action dated Dec. 16, 2014 in U.S. Appl. No. 13/516,173.
Office Action dated May 30, 2017 U.S. Appl. No. 15/099,234.
Office Action dated Apr. 12, 2018 in Australain Patent Application Np. 2017201930.
Office Action dated Jun. 2, 2016 U.S. Appl. No. 13/901,483.
Office Action dated Feb. 9, 2018 in U.S. Appl. No. 15/368,376.
Office Action dated Apr. 6, 2017 Canadian Patent Application No. 2,795,667.
Office Action dated Dec. 29, 2017 Canadian Patent Application No. 2,795,667.
Office Action in CN Application No. 201180028682.1, dated Aug. 21, 2014.
Office Action in CN Application No. 201180028682.1, dated Jan. 26, 2015.
Office Action in CN Application No. 20118002868.1, dated Aug. 11, 2015.
Office Action received in European Patent Application No. 11769715.1 dated Nov. 9, 2017.
Office Action in JP Application No. 2015-165282, dated Aug. 15, 2016.
Office Action in JP Application No. 2015-165282, dated Aug. 1, 2017.
Office Action in KR Application No. 10-2012-7029878, dated Mar. 8, 2017.
Office Action dated Mar. 9, 2018 in KR Application No. 10-217-703456.

(56) References Cited

OTHER PUBLICATIONS

Office Action dated Jan. 24, 2018 in U.S. Appl. No. 14/916,180.
Office Action dated Feb. 27, 2017 in U.S. Appl. No. 14/753,824.
Office Action dated May 8, 2017 in U.S. Appl. No. 14/932,913.
Office Action dated Aug. 16, 2017 in U.S. Appl. No. 14/932,913.
Office Action dated Dec. 15, 2017 in U.S. Appl. No. 14/932,913.
Patent Examination Report No. 1 in AU Application No. 2010330727, dated Nov. 19, 2014.
Patent Examination Report in AU Application No. 2011239434, dated Mar. 19, 2014.
Patent Examination Report in AU Application No. 2015207898, dated Mar. 23, 2016.
Patent Examination Report in AU Application No. 2015207898, dated May 27, 2017.
PCT Invitation to Pay Additional Fees dated Feb. 3, 2016 in International Application No. PCT/US2015/056112.
Restriction Requirement dated Jun. 20, 2011 in U.S. Appl. No. 12/28107.
Restriction Requirement dated Jul. 15, 2015 in U.S. Appl. No. 14/265,174.
Restriction Requirement dated Aug. 14, 2013 in U.S. Appl. No. 13/515,913.
Restriction Requirement dated Sep. 3, 2013 in U.S. Appl. No. 13/516,173.
Restriction Requirement dated Feb. 9, 2017 U.S. Appl. No. 15/099,234.
Restriction Requirement dated Nov. 3, 2015 U.S. Appl. No. 13/901,483.
Restriction Requirement dated Aug. 21, 2017 in U.S. Appl. No. 15/368,376.
Restriction Requirement dated Jan. 31. 2017in U.S. Appl. No. 14/916,180.
Restriction Requirement dated Aug. 16, 2017in U.S. Appl. No. 14/916,180.
Restriction Requirement dated Jan. 13, 2017in U.S. Appl. No. 14/932,913.
Supplemental European Search Report received in European Patent Application No. EP 07752096.3 dated Feb. 19, 2013.
Supplemental European Search Report dated Feb. 2, 2015 in European Patent Application No. EP 10838353.0 dated Feb. 2, 2015.
Office Action dated May 4, 2018 in U.S. Appl. No. 14/932,913.
Engelgau, M et al. Evolving Diabetes Burden in the United States. Ann of Int Med. 140 (11): 945-951, 2004.
Meng, X. et al. New Generation Recombinant hBuChe-FC Fusion with In-Vivo Performance Equivilanet to Gold Standard Plasma-Derive hbuChe-A First-in-Class Broad Spectrum Bioscanvenger that is Sustainable, Scalable, and Highly Cost-Effective on a Troop-Equivalent-Dose (TED) Basis.
File History of U.S. Appl. No. 13/959,563, filed Aug. 5, 2013.
File History of U.S. Appl. No. 14/456,875, filed Aug. 11, 2014.
File History of U.S. Appl. No. 12/281,071, filed Aug. 28, 2008.
File History of U.S. Appl. No. 14/265,174, filed Apr. 29, 2014.
File History of U.S. Appl. No. 15/182,278, filed Jun. 14, 2016.
File History of U.S. Appl. No. 13/515,913, filed Aug. 27, 2012.
File History of U.S. Appl. No. 13/516,173, filed Aug. 27, 2012.
File History of U.S. Appl. No. 15/099,234, filed Apr. 14, 2016.
File History of U.S. Appl. No. 13/901,483, filed May 23, 2013.
File History of U.S. Appl. No. 14/916,180, filed Mar. 2, 2016.
File History of U.S. Appl. No. 14/753,824, filed Jun. 29, 2015.
File History of U.S. Appl. No. 15/820,325, filed Nov. 21, 2017.
File History of U.S. Appl. No. 14/932,913, filed Nov. 4, 2015.
International Preliminary Report on Patentability on dated Jul. 3, 2018 for International Patent Application No. PCT/US2016/069336 filed Dec. 29, 2016.
International Search Report and Written Opinion for PCT/US2018/027378 dated Sep. 27, 2018.
Notice of Allowance dated Sep. 26, 2018 in Canadian Patent Application No. 2,783,615.
Notice of Allowance dated Sep. 11, 2018 in U.S. Appl. No. 14/932,913.
Notice to File a Response received in Korean Patent Application No. 10-2012-7018788 dated Sep. 13, 2017.
Office Action in U.S. Appl. No. 14/456,875, dated Aug. 28, 2018.
Office Action dated Oct. 19, 2018 U.S. Appl. No. 15/099,234.
Office Action dated Sep. 10, 2018 in U.S. Appl. No. 15/368,376.
Office Action dated Aug. 28, 2018 in KR Application No. 10-217-703456.
Office Action dated Jul. 13, 2018 in Japanese Patent Application No. 2016-540916.
Office Action dated Aug. 10, 2018 in U.S. Appl. No. 14/916,180.
Office Action dated May 8, 2018 in Japanese Patent Application No. 2017-520515.
Office Action dated Jun. 27, 2018 in Indian Patent Application No. 9476/CHENP/2012.
File History of U.S. Appl. No. 15/952,092, filed Apr. 12, 2018.
Office Action dated May 14, 2019 U.S. Appl. No. 15/099,234.
U.S. Appl. No. 09/253,689, filed Feb. 20, 1999, Fung et al.
Casset, F. et al. A Peptide Mimetic of an Anti0CD4 Monoclonal Antibody by Rational Design, Biochemical and Biophysical Research Communications, vol. 307, pp. 198-205, (2003).
Chen, Y et al. Selection and Analysis an Optimized Anti-VEGF Antibody: Crystal Structure of an Affinity-Matured Complex with Antigen, J. Mol, Biol,, vol. 293, pp. 865-881 , (1999).
Janssen, Alzheimer Immunotherapy Research & Development, LLC, AAB-001 in Patients With Mild to Moderate Alzheimer's Disease, Clinical Trials, gov, NIH, 2005, [retrieved on Jun. 19, 2012]. Retrieved from the Internet: <http://clinicaltrials.gov/ct2/show/NCT00112073?term=aab-001&rank=3>.
Maccallum, R. et al., Antibody-Antigen Interactions: Contact Analysis and Binding Site Toopgraphy, J/. Mol Biol., vol. 262, pp. 732-745, (1996).
Mayadunne, R. et al. Living Free Radical Polymerization with Reversible Addition-Fragmentation Chain Transfer (RAFT Polymerization): Approaches to Star Polymers, Macromolecules, vol. 36, pp. 1505-1513, (2003).
Robinson, K. et al. Controlled Polymerization of 2-Hydroxyethyl Methacrylate by ATRP at Ambient Temperature, Macromolecules, vol. 34, pp. 3155-3158, (2001).
Rudikoff, S. et al, Single Amino Acid Subs Altering Antigen-Binding Specificity, Proc Natl. Acad. Sci. USA, vol. 79, pp. 1979-1983, (1982).
Vafa, O. et al. An Engineered FC Variant of an IG Eliminates All Immune Effecotr Functions via Structural Perturbations, Methods, vol. 65, pp. 114-126, (2014).
Wu, H et al., Humanization of a Murine Monoclonal Antibody by Simultaneous Optimization of Framework and CDR Residues, J. Mol. Biol., vol. 294, pp. 151-162, (1999).
Xiaoying, S. et al. Synthesis and Characterization of a Multiarm Star Polymer, Journal of Polymer Science, vol. 42, pp. 2356-2364, (2004).
Zhang, X et al. Synthesis of Functional Polystyrenes by Atom Transfer Radical Polymerization Using Protected and Unprotected Carboxylic Acid Initiators, Macromolecules, vol. 32, pp. 7349-7353, (1999).
Advisory Action dated Nov. 29, 2018 in U.S. Appl. No. 14/916,180.
Advisory Action dated Dec. 11, 2018 in U.S. Appl. No. 14/916,180.
Notice of Allowance dated Jan. 30, 2019 in U.S. Appl. No. 14/932,913.
Office Action in U.S. Appl. No. 14/456,875, dated Mar. 8, 2019.
Office Action Received in Chinese Patent Application No. 201080062252.7 dated Apr. 20, 2017.
Office Action Received in Chinese Patent Application No. 201610439969.8 dated Jul. 24, 2018.
Office Action in European Patent Application No. 17181272.0 dated Oct. 31, 2018.
Office Action in European Patent Application No. 17181272.0 dated Mar. 22, 2019.
Office Action in KR Application No. 10-2012-7018788, dated Mar. 10, 2017.
Office Action dated Mar. 27, 2019 in Australian Patent Application Np. 2017201930.
Office Action dated Mar. 11, 2019 in U.S. Appl. No. 15/368,376.
Office Action received in Chinese Patent Application No. 201610446624.5 dated Mar. 12, 2018 in 12 pages.

(56) References Cited

OTHER PUBLICATIONS

Office Action received in Chinese Patent Application No. 201610446624.5 dated Nov. 26, 2018.
Office Action in JP Application No. 2015-165282, dated Sep. 27, 2018.
Office Action dated Nov. 27, 2018 in Japanese Patent Application No. JP 2017-231724.
Office Action dated Oct. 26, 2018 in KR Application No. 10-2017-703456.
Office Action received in Mexican Patent Application No. Mx/a/2012/011876 dated Jul. 13, 2017.
Office Action dated Jan. 16, 2018 in MX Application No. Mx/a/2012/011876.
Office Action dated Jun. 6, 2018 in Mexican patent Application No. Mx/a/2012/011876.
Office Action dated Dec. 17, 2018 in Mexican patent Application No. Mx/a/2012/011876.
Office Action dated Jan. 23, 2019 in European Patent Application No. EP 14841835.3.
Office Action dated Mar. 8, 2019 in U.S. Appl. No. 14/916,180.
Office Action dated Jan. 9, 2019 in U.S. Appl. No. 15/820,325.
Office Action dated Feb. 21, 2019 in European Patent Application No. 15851363.0.
Office Action dated Dec. 18, 2018 in Japanese Patent Application No. 2017-520515.
Office Action dated Apr. 23, 2019 in Korean Patent Application No. KR 10-2017-7013268.
Office Action Received in Chinese Patent Application No. 201610439969.8 dated Mar. 19, 2019.
File History of U.S. Appl. No. 16/290,128, filed Mar. 1, 2019.
Bock, F. et al. Safety Profile of Topical VEGF Neutralization at the Cornea, Investigative Opthalmology & Visual Science, vol. 50, No. 5, pp. 2095-2012, (2009).
Pan, C. et al. Comparison of Long-Acting Bevacizumab Formulations in the Treatment of Choroidal Neovascularization in a Rat Model, Journal of Ocular Pharmacology and Therapeutics., vol. 27, No. 3, pp. 219-224, (2011).
Partial Supplementary European Search Report dated Jul. 11, 2019 in European Patent Application No. 16882707.9.
Geng, J. et al. Site-Directed Conjugation of "Clicked" Glycopolymers to Form Glycoprotein Mimics: Binding to Mammalian Lectin and Induction of Immunological Function, J. Am. Chem. Soc., 2007, 127, pp. 15156-15163.
Advisory Action dated Sep. 9, 2019 in U.S. Appl. No. 14/916,180.
International Search Report and Written Opinion dated Jun. 20, 2019 in International Application No. PCT/US2019/020418.
Notice of Hearing dated Jun. 24, 2019 in Indian Patent Application No. 6116/CHENP/2012.
Notice of Hearing dated Aug. 19, 2019 in Indian Patent Application No. 9476/CHENP/2012.
Office Action dated Apr. 5, 2019 in Mexican Patent Application No. Mx/a/2016/010818.
Office Action dated Aug. 2, 2019 in U.S. Appl. No. 15/368,376.
Office Action dated Jun. 4, 2019 in Japanese Patent Application No. JP 2017-231724.
Office Action dated May 21, 2019 in Korean Patent Application No. 10-2018-7034569.
Office Action dated Jun. 26, 2019 in U.S. Appl. No. 14/916,180.
Office Action dated Jul. 29, 2019 in U.S. Appl. No. 15/820,325.
Office Action dated Jun. 4, 2019 in Japanese Patent Application No. JP 2016-575823.
Trial Decision in KR Application No. 10-2012-7029878, dated Jul. 23, 2019.
Chames, Patrick et al., "Therapeutic antibodies: successes, limitation and hopes for the future, " British Journal of Pharmacology, Wiley-Blackwell, UK; Biosciences Information Service, vol. 157, No. 2, May 1, 2009, pp. 220-233.
Jorg T. Regula, et al., "Targeting key angiogenic pathways with a bispecific CrossMab, optimized for neovascular eye diseases," EMBO Molecular Medicine (online), vol. 8, No. 11, Oct. 14, 2016, pp. 1265-1288.
Written Opinion, Singapore Patent Application No. 11201805420S, dated Dec. 22, 2019.
Search Report, Singapore Patent Application No. 11201805420S, dated Dec. 22, 2019.
Extended European Search Report, EP16882707.9, dated Nov. 19, 2019.
Office Action, BR112012014556-8, dated Nov. 6, 2019.
Rejection Decision Received in Chinese Patent Application No. 201610439969.8 dated Sep. 20, 2019.
Japanese Office Action, JP 2018-189049, dated Dec. 3, 2019.
Office Action, BR112012026118.5, dated Aug. 23, 2019.
Office Action dated Dec. 24, 2019 in Japanese Patent Application No. JP 2017-231724.
Office Action, EP 14 841 835.3 dated Jan. 23, 2019.
Office Action, JP2019-000261, dated Feb. 12, 2020.
Office Action dated Jul. 29, 2019, U.S. Appl. No. 15/820,325.
Office Action dated Jan. 20, 2020 in Japanese Patent Application No. JP 2016-575823.
Office Action dated Oct. 18, 2019, European Patent Application No. 15851363.0.
OA Japanese Patent Application No. 2017-520515, mailed May 8, 2018.
OA Japanese Patent Application No. 2017-520515, mailed Feb. 17, 2020.
Office Action dated Nov. 14, 2019 in Korean Patent Application 10-2017-7013268.
Office Action dated Feb. 17, 2020 in Korean Patent Application 10-2017-7013268.
Office Action dated Apr. 3, 2020 in Chinese Application No. 201580046779.3 with English Translation.
Notice of Allowance dated Nov. 15, 2019 in U.S. Appl. No. 15/820,325.
Corrected Notice of Allowability dated Feb. 27, 2020 in U.S. Appl. No. 15/820,325.
Notice of Allowance dated Apr. 2, 2020 in U.S. Appl. No. 15/820,325.
Corrected Notice of Allowability dated Apr. 29, 2020 in U.S. Appl. No. 15/820,325.
Supplementary Partial European Search Report dated Dec. 21, 2017 in European Patent Application No. 15812238.2.
Extended European Search Report dated Mar. 29, 2018 in European Patent Application No. 15812238.2.
Office Action dated Mar. 18, 2020 in Australian Application No. 2015279560.
U.S. Appl. No. 16/795,450, filed Feb. 19, 2020, Perlroth et al.
Office Action dated Sep. 28, 2020 in European Application No. 1682707.9.
Office Action received in Chinese Patent Application No. 2015800564492 dated Oct. 27, 2020.
Office Communication received in U.S. Appl. No. 16/290,128 dated Nov. 12, 2020.
Office Action in U.S. Appl. No. 16/402,602, dated Nov. 20, 2020.
Allen et al., "Combined antiangiogenic and anti-PD-L1 therapy stimulates tumor immunity through HEV formation", Science Translational Medicine, 9(385): dated Apr. 12, 2017.
Boyd et al., "The effect of the removal of sialic acid, galactose and total carbohydrate on the functional activity of Campath-1H", Molecular Immunology, vol. 32: dated Dec. 1995, pp. 1311-1318.
Capel et al., "Heterogeneity of human IgG Fc receptors", Immunomethods, 4(1): dated Feb. 1994 pp. 25-34.
Connelly "In Vivo Gene Delivery and Expression of Physiological Levels of Functional Human Factor VIII in Mice" Human Gene Therapy, 1995, 1:185.
Curiel, "High-Efficiency Gene Transfer Mediated by Adenovirus Coupled to DNA—Polylysine Complexes" Hum. Gene Ther., 1992, 3:147.
De Haas et al., "Fc gamma receptors of phagocytes", Journal of Laboratory and Clinical Medicine, 126(4): dated Oct. 1995, pp. 330-341.

(56) References Cited

OTHER PUBLICATIONS

Eppstein et al., "Biological activity of liposome-encapsulated murine interferon gamma is mediated by a cell membrane receptor", Proc. Natl. Acad. Sci. USA, vol. 82: dated Jun. 1985 pp. 3688-3692.
Findeis et al., "Targeted delivery of DNA for gene therapy via receptors" Trends Biotechnol., 1993, 11:202.
Guyer et al., "Immunoglobulin Binding by Mouse Intestinal Epithelial Cell Receptors", The Journal of Immunology, 117(2): dated Aug. 1, 1976, pp. 587-893.
Hein J., 1990, Unified Approach to Alignment and Phylogenies pp. 626-645 Methods in Enzymology vol. 183, Academic Press, Inc., San Diego, CA.
Higgins, D.G. and Sharp, P.M., "Fast and sensitive multiple sequence alignments on a microcomputer" CABIOS 5: dated 1989, pp. 151-153.
Hinton et al., "Engineered human IgG antibodies with longer serum half-lives in primates", Journal of Biological Chemistry, 279(8): dated Feb. 20, 2004 in 5 pages.
Hsu et al., "Differential N-Glycan Patterns of Secreted and Intracellular IgG Produced in Trichoplusia ni Cells" Journey of Biol. Chem. vol. 272: dated 1997, pp. 9062-9070.
Hwang et al., "Hepatic uptake and degradation of unilamellar sphingomyelin/cholesterol liposomes: a kinetic study", Proceedings of the National Academy of Sciences of the United States of America, 77(7): dated Jul. 1980, pp. 4030-4034.
Jefferis et al., "Glycosylation of Antibody Molecules: Structural and Functional Significance", Antibody Engineering, vol. 65: dated 1997, pp. 111-128.
Johnson et al., "Kabat Database and its applications: 30 years after the first variability plot", Nucleic Acids Research, 28(1): Jan. 1, 2000, pp. 214-218.
Kaplitt, "Long-term gene expression and phenotypic correction using adeno-associated virus vectors in the mammalian brain" Nature Genetics, 1994, 8:148.
Kimura, "Retroviral Delivery of DNA into the Livers of Transgenic Mice Bearing Premalignant and Malignant Hepatocellular Carcinomas" Human Gene Therapy, 1994, 5:845.
Kim et al., "Identifying amino acid residues that influence plasma clearance of murine IgG1 fragments by site-directed mutagenesis", European Journal of Immunology, 24(3): dated Mar. 1994.
Kohler et al, "Continuous cultures of fused cells secreting antibody of predefined specificity", Nature, vol. 256: dated 1975, pp. 495-497.
Kunik et al., "Paratome: an online tool for systematic indentification of antigen-binding regions in antibodies based on sequence or structure", Nucleic Acids Research, vol. 40: Jun. 6, 2012, W521-524.
Lazar et al., "Engineered antibody Fc variants with enhanced effector function", Proc Natl Acad Sci U S A, 103(11): dated Mar. 14, 2006 in 6 pages.
Lefranc et al., "IMGT unique numbering for immunoglobulin and T cell receptor variable domains and Ig superfamily V-like domains", Developmental and Comparative Immunology, vol. 27: dated 2003, pp. 55-77.
Makabe et al., "Thermodynamic Consequences of Mutations in Vernier Zone Residues of a Humanized Anti-human Epidermal Growth Factor Receptor Murine Antibody, 528", Journal of Biological Chemistry, vol. 283: dated Jan. 11, 2008, pp. 1156-1166.
Martin et al., "Modeling antibody hypervariable loops: A combined algorithm", Proc. Natl. Acad. Sci. USA, vol. 86: dated Dec. 1989, pp. 9268-9272.
Mccafferty et al., "Phage antibodies: filamentous phage displaying antibody variable domains", Nature, vol. 348: dated 1990, pp. 552-554.
Myers, E.W. and Muller W., "Optimal alignments in linear space" CABIOS 4: dated 1988, pp. 11-17.
Philip, "Efficient and sustained gene expression in primary T lymphocytes and primary and cultured tumor cells mediated by adeno-associated virus plasmid DNA complexed to cationic liposomes." Mol. Cell Biol., 1994, 14:2411.

Samudrala et al., "Ab initio protein structure prediction using a combined hierarchical approach", Proteins, Structure, Function, Bioinformatics, 37(S3): dated 1999, pp. 194-198.
Saitou, N., Nei, M., "The neighbor-joining method: a new method for reconstructing phylogenetic trees." Mol. Biol. Evol. vol. 4: dated 1987, pp. 406-425.
Takahara, et al., Int. Symp. Nano-bio-Interfaces Rel. Mol. Molecular Mobility, Program and Abstracts Book, p. 25-26, https://www.nof.co.jp/business/life/product01.html (2009).
Tsukamoto et al., "Combined Blockade of IL6 and PD-1/PD-L1 Signaling Abrogates Mutual Regulation of Their Immunosuppressive Effects in the Tumor Microenvironment", Cancer Research, 78(17): dated Sep. 2018 in 12 pages.
Umana et al., "Engineered glycoforms of an antineuroblastoma IgG1 with optimized antibody-dependent cellular cytotoxic activity." 1999, Nature Biotech. 17:176-180.
Wilbur, W.J. and Lipman, D.J., "Rapid similarity searches of nucleic acid and protein data banks" 1983, Proc. Natl. Acad. Sci. USA 80: pp. 726-730.
Wittwer et al., "Glycosylation at Asn-184 inhibits the conversion of single-chain to two-chain tissue-type plasminogen activator by plasmin", Biochemistry, 29(17): dated May 1, 1990, pp. 4175-4180.
Woffendin, "Nonviral and viral delivery of a human immunodeficiency virus protective gene into primary human T cells" Proc. Natl. Acad. Sci., 1994, 91:1581.
Wright et al., "Effect of glycosylation on antibody function: implications for genetic engineering", Trends Biotechnol, 15(1): dated Jan. 1997, pp. 26-32.
Wu et al., "Receptor-mediated Gene Delivery and Expression in Viuo" J. Biol. Chem., 1988, 263.
Wu et al., "Receptor-mediated Gene Delivery in Vivo" J. Biol. Chem., 1991, 266.
Wu et al., "Incorporation of Adenovirus into a Ligand-based DNA Carrier System Results in Retention of Original Receptor Specificity and Enhances Targeted Gene Expression" J. Biol. Chem., 1994, 269.
Wu, "Targeting Genes: Delivery and Persistent Expression of a Foreign Gene Driven by Mammalian Regulatory Elements in Vivo" J. Biol. Chem., 1989, 264:16985.
Zenke et al., "Receptor-mediated endocytosis of transferrin-polycation conjugates: an efficient way to introduce DNA into hematopoietic cells." Proc. Natl. Acad. Sci. USA, 1990, 87:3655.
Edwards et al., "The Remarkable Flexibility of the Human Antibody Repertoire; Isolation of Over One Thousand Different Antibodies to a Single Protein, BLyS", J. Mol. Biol., vol. 334, pp. 103-118, 2003.
Katschke et al., "Inhibiting Alternative Pathway Complement Activation by Targeting the Factor D Exosite", The Journal of Biological Chemistry, vol. 287, No. 16, pp. 12886-12892, Apr. 13, 2012.
Lloyd et al., "Modelling the human immune response: performance of a $10^{11}$ human antibody repertoire against a broad panel of therapeutically relevant antigens", Protein Engineering Design & Selection, vol. 22, No. 3, pp. 159-168, 2009.
Roitt, I.M., "Immunology— Second Edition", Gower Medical Publishing, 1989, pp. 5.8, 5.9.
Office Action received in Chinese Patent Application No. 2015800564492 dated Apr. 22, 2020.
Office Action, U.S. Appl. No. 16/290,128, dated May 22, 2020.
Brazilian Office Action, BR application No. BR11 2012 014556-8 dated Jun. 12, 2020, 5 pages.
Office Action dated Jul. 15, 2020 in Mexican patent Application No. Mx/a/2016/017290.
Notice of Allowance dated Sep. 4, 2020 in U.S. Appl. No. 15/820,325.
Office Action dated Apr. 13, 2020 in U.S. Appl. No. 16/402,602.
Office Action dated Aug. 3, 2020 in U.S. Appl. No. 16/402,602.
Office Action dated Jul. 9, 2020 in European Patent Application No. 15812238.2.
Pakula, et al., "Genetic Analysis of Protein Stability and Function," Annual Reviews of Genetics, vol. 23, pp. 289-310, Dec. 1989.
Office Action dated Sep. 8, 2020 in Russian Patent Application No. 2018126519.
Perederni, et al., "Endocrine Ophthalmopathy," Eye Diseases 5. Complete reference, Feb. 6, 2008, pp. 154-158, 162.

(56) References Cited

OTHER PUBLICATIONS

Notice of Acceptance for Patent Application, Australian Application No. 2015279560, dated Sep. 2, 2020, in 3 pages.
Advisory Action dated Apr. 1, 2020 in U.S. Appl. No. 15/099,234.
Notice of Allowance dated Jun. 10, 2020 in U.S. Appl. No. 15/820,325.
Office Action dated May 19, 2020 in Japanese Application No. 2018-189049 with English Translation.
Office Action dated May 27, 2020 in European Application No. 15 851 363.0.
Office Action, Russian Patent Application No. 2018126519, dated Apr. 28, 2020 with English Translation.
Brazilian Office Action, BR Application No. BR11 2012 014556-8, dated May 12, 2020, in 5 pages with English Translation.
Restriction Requirement dated Apr. 21, 2020 in U.S. Appl. No. 16/424,265.
Restriction Requirement dated Mar. 3, 2020 in U.S. Appl. No. 15/952,092.
Office Action received in Chinese Patent Application No. 201610446624.5 dated Feb. 6, 2020 with English Translation.
Office Action received in Chinese Patent Application No. 201610446624.5 dated Jun. 14, 2019, with English Summary.
Extended European Search Report in EP Application No. 19175761.6, dated Nov. 27, 2019.
Office Action, U.S. Appl. No. 15/952,092, dated Jun. 30, 2020.
Binder S, Stanzel BV, Krebs I, Glittenberg C. 2007. Transplantation of the RPE in AMD. Prog Retn Eye Res. 26:516-554.
Chiou et al., Gene Therapeutics: Methods and Applications of Direct Gene Transfer, J.A. Wolff, ed., 1994.
Dayhoff, M.O. (ed.) Atlas of Protein Sequence and Structure, National Biomedical Research Foundation, Washington DC vol. 5, Suppl. 3, pp. 345-358.
Iwahashi et al., " CDR substitutions of a humanized monoclonal antibody (CC49): contributions of individual CDRs to antigen binding and immunogenicity," Mol. Immunol. 36: Issue 15-16, 1079-1091, 1999.
Klein R, Klein BE, Jensen SC, Meuer SM. 1997. The five-year incidence and progression of age-related maculopathy: The Beaver Dam Eye Study. Ophthal. 104:7-21.
Robinson, D.F, "Comparison of Labeled Trees with Valency Three," Journal of Combinational Theory 11: pp. 105-119 (1997).
Wyss et al., " Current Opinion in Biotechnology," vol. 7 (4): pp. 409-146, 1996.
U.S. Appl. No. 17/066,856, filed Oct. 9, 2020, Ehrlich et al.
Office Action dated Sep. 2, 2020 in Japanese Application No. 2017-520515 with English Translation.
Office Action dated Sep. 30, 2020 in Canadian Application No. 3,059,938.
File History of U.S. Appl. No. 16/424,265, filed Aug. 11, 2014.
File History of U.S. Appl. No. 15/368,376, filed Dec. 2, 2016.
File History of U.S. Appl. No. 13/641,342, filed Dec. 2, 2016.
File History of U.S. Appl. No. 16/7818,69, filed Mar. 2, 2016.
File History of U.S. Appl. No. 16/795,450 filed Jun. 29, 2015.
File History of U.S. Appl. No. 16/402,602 filed Nov. 4, 2015.
Notice of Allowance dated Oct. 26, 2020 in Korean Application No. 10-2017-7013268.
Office Action with English Translation dated Jan. 26, 2021 in Japanese Application No. 2018-534732 in 9 pages.
Restriction Requirement dated Feb. 2, 2021 in U.S. Appl. No. 17/066,856 in 6 pages.
Decision of Refusal dated Oct. 21, 2020 in Japanese Patent Application No. 2016-575823.
Notice of Allowance dated Dec. 22, 2020 in U.S. Appl. No. 15/820,325 in 15 pages.
International Search Report with written Opinion dated Feb. 8, 2021 in PCT Application No. US2020/055074.
Kernt et al. "Improvement of Diabetic Retinopathy with Intravitreal Ranibizumab," Diabetes Research and clinical Practice, Feb. 5, 2013 (Feb. 5, 2013), vol. 100, No. 1, pp. 11-13. entire document.
Paul, "Fv Structure and Diversity in Three Dimensions," Fundamental Immunology, 1993, 3rd Edition, pp. 292-295.
Decision to Grant with English Translation dated Jan. 21, 2021 in Russian Application No. 2018126519/10.
Examination Report dated Jan. 22, 2021 in Singapore Application No. 11201805420S.
Bakri et al., "Pharmacokinetics of Intravitreal Ranibizumab [Lucentis]," Dec. 2007, Ophthalmology vol. 114, Issue 12, pp. 2179-2182.
Daniel et al., Risk of Scar in the Comparison of Age-related Macular Degeneration Treatments Trials, Ophthalmology, vol. 121, No. 3, pp. 656-666, 2014.
Drolet et al., "Pharmacokinetics and Safety of an Anti-Vascular Endothelial Growth Factor Aptamer Following Injection into the Vitreous Humor of Rhesus Monkeys," 2000, Pharm Res. 17:1503-1510.
Dvorak, et al., "Vascular Permeability Factor/Vascular Endothelial Growth Factor and the Significance of Microvascular Hyperpermeability in Angiogenesis," 1999, Curr Top Microbiol Immunol, 237: 97-132.
Gaudreault et al., "Pharmacokinetics and retinal distribution of ranibizumab, a humanized antibody fragment directed against VEGF-A following intravitreal administration in rabbits," Nov. 2007 Retina vol. 27, Issue 9, pp. 1260-1266.
Halekoh et al., "The R Package geepack for Generalized Estimating Equations," Jan. 2006, Journal of Statistical Software vol. 15, Issue 2, pp. 1-11.
Kong, et al., "Platelet-Derived Growth Factor-D Overexpression Contributes to Epithelial-Mesenchymal Transition of PC3 Prostate Cancer Cells," Jun. 2008, Stem Cells vol. 26, Issue 6 pp. 1425-1435.
Lloyd et al., "Food and Drug Administration approval process for ophthalmic drugs in the U.S.," May 2008, Current Opinion Opthalmology, vol. 19 Issue 3 pp. 190-194.
Nork et al., "Prevention of Experimental Choroidal Neovascularization and Resolution of Active Lesions by VEGF trap in Nonhuman Primates," 2011, Arch Opthalmol, 129(8):1042-1052.
Ray et al., "Platelet-derived Growth Factor D, Tissue-specific Expression in the Eye, and a Key Role in Control of Lens Epithelial Cell Proliferation," Mar. 2005, J Biol Chem., vol. 280, No. 9 pp. 8494-8502.
Sinapis et al., "Pharmacokinetics of intravitreal bevacizumab (Avastin®) in rabbits," 2011, Clinical Ophthalmology 5:697-704.
Strohl, William R, "Optimization of Fc-mediated effector functions of monoclonal antibodies," Dec. 2009, Curr Opin. In Biotech vol. 20 Issue 6, pp. 685-691.
Struble et al., "Pharmacokinetics and ocular tissue penetration of VEGF Trap after intravitreal injections in rabbits," Sep. 2008, vol. 86, Issue s243.
Causes and Risk Factors. Diabetic Retinopathy. United States National Library of Medicine. Sep. 15, 2009. This is an archived web page of http://www.nei.nih.gov/health/diabetic/retinopathy.asp and lists a date of Sep. 23, 2009.
Williams AF, et al., The Immunoglobulin Superfamily-Domains for Cell Surface Recognition Annual Review of Immunology, vol. 6, pp. 381-405, 1988.
Ravetch et al., "FC Receptors," Ann. Rev. Immunol., vol. 9:457-92. 1991.
Final Office Action in U.S. App. No. 15/952,092 dated Nov. 27, 2020 in 60 pages.
Claims filed Nov. 4, 2020 in U.S. Appl. No. 17/066,856.
Extended European Search Report dated Jan. 21, 2021 in EP Application No. 18784891.6 in 15 pages.
Joralemon et al., PEGylated Polymers for Medicine From Conjugation to Self-Assembled Systems, Chemical Communications, vol. 46, No. 9, pp. 1377, 2010.
RecName: Full=Complement factor D; EC=3.4.21.46; AltName: Full=Adipsin; AltName: Full=C3 convertase activator; AltName: Full=Properdin factor D; Flags: Precursor, UNIPROT, Jul. 21, 1986 (Jul. 21, 1986), XP002614847. This appears to refer to a web page, which indicates that the page was last modified on Nov. 30, 2010. Contents of the web page may have been available at an earlier date.
Office Action with English translation dated Feb. 26, 2021 in Chinese Patent Application No. 201580046779.3 in 29 pages.

(56) References Cited

OTHER PUBLICATIONS

Examiners Comments Letter Received Feb. 10, 2021 in Singaporean patent Application No. 11201805420S in 3 pages.
Notice of Allowance in U.S. Appl. No. 16/402,602 in 13 pages.
Final Office Action dated Mar. 22, 2021 received in U.S. Appl. No. 16/290,128 in 78 pages.
Technical Report with English translation dated Mar. 19, 2021 in Brazilian Patent Application No. BR 11 2018 013407 4 in 8 pages.
Office Action dated Mar. 26, 2021 in Canadian Patent Application No. 2953698 in 4 pages.
Examination Report dated Feb. 22, 2021 received in Australian Patent Application No. 2018250695 in 4 pages.
Office Action with English Translation dated Apr. 1, 2021 in Chinese Application No. 201580056449.2 in 9 pages.
Restriction Requirement dated Mar. 24, 2021 in U.S. Appl. No. 16/795,450 in 5 pages.
Notice of Allowance dated Apr. 15, 2021 in U.S. Appl. No. 15/820,325 in 17 pages.
Office Action with English translation dated Apr. 23, 2021 in Chinese Application No. 201680082940.7 in 18 pages.
Notification of Reason for Refusal dated May 11, 2021 with English Translation in 10 pages, in Korean Patent Application No. 10-2021-7002410.
Office Action dated May 21, 2021 in U.S. Appl. No. 15/952,092 in 29 pages.
Office Action dated May 24, 2021 in U.S. Appl. No. 17/066,856 in 87 pages.

\* cited by examiner

COMPOUND K

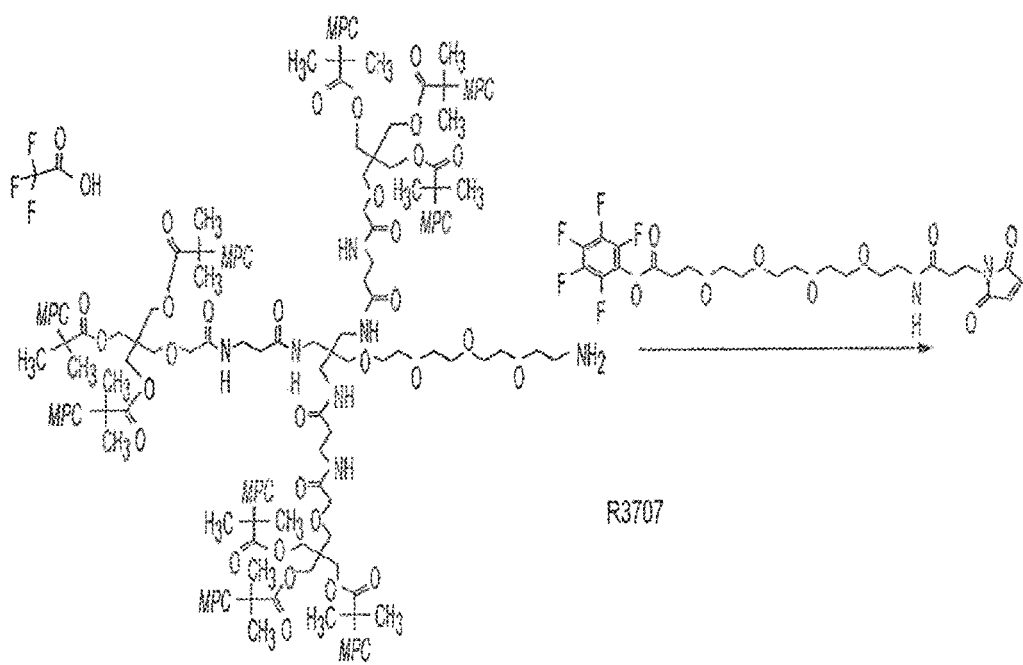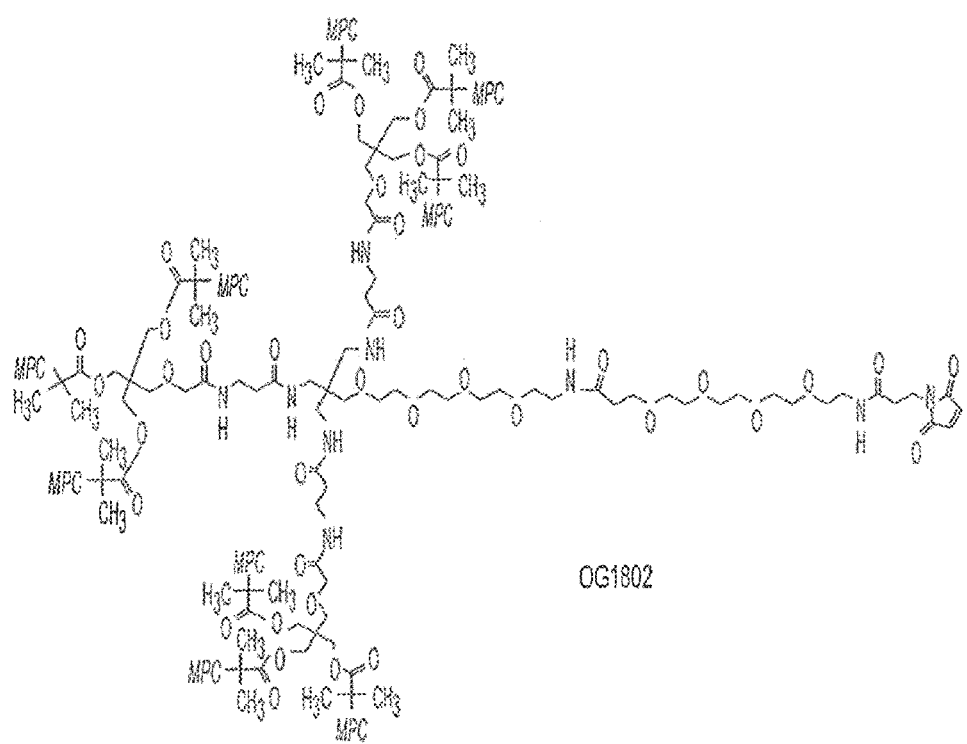
FIG. 3

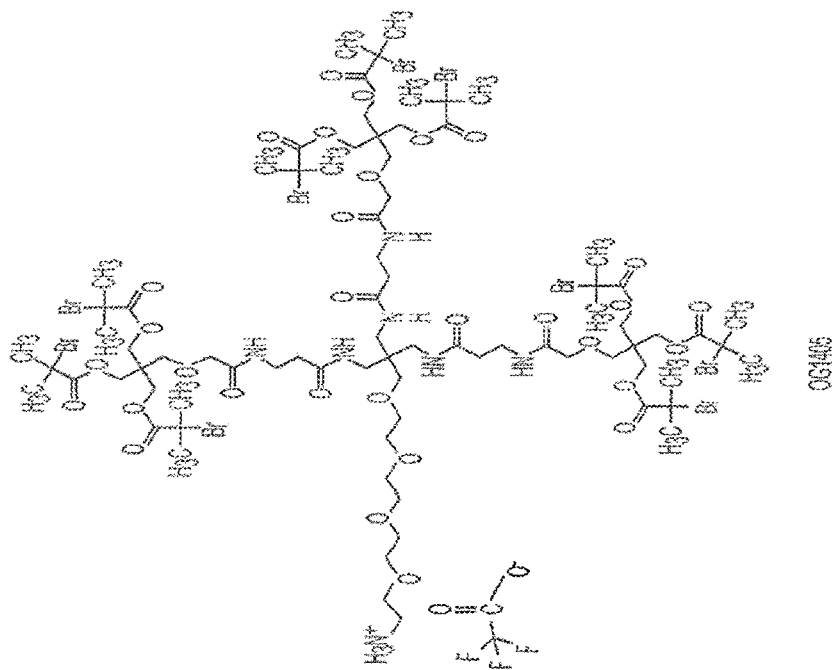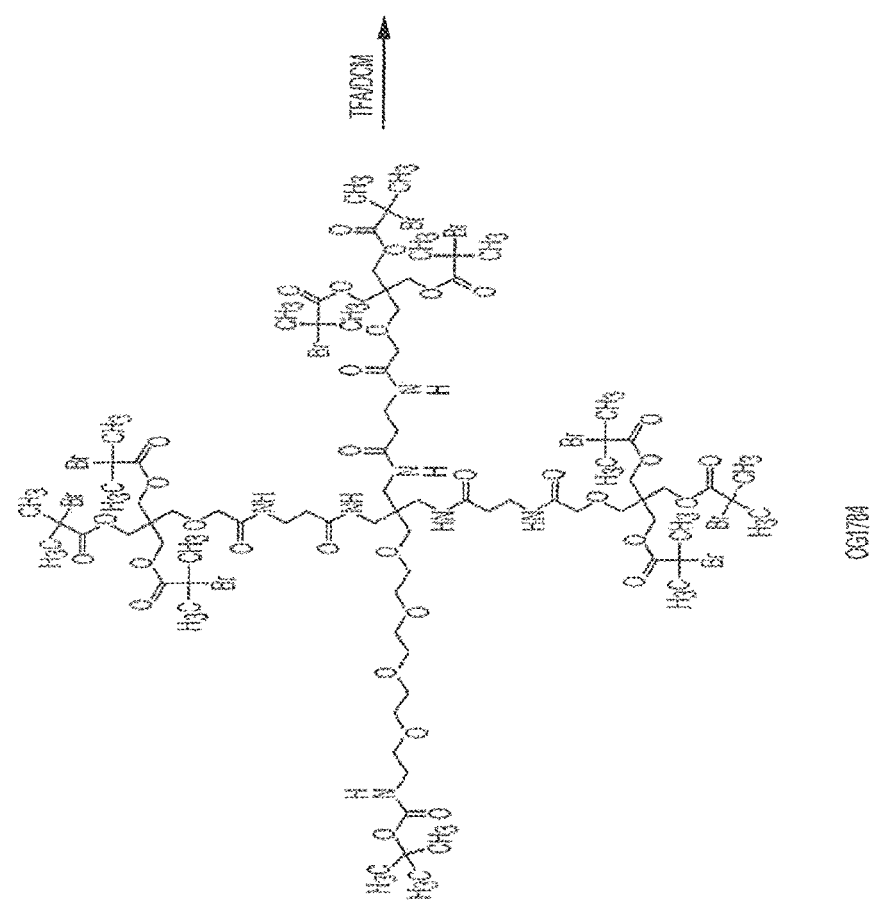
FIG. 7

COMPOUND E

SEQ ID NO. 1

```
  1 EVQLVESGGG LVQPGGSLRL SCAASGYDFT HYGMNWVRQA PGKGLEWVGW INTYTGEPTY
AADFKRRFTF SLDTSKSTAY
 81 LQMNSLRAED TAVYYCAKYP YYYGTSHWYF DVWGQGTLVT VSSASTKGPS VFPLAPSSKS
TSGGTAALGC LVKDYFPEPV
161 TVSWNSGALT SGVHTFPAVL QSSGLYSLSS VVTVPSSSLG TQTYICNVNH KPSNTKVDKK
VEPKSCDKTH TCPPCPAPEA
241 AGAPSVFLFP PKPKDTLMIS RTPEVTCVVV DVSHEDPEVK FNWYVDGVEV HNAKTKPREE
QYNSTYRVVS VLTVLHQDWL
321 NGKEYKCKVS NKALPAPIEK TISKAKGQPR EPQVYTLPPS REEMTKNQVS LTCLVKGFYP
SDIAVEWESN GQPENNYKTT
401 PPVLDSDGSF FLYSKLTVDK SRWQQGNVFS CSVMHEALHN HYTQKSLSCS PGK
```

FIG.12

SEQ ID NO. 2

```
  1 DIQLTQSPSS LSASVGDRVT ITCSASQDIS NYLNWYQQKP GKAPKVLIYF TSSLHSGVPS
RFSGSGSGTD FTLTISSLQP
 81 EDFATYYCQQ YSTVPWTFGQ GTKVEIKRTV AAPSVFIFPP SDEQLKSGTA SVVCLLNNFY
PREAKVQWKV DNALQSGNSQ
161 ESVTEQDSKD STYSLSSTLT LSKADYEKHK VYACEVTHQG LSSPVTKSFN RGEC
```

FIG. 13

SEQ ID NO. 3

1 EVQLVESGGG LVQPGGSLRL SCAASGYTFT NYGMNWVRQA PGKGLEWVGW INTYTGEPTY
AADFKRRFTF SLDTSKSTAY
   81 LQMNSLRAED TAVYYCAKYP HYYGSSHWYF DVWGQGTLVT VSSASTKGPS VFPLAPSSKS
TSGGTAALGC LVKDYFPEPV
  161 TVSWNSGALT SGVHTFPAVL QSSGLYSLSS VVTVPSSSLG TQTYICNVNH KPSNTKVDKK
VEPKSCDKTH TCPPCPAPEL
  241 LGGPSVFLFP PKPKDTLMIS RTPEVTCVVV DVSHEDPEVK FNWYVDGVEV HNAKTKPREE
QYNSTYRVVS VLTVLHQDWL
  321 NGKEYKCKVS NKALPAPIEK TISKAKGQPR EPQVYTLPPS REEMTKNQVS LTCLVKGFYP
SDIAVEWESN GQPENNYKTT
  401 PPVLDSDGSF FLYSKLTVDK SRWQQGNVFS CSVMHEALHN HYTQKSLSLS PGK

FIG. 14

SEQ ID NO. 4
  1 DIQMTQSPSS LSASVGDRVT ITCSASQDIS NYLNWYQQKP GKAPKVLIYF TSSLHSGVPS
RFSGSGSGTD FTLTISSLQP
 81 EDFATYYCQQ YSTVPWTFGQ GTKVEIKRTV AAPSVFIFPP SDEQLKSGTA SVVCLLNNFY
PREAKVQWKV DNALQSGNSQ
161 ESVTEQDSKD STYSLSSTLT LSKADYEKHK VYACEVTHQG LSSPVTKSFN RGEC

FIG. 15

SEQ ID NO. 5

```
  1 EVQLVESGGG LVQPGGSLRL SCAASGYDFT HYGMNWVRQA PGKGLEWVGW INTYTGEPTY
AADFKRRFTF SLDTSKSTAY
 81 LQMNSLRAED TAVYYCAKYP YYYGTSHWYF DVWGQGTLVT VSSASTKGPS VFPLAPSSKS
TSGGTAALGC LVKDYFPEPV
161 TVSWNSGALT SGVHTFPAVL QSSGLYSLSS VVTVPSSSLG TQTYICNVNH KPSNTKVDKK
VEPKSCDKTH L
```

FIG. 16

SEQ ID NO. 6
1 DIQLTQSPSS LSASVGDRVT ITCSASQDIS NYLNWYQQKP GKAPKVLIYF TSSLHSGVPS RFSGSGSGTD FTLTISSLQP
81 EDFATYYCQQ YSTVPWTFGQ GTKVEIKRTV AAPSVFIFPP SDEQLKSGTA SVVCLLNNFY PREAKVQWKV DNALQSGNSQ
161 ESVTEQDSKD STYSLSSTLT LSKADYEKHK VYACEVTHQG LSSPVTKSFN RGEC

FIG. 17

Effect of Various anti-VEGF Molecules on Binding of biotin-VEGF to Plate bound VEGFR EDC-Fc Protein OG1950 binding affinity to VEGF measured by BIAcore single cycle kinetics Binding of OG1950 to Fc gamma receptor I
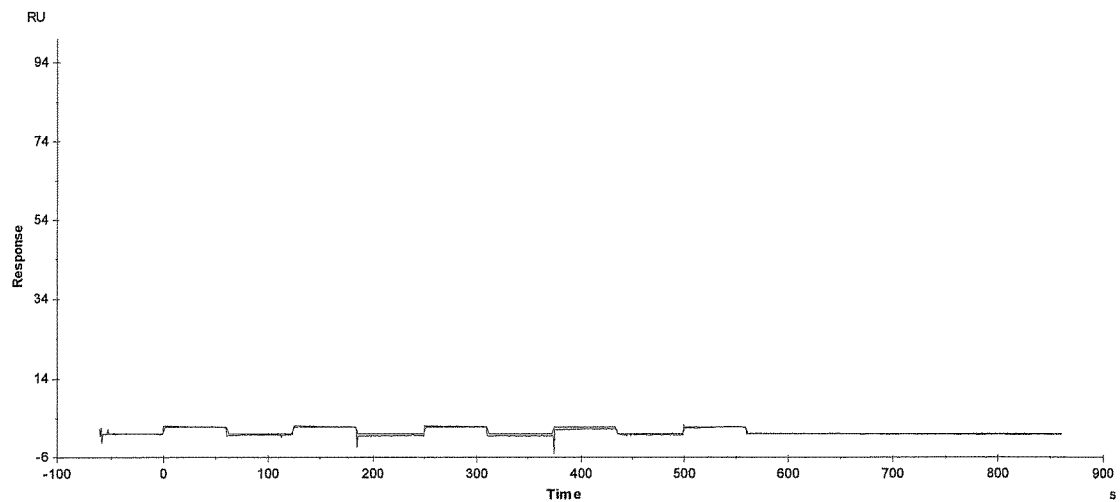
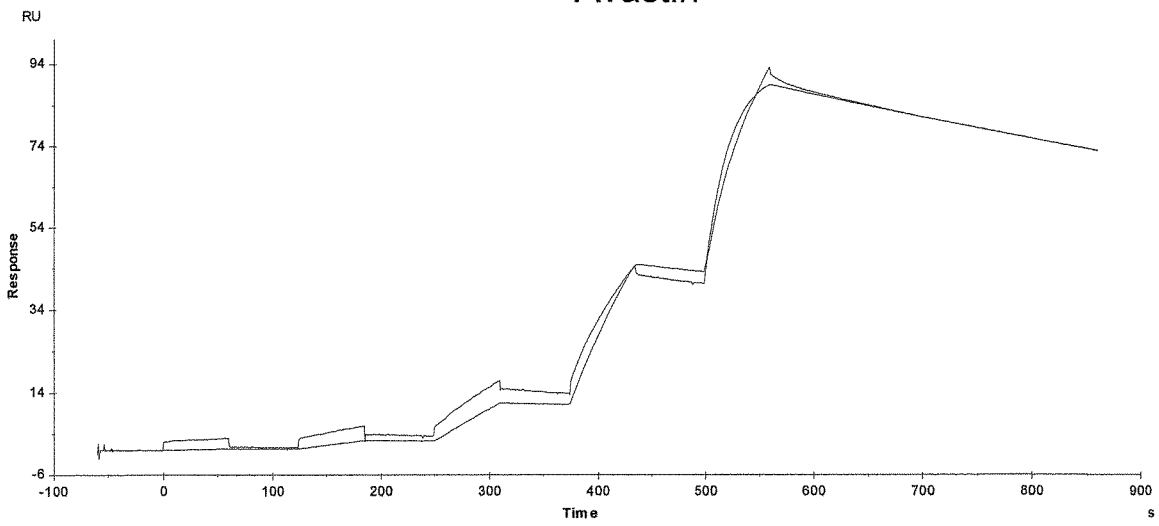
FIG. 22

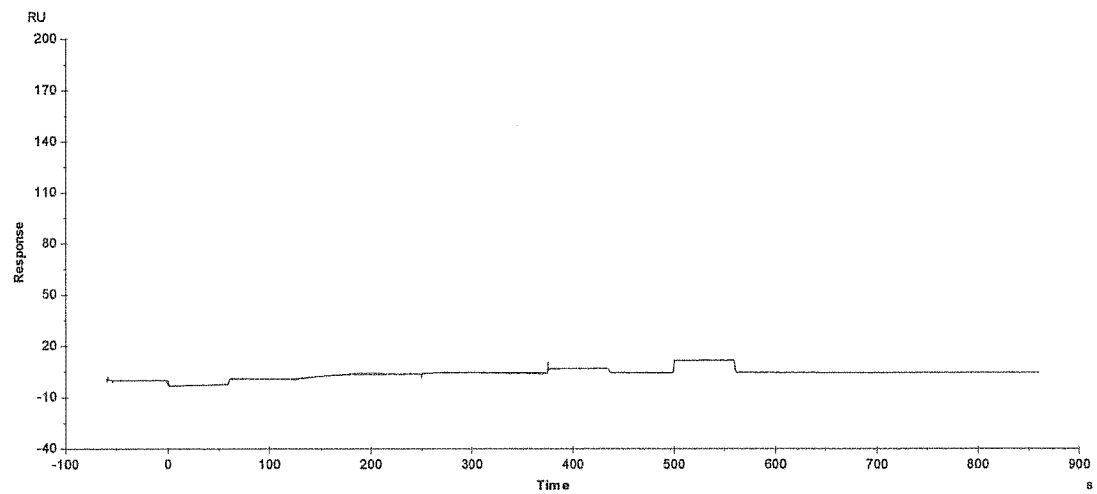
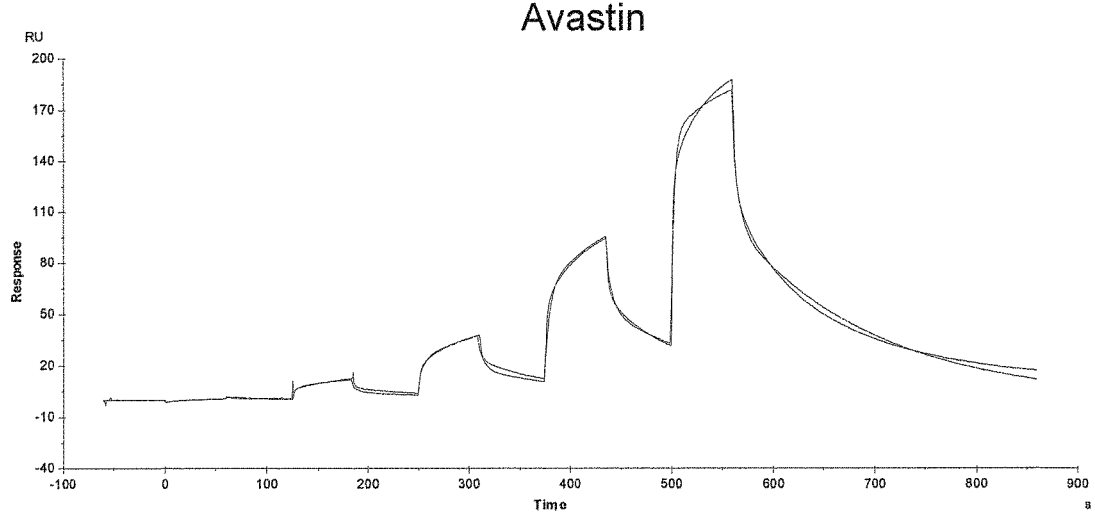
FIG. 23

Single Cycle Kinetics (SCK) of VEGF Binding to Anti-VEGF Agents captured on Protein A chip at 25 Degrees

| Ligand | ka (1/Ms) | kd (1/s) | KD (M) | Rmax (RU) | Chi$^2$ (RU$^2$) |
|---|---|---|---|---|---|
| Avastin | 3.49E+06 | 8.23E-05 | 2.36E-11 | 84.6 | 0.419 |
| OG1950 | 2.95E+06 | 3.86E-05 | 1.31E-11 | 82 | 0.171 |
| OG1953 | 2.11E+06 | 4.09E-05 | 1.94E-11 | 73.9 | 0.343 |

SEQ ID NO. 7

Heavy chain
Atgaaagctgtggtgctggccgtggctctggtcttcctgacagggagccaggctgaggtgcagctggtggaatccgg
cggaggcctggtccagcctggcggatccctgagactgtcctgtgccgcctccggctacgacttcacccattacggca
tgaactgggtccgacaggcccctggcaagggcctggaatgggtcggatggatcaacacctacaccggcgagcccacc
tacgccgccgacttcaagcggcggttcaccttctcctggacacctccaagtccaccgcctacctgcagatgaactc
cctgcgggccgaggacaccgccgtgtactactgcgccaagtaccctactactacggcacctccactggtacttcg
acgtgtggggccagggcaccctggtcaccgtgtcctccgcctctaccaagggcccctccgtgttccctctggccccc
tccagcaagtccacctctggcggcaccgccgctctgggctgcctggtcaaggactacttccccgagccgtgaccgt
gtcctggaactctggcgccctgacctccggcgtgcacaccttccagccgtgctgcagtcctccggcctgtactccc
tgtcctccgtcgtgaccgtgccctccagctctctgggcacccagacctacatctgcaacgtgaaccacaagcccctcc
aacaccaaggtggacaagaaggtggaacccaagtcctgcgacaagacccacacctgtccccctgccctgccctga
gcagccggtgcacccagcgtgttcctgttccccccaaagcccaaggacaccctgatgatctcccggaccccgaag
tgacctgcgtggtggtggacgtgtcccacgaggaccctgaagtgaagttcaattggtacgtggacggcgtggaagtg
cacaatgccaagaccaagccagagaggaacagtacaactccacctaccgggtggtgtccgtgctgaccgtgctgca
tcaggactggctgaacggcaaagagtacaagtgcaaggtctccaacaaggccctgcctgcccccatcgaaaagacca
tctccaaggccaagggccagccccgcgagcctcaggtgtacacactgccacccagccgggaagagatgaccaagaac
caggtctccctgacctgtctggtcaagggcttctaccccctccgatatcgccgtcgaatgggagtccaacggccagcc
cgagaacaactacaagaccaccccccctgtgctggactccgacggctcattcttcctgtactccaagctgaccgtgg
acaagtcccggtggcagcagggcaacgtgttctcctgctccgtgatgcacgaggccctgcacaaccactacacccag
aagtccctgtcctgcagccccggcaagtga

SEQ ID NO. 8

Light chain:
Atgggatggagctgtatcatcctcttcttggtggcaacagctacaggcgtgcactccgacatccagctgacccagtc
cccctccagcctgtccgcctctgtgggcgacagagtgaccatcacctgttccgccagccaggacatctccaactacc
tgaactggtatcagcagaagcccggcaaggccccaaggtgctgatctacttcacctcccctgcactccggcgtg
ccctccagattctccggctctggctccggcaccgactttaccctgaccatctccagcctgcagccgaggacttcgc
cacctactactgccagcagtactccaccgtgccctggaccttcggccagggcaccaaggtggaaatcaagcggaccg
tggccgctcccctccgtgttcatcttccacctccgacgagcagctgaagtccggaaccgcctccgtcgtgtgcctg
ctgaacaacttctaccccgcgaggccaaggtgcagtggaaggtggacaacgccctgcagagcggcaactcccagga
atccgtcaccgagcaggactccaaggacagcacctactccctgtccagcaccctgaccctgtccaaggccgactacg
agaagcacaaggtgtacgcctgcgaagtgacccaccagggcctcagctcccagtgaccaagtccttcaaccggggc
gagtgctag

FIG. 27

SEQUENCE LISTING

```
<160> NUMBER OF SEQ ID NOS: 14

<210> SEQ ID NO 1
<211> LENGTH: 453
<212> TYPE: PRT
<213> ORGANISM: Artificial Sequence
<220> FEATURE:
<223> OTHER INFORMATION: Anti-VEGF-A heavy chain

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95
```

Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Cys Ser Pro Gly Lys
        450

<210> SEQ ID NO 2
<211> LENGTH: 214
<212> TYPE: PRT
<213> ORGANISM: Artificial Sequence
<220> FEATURE:
<223> OTHER INFORMATION: Anti-VEGF-A light chain

<400> SEQUENCE: 2

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
                35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 3
<211> LENGTH: 453
<212> TYPE: PRT
<213> ORGANISM: Artificial Sequence
<220> FEATURE:
<223> OTHER INFORMATION: Antigen binding protein components

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
                35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
130                 135                 140

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 4
<211> LENGTH: 214
<212> TYPE: PRT
```

<213> ORGANISM: Artificial Sequence
<220> FEATURE:
<223> OTHER INFORMATION: Antigen binding protein components

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 231
<212> TYPE: PRT
<213> ORGANISM: Artificial Sequence
<220> FEATURE:
<223> OTHER INFORMATION: Antigen binding protein components

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

```
Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Leu
225                 230

<210> SEQ ID NO 6
<211> LENGTH: 214
<212> TYPE: PRT
<213> ORGANISM: Artificial Sequence
<220> FEATURE:
<223> OTHER INFORMATION: Antigen binding protein components

<400> SEQUENCE: 6

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 7
<211> LENGTH: 235
<212> TYPE: DNA
<213> ORGANISM: Artificial Sequence
<220> FEATURE:
<223> OTHER INFORMATION: Heavy chain

<400> SEQUENCE: 7

| atgaaagctg tggtgctggc cgtggctctg gtcttcctga cagggagcca ggctgaggtg | 60 |
| cagctggtgg aatccggcgg aggcctggtc cagcctggcg atccctgag actgtcctgt | 120 |
| gccgcctccg gctacgactt cacccattac ggcatgaact gggtccgaca ggcccctggc | 180 |
| aagggcctgg aatgggtcgg atggatcaac acctacaccg gcgagcccac ctacg | 235 |

<210> SEQ ID NO 8
<211> LENGTH: 702
<212> TYPE: DNA
<213> ORGANISM: Artificial Sequence
<220> FEATURE:
<223> OTHER INFORMATION: Light chain

<400> SEQUENCE: 8

| atgggatgga gctgtatcat cctcttcttg gtggcaacag ctacaggcgt gcactccgac | 60 |
| atccagctga cccagtcccc ctccagcctg tccgcctctg tgggcgacag agtgaccatc | 120 |
| acctgttccg ccagccagga catctccaac tacctgaact ggtatcagca gaagcccggc | 180 |
| aaggccccca aggtgctgat ctacttcacc tcctccctgc actccggcgt gccctccaga | 240 |
| ttctccggct ctggctccgg caccgacttt accctgacca tctccagcct gcagcccgag | 300 |
| gacttcgcca cctactactg ccagcagtac tccaccgtgc cctggacctt cggccagggc | 360 |
| accaaggtgg aaatcaagcg gaccgtggcc gctccctccg tgttcatctt cccacccctcc | 420 |
| gacgagcagc tgaagtccgg aaccgcctcc gtcgtgtgcc tgctgaacaa cttctacccc | 480 |
| cgcgaggcca aggtgcagtg gaaggtggac aacgccctgc agagcggcaa ctcccaggaa | 540 |
| tccgtcaccg agcaggactc caaggacagc acctactccc tgtccagcac cctgaccctg | 600 |
| tccaaggccg actacgagaa gcacaaggtg tacgcctgcg aagtgaccca ccagggcctc | 660 |
| agctccccag tgaccaagtc cttcaaccgg ggcgagtgct ag | 702 |

<210> SEQ ID NO 9
<211> LENGTH: 10
<212> TYPE: PRT
<213> ORGANISM: Artificial Sequence
<220> FEATURE:
<223> OTHER INFORMATION: Antigen binding protein components

<400> SEQUENCE: 9

Gly Tyr Asp Phe Thr His Tyr Gly Met Asn
1               5                   10

<210> SEQ ID NO 10
<211> LENGTH: 17
<212> TYPE: PRT

```
<213> ORGANISM: Artificial Sequence
<220> FEATURE:
<223> OTHER INFORMATION: Antigen binding protein components

<400> SEQUENCE: 10

Trp Ile Asn Thr Tyr Thr Gly Glu Pro Thr Tyr Ala Ala Asp Phe Lys
1               5                   10                  15
Arg

<210> SEQ ID NO 11
<211> LENGTH: 14
<212> TYPE: PRT
<213> ORGANISM: Artificial Sequence
<220> FEATURE:
<223> OTHER INFORMATION: Antigen binding protein components

<400> SEQUENCE: 11

Tyr Pro Tyr Tyr Tyr Gly Thr Ser His Trp Tyr Phe Asp Val
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Antigen binding protein components

<400> SEQUENCE: 12

Ser Ala Ser Gln Asp Ile Ser Asn Tyr Leu Asn
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Antigen binding protein components

<400> SEQUENCE: 13

Phe Thr Ser Ser Leu His Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Antigen binding protein components

<400> SEQUENCE: 14

Gln Gln Tyr Ser Thr Val Pro Trp Thr
1               5
```

ANTIBODIES AND CONJUGATES THEREOF

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR § 1.57.

SEQUENCE LISTING

The present application is being filed along with a Sequence Listing in electronic format. The Sequence Listing is provided as a file entitled KDIAK004.txt, created Dec. 28, 2016, which is 18,231 bytes in size. The information in the electronic format of the Sequence Listing is incorporated herein by reference in its entirety.

FIELD OF THE INVENTION

The present invention relates to antibodies and conjugates thereof and methods of using and manufacturing said antibodies, conjugates thereof, and other protein conjugates.

BACKGROUND

Diabetic retinopathy is a leading cause of blindness in people between the ages of about 20 to 64 years of age. Engelgau M, Geiss L, Saaddine J, Boyle J, et al. 2004. The Evolving Diabetes Burden in the United States. Ann of Int Med. 140 (11): 945-951. In the United States, diabetic retinopathy accounts for some 12% of new cases of blindness. Typically, in cases of diabetic retinopathy, retinal blood vessels will swell and leak fluid into the rear of the eye. Hyperglycemia induces intramural and thickening of the basement membrane, resulting in leaky or permeable blood vessels.

In diabetic retinopathy, changes in blood glucose level cause changes to retinal blood vessels. All people with diabetes mellitus are at risk. The longer a person has diabetes, the higher their risk of developing some ocular problem. Between 40 to 45 percent of Americans diagnosed with diabetes have some stage of diabetic retinopathy. Causes and Risk Factors. Diabetic Retinopathy. United States National Library of Medicine. 15 Sep. 2009.

Diabetic retinopathy is first exhibited in the development of microaneurysms in the retina. Microaneurysms occur when there is a swelling of capillaries (very small blood vessels) that feed the retina. The presence of relatively small numbers of microaneurysms will not usually cause problems with vision. However, if the retinopathy develops to later stages, there are significant chances of vision loss. Such early stage retinopathy are referred to as background diabetic retinopathy or non-proliferative diabetic retinopathy (NPDR). While NPDR patients are generally asymptomatic, early detection of retinopathy is crucial because if the disease proceeds to later stages, significant vision loss is very likely.

In the next stage of diabetic retinopathy, neovascularization occurs in the back of the eye (proliferative diabetic retinopathy). The neovasculature is leaky and the vessels can burst, followed by bleeding and resulting in blurred or obscured vision. Due to lack of oxygen in the eye, still further neovascularization occurs. Blood vessels grow along the retina and in the vitreous humor. As these vessels burst, there is further bleeding and the retina can be badly damaged or destroyed. The accumulation of fluid in the macula due to leaking blood vessels is called diabetic macular edema. Many patients with diabetic retinopathy will develop diabetic macular edema.

There are generally three treatment pathways for patients with diabetic retinopathy: laser surgery, injection of corticosteroids and injection of anti-VEGF agents (e.g. AVASTIN®(bevacizumab), LUCENTIS®(ranibizumab) and Eylea®(aflibercept)). While laser surgery is generally effective in treating diabetic retinopathy, retinal damage induced by the laser is a frequent side effect. Steroid preparations such as triamcinolone acetonide have been administered via intravitreal injection to treat diabetic retinopathy. However, to treat diabetic retinopathy, the steroid solutions must be frequently administered. Moreover, intravitreal treatment with steroids has been associated with cataracts, steroid-induced glaucoma and endophthalmitis.

Another way to treat diabetic retinopathy is the intravitreal injection of anti-VEGF agents. In this regard, LUCENTIS®(ranibizumab) and EYLEA®(aflibercept) have been recently approved for treatment of diabetic retinopathy in patients with diabetic macular edema. VEGF-directed therapies are effective not just for diabetic retinopathy, but also for Age-Related Macular Degeneration (AMD), such as neovascular (wet) AMD.

SUMMARY OF THE INVENTION

Provided herein is an antibody conjugate of an anti-VEGF-A antibody bonded at a cysteine outside a variable region of the antibody to a phosphorylcholine containing polymer, wherein said cysteine has been added via recombinant DNA technology. Optionally the anti-VEGF-A antibody comprises a light chain and a heavy chain and the heavy chain comprises an Fc region. Optionally, the anti-VEGF-A antibody is an immunoglobulin G (IgG). Optionally, the cysteine is in the Fc region of the heavy chain. Optionally, the anti-VEGF-A heavy chain comprises $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11), and position 231 (via sequential counting as in SEQ ID NO. 3) is T, and the anti-VEGF-A light chain comprises $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14), and Kabat position 4 is L. Optionally, the anti-VEGF-A heavy chain isotype is human IgG1.

Optionally, the heavy chain constant domain of the anti-VEGF-A antibody IgG1 has one or more mutations relative to an IgG1 constant domain to modulate effector function. The mutations are optionally to one or more of the following amino acid positions (EU numbering): E233X, L234X, L235X, G236X, G237X, A327X, A330X, and P331X wherein X is any natural or unnatural amino acid. Optionally, the mutations are selected from the group consisting of (EU numbering): E233P, L234V, L234A, L235A, G237A, A327G, A330S, and P331S. Optionally, the mutations are (EU numbering) L234A, L235A, and G237A. In some embodiments, the effector function is decreased. In some embodiments, CDC, ADCC, and/or ADCP is decreased at least 10, 20, 30, 40, 50, 60, 70, or more percent. In some embodiments, CDC is mediated by Fc binding to C1q, ADCC and ADCP are mediated by Fc binding to various Fc gamma receptors and each of these binding interactions is decreased at least 10, 20, 30, 40, 50, 60, 70, or more percent.

The cysteine residue is optionally in the anti-VEGF-A heavy chain and is optionally Q347C (EU numbering) or L443C (EU numbering). Optionally, the anti-VEGF-A heavy chain is SEQ ID NO. 1 and the sequence of the anti-VEGF-A light chain is SEQ ID NO. 2. Optionally, the cysteine is L443C (EU numbering).

Optionally, the phosphorylcholine containing polymer comprises 2-(methacryloyloxyethyl)-2'-(trimethylammonium)ethyl phosphate (MPC) monomers as set forth below:

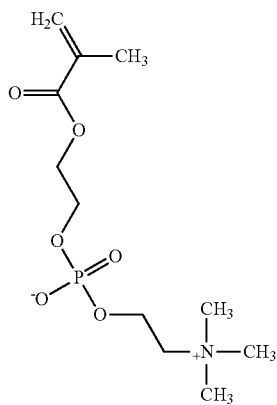

Such that the polymer comprises the following repeating units:

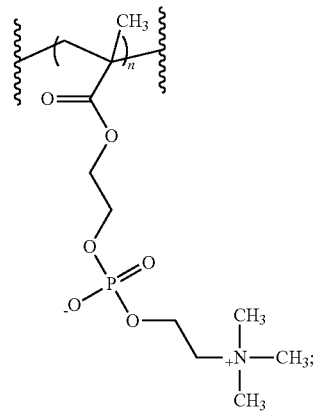

where n is an integer from 1 to 3000 and the wavy lines indicate the points of attachment between monomer units in the polymer.

The polymer optionally has three or more arms, or is synthesized with an initiator comprising 3 or more polymer initiation sites. Optionally, the polymer has 2, 3, 4, 5, 6, 7, 8, 9, 10, 11 or 12 arms, or is synthesized with an initiator comprising 2, 3, 4, 5, 6, 7, 8, 9, 10, 11 or 12 polymer initiation sites. Optionally, the polymer has 2, 3, 6, or 9 arms, or is synthesized with an initiator comprising 2, 3, 6 or 9 polymer initiation sites. Optionally, the polymer has 9 arms, or is synthesized with an initiator comprising 9 polymer initiation sites.

Optionally, the polymer has a molecular weight between about 300,000 and about 1,750,000 Da, as measured by size exclusion chromatography—multi angle light scattering (hereinafter "SEC-MALS"). Optionally, the polymer has a molecular weight between about 500,000 and about 1,000,000 Da. Optionally, the polymer has a molecular weight of between about 600,000 to about 800,000 Da.

Optionally, the antibody conjugate is purified and the polymer is polydisperse. Optionally, the polymer has a polydispersity value (PDI) of less than 1.2. In some embodiments, any of the conjugate solutions provided herein can have a PolyDispersity Index (PDI) that is equal to or less than 1.8, for example, less than or equal to: 1.7, 1.6, 1.5, 1.4, 1.3, 1.2, 1.1, 1.

Optionally, an antibody conjugate comprising an anti-VEGF-A immunoglobulin G (IgG) bonded to a polymer, which polymer comprises MPC monomers, wherein the sequence of the anti-VEGF-A heavy chain is SEQ ID NO. 1, and the sequence of the anti-VEGF-A light chain is SEQ ID NO. 2, and wherein the antibody is bonded only at C449 in SEQ ID NO. 1 to the polymer. Optionally, the polymer has 9 arms; and the polymer has a molecular weight of between about 600,000 to about 800,000 Da.

Optionally, an antibody conjugate comprising an anti-VEGF-A immunoglobulin G (IgG) bonded to a polymer, which polymer comprises MPC monomers, wherein the sequence of the anti-VEGF-A heavy chain is SEQ ID NO. 1, and the sequence of the anti-VEGF-A light chain is SEQ ID NO. 2, and wherein the antibody is bonded only at C443 (EU numbering) to the polymer. Optionally, the polymer has 9 arms; and the polymer has a molecular weight of between about 600,000 to about 800,000 Da.

Optionally, the antibody conjugate has the following structure:

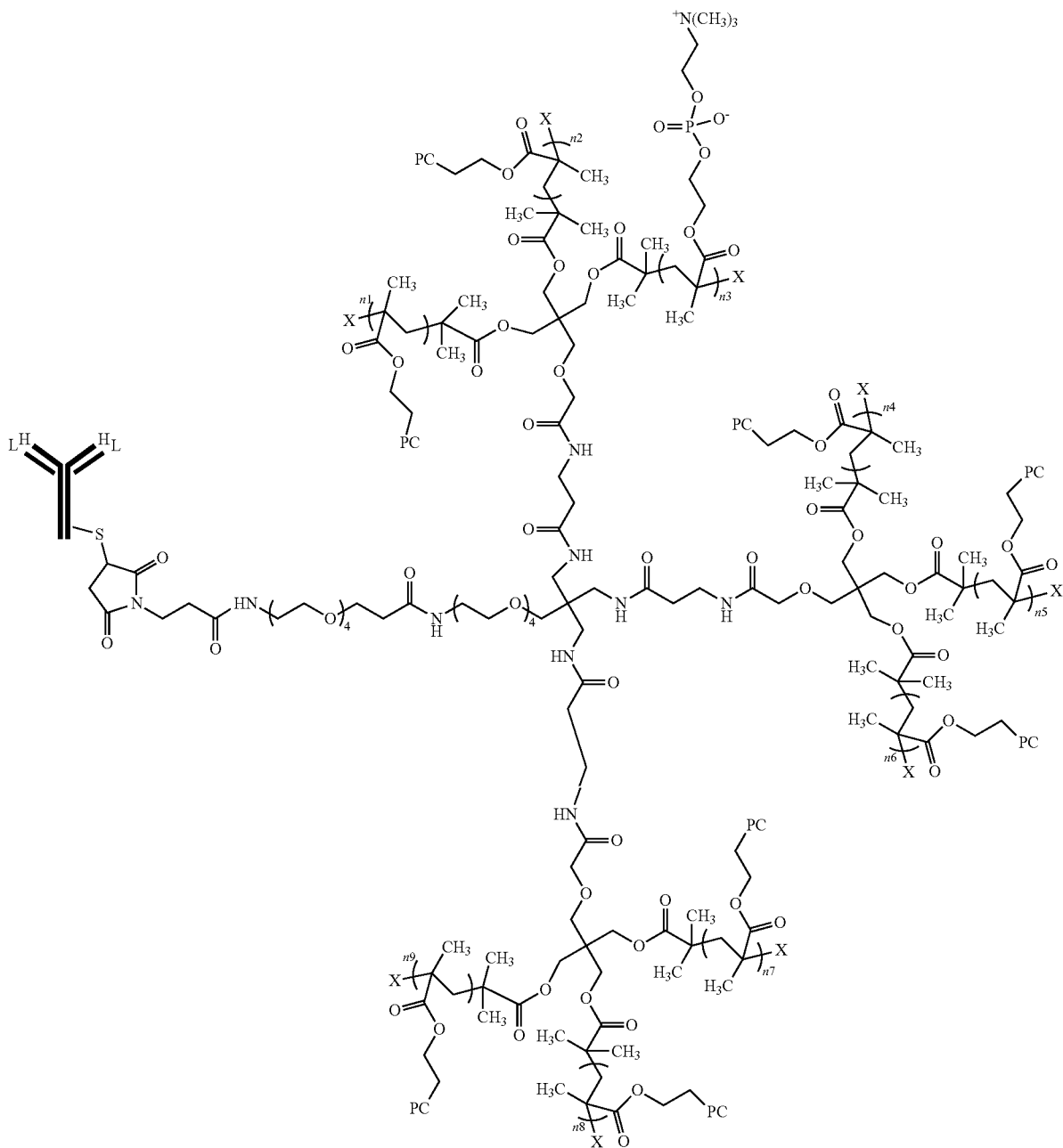

wherein: each heavy chain of the anti-VEGF-A antibody is denoted by the letter H, and each light chain of the anti-VEGF-A antibody is denoted by the letter L; the polymer is bonded to the anti-VEGF-A antibody through the sulfhydryl of C449 in SEQ ID NO: 1, which bond is depicted on one of the heavy chains; PC is

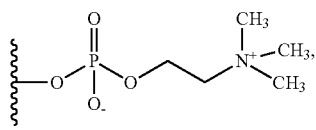

where the curvy line indicates the point of attachment to the rest of the polymer; where X=a) OR where R=H, Methyl, ethyl, propyl, isopropyl, b) H, or c) any halide, including Br; and n1, n2, n3, n4, n5, n6, n7, n8 and n9 are the same or different such that the sum of n1, n2, n3, n4, n5, n6, n7, n8 and n9 is 2500 plus or minus 15%. Optionally, n1, n2, n3, n4, n5, n6, n7, n8 and n9 are independently integers from 0 to 3000. Optionally, n1, n2, n3, n4, n5, n6, n7, n8 and n9 are independently integers from 0 to 500. In some embodiments, X=OR, where R is a sugar, an aminoalkyl, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, —CO—O—$R_7$, carbonyl —CCO—$R_7$, —CO—$NR_8R_9$, —$(CH_2)_n$—$COOR_7$, —CO—$(CH)_n$—$COOR_7$, —$(CH_2)_n$—$NR_8R_9$, ester, alkoxycarbonyl, aryloxycarbonyl, wherein n is an integer from 1 to 6, wherein each $R_7$, $R_8$ and $R_9$ is separately selected from the group consisting of a hydrogen atom, halogen atom, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, a 5-membered ring, and a 6-membered ring.

Optionally, the antibody conjugate has the following structure:

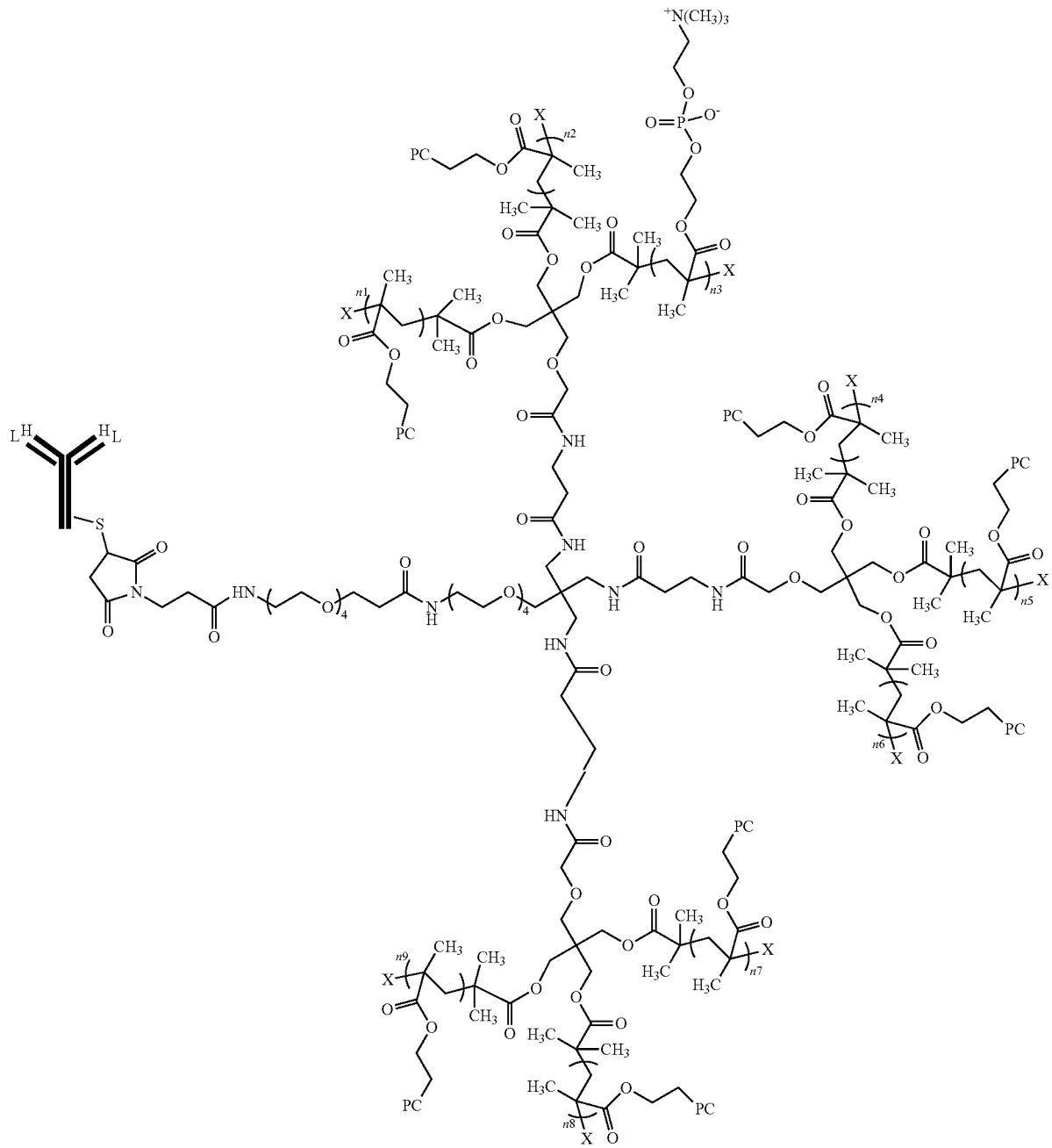

wherein: each heavy chain of the anti-VEGF-A antibody is denoted by the letter H, and each light chain of the anti-VEGF-A antibody is denoted by the letter L; the polymer is bonded to the anti-VEGF-A antibody through the sulfhydryl of C443 (EU numbering), which bond is depicted on one of the heavy chains; PC is

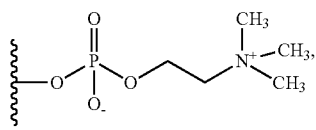

where the curvy line indicates the point of attachment to the rest of the polymer; where X=a) OR where R=H, Methyl, ethyl, propyl, isopropyl, b) H, or c) any halide, including Br; and n1, n2, n3, n4, n5, n6, n7, n8 and n9 are the same or different such that the sum of n1, n2, n3, n4, n5, n6, n7, n8 and n9 is 2500 plus or minus 15%. Optionally, n1, n2, n3, n4, n5, n6, n7, n8 and n9 are independently integers from 0 to 3000. Optionally, n1, n2, n3, n4, n5, n6, n7, n8 and n9 are independently integers from 0 to 500. In some embodiments, X=OR, where R is a sugar, an aminoalkyl, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including poly-halogenated alkyl, —CO—O—$R_7$, carbonyl —CCO—$R_7$, —CO—$NR_8R_9$, —$(CH_2)_n$—$COOR_7$, —CO—$(CH)_n$—$COOR_7$, —$(CH_2)_n$—$NR_8R_9$, ester, alkoxycarbonyl, aryloxycarbonyl, wherein n is an integer from 1 to 6, wherein each $R_7$, $R_8$ and $R_9$ is separately selected from the group consisting of a hydrogen atom, halogen atom, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including poly-halogenated alkyl, a 5-membered ring, and a 6-membered ring.

In some embodiments an antibody conjugate as described above in a liquid solution is provided. Optionally, the liquid solution has a pharmaceutically acceptable carrier.

In some embodiments an anti-VEGF-A antibody which comprises a heavy chain and a light chain, wherein is provided. The heavy chain comprises $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11), and position 231 (via sequential counting as in SEQ ID NO. 3) is T and the light chain comprises $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14), and Kabat position 4 is L. Optionally, the heavy chain isotype is IgG1, wherein the IgG1 constant domain comprises one or more of the following mutations to modulate effector function (EU numbering): E233P, L234V, L234A, L235A, G237A, A327G, A330S, and P331S. Optionally, the antibody has (EU numbering) L234A, L235A, and G237A. Optionally, the sequence of the anti-VEGF-A heavy chain is SEQ ID NO. 1 and sequence of the anti-VEGF-A light chain is SEQ ID NO. 2.

In some embodiments a method for treatment or prophylaxis of an ocular disease is provided. The method comprises administering an antibody conjugate as described above, or the pharmaceutical composition as described above. Optionally, the the ocular disease is selected from the group consisting of diabetic retinopathy, choroidal neovascularization (CNV), age-related macular degeneration (AMD), diabetic macular edema (DME), pathological myopia, von Hippel-Lindau disease, histoplasmosis of the eye, central retinal vein occlusion (CRVO), branched central retinal vein occlusion (BRVO), corneal neovascularization, retinal neovascularization, retinopathy of prematurity (ROP), subconjunctival hemorrhage, and hypertensive retinopathy. Optionally, the disease is diabetic retinopathy.

In some embodiments a method of making an antibody conjugate comprising an anti-VEGF-A antibody conjugated to a phosphorylcholine containing polymer is provided. The method comprises the step of: conjugating an anti-VEGF-A antibody to a phosphorylcholine containing polymer; wherein the anti-VEGF-A antibody comprises a cysteine residue added via recombinant DNA technology and wherein the cysteine is outside a variable region of the antibody; wherein the phosphorylcholine containing polymer comprises a sulfhydryl specific reacting group selected from the group consisting of a maleimide, a vinylsulfone, an orthopyridyl-disulfide, and an iodoacetamide; and wherein the sulfhydryl specific reacting group on the phosphorylcholine containing polymer reacts with the cysteine residue on the anti-VEGF-A antibody to make the antibody conjugate.

Optionally, the anti-VEGF-A antibody is an immunoglobulin G (IgG) and the cysteine is in the Fc region of the antibody. Optionally, the anti-VEGF-A antibody comprises a light chain and a heavy chain, wherein the anti-VEGF-A antibody heavy chain comprises $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11), and position 231 (via sequential counting as in SEQ ID NO. 3) is T, and the anti-VEGF-A antibody light chain comprises $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14), and Kabat position 4 is L. Optionally, the anti-VEGF-A antibody heavy chain isotype is IgG1.

Optionally, the IgG1 constant domain has one or more mutations relative to an IgG1 constant domain to modulate effector function. Optionally, the mutations are to one or more of the following amino acid positions (EU numbering): E233X, L234X, L235X, G236X, G237X, G236X, D270X, K322X, A327X, P329X, A330X, A330X, P331X, and P331X, wherein X is any natural or non-natural amino acid. Optionally, the mutations are selected from the group consisting of (EU numbering) E233P, L234V, L234A, L235A, G237A, A327G, A330S, and P331S. Optionally, the mutations are (EU numbering) L234A, L235A, and G237A.

Optionally, the cysteine residue added by recombinant DNA technology is selected from the group consisting of Q347C (EU numbering) and L443C (EU numbering). Optionally, the cysteine residue added by recombinant DNA technology is L443C (EU numbering). Optionally, the sequence of the anti-VEGF-A heavy chain is SEQ ID NO. 1 and sequence of the anti-VEGF-A light chain is SEQ ID NO. 2.

Optionally, the phosphorylcholine containing polymer comprises 2-(methacryloyloxyethyl)-2'-(trimethylammonium)ethyl phosphate (MPC) monomers as set forth below:

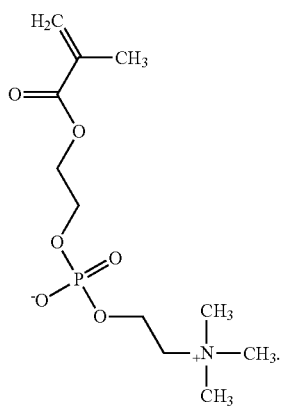

Such that the polymer comprises the following repeating units:

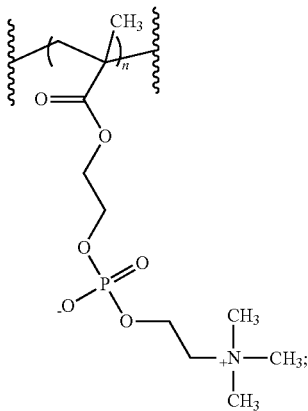

where n is an integer from 1 to 3000 and the wavy lines indicate the points of attachment between monomer units in the polymer.

Optionally, the polymer has three or more arms. Optionally, the polymer has 2, 3, 4, 5, 6, 7, 8, 9, 10, 11 or 12 arms. Optionally, the polymer has 2, 3, 6, or 9 arms. Optionally, the polymer has 9 arms.

Optionally, the polymer has a molecular weight between about 300,000 and 1,750,000 Da. Optionally, the polymer has a molecular weight between about 500,000 and 1,000,000 Da. Optionally, the polymer has a molecular weight of between about 600,000 to 800,000 Da.

Optionally, the method has a further step comprising the step of contacting the anti-VEGF-A antibody with a thiol reductant under conditions that produce a reduced cysteine sulfhydryl group to produce a reduced anti-VEGF-A antibody in which all cysteine residues are reduced. Optionally, the thiol reductant is selected from the group consisting of Tris[2-carboxyethyl]phosphine hydrochloride (TCEP), dithiothreitol (DTT), dithioerythritol (DTE), sodium borohydride ($NaBH_4$), sodium cyanoborohydride ($NaCNBH_3$), β-mercaptoethanol (BME), cysteine hydrochloride, and cysteine. Optionally, the thiol reductant is TCEP. Optionally, the thiol reductant is between 1 and 100 fold molar excess relative to the concentration of the anti-VEGF-A antibody. Optionally, the thiol reductant is between 20 to 50 fold molar excess relative to the concentration of the anti-VEGF-A antibody.

Optionally, the method further comprising the steps of removing the thiol reductant from the reduced anti-VEGF-A antibody, and treating the reduced anti-VEGF-A antibody with an oxidizing agent. Optionally, the oxidizing agent is air, aqueous $CuSO_4$, or dehydroascorbic acid (DHAA). Optionally, the method further comprises the step of purifying the antibody conjugate.

Optionally, the antibody conjugate is purified using a technique selected from the group consisting of ion exchange chromatography, hydrophobic interaction chromatography, size exclusion chromatography, affinity chromatography, and combinations thereof. Optionally, the purified antibody conjugate retains at least 20% biological activity relative to an unconjugated anti-VEGF-A antibody. Optionally, the purified antibody conjugate retains at least 50% biological activity relative to an unconjugated anti-VEGF-A antibody. Optionally, the purified antibody conjugate retains at least 90% biological activity relative to an unconjugated anti-VEGF-A antibody. Optionally, the purified antibody conjugate has an increased half-life relative to an unconjugated anti-VEGF-A antibody. Optionally, the purified antibody conjugate has at least a 1.5 fold increase in half-life relative to an unconjugated anti-VEGF-A antibody.

Optionally, the method further comprises the step of polymerizing a free radically polymerizable phosphorylcholine containing monomer in a polymerization medium to provide the phosphorylcholine containing polymer, the medium comprising: the radically polymerizable phosphorylcholine containing monomer; a transition metal catalyst $M_t^{(q-1)+}$ wherein $M_t$ is a transition metal, q is the maximum oxidation state of the metal and q−1 is the oxidation state of the metal, wherein the metal can act as a catalyst, wherein the transition metal catalyst is supplied as a salt of the form $M_t^{(q-1)+}X'_{(q-1)}$, wherein X' is a counterion or group, or wherein the transition metal catalyst is supplied in situ by providing the inactive metal salt at its highest oxidation state $M_t^{q+}X'_q$ together with a reducing agent that is capable of reducing the transition metal from the oxidized inactive state to the reduced active state; a ligand; and an initiator.

Optionally, the radically polymerizable phosphorylcholine containing monomer is

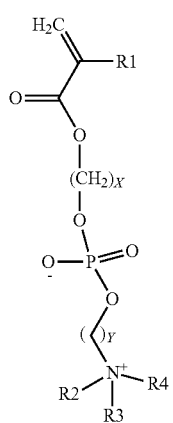

wherein R1 is H or $C_{1-6}$ alkyl; R2, R3, R4 are each methyl; and X and Y are each 2.

Optionally, Mt is selected from the group consisting of Cu, Fe, Ru, Cr, Mo, W, Mn, Rh, Re, Co, V, Zn, Au, and Ag. Optionally, the metal catalyst is supplied as a salt of the form $Mt^{(q-1)+}X'_{(q-1)}$. Optionally, $M_t^{(q-1)+}$ is selected from the group consisting of $Cu^{1+}$, $Fe^{2+}$, $Ru^{2+}$, $Cr^{2+}$, $Mo^{2+}$, $W^{2+}$, $Mn^{3+}$, $Rh^{3+}$, $Re^{2+}$, $Co^+$, $V^{2+}$, $Zn^+$, $Au^+$, and $Ag^+$ and X' is selected from the group consisting of halogen, $C_{1-6}$ alkoxy, $(SO_4)_{1/2}$, $(PO_4)_{1/3}$, $(R7PO_4)_{1/2}$, $(R7_2PO_4)$, triflate, hexaluorophosphate, methanesulfonate, arylsulfonate, CN and $R7CO_2$, where R7 is H or a straight or branched $C_{1-6}$ alkyl group which may be substituted from 1 to 5 times with a halogen. Optionally, $M_t^{(q-1)+}$ is $Cu^{1+}$ and X' is Br. Optionally, $M_t^{(q-1)+}$ is supplied in situ. Optionally, $M_t^{q+}X_q$ is $CuBr_2$.

Optionally, the reducing agent is an inorganic compound. Optionally, the inorganic compound is selected from the group consisting of a sulfur compound of a low oxidation level, sodium hydrogen sulfite, sodium sulfite, an inorganic salt comprising a metal ion, a metal, hydrazine hydrate, and derivatives of such compounds.

Optionally, the reducing agent is a metal. Optionally, the reducing agent is $Cu^0$.

Optionally, the reducing agent is an organic compound. Optionally, the organic compound is selected from the group consisting of alkylthiols, mercaptoethanol, or carbonyl compounds that can be easily enolized, ascorbic acid, acetyl acetonate, camphosulfonic acid, hydroxy acetone, reducing sugars, monosaccharides, glucose, aldehydes, and derivatives of such organic compounds.

Optionally, the ligand is selected from the group consisting of 2,2'-bipyridine, 4,4'-Di-5-nonyl-2,2'-bipyridine, 4,4-dinonyl-2,2'-dipyridyl, 4,4',4"-tris(5-nonyl)-2,2':6',2"-terpyridine, N,N,N',N',N"-Pentamethyldiethylenetriamine, 1,1,4,7,10,10-Hexamethyltriethylenetetramine, Tris(2-dimethylaminoethyl)amine, N,N-bis(2-pyridylmethyl) octadecylamine, N,N,N',N'-tetra[(2-pyridal)methyl] ethylenediamine, tris[(2-pyridyl)methyl]amine, tris(2-aminoethyl)amine, tris(2-bis(3-butoxy-3-oxopropyl) aminoethyl)amine, tris(2-bis(3-(2-ethylhexoxy)-3-oxopropyl)aminoethyl)amine, and Tris(2-bis(3-dodecoxy-3-oxopropyl)aminoethyl)amine. Optionally, the ligand is 2,2'-bipyridine.

Optionally, the initiator has the structure:

R1-R2(-R3)$_s$ wherein R1 is a nucleophilic reactive group, R2 comprises a linker, and R3 comprises a polymer synthesis initiator moiety having the structure

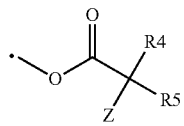

wherein R4 and R5 and are the same or different and are selected from the group consisting of alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido, and any combination thereof; Z is a halogen or CN; and s is an integer between 1 and 20.

Optionally, Z is Br and R4 and R5 are each methyl. Optionally, R1 is selected from the group consisting of $NH_2-$, OH-, and SH-. Optionally, R1 is $NH_2-$. Optionally, R2 is alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido, and any combination thereof. Optionally, R2 is

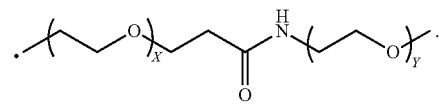

wherein X and Y are the same or different and are integers from 1-20.

Optionally, X and Y are each 4. Optionally, R3 further comprises

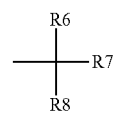

wherein R6, R7 and R8 are the same or different and are selected from the group consisting of

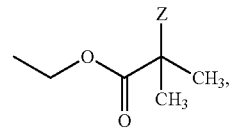

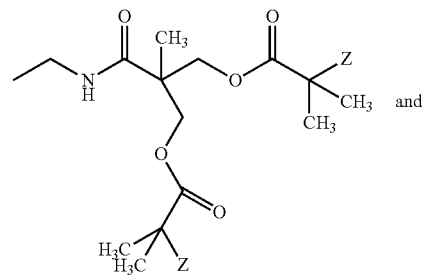

and

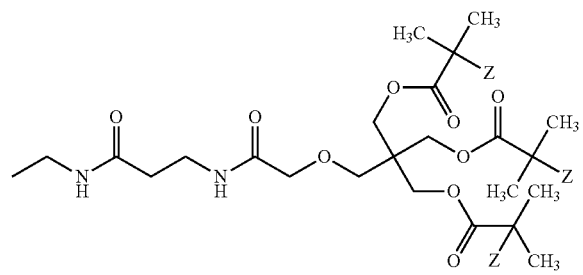

wherein Z is NCS, F, Cl, Br or I. Optionally, Z is Br. Optionally, R6, R7 and R8 are each Optionally, the initiator has the structure

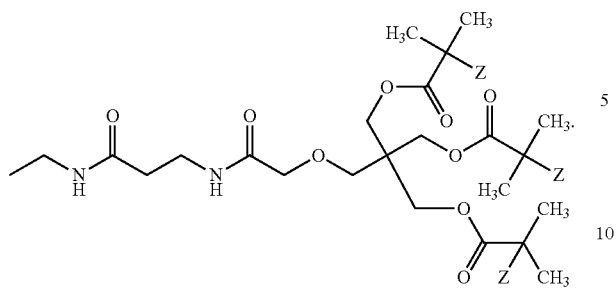

wherein A and B are the same or different and are integers from 2 to 12 and Z is any halide, such as Br. Optionally, A and B are each 4.

Optionally, the method further comprising the step of reacting the polymer with a maleimide reagent to provide a polymer having a terminal maleimide. Optionally, the maleimide compound is

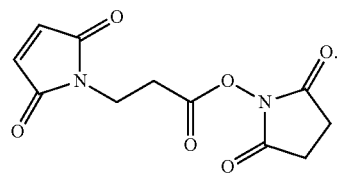

In some embodiments, the options provided herein avoid one or more issues with other methods or forms of therapy. For example, they can reduce the frequency of administration to less than once a month intravitreal injection, as such intravitreal injections can be painful and require a clinical setting. Furthermore, diabetic retinopathy patients whose vision is relatively unimpaired could be resistant to monthly intravitreal injections and thus may go untreated under other forms of therapy. There is thus a need for diabetic retinopathy treatments with less frequent dosing. In this context, a

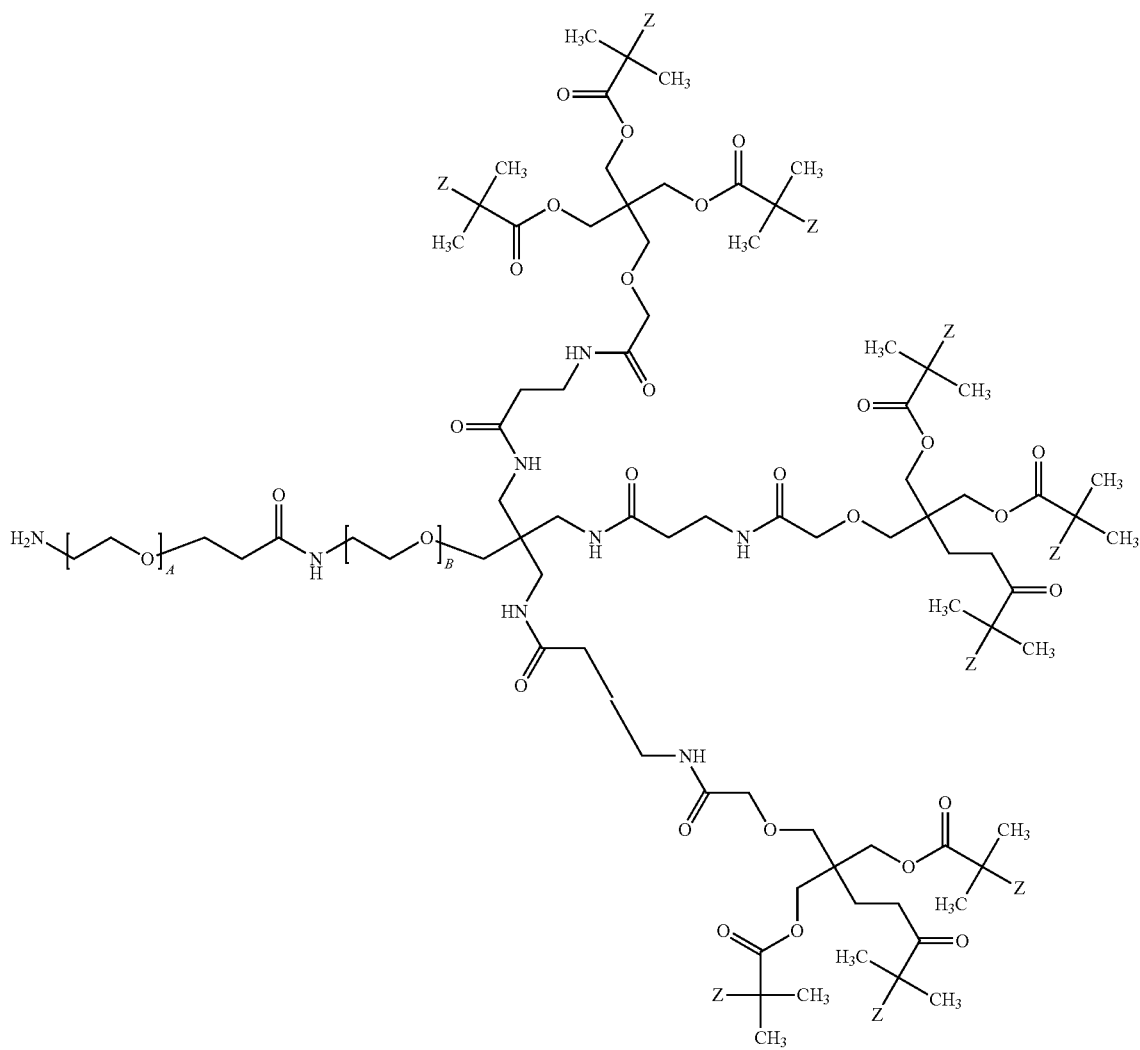

treatment for diabetic retinopathy could be used early in the disease to prevent progression of the disease and associated vision threatening events.

In some embodiments, the antibody conjugate comprises (1) an anti-VEGF-A antibody and (2) a phosphorylcholine containing polymer. The polymer is covalently bonded to the antibody at a cysteine outside a variable region of the antibody and said cysteine has been added via recombinant DNA technology.

In some embodiments, the anti-VEGF-A antibody heavy chain comprises $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11), and the anti-VEGF-A light chain comprises $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14).

In some embodiments, the polymer conjugated to the antibody has a molecular weight between about 300,000 and about 1,750,000 Da as measured by size exclusion chromatography—multi angle light scattering (hereinafter "SEC-MALS").

In some embodiments, the anti-VEGF-A antibody comprises a heavy chain and a light chain. The heavy chain comprises $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11) and the light chain comprises $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14), and the heavy chain isotype is IgG1. The IgG1 constant domain comprises one or more of the following mutations to reduce effector function (EU numbering): E233P, L234V, L234A, L235A, G237A, A327G, A330S, and P331S.

In some embodiments, any of the methods can employ an anti-VEGF-A antibody that comprises a light chain and a heavy chain, wherein the anti-VEGF-A antibody heavy chain comprises $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11), and the anti-VEGF-A antibody light chain comprises $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14).

In some embodiments, the antibody comprises a heavy chain amino acid variable region that comprises SEQ ID NO 1 and a light chain amino acid variable region that comprises SEQ ID NO. 2.

In some embodiments, the antibody is a human IgG1, and the heavy chain constant domain comprises one or more mutations that reduce an immune-mediated effector function.

In some embodiments, the antibody is further conjugated to a polymer to form a bioconjugate, and wherein the bioconjugate has a molecular weight between about 450,000 and 1,900,000 Daltons.

In some embodiments, the PolyDispersity Index (PDI) is equal to or less than 1.5.

In some embodiments, the antibody that binds to VEGF-A comprises a $CDR_H1$ that is the $CDR_H1$ in SEQ ID NO: 1; a $CDR_H2$ that is the $CDR_H2$ in SEQ ID NO: 1; a $CDR_H3$ that is the $CDR_H3$ in SEQ ID NO: 1; a $CDR_L1$ that is the $CDR_L1$ in SEQ ID NO: 2; a $CDR_L2$ that is the $CDR_L2$ in SEQ ID NO: 2; a $CDR_L3$ that is the $CDR_L3$ in SEQ ID NO: 2; at least one of the following mutations: L234A, L235A, and G237A (EU numbering); and at least one of the following mutations: Q347C (EU numbering) or L443C (EU numbering).

In some embodiments, the antibody comprises all three of the following mutations (EU numbering) L234A, L235A, and G237A, and wherein the antibody comprises L443C (EU numbering).

In some embodiments, a process for preparing a conjugated protein comprises reducing one or more cysteines in a protein to form a decapped protein in a solution, reoxidizing the decapped protein to restore at least one disulfide linkage in the reduced protein while ensuring that an engineered cysteine residue in the protein remains in a free thiol form to thereby form a reoxidized decapped protein in the solution, and adding at least one excipient to the solution, wherein the excipient reduces a polymer induced protein precipitation. The process further includes adding a polymer to the solution, and conjugating the polymer to the reoxidized decapped protein at the engineered cysteine residue to form a conjugated protein. In some embodiments, the protein is an antibody, an antibody protein fusion or a binding fragment thereof. In some embodiments, the excipient is an acid or a base. In some embodiments, the excipient is selected from the group consisting of at least one of: a detergent, a sugar, and a charged amino acid. In some embodiments, reaction of a polymer with the reduced protein occurs under aqueous conditions between pH 6.0 to pH 8.5. In some embodiments, an amount of the reduced protein is less than an amount of the polymer. In some embodiments, the polymer is conjugated to the protein at 2-37 degrees Celsius. In some embodiments, the process further comprises the process of contacting a solution comprising the conjugated protein to an ion exchange medium or hydrophobic interaction chromatography or affinity chromatography medium. In some embodiments, the ion exchange medium or hydrophobic interaction chromatography or affinity chromatography medium separates the conjugated protein from the free polymer and from the reoxidized decapped protein. In some embodiments, the polymer comprises a zwitterion. In some embodiments, the polymer comprises a phosphorylcholine. In some embodiments, the polymer comprises a PEG linker bridging a center of a polymer branching point to the maleimide functional group.

In some embodiments, an anti-VEGF antibody conjugate is provided that is capable of blocking at least 90% of an interaction between a VEGF ligand and a VEGF-receptor.

In some embodiments, an anti-VEGF antibody conjugate is provided that blocks at least 95% of an interaction between a VEGF ligand and a VEGF-receptor.

In some embodiments, an anti-VEGF antibody is provided that blocks at least 90% of an interaction between a VEGF ligand and a VEGF-receptor.

BRIEF DESCRIPTION OF THE DRAWINGS

FIG. 3 shows the synthesis of OG1802 from R3707.
FIG. 7 shows the synthesis of OG1405 from OG1784.

FIG. 12 depicts some embodiments of anti-VEGF-A heavy chain with certain effector function mutations and L443C (EU numbering, which is position 449 in SEQ ID NO. 1).

FIG. 13 depicts some embodiments of an anti-VEGF-A light chain (SEQ ID NO. 2).

FIG. 14 depicts some embodiments of a Bevacizumab heavy chain (SEQ ID NO. 3).

FIG. 15 depicts some embodiments of a Bevacizumab light chain (SEQ ID NO. 4).

FIG. 16 depicts some embodiments of a Ranibizumab heavy chain (SEQ ID NO. 5).

FIG. 17 depicts some embodiments of a Ranibizumab light chain (SEQ ID NO. 6).

FIG. 22 depicts binding of the OG1950 to Fc gamma receptor I.

FIG. 23 depicts binding of the OG1950 to Fc gamma receptor IIIa.

FIG. 27 depicts some embodiments of nucleic acid sequences encoding heavy and light chain variable regions.

DETAILED DESCRIPTION OF THE PREFERRED EMBODIMENT

Figure 1:
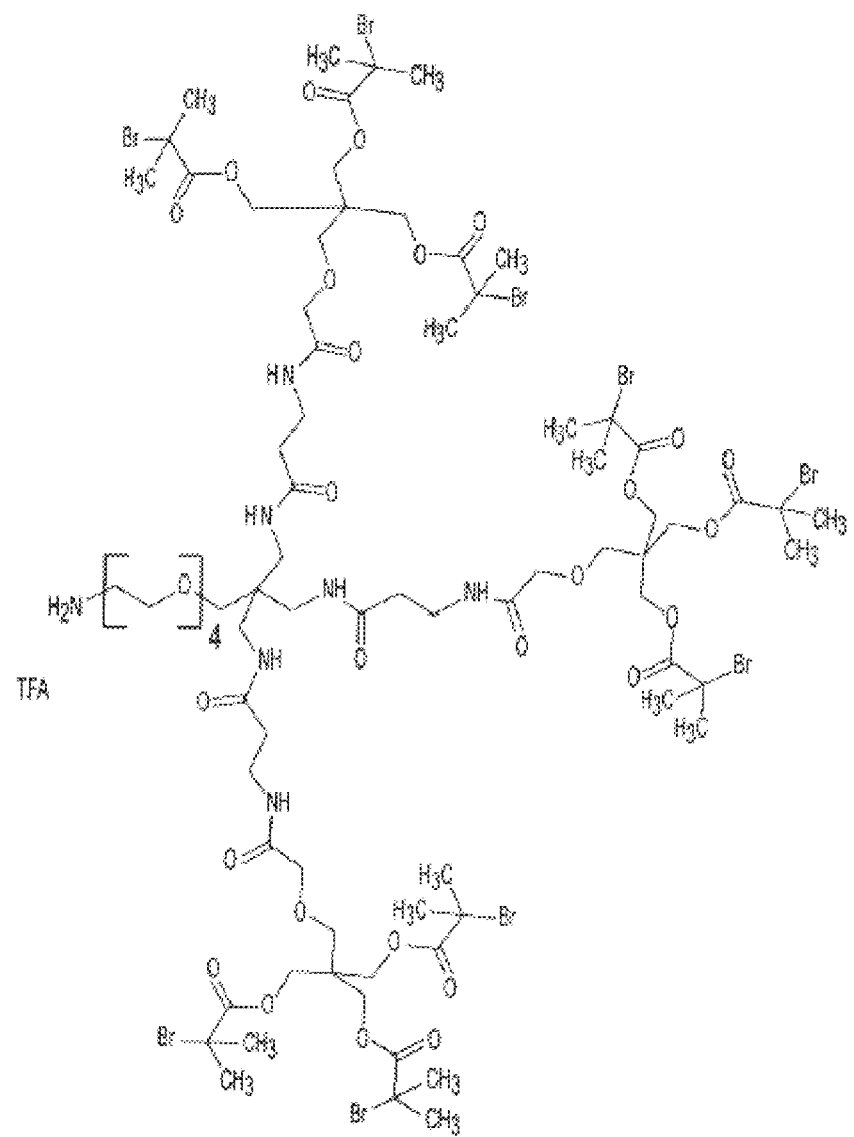
FIG. 1 shows Compound L.

Provided herein are anti-VEGF-A antibodies. In some embodiments, these antibodies can be conjugated to a half-life extending moiety. In some embodiments, the conjugate can be used for the treatment of certain conditions, such as diabetic retinopathy and/or age-related macular degeneration.

Further provided herein are methods for preparing conjugate compositions of antibodies (of any type of antibody). In some embodiments, these methods allow for lower aggregate formation or higher efficiency of formation of the desired antibody conjugate.

These and additional embodiments are provided below, following the definition section.

Definitions

A "neovascular disorder" is a disorder or disease state characterized by altered, dysregulated or unregulated angiogenesis. Examples of neovascular disorders include neoplastic transformation (e.g. cancer) and ocular neovascular disorders including diabetic retinopathy and age-related macular degeneration.

An "ocular neovascular" disorder is a disorder characterized by altered, dysregulated or unregulated angiogenesis in the eye of a patient. Such disorders include optic disc neovascularization, iris neovascularization, retinal neovascularization, choroidal neovascularization, corneal neovascularization, vitreal neovascularization, glaucoma, pannus, pterygium, macular edema, diabetic retinopathy, diabetic macular edema, vascular retinopathy, retinal degeneration, uveitis, inflammatory diseases of the retina, and proliferative vitreoretinopathy.

The term antibody includes intact antibodies and binding fragments thereof. A binding fragment refers to a molecule other than an intact antibody that comprises a portion of an intact antibody that binds the antigen to which the intact antibody binds. Examples of binding fragments include Fv, Fab', Fab'-SH, F(ab')2; diabodies; linear antibodies; single-chain antibody molecules (e.g. scFv); and multispecific antibodies formed from antibody fragments. scFv antibodies are described in Houston J S. 1991. Methods in Enzymol. 203:46-96. In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

Specific binding of an antibody to its target antigen(s) means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody or fusion protein binds one and only one target.

A basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. However, reference to a variable region does not mean that a signal sequence is necessarily present; and in fact signal sequences are cleaved once the antibodies or fusion proteins have been expressed and secreted. A pair of heavy and light chain variable regions defines a binding region of an antibody. The carboxy-terminal portion of the light and heavy chains respectively defines light and heavy chain constant regions. The heavy chain constant region is primarily responsible for effector function. In IgG antibodies, the heavy chain constant region is divided into CH1, hinge, CH2, and CH3 regions. The CH1 region binds to the light chain constant region by disulfide and noncovalent bonding. The hinge region provides flexibility between the binding and effector regions of an antibody and also provides sites for intermolecular disulfide bonding between the two heavy chain constant regions in a tetramer subunit. The CH2 and CH3 regions are the primary site of effector functions and FcR binding.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" segment of about 12 or more amino acids, with the heavy chain also including a "D" segment of about 10 or more amino acids. (See generally, Fundamental Immunology (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites, i.e., is divalent. In natural antibodies, the binding sites are the same. However, bispecific antibodies can be made in which the two binding sites are different (see, e.g., Songsivilai S, Lachmann P C. 1990. Bispecific antibody: a tool for diagnosis and treatment of disease. Clin Exp Immunol. 79:315-321; Kostelny S A, Cole M S, Tso J Y. 1992. Formation of bispecific antibody by the use of leucine zippers. J Immunol. 148: 1547-1553). The variable regions all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. For convenience, the variable heavy CDRs can be referred to as $CDR_H1$, $CDR_H2$ and $CDR_H3$; the variable light chain CDRs can be referred to as $CDR_L1$, $CDR_L2$ and $CDR_L3$. The assignment of amino acids to each domain is in accordance with the definitions of Kabat E A, et al. 1987 and 1991. Sequences of Proteins of Immunological Interest (National Institutes of Health, Bethesda, Md.) or Chothia C, Lesk A M. 1987. Canonical Structures for the Hypervariable Regions of Immunoglobulins. J Mol Biol 196:901-917; Chothia C, et al. 1989. Conformations of Immunoglobulin Hypervariable Regions. Nature 342:877-883. Kabat also provides a widely used numbering convention (Kabat numbering) in which corresponding residues between different heavy chain variable regions or between different light chain variable regions are assigned the same number. Although Kabat numbering can be used for antibody constant regions, EU numbering is more commonly used, as is the case in this application. Although specific sequences are provided for exemplary antibodies disclosed herein, it will be appreciated that after expression of protein chains one to several amino acids at the amino or carboxy terminus of the light and/or heavy chain, particularly a heavy chain C-terminal lysine residue, may be missing or derivatized in a proportion or all of the molecules.

The term "epitope" refers to a site on an antigen to which an antibody or extracellular trap segment binds. An epitope on a protein can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody (or Fab fragment) bound to its antigen to identify contact residues.

Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50: 1495, 1990). A test antibody competes with a reference antibody if an excess of a test antibody (e.g., at least 2×, 5×, 10×, 20× or 100×) inhibits binding of the reference antibody by at least 50%. In some embodiments the test antibody inhibits binding of the reference antibody by 75%, 90%, or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention for a variable region or EU numbering for a constant region. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage. Sequence identities of other sequences can be determined by aligning sequences using algorithms, such as BESTFIT, FASTA, and TFASTA in the Wisconsin Genetics Software Package Release 7.0, Genetics Computer Group, 575 Science Dr., Madison, Wis., using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of positions in the window of comparison (i.e., the window size), and multiplying the result by 100 to yield the percentage of sequence identity.

Compositions or methods "comprising" one or more recited elements may include other elements not specifically recited. For example, a composition that comprises antibody may contain the antibody alone or in combination with other ingredients.

The term "antibody-dependent cellular cytotoxicity", or ADCC, is a mechanism for inducing cell death that depends upon the interaction of antibody-coated target cells (i.e., cells with bound antibody) with immune cells possessing lytic activity (also referred to as effector cells). Such effector cells include natural killer cells, monocytes/macrophages and neutrophils. ADCC is triggered by interactions between the Fc region of an antibody bound to a cell and Fcγreceptors, particularly FcγRI and FcγRIII, on immune effector cells such as neutrophils, macrophages and natural killer cells. The target cell is eliminated by phagocytosis or lysis, depending on the type of mediating effector cell. Death of the antibody-coated target cell occurs as a result of effector cell activity.

The term opsonization also known as "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an immunoglobulin Fc region.

The term "complement-dependent cytotoxicity" or CDC refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (which can be as defined by Kabat) from a mouse antibody, they can also be made with less than all CDRs (e.g., at least 3, 4, or 5 CDRs from a mouse antibody) (e.g., De Pascalis R, Iwahashi M, Tamura M, et al. 2002. Grafting "Abbreviated" Complementary-Determining Regions Containing Specificity-Determining Residues Essential for Ligand Contact to Engineer a Less Immunogenic Humanized Monoclonal Antibody. J Immunol. 169:3076-3084; Vajdos F F, Adams C W, Breece T N, Presta L G, de Vos A M, Sidhu, S S. 2002. Comprehensive functional maps of the antigen-binding site of an anti-ErbB2 antibody obtained with shotgun scanning mutagenesis. J Mol Biol. 320: 415-428; Iwahashi M, Milenic D E, Padlan E A, et al. 1999. CDR substitutions of a humanized monoclonal antibody (CC49): Contributions of individual CDRs to antigen binding and immunogenicity. Mol Immunol. 36:1079-1091; Tamura M, Milenic D E, Iwahashi M, et al. 2000. Structural correlates of an anticarcinoma antibody: Identification of specificity-determining regions (SDRs) and development of a minimally immunogenic antibody variant by retention of SDRs only. J Immunol. 164:1432-1441).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan E A. 1991. A possible procedure for reducing the immunogenicity of antibody variable domains while preserving their ligand-binding properties. Mol Immunol. 28:489-98) with residues from the corresponding positions of a human antibody sequence. The result is an antibody in which the CDRs are entirely or substantially from a non-human antibody and the variable region frameworks of the non-human antibody are made more human-like by the substitutions. A human antibody can be isolated from a human, or otherwise result from expression of human immunoglobulin genes (e.g., in a transgenic mouse, in vitro or by phage display). Methods for producing human antibodies include the trioma method of Ostberg L, Pursch E. 1983. Human×(mouse×human) hybridomas stably producing human antibodies. Hybridoma 2:361-367; Ostberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741 (1991) and phage display methods (see, e.g. Dower et al., WO 91/17271 and McCafferty et al., WO 92/01047, U.S. Pat. Nos. 5,877,218, 5,871,907, 5,858,657, 5,837,242, 5,733,743 and 5,565,332.

"Polymer" refers to a series of monomer groups linked together. A polymer is composed of multiple units of a single monomer (a homopolymer) or different monomers (a heteropolymer). High MW polymers are prepared from monomers that include, but are not limited to, acrylates, methacrylates, acrylamides, methacrylamides, styrenes, vinylpyridine, vinyl-pyrrolidone and vinyl esters such as vinyl acetate. Additional monomers are useful in high MW polymers. When two different monomers are used, the two monomers are called "comonomers," meaning that the different monomers are copolymerized to form a single polymer. The polymer can be linear or branched. When the polymer is branched, each polymer chain is referred to as a "polymer arm." The end of the polymer arm linked to the initiator moiety is the proximal end, and the growing-chain end of the polymer arm is the distal end. On the growing chain-end of the polymer arm, the polymer arm end group can be the radical scavenger, or another group.

"Initiator" refers to a compound capable of initiating a polymerization using monomers or comonomers. The polymerization can be a conventional free radical polymerization or a controlled/"living" radical polymerization, such as Atom Transfer Radical Polymerization (ATRP), Reversible Addition-Fragmentation-Termination (RAFT) polymerization or nitroxide mediated polymerization (NMP). The polymerization can be a "pseudo" controlled polymerization, such as degenerative transfer. When the initiator is suitable for ATRP, it contains a labile bond which can be homolytically cleaved to form an initiator fragment, I, being a radical capable of initiating a radical polymerization, and a radical scavenger, I', which reacts with the radical of the growing polymer chain to reversibly terminate the polymerization. The radical scavenger I' is typically a halogen, but can also be an organic moiety, such as a nitrile. In some embodiments, the initiator contains one of more 2-bromoisobutyrate groups as sites for polymerization via ATRP.

A "chemical linker" refers to a chemical moiety that links two groups together, such as a half-life extending moiety and a protein. The linker can be cleavable or non-cleavable. Cleavable linkers can be hydrolyzable, enzymatically cleavable, pH sensitive, photolabile, or disulfide linkers, among others. Other linkers include homobifunctional and heterobifunctional linkers. A "linking group" is a functional group capable of forming a covalent linkage consisting of one or more bonds to a bioactive agent. Non-limiting examples include those illustrated in Table 1 of WO2013059137 (incorporated by reference).

The term "reactive group" refers to a group that is capable of reacting with another chemical group to form a covalent bond, i.e. is covalently reactive under suitable reaction conditions, and generally represents a point of attachment for another substance. The reactive group is a moiety, such as maleimide or succinimidyl ester, is capable of chemically reacting with a functional group on a different moiety to form a covalent linkage. Reactive groups generally include nucleophiles, electrophiles and photoactivatable groups.

"Phosphorylcholine," also denoted as "PC," refers to the following:

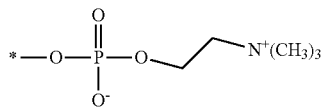

where * denotes the point of attachment. The phosphorylcholine is a zwitterionic group and includes salts (such as inner salts), and protonated and deprotonated forms thereof.

"Phosphorylcholine containing polymer" is a polymer that contains phosphorylcholine. "Zwitterion containing polymer" refers to a polymer that contains a zwitterion.

Poly(acryloyloxyethyl phosphorylcholine) containing polymer refers to a polymer containing 2-(acryloyloxy) ethyl-2-(trimethylammonium)ethyl phosphate (HEA-PC shown below in Example 6) as monomer.

Poly(methacryloyloxyethyl phosphorylcholine) containing polymer refers to a polymer containing 2-(methacryloyloxy)ethyl-2-(trimethylammonium)ethyl phosphate (HEMA-PC or MPC) as monomer (see below):

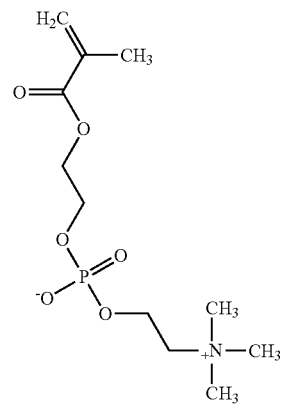

As used herein, "MPC" and "HEMA-PC" are interchangeable.

Molecular weight" in the context of the polymer can be expressed as either a number average molecular weight, or a weight average molecular weight or a peak molecular weight. Unless otherwise indicated, all references to molecular weight herein refer to the peak molecular weight. These molecular weight determinations, number average (Mn), weight average (Mw) and peak (Mp), can be measured using size exclusion chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight, or the use of light scattering techniques, ultracentrifugation or viscometry to determine weight average molecular weight. In some embodiments, the molecular weight is measured by SEC-MALS (size exclusion chromatography—multi angle light scattering). In some embodiments, the polymeric reagents are typically polydisperse (i.e., number average molecular weight and weight average molecular weight of the polymers are not equal), and can possess low polydispersity values of, for example, less than about 1.5, as judged, for example, by the PDI value derived from the SEC-MALS measurement. In some embodiments, the polydispersities (PDI) are in the range of about 1.4 to about 1.2. In some embodiments the PDI is less than about 1.15, 1.10, 1.05, or 1.03.

The phrase "a" or "an" entity refers to one or more of that entity; for example, a compound refers to one or more compounds or at least one compound. As such, the terms "a" (or "an"), "one or more", and "at least one" can be used interchangeably herein.

"About" means variation one might see in measurements taken among different instruments, samples, and sample preparations.

"Protected," "protected form," "protecting group" and "protective group" refer to the presence of a group (i.e., the protecting group) that prevents or blocks reaction of a particular chemically reactive functional group in a molecule under certain reaction conditions. Protecting groups vary depending upon the type of chemically reactive group being protected as well as the reaction conditions to be employed and the presence of additional reactive or protecting groups in the molecule, if any. Suitable protecting groups include those such as found in the treatise by Greene et al., "Protective Groups In Organic Synthesis," $3^{rd}$ Edition, John Wiley and Sons, Inc., New York, 1999.

"Alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "lower" referred to above and hereinafter in connection with organic radicals or compounds respectively defines a compound or radical which can be branched or unbranched with up to and including 7 or up to and including 4 and (as unbranched) one or two carbon atoms.

"Alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2 m'+1), where m' is the total number of carbon atoms in such radical. R', R" and R''' each independently refer to hydrogen, unsubstituted ($C_1$-$C_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. The term "alkyl" is include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). In some embodiments, the substituted alkyl and heteroalkyl groups have from 1 to 4 substituents. In some embodiments, the substituted alkyl and heteroalkyl groups have 1, 2 or 3 substituents. Exceptions are those perhalo alkyl groups (e.g., pentafluoroethyl and the like).

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R''' and R'''' each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

"Alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group.

"Carboxyalkyl" means an alkyl group (as defined herein) substituted with a carboxy group. The term "carboxycycloalkyl" means a cycloalkyl group (as defined herein) substituted with a carboxy group. The term alkoxyalkyl means an alkyl group (as defined herein) substituted with an alkoxy group. The term "carboxy" employed herein refers to carboxylic acids and their esters.

"Haloalkyl" refers to alkyl as defined above where some or all of the hydrogen atoms are substituted with halogen atoms. Halogen (halo) represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has all available hydrogens that are replaced with fluorine. For example, perfluorophenyl refers to 1,2,3,4,5-pentafluorophenyl, perfluoromethyl refers to 1,1,1-trifluoromethyl, and perfluoromethoxy refers to 1,1,1-trifluoromethoxy.

"Fluoro-substituted alkyl" refers to an alkyl group where one, some, or all hydrogen atoms have been replaced by fluorine.

"Cytokine" is a member of a group of protein signaling molecules that may participate in cell-cell communication in immune and inflammatory responses. Cytokines are typically small, water-soluble glycoproteins that have a mass of about 8-35 kDa.

"Cycloalkyl" refers to a cyclic hydrocarbon group that contains from about 3 to 12, from 3 to 10, or from 3 to 7 endocyclic carbon atoms. Cycloalkyl groups include fused, bridged and spiro ring structures.

"Endocyclic" refers to an atom or group of atoms which comprise part of a cyclic ring structure.

"Exocyclic" refers to an atom or group of atoms which are attached but do not define the cyclic ring structure.

"Cyclic alkyl ether" refers to a 4 or 5 member cyclic alkyl group having 3 or 4 endocyclic carbon atoms and 1 endocyclic oxygen or sulfur atom (e.g., oxetane, thietane, tetrahydrofuran, tetrahydrothiophene); or a 6 to 7 member cyclic alkyl group having 1 or 2 endocyclic oxygen or sulfur atoms (e.g., tetrahydropyran, 1,3-dioxane, 1,4-dioxane, tetrahydrothiopyran, 1,3-dithiane, 1,4-dithiane, 1,4-oxathiane).

"Alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl group is typically monovalent, but can be divalent, such as when the alkenyl group links two moieties together.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

"Alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl group is typically monovalent, but can be divalent, such as when the alkynyl group links two moieties together.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

"Cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

"Cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

"Heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

"Heterocycloalkylene" refers to a heterocyclalkyl group, as defined above, linking at least two other groups. The two moieties linked to the heterocycloalkylene can be linked to the same atom or different atoms of the heterocycloalkylene.

"Aryl" refers to a monocyclic or fused bicyclic, tricyclic or greater, aromatic ring assembly containing 6 to 16 ring carbon atoms. For example, aryl may be phenyl, benzyl or naphthyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

In some embodiments the aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phenyl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

"Arylene" refers to an aryl group, as defined above, linking at least two other groups. The two moieties linked to the arylene are linked to different atoms of the arylene. Arylene groups include, but are not limited to, phenylene.

"Arylene-oxy" refers to an arylene group, as defined above, where one of the moieties linked to the arylene is linked through an oxygen atom. Arylene-oxy groups include, but are not limited to, phenylene-oxy.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O) R', —OC(O)NR'R", —NR"C(O)R', —NR"C(O)$_2$R', —NR'—C(O)NR"R'", —NH—C(NH$_2$)═NH, —NR'C(NH$_2$)═NH, —NH—C(NH$_2$)═NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

"Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. In some embodiments, quinolinyl represents 2-, 3- or 4-quinolinyl. In some embodiments, isoquinolinyl represents 1-, 3- or 4-isoquinolinyl. In some embodiments, benzopyranyl, benzothiopyranyl can represent 3-benzopyranyl or 3-benzothiopyranyl, respectively. In some embodiments, thiazolyl can represent 2- or 4-thiazolyl. In some embodiments, triazolyl can be 1-, 2- or 5-(1,2,4-triazolyl). In some embodiments, tetrazolyl can be 5-tetrazolyl.

In some embodiments, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

The term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers, alkyl-amines and alkyl-thiols.

The term "heteroalkylene" refers to a heteroalkyl group, as defined above, linking at least two other groups. The two moieties linked to the heteroalkylene can be linked to the same atom or different atoms of the heteroalkylene.

"Electrophile" refers to an ion or atom or collection of atoms, which may be ionic, having an electrophilic center, i.e., a center that is electron seeking, capable of reacting with a nucleophile. An electrophile (or electrophilic reagent) is a reagent that forms a bond to its reaction partner (the nucleophile) by accepting both bonding electrons from that reaction partner.

"Nucleophile" refers to an ion or atom or collection of atoms, which may be ionic, having a nucleophilic center, i.e., a center that is seeking an electrophilic center or capable of reacting with an electrophile. A nucleophile (or nucleophilic reagent) is a reagent that forms a bond to its reaction partner (the electrophile) by donating both bonding electrons. A "nucleophilic group" refers to a nucleophile after it has reacted with a reactive group. Non limiting examples include amino, hydroxyl, alkoxy, haloalkoxy and the like.

"Maleimido" refers to a pyrrole-2,5-dione-1-yl group having the structure:

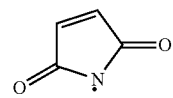

which upon reaction with a sulfhydryl (e.g., a thio alkyl) forms an —S-maleimido group having the structure

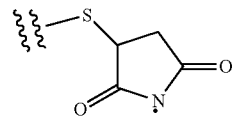

where "•" indicates the point of attachment for the maleimido group and "⚡" indicates the point of attachment of the sulfur atom the thiol to the remainder of the original sulfhydryl bearing group.

For the purpose of this disclosure, "naturally occurring amino acids" found in proteins and polypeptides are L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and or L-valine. "Non-naturally occurring amino acids" found in proteins are any amino acid other than those recited as naturally occurring amino acids. Non-naturally occurring amino acids include, without limitation, the D isomers of the naturally occurring amino acids, and mixtures of D and L isomers of the naturally occurring amino acids. Other amino acids, such as N-alpha-methyl amino acids (e.g. sarcosine), 4-hydroxyproline, desmosine, isodesmosine, 5-hydroxylysine, epsilon-N-methyllysine, 3-methylhistidine, although found in naturally occurring proteins, are considered to be non-naturally occurring amino acids found in proteins for the purpose of this disclosure as they are generally introduced by means other than ribosomal translation of mRNA.

"Linear" in reference to the geometry, architecture or overall structure of a polymer, refers to polymer having a single polymer arm.

"Branched," in reference to the geometry, architecture or overall structure of a polymer, refers to a polymer having 2 or more polymer "arms" extending from a core structure contained within an initiator. The initiator may be employed in an atom transfer radical polymerization (ATRP) reaction. A branched polymer may possess 2 polymer chains (arms), 3 polymer arms, 4 polymer arms, 5 polymer arms, 6 polymer arms, 7 polymer arms, 8 polymer arms, 9 polymer arms or more. Each polymer arm extends from a polymer initiation site. Each polymer initiation site is capable of being a site for the growth of a polymer chain by the addition of monomers. For example and not by way of limitation, using ATRP, the site of polymer initiation on an initiator is typically an organic halide undergoing a reversible redox process catalyzed by a transition metal compound such as cuprous halide. In some embodiments, the halide is a bromine.

"Pharmaceutically acceptable excipient" refers to an excipient that can be included in compositions and that causes no significant adverse toxicological effect on the patient and is approved or approvable by the FDA for therapeutic use, particularly in humans. Non-limiting examples of pharmaceutically acceptable excipients include water, NaCl, normal saline solutions, lactated Ringer's, normal sucrose, normal glucose and the like.

Therapeutic proteins are administered in an effective regime meaning a dosage, route of administration and frequency of administration that delays the onset, reduces the severity, inhibits further deterioration, and/or ameliorates at least one sign or symptom of a disorder. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

The "biological half-life" of a substance is a pharmacokinetic parameter which specifies the time required for one half of the substance to be removed from a tissue or an organism following introduction of the substance.

"OG1786" is a 9-arm initiator used for polymer synthesis with the structure shown in FIG. 30, which depicts that salt form of OG1786 with trifluororacetic acid. OG1786 may be used as other salts are used or as the free base.

"OG1801" is an approximately (+/-15%) 750 kDa polymer (either by Mn or Mp) made using OG1786 as an intiator for ATRP synthesis using the monomer HEMA-PC.

"OG1802" is OG1801 with a maleimide functionality added and is shown in FIG. 36 wherein each of $n_1$, $n_2$, $n_3$, $n_4$, $n_5$, $n_6$, $n_7$, $n_8$ and $n_9$ is an integer (positive) (from 0 up to about 3000) such that the total molecular weight of the polymer is (Mw) 750,000±15% daltons.

Multi-angle light scattering (MALS) is a technique of analyzing macromolecules where the laser light impinges on the molecule, the oscillating electric field of the light induces an oscillating dipole within it. This oscillating dipole will re-radiate light and can be measured using a MALS detector such as Wyatt miniDawn TREOS. The intensity of the radiated light depends on the magnitude of the dipole induced in the macromolecule which in turn is proportional to the polarizability of the macromolecule, the larger the induced dipole, and hence, the greater the intensity of the scattered light. Therefore, in order to analyze the scattering from a solution of such macromolecules, one should know their polarizability relative to the surrounding medium (e.g., the solvent). This may be determined from a measurement of the change, $\Delta n$, of the solution's refractive index n with the molecular concentration change, $\Delta c$, by measuring the do/dc ($=\Delta n/\Delta c$) value using a Wyatt Optilab T-rEX differential refractometer. Two molar weight parameters that MALS determination employ are number average molecular weight (Mn) and weight average molecular weight (Mw) where the polydispersity index (PDI) equals Mw divided by Mn. SEC also allows another average molecular weight determination of the peak molecular weight Mp which is defined as the molecular weight of the highest peak at the SEC.

The PDI is used as a measure of the broadness of a molecular weight distribution of a polymer and bioconjugate which is derived from conjugation of a discrete protein (e.g. OG1950) to a polydisperse biopolymer (e.g., OG1802). For a protein sample, its polydispersity is close to 1.0 due to the fact that it is a product of translation where every protein molecule in a solution is expected to have almost the same length and molar mass. In contrast, due to the polydisperse nature of the biopolymer where the various length of polymer chains are synthesized during the polymerization process, it is very important to determine the PDI of the sample as one of its quality attribute for narrow distribution of molecular weight.

Size exclusion chromatography (SEC) is a chromatography technique in which molecules in solution are separated by their size. Typically an aqueous solution is applied to transport the sample through the column which is packed with resins of various pore sizes. The resin is expected to be inert to the analyte when passing through the column and the analytes separate from each other based on their unique size and the pore size characteristics of the selected column.

Coupling the SEC with MALS or SEC/MALS provides accurate distribution of molar mass and size (root mean square radius) as opposed to relying on a set of SEC calibration standards. This type of arrangement has many advantages over traditional column calibration methods. Since the light scattering and concentration are measured for each eluting fraction, the molar mass and size can be determined independently of the elution position. This is particularly relevant for species with non-globular shaped macromolecules such as the biopolymers (OG1802) or bioconjugates (OG1953); such species typically do not elute in a manner that might be described by a set of column calibration standards.

In some embodiments, a SEC/MALS analysis includes a Waters HPLC system with Alliance 2695 solvent delivery module and Waters 2996 Photodiole Array Detector equipped with a Shodex SEC-HPLC column (7.8×300 mm). This is connected online with a Wyatt miniDawn TREOS and Wyatt Optilab T-rEX differential refractometer. The Empower software from Waters can be used to control the Waters HPLC system and the ASTRA V 6.1.7.16 software from Wyatt can be used to acquire the MALS data from the Wyatt miniDawn TREOS, dn/dc data from the T-rEX detector and the mass recovery data using the A280 absorbance signal from the Waters 2996 Photodiole Array detector. SEC can be carried out at 1 ml/min in 1×PBS pH 7.4, upon sample injection, the MALS and RI signals can be analyzed by the ASTRA software for determination of absolute molar mass (Mp, Mw, Mn) and polydisperse index (PDI). In addition, the calculation also involves the input dn/dc values for polymer and protein as 0.142 and 0.183, respectively. For OG1953 bioconjugates dn/dc value, the dn/dc is calculated based on the weighted MW of the polymer and the protein to be about 0.148 using the formula below:

Conjugate $dn/dc$=0.142×[MWpolymer/(MWpolymer+MWprotein)]+0.183×[MWprotein/(MWpolymer+MWprotein)]

Where MWpolymer for OG1802 is 800 kDa and the MW protein for OG1950 is 146 kDa.

General

Provided herein are anti-VEGF antibodies and conjugates thereof. In some embodiments, the antibodies themselves are different from other anti-VEGF agents and provide superior results over other anti-VEGF agents. In some embodiments, the anti-VEGF antibody conjugate displays a surprising superiority over other antibodies and/or the expectation of the activity other antibody conjugates.

Historically, conjugating a molecule to a protein often resulted in a decrease in the protein's binding interaction to its intended target. In some embodiments of the present disclosure, when conjugating to a location that is outside of the active site, the same level of decrease as might have been expected is not necessarily observed. The evidence provided herein shows the opposite effect as to what may have been expected. In some embodiments, and without intending to be limited by theory, the conjugate can be superior to the antibody alone. For example, the interaction of a ligand and its specific receptor is often driven through the stereospecific interaction of the ligand and the receptor, as directed by the interactions of the hydrophilic amino acids on the ligand with the hydrophilic amino acids on the receptor, and water molecules are front and center in those interactions. At the same time, this hydrophilic stereospecificity is further enhanced by de-emphasizing and/or suppressing non-specific hydrophobic interactions that might generally be mediated/created by hydrophobic-to-hydrophobic amino acids.

In some embodiments, an anti-VEGF antibody conjugate is provided that is capable of blocking at least 90% of an interaction between a VEGF ligand ("VEGFL") and a VEGF-receptor ("VEGFR"). For example, it can block at least 90, 91, 92, 93, 94, 95, 96, 97, 98, 99, or effectively all of the interaction between VEGFR and VEGFL. In some embodiments, the noted blocking occurs at saturating concentrations. In some embodiments, an anti-VEGF antibody conjugate is provided that blocks at least 95% of an interaction between a VEGF ligand and a VEGF-receptor. As an example of such superiority of blocking, see FIG. 20, regarding the ability of OG1953 (and antibody conjugate provided herein) to block to a higher degree than Lucentis® (ranibizumab) or Avastin®(bevacizumab) or even the antibody OG1950 (unconjugated). Indeed, this result was unexpected in that while the addition of a polymer to an antibody (to form an antibody conjugate), could be expected to have some or no detrimental impact on binding/activity of the antibody, it was unexpected that it would actually improve the blocking ability of the antibody in this manner.

In some embodiments, the antibodies or conjugates thereof inhibit at least 70, 80, 85, 86, 87, 88, 89, 90, 91, 92, 93, 94, 95, 96, 97, 98, 99, or 100% of the activity and/or interaction between VEGFR and VEGFL. In some embodiments, the IC50 value can be 0.1, 1, 2, 3, 4, 5, 6, 7, 8, 9, 10, 20, 30, 40, 50, 100 nM or less than any one or more of the preceding values. In some embodiments, the KD can be 2*10^-13, 1*10^-13, 1*10^-12, 1*10^-11, 1*10-^10 M or less than any one of the preceding values. In some embodiments, the IC50 value can be 1, 5, 10, 20, 30, 40, 50, 60, 70 80, 90, 100, 200, 300, 400, 500, 600, 700, 800, 900, 1,000, 1,100, 1,200, 1,300, or less than any one of the preceding values.

In some embodiments, an anti-VEGF antibody is provided that blocks at least 90% of an interaction between a VEGF ligand and a VEGF-receptor. For example, it can block at least 91, 92, 93, 94, 95, 96, 97, 98, 99, or effectively all of the interaction between VEGFR and VEGFL. As an example of such superiority of blocking, see FIG. 20, regarding the ability of OG1950 (and antibody provided herein) to block to a higher degree than Lucentis®(ranibizumab) or Avastin®(bevacizumab).

In some embodiments, other antibodies, such as Lucentis®(ranibizumab) or Avastin®(bevacizumab) can be conjugated to one or more of the polymers as described herein, by one or more of the processes described herein. In some embodiments, any antibody, or fragment thereof, can be conjugated to one or more of the polymers as described herein, by one or more of the processes described herein.

In some embodiments the antibody comprises a heavy chain amino acid variable region that comprises SEQ ID NO 1 and a light chain amino acid variable region that comprises SEQ ID NO. 2. In some embodiments, the antibody is conjugated to one or more of the polymers provided herein. In some embodiments, the conjugated antibody is at least 90% identical to SEQ ID NO: 1 and/or 2. In some embodiments, the antibody contains the 6 CDRs within SEQ ID NO:1 and SEQ ID NO: 2, as well as a point mutation of L443C (EU numbering, or 449C in SEQ ID NO: 1). In some embodiments, the conjugated antibody is at least 90% identical to SEQ ID NO: 1 and/or 2 and includes the following mutations: L234A, L235A, and G237A (EU numbering), and at least one of the following mutations: Q347C (EU numbering) or L443C (EU numbering).

In some embodiments an antibody that binds to VEGF-A is provided. The antibody comprises: a $CDR_H1$ that is the $CDR_H1$ in SEQ ID NO: 1, a $CDR_H2$ that is the $CDR_H2$ in SEQ ID NO: 1, a $CDR_H3$ that is the $CDR_H3$ in SEQ ID NO: 1, a $CDR_L1$ that is the $CDR_L1$ in SEQ ID NO: 2, a $CDR_L2$ that is the $CDR_L2$ in SEQ ID NO: 2, a $CDR_L3$ that is the $CDR_L3$ in SEQ ID NO: 2, at least one of the following mutations: L234A, L235A, and G237A (EU numbering), and at least one of the following mutations: Q347C (EU numbering) or L443C (EU numbering).

As will be appreciated by one of skill in the art, inlight of the present specification, any of the antibodies provided herein can be conjugated to any of the polymers provided herein and/or any antibody provided herein can have a cysteine added such that it allows for site specific conjugation to a polymer.

"VEGF" or "vascular endothelial growth factor" is a human vascular endothelial growth factor that affects angiogenesis or an angiogenic process. In particular, the term VEGF means any member of the class of growth factors that (i) bind to a VEGF receptor such as VEGFR-1 (Flt-1), VEGFR-2 (KDR/Flk-1), or VEGFR-3 (FLT-4); (ii) activates a tyrosine kinase activity associated with the VEGF receptor; and (iii) thereby affects angiogenesis or an angiogenic process.

The VEGF family of factors is made up of five related glycoproteins: VEGF-A (also known as VPE), -B, -C, -D and PGF (placental growth factor). Of these, VEGF-A is the most well studied and is the target of anti-angiogenic therapy. Ferrara et al, (2003) Nat. Med. 9:669-676. VEGF-A exists as a number of different isotypes which are generated both by alternative splicing and proteolysis: VEGF-$A_{206}$, VEGF-$A_{189}$, VEGF-$A_{165}$, and VEGF-$A_{121}$. The isoforms differ in their ability to bind heparin and non-signaling binding proteins called neuropilins. The isoforms are all biologically active as dimers.

The various effects of VEGF are mediated by the binding of a VEGF, e.g., VEGF-A (P15692), -B (P49766), -C (P49767) and -D (Q43915), to receptor tyrosine kinases (RTKs). The VEGF family receptors belong to class V RTKs and each carry seven Ig-like domains in the extracellular domain (ECD). In humans, VEGF binds to three types of RTKs: VEGFR-1 (Flt-1) (P17948), VEGFR-2 (KDR, Flk-1) (P935968) and VEGFR-3 (Flt-4) (P35916). Unless otherwise apparent from the context reference to a VEGF means any of VEGF-A, -B, -C, -D, and PGF, in any of the natural isoforms or natural variants or induced variants having at least 90, 95, 98 or 99% or 100% sequence identity to a natural form. In some embodiments, such VEGFs are human VEGFs. Likewise reference to a VEGFR means any of VEGR-1, R-2 or R-3, including any natural isoform or natural variant, or an induced variant having at least 90, 95, 98 or 99% or 100% sequence identity to a natural sequences.

VEGF antagonist therapies have been approved for the treatment of certain cancers and wet AMD. Bevacizumab (AVASTIN, Genentech/Roche) is a humanized mouse monoclonal antibody that binds to and neutralizes human VEGF, in particular to all isoforms of VEGF-A and to bioactive proteolytic fragments of VEGF-A. See, e.g., Ferrara N, Hillan K J, Gerber H P, Novotny W. 2004. Discovery and development of bevacizumab, an anti-VEGF antibody for treating cancer. Nat Rev Drug Discov. 3(5):391-400. Bevacizumab has been approved for the treatment of certain cancers. The protein sequence of the heavy and light chains of bevacizumab (DrugBank DB00112) are set forth in SEQ ID NO. 3 (heavy) and SEQ ID NO. 4 (light).

Bevacizumab variable light chain CDRs are $CDR_L1$: SASQDISNYLN (SEQ ID NO: 12), $CDR_L2$: FTSSLHS (SEQ ID NO: 13) and $CDR_L3$: QQYSTVPWT (SEQ ID NO: 14). Bevacizumab variable heavy chain CDRs are $CDR_H1$: GYTFTNYGMN, $CDR_H2$: WINTYTGEPTYAADFKR (SEQ ID NO: 10), and $CDR_H3$: YPHYYGSSHWYFDV. CDRs are defined by Kabat except CDRH1 uses the composite Kabat/Chothia definition. In some embodiments, a cysteine can be added to the Bevacizumab sequence and the antibody (and/or a variant that includes the 6 CDRs of Bevacizumab) can be conjugated to any one or more of the polymers provided herein.

Another anti-VEGF molecule, derived from the same mouse monoclonal antibody as bevacizumab has been approved as a treatment for wet AMD: ranibizumab (LUCENTIS®(ranibizumab), Genentech/Roche). Ranibizumab is an antibody fragment or Fab. Ranibizumab was produced by affinity maturation of the variable heavy and light chains of bevacizumab. The sequence of the heavy and light chains of ranibizumab (as published by Novartis) is set forth in SEQ ID NO. 5 and 6 respectively. In some embodiments, a cysteine can be added to the ranibizumab sequence and the antibody (and/or a variant that includes the 6 CDRs of ranibizumab) can be conjugated to any one or more of the polymers provided herein.

The Ranibizumab CDRS are the same as Bevacizumab except where an improvement was added after affinity maturation: Ranibizumab variable light chain CDRs are $CDR_L1$: SASQDISNYLN (SEQ ID NO: 12), $CDR_L2$: FTSSLHS (SEQ ID NO: 13) and $CDR_L3$: QQYSTVPWT (SEQ ID NO: 14). Ranibizumab variable heavy chain CDRs are $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11).

In some embodiments, an antibody conjugate is presented having an anti-VEGF-A antibody bonded at a cysteine outside a variable region of the antibody to a phosphorylcholine containing polymer, wherein the cysteine has been added via recombinant DNA technology. In some embodiments, the polymer is bonded to a single cysteine. In some embodiments, "added by recombinant DNA technology" means that the cysteine residue replaces a non-cysteine amino acid that occurs in the same position in a known or existing antibody or in a consensus antibody sequence. Thus, for example where the antibody is an IgG1 and the heavy chain possess a leucine at EU position 443, the leucine is replaced via recombinant DNA technology with a cysteine (L443C, EU numbering, or 449C in SEQ ID NO: 1). Correspondingly, the native IgG1 sequence at EU position 347 is Q (glutamine) and the Q is replaced with cysteine via recombinant DNA technology to yield Q347C.

In some embodiments, the anti-VEGF-A antibody comprises a light chain and a heavy chain where the heavy chain has an Fc region. In some embodiments, the cysteine is in the Fc region and the anti-VEGF-A antibody is an immunoglobulin G (IgG). In some embodiments, the anti-VEGF-A heavy chain has $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11), and position 231 (via sequential counting as in SEQ ID NO. 3) is T, and the anti-VEGF-A light chain has $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14), and Kabat position 4 is L.

In some embodiments, the anti-VEGF-A heavy chain isotype is IgG1. In some embodiments, the IgG1 constant domain has one or more mutations relative to an IgG1 constant domain (e.g. constant region of SEQ ID NO. 3) to modulate effector function. In some embodiments, the effector function mutations are one or more of the following: (EU numbering) E233X, L234X, L235X, G236X, G237X, A327X, A330X, and P331X wherein X is any natural or unnatural amino acid. In some embodiments, the mutations are selected from the group consisting of (EU numbering): E233P, L234V, L234A, L235A, G237A, A327G, A330S, and P331S. In some embodiments, antibody conjugate has the following mutations (EU numbering): L234A, L235A, and G237A.

In some embodiments, the cysteine residue is in the anti-VEGF-A heavy chain and is Q347C (EU numbering) or L443C (EU numbering). In some embodiments, the cysteine residue is L443C (EU numbering, or 449C in SEQ ID NO: 1). In some embodiments, the sequence of the anti-VEGF-A heavy chain is SEQ ID NO. 1 and the sequence of the anti-VEGF-A light chain is SEQ ID NO. 2.

In some embodiments, the phosphorylcholine containing polymer comprises 2-(methacryloyloxyethyl)-2'-(trimethylammonium)ethyl phosphate (MPC) monomers as set forth below:

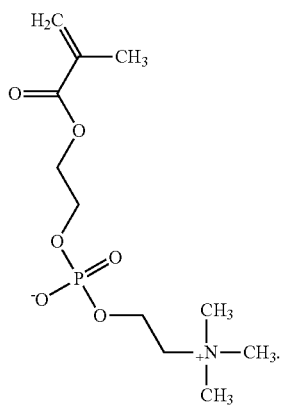

Such that the polymer comprises the following repeating units:

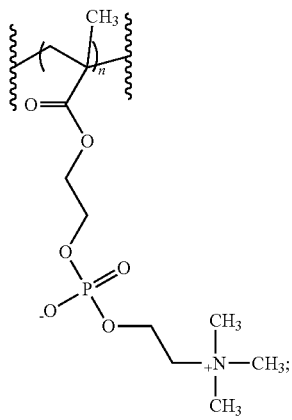

where n is an integer from 1 to 3000 and the wavy lines indicate the points of attachment between monomer units in the polymer.

In some embodiments, the polymer has three or more arms, or is synthesized with an initiator comprising 3 or more polymer initiation sites. In some embodiments, the polymer has 2, 3, 4, 5, 6, 7, 8, 9, 10, 11 or 12 arms, or is synthesized with an initiator comprising 2, 3, 4, 5, 6, 7, 8, 9, 10, 11, or 12 polymer initiation sites. More preferably, the polymer has 3, 6, or 9 arms, or is synthesized with an initiator comprising 3, 6, or 9 polymer initiation sites. In some embodiments, the polymer has 9 arms, or is synthesized with an initiator comprising 9 polymer initiation sites.

In some embodiments, the polymer that is added has a molecular weight between about 300,000 and about 1,750,000 Da (SEC-MALs). In some embodiments, the polymer has a molecular weight between about 500,000 and about 1,000,000 Da. In some embodiments, the polymer has a molecular weight of between about 600,000 to about 900,000 Da. In some embodiments, the polymer has a molecular weight of between about 750,000 to about 850,000 Da. In some embodiments, the polymer has a molecular weight of between about 800,000 to about 850,000 Da. In some embodiments, the polymer has a molecular weight of between about 750,000 to about 800,000 Da.

In some embodiments, any of the antibodies described herein can be further conjugated to a polymer to form a bioconjugate. The molecular weight of the bioconjugate (in total, SEC-MALs) can be between about 350,000 and 2,000,000 Daltons, for example, between about 450,000 and 1,900,000 Daltons, between about 550,000 and 1,800,000 Daltons, between about 650,000 and 1,700,000 Daltons, between about 750,000 and 1,600,000 Daltons, between about 850,000 and 1,500,000 Daltons, between about 900,000 and 1,400,000 Daltons, between about 950,000 and 1,300,000 Daltons, between about 900,000 and 1,000,000 Daltons, between about 1,000,000 and 1,300,000 Daltons, between about 850,000 and 1,300,000 Daltons, between about 850,000 and 1,000,000 Daltons, and between about 1,000,000 and 1,200,000 Daltons.

In some embodiments, the antibody conjugate is purified. In some embodiments, the polymer is aspect of the antibody conjugate is polydisperse, i.e. the polymer PDI is not 1.0. In some embodiments, the PDI is less than 1.5. In some embodiments, the PDI is less than 1.4. In some embodiments, the PDI is less than 1.3. In some embodiments the PDI is less than 1.2. In some embodiments the PDI is less than 1.1.

In some embodiments, the antibody conjugate has an anti-VEGF-A immunoglobulin G (IgG) bonded to a polymer, which polymer comprises MPC monomers, wherein the sequence of the anti-VEGF-A heavy chain is SEQ ID NO. 1, and the sequence of the anti-VEGF-A light chain is SEQ ID NO. 2, and wherein the antibody is bonded only at C449 in SEQ ID NO. 1 to the polymer. In some embodiments, the polymer has 9 arms and has a molecular weight of between about 600,000 to about 1,000,000 Da.

In some embodiments, the antibody conjugate has an anti-VEGF-A immunoglobulin G (IgG) bonded to a polymer, which polymer comprises MPC monomers, wherein the sequence of the anti-VEGF-A heavy chain is SEQ ID NO. 1, and the sequence of the anti-VEGF-A light chain is SEQ ID NO. 2, and wherein the antibody is bonded only at C443 (EU numbering, or 449C in SEQ ID NO: 1) to the polymer. In some embodiments, the polymer has 9 arms and has a molecular weight of between about 600,000 to about 1,000,000 Da.

In some embodiments, the antibody conjugate has the following structure:

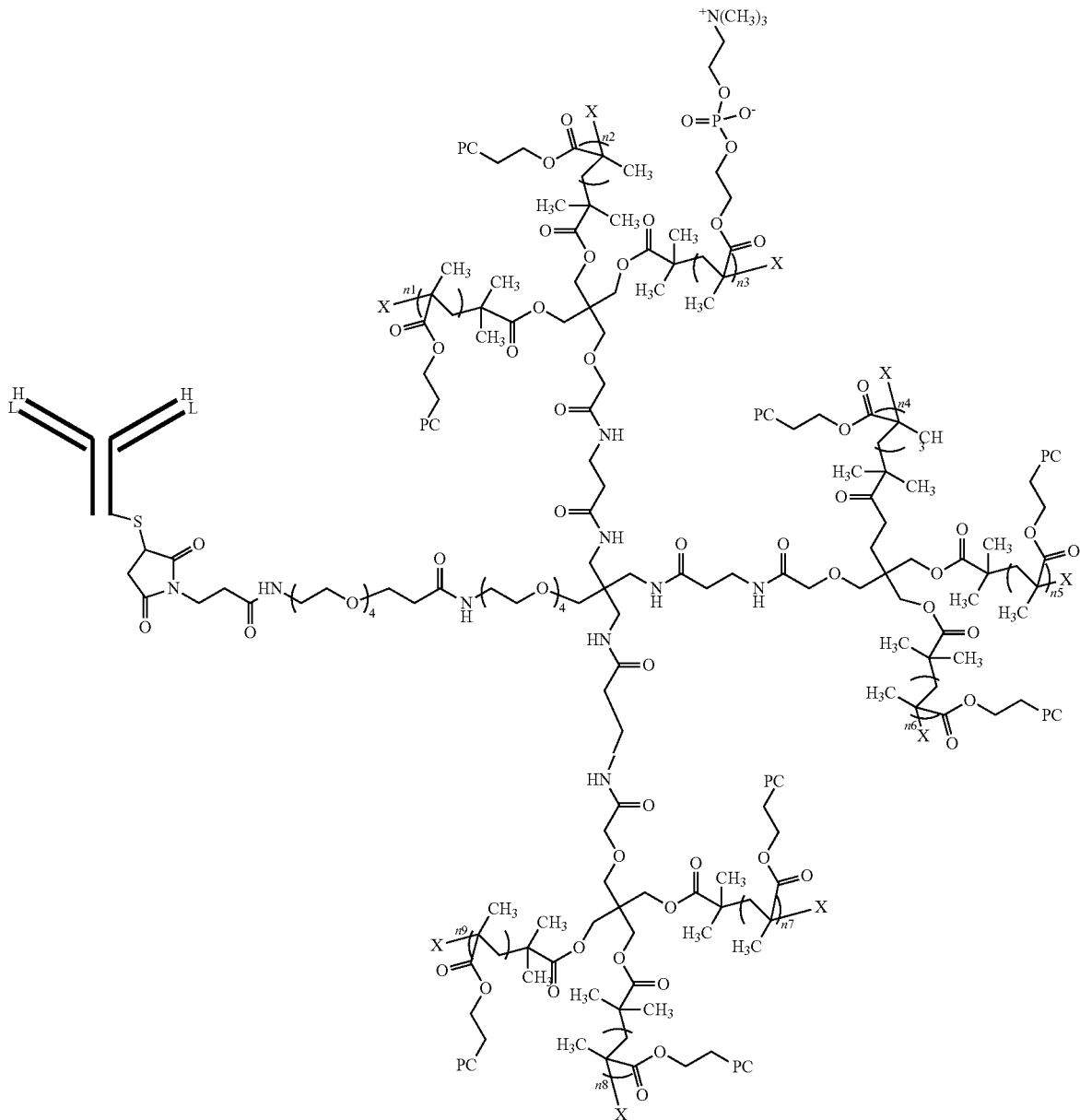

wherein: each heavy chain of the anti-VEGF-A antibody is denoted by the letter H, and each light chain of the anti-VEGF-A antibody is denoted by the letter L; the polymer is bonded to the anti-VEGF-A antibody through the sulfhydryl of C449 of SEQ ID NO: 1, which bond is depicted on one of the heavy chains; PC is,

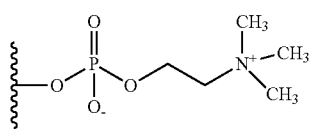

where the curvy line indicates the point of attachment to the rest of the polymer; wherein X=a) OR where R=H, Methyl, ethyl, propyl, isopropyl, b) H, or c) any halide, including Br; and n1, n2, n3, n4, n5, n6, n7, n8 and n9 are the same or different such that the sum of n1, n2, n3, n4, n5, n6, n6, n7, n8 and n9 is 2500 plus or minus 10%. In certain embodiments, n1, n2, n3, n4, n5, n6, n7, n8 and n9 are the same or different and are integers from 0 to 3000. In certain embodiments, n1, n2, n3, n4, n5, n6, n7, n8 and n9 are the same or different and are integers from 0 to 500. In some embodiments, X=OR, where R is a sugar, an aminoalkyl, monosubstituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, —CO—O—$R_7$, carbonyl —CCO—$R_7$, —CO—$NR_8R_9$, —$(CH_2)_n$—$COOR_7$, —CO—$(CH)_n$—$COOR_7$, —$(CH_2)_n$—$NR_8R_9$, ester, alkoxycarbonyl, aryloxycarbonyl, wherein n is an integer from 1 to 6, wherein each $R_7$, $R_8$ and $R_9$ is separately selected from the group consisting of a hydrogen atom, halogen atom, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, a 5-membered ring, and a 6-membered ring.

In some embodiments, the antibody conjugate has the following structure:

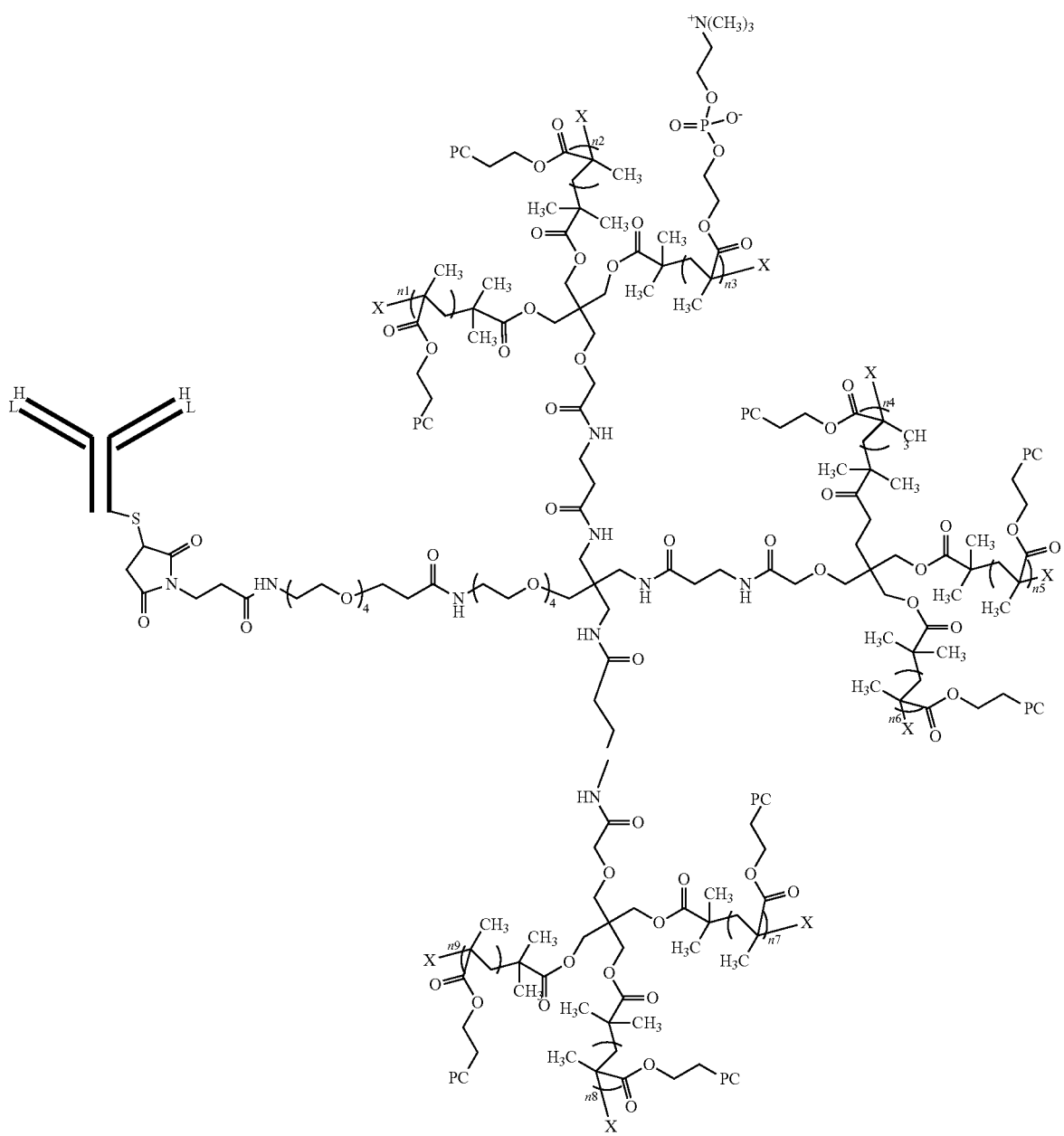

wherein: each heavy chain of the anti-VEGF-A antibody is denoted by the letter H, and each light chain of the anti-VEGF-A antibody is denoted by the letter L;
the polymer is bonded to the anti-VEGF-A antibody through the sulfhydryl of C443 (EU numbering, or 449C in SEQ ID NO: 1), which bond is depicted on one of the heavy chains; PC is,

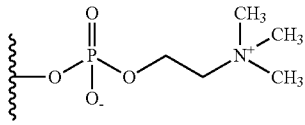

where the curvy line indicates the point of attachment to the rest of the polymer; wherein X=a) OR where R=H, Methyl, ethyl, propyl, isopropyl, b) H, or c) any halide, including Br; and n1, n2, n3, n4, n5, n6, n7, n8 and n9 are the same or different such that the sum of n1, n2, n3, n4, n5, n6, n6, n7, n8 and n9 is 2500 plus or minus 10%. In certain embodiments, n1, n2, n3, n4, n5, n6, n7, n8 and n9 are the same or different and are integers from 0 to 3000. In certain embodiments, n1, n2, n3, n4, n5, n6, n7, n8 and n9 are the same or different and are integers from 0 to 500. In some embodiments, X=OR, where R is a sugar, an aminoalkyl, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, —CO—O—$R_7$, carbonyl —CCO—$R_7$, —CO—$NR_8R_9$, —$(CH_2)_n$—$COOR_7$, —CO—$(CH)_n$—$COOR_7$, —$(CH_2)_n$—$NR_8R_9$, ester, alkoxycarbonyl, aryloxycarbonyl, wherein n is an integer from 1 to 6, wherein each $R_7$, $R_8$ and $R_9$ is separately selected from the group consisting of a hydrogen atom, halogen atom, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, and halogenated alkyl including polyhalogenated alkyl, a 5-membered ring, and a 6-membered ring.

In some embodiments, the antibody conjugate is present in a liquid formulation. In some embodiments, the antibody conjugate is combined with a pharmaceutically acceptable carrier.

In some embodiments, an anti-VEGF-A antibody is presented. The anti-VEGF-A antibody heavy chain has at least the following CDR sequences: $CDR_H1$: GYDFTHYGMN (SEQ ID NO: 9), $CDR_H2$: WINTYTGEPTYAADFKR (SEQ ID NO; 10), and $CDR_H3$: YPYYYGTSHWYFDV (SEQ ID NO: 11). In some embodiments, the anti-VEGF-A heavy chain has those CDRs and in addition has threonine (T) at position 231 (via sequential counting as in SEQ ID NO: 3). In some embodiments, the anti-VEGF-A light chain has at least the following CDRs: $CDR_L1$: SASQDISNYLN (SEQ ID NO: 12), $CDR_L2$: FTSSLHS (SEQ ID NO: 13) and $CDR_L3$: QQYSTVPWT (SEQ ID NO: 14). In some embodiments, the anti-VEGF-A antibody has those CDRs and in addition has leucine (L) at Kabat position 4. In some embodiments, the isotype of the anti-VEGF-A antibody heavy chain, is IgG1 and has a $CH_1$, hinge, $CH_2$ and $CH_3$ domains. In some embodiments the light chain isotype is kappa.

In some embodiments, the IgG1 domain of the anti-VEGF-A antibody has one or more mutations to modulate effector function, such as ADCC, ADCP, and CDC. In some embodiments, the IgG1 mutations reduce effector function. In some embodiments the amino acids to use for effector function mutations include (EU numbering) E233X, L234X, L235X, G236X, G237X, G236X, D270X, K322X, A327X, P329X, A330X, A330X, P331X, and P331X, in which X is any natural or non-natural amino acid. In some embodiments, the mutations include one or more of the following: E233P, L234V, L234A, L235A, G237A, A327G, A330S and P331S (EU numbering). In some embodiments, the anti-VEGF-A heavy chain has the following mutations (EU numbering): L234A, L235A and G237A. In some embodiments, the number of effector function mutations relative to a natural human IgG1 sequence is no more than 10. In some embodiments the number of effector function mutations relative to a natural human IgG1 sequence is no more than 5, 4, 3, 2 or 1. In some embodiments, the antibody has decreased Fc gamma binding and/or complement C1q binding, such that the antibody's ability to result in an effector function is decreased. This can be especially advantageous for ophthalmic indications/disorders.

In some embodiments, the anti-VEGF-A antibody comprises one or more of the following amino acid mutations: L234A, L235A, G237A (EU numbering), and L443C (EU numbering, or 449C in SEQ ID NO: 1).

In some embodiments, the anti-VEGF-A antibody is or is part of a human immunoglobulin G (IgG1).

In some embodiments, the VEGF-A antibody comprises a heavy chain constant domain that comprises one or more mutations that reduce an immune-mediated effector function.

In some embodiments an anti-VEGF-A antibody is provided. The anti-VEGF-antibody comprises a heavy chain that comprises a $CDR_H1$ comprising the sequence GYDFTHYGMN (SEQ ID NO: 9), a $CDR_H2$ comprising the sequence WINTYTGEPTYAADFKR (SEQ ID NO: 10), a $CDR_H3$ comprising the sequence YPYYYGTSHWYFDV (SEQ ID NO: 11), a $CDR_L1$ comprising the sequence SASQDISNYLN (SEQ ID NO: 12), a $CDR_L2$ comprising the sequence FTSSLHS (SEQ ID NO: 13), and a $CDR_L3$ comprising the sequence QQYSTVPWT (SEQ ID NO: 14).

Alternatively, the IgG domain can be IgG2, IgG3 or IgG4 or a composite in which a constant regions is formed from more than one of these isotypes (e.g., CH1 region from IgG2 or IgG4, hinge, CH2 and CH3 regions from IgG1). Such domains can contain mutations to reduce and/or modulate effector function at one or more of the EU position mentioned for IgG1. Human IgG2 and IgG4 have reduced effector functions relative to human IgG1 and IgG3.

The anti-VEGF-A heavy chain has a cysteine residue added as a mutation by recombinant DNA technology which can be used to conjugate a half-life extending moiety. In some embodiments, the mutation is (EU numbering) Q347C (EU numbering) and/or L443C (EU numbering, or 449C in SEQ ID NO: 1). In some embodiments, the mutation is L443C (EU numbering, or 449C in SEQ ID NO: 1). In some embodiments, the stoichiometry of antibody to polymer is 1:1; in other words, a conjugate has one molecule of antibody conjugated to one molecule of polymer.

The half-life of the anti-VEGF-A antibodies can be extended by attachment of a "half-life ("half life") extending moieties" or "half-life ("half life") extending groups". Half-life extending moieties include peptides and proteins which can be expressed in frame with the biological drug of issue (or conjugated chemically depending on the situation) and various polymers which can be attached or conjugated to one or more amino acid side chain or end functionalities such as —SH, —OH, —COOH, —CONH2, —NH2, or one or more N- and/or O-glycan structures. Half-life extending moieties generally act to increase the in vivo circulatory half-life of biologic drugs.

Examples of peptide/protein half-life extending moieties include Fc fusion (Capon D J, Chamow S M, Mordenti J, et al. Designing CD4 immunoadhesions for AIDS therapy. Nature. 1989. 337:525-31), human serum albumin (HAS) fusion (Yeh P, Landais D, Lemaitre M, et al. Design of yeast-secreted albumin derivatives for human therapy: biological and antiviral properties of a serum albumin-CD4 genetic conjugate. Proc Natl Acad Sci USA. 1992. 89:1904-08), carboxy terminal peptide (CTP) fusion (Fares F A, Suganuma N. Nishimori K, et al. Design of a long-acting follitropin agonist by fusing the C-terminal sequence of the chorionic gonadotropin beta subunit to the follitropin beta subunit. Proc Natl Acad Sci USA. 1992. 89:4304-08), genetic fusion of non-exact repeat peptide sequence (XTEN) fusion (Schellenberger V, Wang C W, Geething N C, et al. A recombinant polypeptide extends the in vivo half-life of peptides and proteins in a tunable manner. Nat Biotechnol. 2009. 27:1186-90), elastin like peptide (ELPylation) (MCpherson D T, Morrow C, Minehan D S, et al. Production and purification of a recombinant elastomeric polypeptide, G(VPGVG19-VPGV, from *Escheriachia coli*. Biotechnol Prog. 1992. 8:347-52), human transferrin fusion (Prior C P, Lai C-H, Sadehghi H et al. Modified transferrin fusion proteins. Patent WO2004/020405. 2004), proline-alanine-serine (PASylation) (Skerra A, Theobald I, Schlapsky M. Biological active proteins having increased in vivo and/or vitro stability. Patent WO2008/155134 A1. 2008), homo-amino acid polymer (HAPylation) (Schlapschy M, Theobald I, Mack H, et al. Fusion of a recombinant antibody fragment with a homo-amino acid polymer: effects on biophysical properties and prolonged plasma half-life. Protein Eng Des Sel. 2007. 20:273-84) and gelatin like protein (GLK) fusion (Huang Y-S, Wen X-F, Zaro J L, et al. Engineering a pharmacologically superior form of granulocyte-colony-stimulating-factor by fusion with gelatin-like protein polymer. Eur J. Pharm Biopharm. 2010. 72:435-41).

Examples of polymer half-life extending moieties include polyethylene glycol (PEG), branched PEG, PolyPEG® (Warwick Effect Polymers; Coventry, UK), polysialic acid (PSA), starch, hydroxylethyl starch (HES), hydroxyalkyl starch (HAS), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anyhydride, polystyrene-co-maleic acid anhydride, poly(l-hydroxymethyethylene hydroxymethylformal) (PHF), a zwitterionic polymer, a phosphorylcholine containing polymer and a polymer comprising MPC, Poly (Gly$_x$-Ser$_y$), Hyaluronic acid (HA), Heparosan polymers (HEP), Fleximers, Dextran, and Poly-sialic acids (PSA).

In one embodiment a half-life extending moiety can be conjugated to an antibody via free amino groups of the protein using N-hydroxysuccinimide (NHS) esters. Reagents targeting conjugation to amine groups can randomly react to ϵ-amine group of lysines, α-amine group of N-terminal amino acids, and δ-amine group of histidines.

However, the anti-VEGF-A antibodies disclosed herein have many amine groups available for polymer conjugation. Conjugation of polymers to free amino groups, thus, might negatively impact the ability of the antibody proteins to bind to VEGF.

In some embodiments, a half-life extending moiety is coupled to one or more free SH groups using any appropriate thiol-reactive chemistry including, without limitation, maleimide chemistry, or the coupling of polymer hydrazides or polymer amines to carbohydrate moieties of the antibody after prior oxidation. In some embodiments maleimide coupling is used In some embodiments, coupling occurs at cysteines naturally present or introduced via genetic engineering.

In some embodiments, polymers are covalently attached to cysteine residues introduced into anti-VEGF-A antibodies by site directed mutagenesis. In some embodiments, the cysteine residues are employed in the Fc portion of the antibody. In some embodiments, the sites to introduce cysteine residues into an Fc region are provided in WO 2013/093809, U.S. Pat. No. 7,521,541, WO 2008/020827, U.S. Pat. Nos. 8,008,453, 8,455,622 and US2012/0213705, incorporated herein by reference for all purposes. In some embodiments, the cysteine mutations are Q347C (EU numbering) and L443C referring to the human IgG heavy chain by EU numbering.

In some embodiments, conjugates of antibody and high MW polymers serving as half-life extenders are provided. In some embodiments, a conjugate comprises an antibody that is coupled to a zwitterionic polymer wherein the polymer is formed from one or more monomer units and wherein at least one monomer unit has a zwitterionic group is provided. In some embodiments, the zwitterionic group is phosphorylcholine.

In some embodiments, one of the monomer units is HEMA-PC. In some embodiments, a polymer is synthesized from a single monomer which is HEMA-PC.

In some embodiments, some antibody conjugates have 2, 3, or more polymer arms wherein the monomer is HEMA-PC. In some embodiments, the conjugates have 2, 3, 4, 5, 6, 7, 8, 9, 10, 11, or 12 polymer arms wherein the monomer is HEMA-PC. In some embodiments, the conjugates have 3, 6 or 9 arms. In some embodiments, the conjugate has 9 arms.

In some embodiments, polymer-antibody conjugates have a polymer portion with a molecular weight of between 100,000 and 1,500,000 Da. In some embodiments, the conjugate has a polymer portion with a molecular weight between 500,000 and 1,000,000 Da. In some embodiments, the conjugate has a polymer portion with a molecular weight between 600,000 to 800,000 Da. In some embodiments, the conjugate has a polymer portion with a molecular weight between 600,000 and 850,000 Da and has 9 arms. When a molecular weight is given for an antibody conjugated to a polymer, the molecular weight will be the addition of the molecular weight of the protein, including any carbohydrate moieties associated therewith, and the molecular weight of the polymer.

In some embodiments, an anti-VEGF-A antibody has a HEMA-PC polymer which has a molecular weight measured by Mw of between about 100 kDa and 1650 kDa is provided. In some embodiments, the molecular weight of the polymer as measured by Mw is between about 500 kDa and 1000 kDa. In some embodiments, the molecular weight of the polymer as measured by Mw is between about 600 kDa to about 900 kDa. In some embodiments, the polymer molecular weight as measured by Mw is 750 kDa plus or minus 15%.

In some embodiments, the polymer is made from an initiator suitable for ATRP having one or more polymer initiation sites. In some embodiments, the polymer initiation site has a 2-bromoisobutyrate site. In some embodiments, the initiator has 3 or more polymer initiation sites. In some embodiments, the initiator has 3, 4, 5, 6, 7, 8, 9, 10, 11 or 12 polymer initiation sites. In some embodiments, the initiator has 3, 6 or 9 polymer initiation sites. In some embodiments, the initiator has 9 polymer initiation sites. In some embodiments, the initiator is OG1786.

The anti-VEGF-A antibodies can be produced by recombinant expression including (i) the production of recombinant DNA by genetic engineering, (ii) introducing recombinant DNA into prokaryotic or eukaryotic cells by, for example and without limitation, transfection, electroporation or microinjection, (iii) cultivating the transformed cells, (iv) expressing antibody, e.g. constitutively or on induction, and (v) isolating the antibody, e.g. from the culture medium or by harvesting the transformed cells, in order to (vi) obtain purified antibody.

The anti-VEGF-A antibodies can be produced by expression in a suitable prokaryotic or eukaryotic host system characterized by producing a pharmacologically acceptable antibody molecule. Examples of eukaryotic cells are mammalian cells, such as CHO, COS, HEK 293, BHK, SK-Hip, and HepG2. Other suitable expression systems are prokaryotic (e.g., *E. coli* with pET/BL21 expression system), yeast (*Saccharomyces cerevisiae* and/or *Pichia pastoris* systems), and insect cells.

A wide variety of vectors can be used for the preparation of the antibodies disclosed herein and are selected from eukaryotic and prokaryotic expression vectors. Examples of vectors for prokaryotic expression include plasmids such as, and without limitation, preset, pet, and pad, wherein the promoters used in prokaryotic expression vectors include one or more of, and without limitation, lac, trc, trp, recA, or araBAD. Examples of vectors for eukaryotic expression include: (i) for expression in yeast, vectors such as, and without limitation, pAO, pPIC, pYES, or pMET, using promoters such as, and without limitation, AOX1, GAP, GAL1, or AUG1; (ii) for expression in insect cells, vectors such as and without limitation, pMT, pAc5, pIB, pMIB, or pBAC, using promoters such as and without limitation PH, p10, MT, Ac5, OpIE2, gp64, or polh, and (iii) for expression in mammalian cells, vectors such as, and without limitation, pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and beta-actin.

Method of Conjugating Proteins to Polymers

In some embodiments, a method is presented of preparing a therapeutic protein-half life extending moiety conjugate having the step of conjugating a therapeutic protein which has a cysteine residue added via recombinant DNA technology to a half-life extending moiety having a sulfhydryl specific reacting group selected from the group consisting of maleimide, vinylsulfones, orthopyridyl-disulfides, and iodo-acetamides to provide the therapeutic protein-half life extending moiety conjugate.

Figure 18:
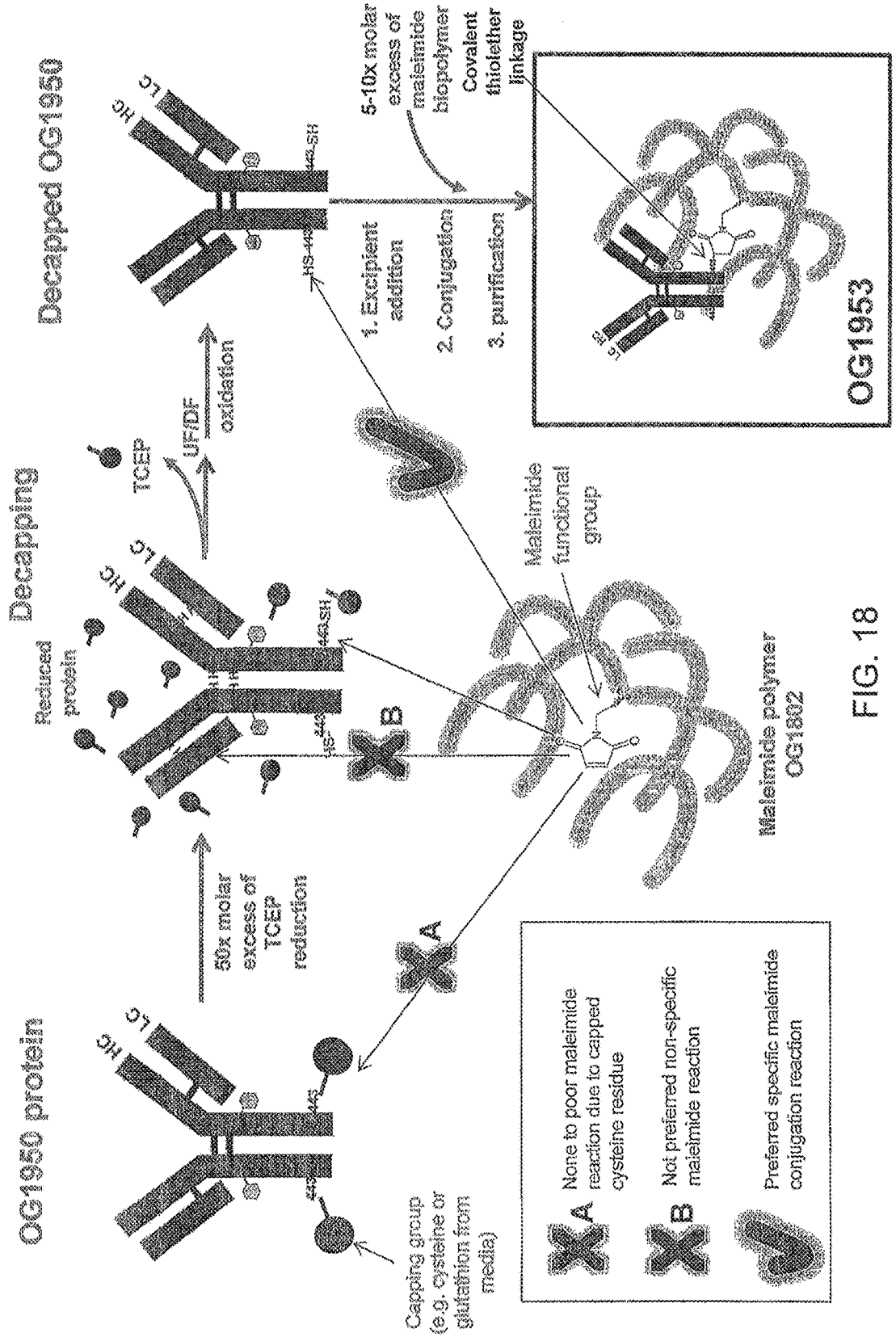
FIG. 18 depicts some embodiments of a method for preparing an antibody conjugate.

In embodiments a method of preparing the OG1953 antibody conjugate from OG1950 is provided. As shown in FIG. 18, the method comprises reducing the OG1950 protein with a 50× molar excess of the TCEP reducing agent (FIG. 18). After reduction, the antibody is oxidized to produce a decapped OG1950 antibody where the inter- and intra-light and heavy chain disulfide bonds naturally occurring in the antibody are formed, but the engineered Cysteine on the heavy chain position L443C (EU numbering, or 449C in SEQ ID NO: 1) remains to be decapped (FIG. 18). The OG1950 is then conjugated by adding an excipient and adding 5-10× molar excess of a maleimide biopolymer. (FIG. 18). The biopolymer links to the OG1950 antibody through a covalent thiolether linkage (FIG. 18). After conjugation, the OG19503 antibody conjugate is purified with both unconjugated antibody and polymer removed (FIG. 18).

The protein and process described above can be varied as well. Thus, in some embodiments, a process for preparing a conjugated protein (which need not be an antibody or an anti-VEGF antibody) is provided. The process includes reducing one or more cysteines in a protein to form a decapped protein in a solution. After reducing the one or more cysteines the decapped protein is reoxidized to restore at least one disulfide linkage in the reduced protein while ensuring that an engineered cysteine residue in the protein remains in a free thiol form to form a reoxidized decapped protein in the solution. At least one excipient is then added to the solution. The excipient reduces a polymer induced protein precipitation. After the excipient is added, a polymer is added to the solution, which is conjugated to the reoxidized decapped protein at the engineered cysteine residue to form a conjugated protein.

In some embodiments, the molar excess of the reducing agent can be altered to any amount that functions. In some embodiments 10, 20, 30, 40, 50, 60, 70, 80, 90× molar excess of the reducing agent (which need not be TCEP in all embodiments) can be employed. In some embodiments, any antibody (therapeutic or otherwise) can be employed. In some embodiments, 1, 2, 3, 4, 5, 6, 7, 8, 9, 10, 11, 12, 13, 14, 15× molar excess of a maleimide biopolymer can be employed. In some embodiments, there is an excess of decapped protein to polymer. In some embodiments, the amount of the reduced protein is less than the amount of the polymer. In some embodiments, the amount of the reduced protein is 90%, 80%, 70%, 60%, 50%, 40%, 30%, 20%, 10%, 5%, 4%, 3%, 2%, 1% of the amount of the polymer. In some embodiments, 10-15 times as much polymer is used as protein. In some embodiments the amount of the reduced antibody is greater than the amount of the polymer. In some embodiments the amount of the polymer is greater than the amount of the reduced antibody.

In some embodiments, the purification step is optional.

In some embodiments, the method of making an antibody conjugate comprises conjugating an anti-VEGF-A antibody to a phosphorylcholine containing polymer. In some embodiments the method comprises the steps of conjugating an anti-VEGF-A antibody to a phosphorylcholine containing polymer. The anti-VEGF-A antibody comprises an amino residue added via recombinant DNA technology. In some embodiments, the added amino acid residue is a cysteine residue. In some embodiments, the cysteine residue is added outside a variable region of the antibody. The cysteine residue can be added to either the heavy chain or light chain of the antibody.

In some embodiments, the polymer comprises or consists of a phosphorylcholine containing polymer. In some embodiments, the phosphorylcholine containing polymer comprises a sulfhydryl specific reacting group selected from the group consisting of a maleimide, a vinylsulfone, an orthopyridyl-disulfide, and an iodoacetamide. In some embodiments, the sulfhydryl specific reacting group on the phosphorylcholine containing polymer reacts with the cysteine residue on the anti-VEGF-A antibody to make the antibody conjugate.

In some embodiments, the protein to be conjugated can be an antibody, an antibody protein fusion, or a binding fragment thereof. In some embodiments, the protein is not an antibody but is an enzyme, a ligand, a receptor, or other protein or mutants or variants thereof. In some embodiments, the native protein contains at least one disulfide bond and at least one non-native cysteine.

In some embodiments, the excipient can be an acid or a base. In some embodiments, the excipient is a detergent, a sugar, or a charged amino acid. In some embodiments, the excipient assists in keeping the protein in solution during the conjugation to the polymer. In some embodiments, the excipient is added to the solution containing the protein, prior to the addition of the polymer to the solution that contains the protein.

In some embodiments, the reaction occurs under aqueous conditions between about pH 5 to about pH 9. In some embodiments, the reaction occurs between 6.0 and 8.5, between 6.5 and 8.0 or between 7.0 and 7.5.

In some embodiments, the polymer is conjugated to the protein at 2-37 degrees Celsius. In some embodiments, the conjugation occurs at 0-40 degrees Celsius, 5-35 degrees Celsius, 10-30 degrees Celsius, and 15-25 degrees Celsius.

In some embodiments, the conjugated proteins described herein can be contacted to an ion exchange medium or hydrophobic interaction chromatography or affinity chromatography medium for purification (to remove the conjugated from the unconjugated). In some embodiments, the ion exchange medium, hydrophobic interaction chromatography, and/or affinity chromatography medium separates the conjugated protein from the free polymer and from the reoxidized decapped protein.

In some embodiments, the processes described herein and outlined in FIG. 18 involves an excipient that is capable of facilitating and/or maintaining a solubility system. In some embodiments, the process allows the solution to maintain the solubility of the two components meant to interact. This can include the solubility of the protein and the polymer and then the end conjugate as well. In some embodiments, without the excipient approach, the issue can be that while the protein it is soluble, when the biopolymer is added, the solubility of the solution (e.g., protein) drops and and it crashes/precipitates out of solution. Of course, when the protein crashes out, it is not available to conjugate efficiently with the biopolymer. Thus, an excipient can be employed to maintain the solubility of the protein in the presence of the biopolymer so the two can couple to form the protein conjugate (or as depicted in FIG. 18, an antibody conjugate). This also allows for the solubility of the conjugate to be maintained.

In some embodiments, the polymers disclosed herein can comprise one or more of the following: a zwitterion, a phosphorylcholine, or a PEG linker bridging a center of a polymer branching point to the maleimide functional group. In some embodiments, any of the polymers provided herein can be added to a protein via the methods provided herein.

In some embodiments, any of the proteins provided herein can be conjugated to any of the polymers provided herein via one or more of the methods provided herein.

In some embodiments, the process(es) provided herein allow(s) for larger scale processing to make and purify protein and/or antibody conjugates. In some embodiments, the volume employed is at least 1 liter, for example 1, 10, 100, 1,000, 5,000, 10,000, liters or more. In some embodiments, the amount of the antibody conjugate produced and/or purified can be 0.1, 1, 10, 100, 1000, or more grams.

In some embodiments, the therapeutic protein may be any of the anti-VEGF-A antibodies described herein having a cysteine residue added via recombinant DNA technology. In some embodiments, the anti-VEGF antibody heavy chain has the following CDRs: $CDR_H1$: GYDFTHYGMN (SEQ ID NO: 9), $CDR_H2$: WINTYTGEPTYAADFKR (SEQ ID NO: 10), and $CDR_H3$: YPYYYGTSHWYFDV (SEQ ID NO: 11). The heavy chain also has threonine (T) at position 231 (via sequential counting as in SEQ ID NO. 3). In some embodiments, the anti-VEGF light chain has the following CDRs: $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14). The anti-VEGF-A light chain can also have leucine (L) at Kabat position 4.

In some embodiments, the anti-VEGF-A antibody is IgG1. In some embodiments, the heavy chain has one or more mutations to modulate effector function. In some embodiments, the mutations are to one or more of the following amino acid positions (EU numbering): E233, L234, L235, G236, G237, A327, A330, and P331. In some embodiments, the mutations are selected from the group consisting of: E233P, L234V, L234A, L235A, G237A, A327G, A330S and P331S (EU numbering). In some embodiments, the mutations are (EU numbering) L234A, L235A and G237A.

In some embodiments, the cysteine residue added to the therapeutic protein via recombinant DNA technology should not be involved in Cys-Cys disulfide bond pairing. In this regard, therapeutic proteins may be dimeric. So for example, an intact anti-VEGF-A antibody has two light chains and two heavy chains. If a Cys residue is introduced into the heavy chain for instance, the intact antibody will have two such introduced cysteines at identical positions and the possibility exists that these cysteine residues will form intra-chain disulfide bonds. If the introduced cysteine residues form Cys-Cys disulfide bonds or have a propensity to do so, that introduced Cys residue will not be useful for conjugation. It is know in the art how to avoid positions in the heavy and light chains that will give rise to intra-chain disulfide pairing. See, e.g., U.S. Patent Application No. 2015/0158952.

In some embodiments, the cysteine residue introduced via recombinant DNA technology is selected from the group consisting of (EU numbering) Q347C and L443C. In some embodiments, the cysteine residue is L443C (EU numbering, or 449C in SEQ ID NO: 1). In some embodiments, the heavy chain the antibody has the amino acid sequence set forth in SEQ ID NO. 1 and the light chain has the amino acid sequence of SEQ ID NO. 2.

In some embodiments, the sulfhydral specific reacting group is maleimide.

In some embodiments, the half-life extending moiety is selected from the group consisting of polyethylene glycol (PEG), branched PEG, PolyPEG® (Warwick Effect Polymers; Coventry, UK), polysialic acid (PSA), starch, hydroxylethyl starch (HES), hydroxyalkyl starch (HAS), carbohydrate, polysaccharides, pullulane, chitosan, hyaluronic acid, chondroitin sulfate, dermatan sulfate, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polycarboxylate, polyvinylpyrrolidone, polyphosphazene, polyoxazoline, polyethylene-co-maleic acid anyhydride, polystyrene-co-maleic acid anhydride, poly(l-hydroxymethyethylene hydroxymethylformal) (PHF), a zwitterionic polymer, a phosphorylcholine containing polymer and a polymer comprising 2-methacryloyloxy-2'-ethyl-trimethylammoniumphosphate (MPC).

In some embodiments, the half-life extending moiety is a zwitterionic polymer. S In some embodiments, the zwitterion is phosphorylcholine, i.e. a phosphorylcholine containing polymer. In some embodiments, the polymer is composed of MPC units.

In some embodiments, the MPC polymer has three or more arms. In some embodiments, the MPC polymer has 2, 3, 4, 5, 6, 7, 8, 9, 10, 11 or 12 arms. In some embodiments, the MPC polymer has 3, 6, or 9 arms. In some embodiments, the MPC polymer has 9 arms. In some embodiments, the polymer is synthesized with an initiator comprising 2, 3, 4, 5, 6, 7, 8, 9, 10, 11, 12, or more polymer initiation sites In some embodiments, the MPC polymer has a molecular weight between about 300,000 and 1,750,000 Da. In some embodiments, the MPC polymer has a molecular weight between about 500,000 and 1,000,000 Da or between about 600,000 to 900,000 Da.

In some embodiments, the method of preparing a therapeutic protein-half life extending moiety conjugate has an additional step of contacting the therapeutic protein with a thiol reductant under conditions that produce a reduced cysteine sulfhydryl group. As discussed above, it is preferable that the cysteine residue added via recombinant DNA technology are unpaired, i.e. are not involved in Cys-Cys intra chain disulfide bonds or are not substantially involved in such bonding. However, Cys residues which are not involved in such Cys-Cys disulfide bonding and are free for conjugation are known to react with with free cysteine in the culture media to form disulfide adducts. See, e.g., WO 2009/052249. A cysteine so derivatized will not be available for conjugation. To free the newly added cysteine from the disulfide adduct, the protein after purification is treated with a reducing agent, e.g., dithiothreitol. However, such treatment with a reducing agent will reduce all of the cysteine residues in the therapeutic protein, including native cysteines many of which are involved in inter and intra chain Cys-Cys disulfides bonds. The native Cys-Cys disulfides are generally crucial to protein stability and activity and they should be reformed. In some embodiments, all native (e.g., inter and intra) Cys-Cys disulfides are reformed.

To reform native inter and intra-chain disulfide residues, after reduction to remove the cysteine disulfide adducts, the therapeutic protein is exposed to oxidizing conditions and/or oxidizing agents for a prescribed period of time, e.g., overnight. In some embodiments, ambient air exposure overnight can be used to achieve reformation of the native disulfide bonds. In some embodiments, an oxidizing agent is employed to restore the native disulfides. In some embodiments, the oxidizing agent is selected from the group consisting of acqueous CuSO4 and dehydroascorbic acid (DHAA). In some embodiments, the oxidizing agent is DHAA. In some embodiments, the range of DHAA used is in the range of 5-30 equivalents. In some embodiments, the range is 10-20 equivalents. In some embodiments, the range is 15 equivalents.

In some embodiments, the thiol reductant is selected from the group consisting of: Tris[2-carboxyehtyl]phosphine hydrochloride (TCEP), dithiothreitol (DTT), dithioerythritol (DTE), sodium borohydride (NaBH$_4$), sodium cyanoborohydride (NaCNBH3), β-mercaptoethanol (BME), cysteine hydrochloride and cysteine. In some embodiments, the thiol reductant is TCEP.

In some embodiments, the thiol reductant concentration is between 1 and 100 fold molar excess relative to the therapeutic protein concentration. In some embodiments, the thiol reductant concentration is between 20 to 50 fold molar excess relative to the therapeutic protein concentration. In some embodiments, the thiol reductant is removed following incubation with the therapeutic protein prior to oxidation of the therapeutic protein.

In some embodiments, the method for conjugating a therapeutic protein to a half-life extending moiety has a further step of purifying the therapeutic protein conjugate after conjugation. In some embodiments, the therapeutic protein conjugate is purified using a technique selected from the group consisting of ion exchange chromatography, hydrophobic interaction chromatography, size exclusion chromatography, and affinity chromatography or combinations thereof.

In some embodiments, the therapeutic protein conjugate retains at least 20% biological activity relative to unconjugated therapeutic protein. In some embodiments, the therapeutic protein conjugate retains at least 50% biological activity relative to unconjugated therapeutic protein. In some embodiments, the therapeutic protein conjugate retains at least 90% biological activity relative to native therapeutic protein.

In some embodiments, the therapeutic protein conjugate has an increased half-life relative to unconjugated therapeutic protein. In some embodiments, the therapeutic protein conjugate has at least a 1.5 fold increase in half-life relative to unconjugated therapeutic protein. In some embodiments, the therapeutic protein conjugate has at least a 5 fold increase in half-life relative to unconjugated therapeutic protein.

In some embodiments, the zwitterionic polymer of the method of conjugating a therapeutic protein to a half-life extending moiety is a radically polymerizable monomer having a zwitterionc group and the method has a further step of polymerizing the free radically polymerizable zwitterionic monomer in a polymerization medium to provide a polymer, the medium comprising: the radically polymerizable zwitterionic monomer; a transition metal catalyst $M_t^{(q-1)+}$ wherein $M_t$ is a transition metal, q is a higher oxidation state of the metal and q−1 is a lower oxidation state of the metal, wherein the metal catalyst is supplied as a salt of the form $Mt^{(q-1)+}X'_{(q-1)}$ wherein X' is a counterion or group or the transition metal catalyst is supplied in situ by providing the inactive metal salt at its higher oxidation state $M_t^{q+}X'_q$ together with a reducing agent that is capable of reducing the transition metal from the oxidized inactive state to the reduced active state; a ligand; and an initiator.

To function as an ATRP transition metal catalyst, the transition metal should have at least two readily accessible oxidation states separated by one electron, a higher oxidation state and a lower oxidation state. In ATRP, a reversible redox reaction results in the transition metal catalyst cycling between the higher oxidation state and the lower oxidation state while the polymer chains cycle between having propagating chain ends and dormant chain ends. See, e.g., U.S. Pat. No. 7,893,173.

In some embodiments, the radically polymerizable zwitterionic monomer is selected from the group consisting of

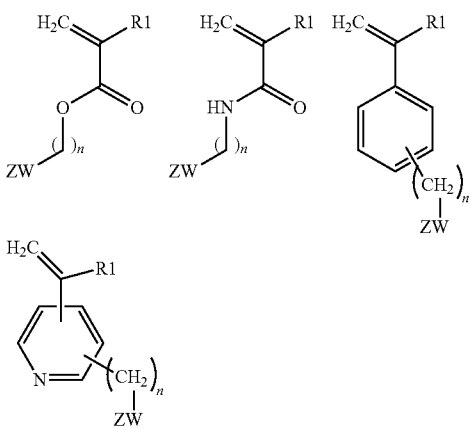

wherein R1 is H or $C_{1-6}$ alkyl, ZW is a zwitterion and n is an integer from 1-6.

In some embodiments, the radically polymerizable monomer is

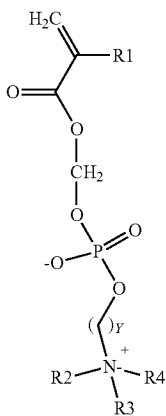

wherein R1 is H or $C_{1-6}$ alkyl, R2, R3, R4 are the same or different and are H or $C_{1-4}$alkyl and X and Y are the same or different and are integers from 1-6. In some embodiments, R1, R2, R3 and R4 are each methyl and X and Y are each 2.

In some embodiments, the radically polymerizable monomer is

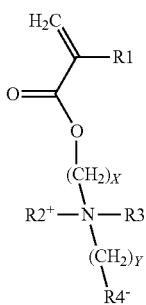

wherein R1 is H or $C_{1-6}$alkyl, R2 and R3 are the same or different and are H or $C_{1-4}$alkyl, R4 is $PO_4-$, $SO_3-$ or $CO_2-$ and X and Y are the same or different and are integers from 1-6. In some embodiments, R1, R2 and R3 are methyl, R4 is $PO_4-$ and X and Y are each 2.

In some embodiments, the monomer is

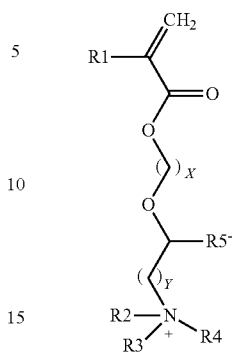

wherein R1 is H or $C_{1-6}$alkyl, R2, R3 and R4 are the same or different and are H or $C_{1-4}$alkyl, R5 is $PO_4-$, $SO_3-$ or $CO_2-$ and X and Y are the same or different and are integers from 1-6. In some embodiments, R1, R2, R3 and R4 are methyl, R5 is $PO_4-$ and X and Y are 2.

In some embodiments, the transition metal Mt is selected from the group consisting of Cu, Fe, Ru, Cr, Mo, W, Mn, Rh, Re, Co, V, Zn, Au, and Ag. In some embodiments, the metal catalyst is supplied as a salt of the form $M_t^{(q-1)+}X'_{(q-1)}$. $M_t^{(q-1)+}$ is selected from the group consisting of $Cu^{1+}$, $Fe^{2+}$, $Ru^{2+}$, $Cr^{2+}$, $Mo^{2+}$, $W^{2+}$, $Mn^{3+}$, $Rh^{3+}$, $Re^{2+}$, $Co^{+}$, $V^{2+}$, $Zn^{+}$, $Au^{+}$, and $Ag^{+}$ and X' is selected from the group consisting of halogen, $C_{1-6}$ alkoxy, $(SO_4)_{1/2}$, $(PO_4)_{1/3}$, $(R7PO_4)_{1/2}$, $(R^7_2PO_4)$, triflate, hexaluorophosphate, methanesulfonate, arylsulfonate, CN and $R7CO_2$, where R7 is H or a straight or branched $C_{1-6}$ alkyl group which may be substituted from 1 to 5 times with a halogen. In some embodiments, $M_t^{(q-1)+}$ is $Cu^{1+}$ and X' is Br.

In some embodiments, $M_t^{(q-1)+}$ is supplied in situ. In some embodiments, $M_t^{q+}X_q$ is $CuBr_2$. In some embodiments, the reducing agent is an inorganic compound. In some embodiments, the reducing agent is selected from the group consisting of a sulfur compound of a low oxidation level, sodium hydrogen sulfite, an inorganic salt comprising a metal ion, a metal, hydrazine hydrate and derivatives of such compounds. In some embodiments, the reducing agent is a metal. In some embodiments, the reducing agent is $Cu^0$.

In some embodiments, the reducing agent is an organic compound. In some embodiments, the organic compound is selected from the group consisting of alkylthiols, mercaptoethanol, or carbonyl compounds that can be easily enolized, ascorbic acid, acetyl acetonate, camphosulfonic acid, hydroxy acetone, reducing sugars, monosaccharides, glucose, aldehydes, and derivatives of such organic compounds.

In some embodiments, the ligand is selected from the group consisting of 2,2'-bipyridine, 4,4'-Di-5-nonyl-2,2'-bipyridine, 4,4-dinonyl-2,2'-dipyridyl, 4,4',4"-tris(5-nonyl)-2,2':6',2"-terpyridine, N,N,N',N',N"-Pentamethyldiethylenetriamine, 1,1,4,7,10,10-Hexamethyltriethylenetetramine, Tris(2-dimethylaminoethyl)amine, N,N-bis(2-pyridylmethyl)octadecylamine, N,N,N',N'-tetra[(2-pyridal)methyl] ethylenediamine, tris[(2-pyridyl)methyl]amine, tris(2-aminoethyl)amine, tris(2-bis(3-butoxy-3-oxopropyl) aminoethyl)amine, tris(2-bis(3-(2-ethylhexoxy)-3-oxopropyl)aminoethyl)amine and Tris(2-bis(3-dodecoxy-3-oxopropyl)aminoethyl)amine. In some embodiments, the ligand is 2,2'-bipyridine.

In some embodiments the initiator has the structure:

R1-R2(-R3)s wherein R1 is a nucleophilic reactive group, R2 comprises a linker, and R3 comprises a polymer synthesis initiator moiety having the structure

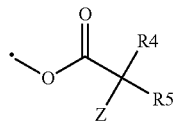

wherein R4 and R5 and are the same or different and are selected from the group consisting of alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof; Z is a halogen or CN; and s is an integer between 1 and 20.

In some embodiments, Z is Br and R4 and R5 are each methyl. In some embodiments, R1 is selected from the group consisting of NH2—, OH—, and SH—.

In some embodiments R2 is alkyl, substituted alkyl, alkylene, alkoxy, carboxyalkyl, haloalkyl, cycloalkyl, cyclic alkyl ether, alkenyl, alkenylene, alkynyl, alkynylene, cycloalkylene, heterocycloalkyl, heterocycloalkylene, aryl, arylene, arylene-oxy, heteroaryl, amino, amido or any combination thereof. In some embodiments, R2 is

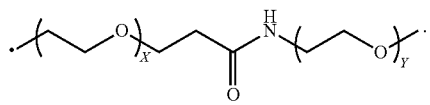

wherein X and Y are the same or different and are integers from 1-20. In some embodiments, X and Y are each 4.

In some embodiments, R3 is

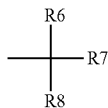

wherein R6, R7 and R8 are the same or different and are selected from the group consisting of

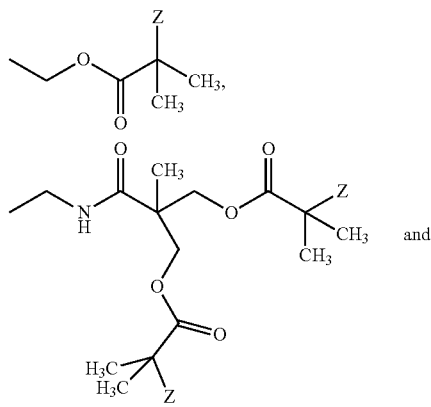

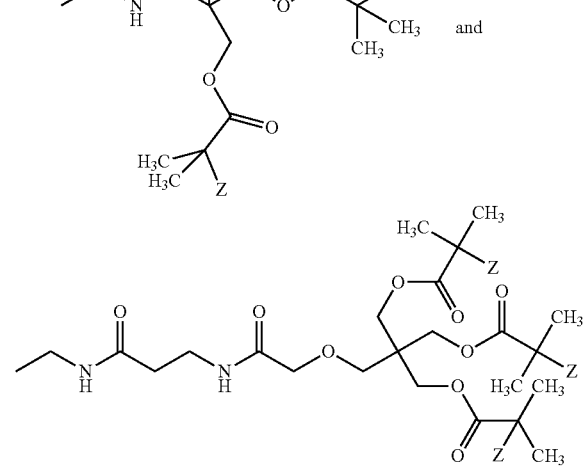

wherein Z is NCS, F, Cl, Br or I. In some embodiments, Z is Br and R6, R7 and R8 are each

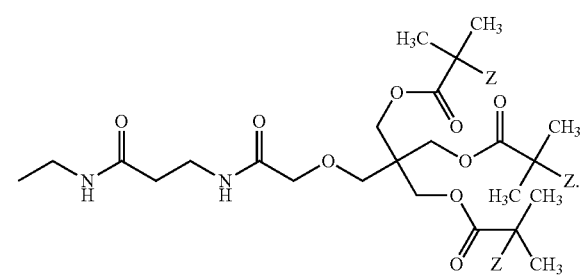

In some embodiments, the initiator has the structure:

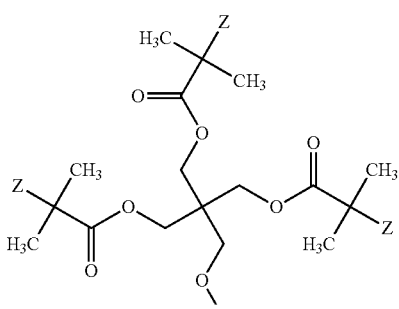

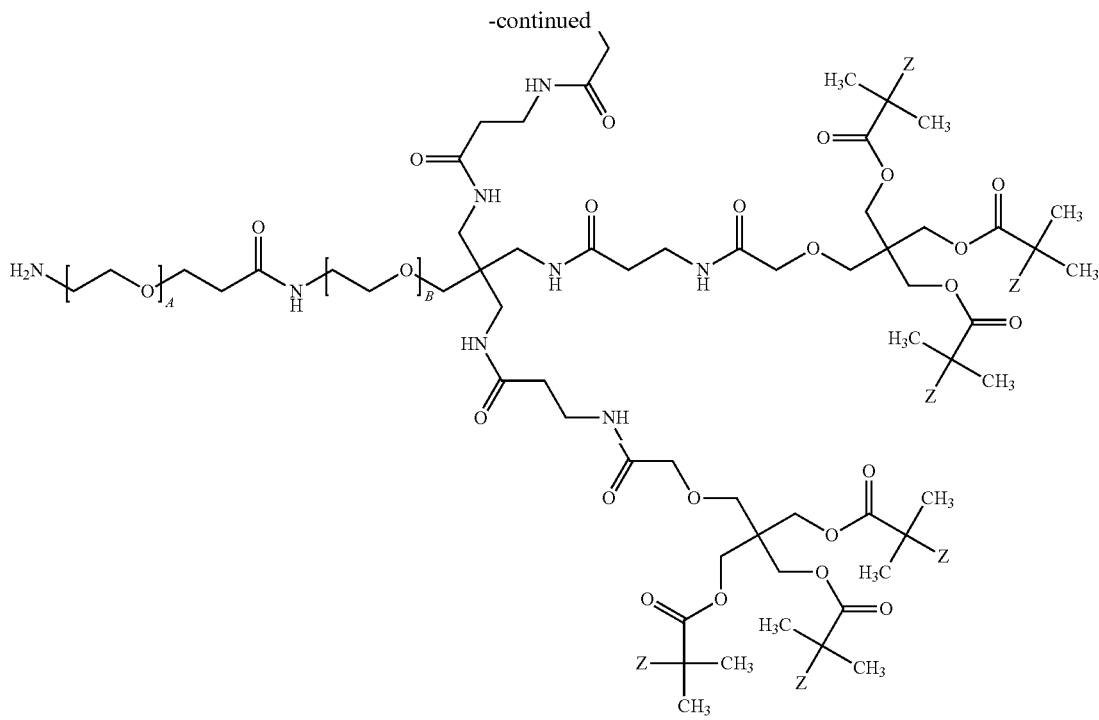

wherein A and B are the same or different and are integers from 2 to 12 and Z is any halide, for example Br. In some embodiments, A and B are each 4.

In some embodiments, the method further has the step of reacting the polymer with a maleimide reagent to provide a polymer having a terminal maleimide. In some embodiments, the maleimide compound is

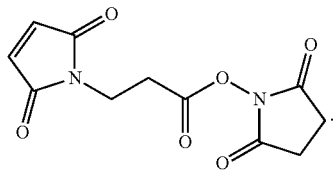 [SMILES: O=C(CCN1C(=O)C=CC1=O)ON1C(=O)CCC1=O]

Method of Treatment

In some embodiments, a method is presented for the treatment or prophylaxis of an ocular disease having the step of administering a therapeutic protein selected from the group consisting of an anti-VEGF-A antibody (and conjugates thereof). In some embodiments, any one or more of the antibodies or antibody conjugates provided herein can be used as treatment and/or prophylaxis for an ocular disease. The method includes administering to the subject any one or more of the antibodies or antibody conjugates provided herein.

In some embodiments a method for treatment or prophylaxis of an ocular disease is provided. The method comprises administering an effective dose of any of the an antibody and/or antibody conjugates described herein to a subject in need thereof. In some embodiments, the disease can be age-related macular degeneration (AMD) or diabetic macular edema (DME). In some embodiments, the disease can be wet AMD.

In some embodiments, the ocular disease is selected from one or more of the group consisting of diabetic retinopathy, choroidal neovascularization (CNV), age-related macular degeneration (AMD), diabetic macular edema (DME), pathological myopia, von Hippel-Lindau disease, histoplasmosis of the eye, central retinal vein occlusion (CRVO), branched central retinal vein occlusion (BRVO), corneal neovascularization, retinal neovascularization, retinopathy of prematurity (ROP), subconjunctival hemorrhage, and hypertensive retinopathy. In some embodiments, the ocular disease is diabetic retinopathy.

In some embodiments, the antibody or antibody conjugate is administered no more frequently than once a month. In some embodiments, the antibody or conjugate thereof is administered two times per month or weekly. In some embodiments, the antibody or conjugate thereof is administered once every two months, once every three months, once every four months, once every five months, once every six months, once every seven months, once every eight months, once every nine months, once every ten months, once every eleven months, or once every twelve months.

In some embodiments, one or more of the compositions provided herein can allow for a reduction in the consequences of high treatment burdens from the use of intravitreal injection of anti-VEGF agents for the treatment of the wet (proliferative) form of age related macular degeneration (AMD). Real world outcomes for patients with wet AMD lag behind the clinical outcomes demonstrated in the phase 3 clinical studies such as the MARINA and ANCHOR studies with Lucentis®(ranibizumab) and the VIEW 1 and VIEW 2 studies with Eylea®(aflibercept). An anti-VEGF therapeutic with a longer ocular residence time such that it can be administered less frequently and therefore with a more patient-tolerable profile can bring real world outcomes closer to phase 3 clinical outcomes for more patients.

In some embodiments, compounds, including antibody conjugates and anti-VEGF-A antibodies described herein are used to treat patients who have background or nonproliferative diabetic retinopathy but have little or no vision impairment. In some embodiments, such patients are dosed less than once a month via intravitreal injection. In some embodiments, such patients are dosed six times a year. In some embodiments, such pateints are dosed no more than four times a year. In some embodiments, the patients are dose no more than three times a year. In some embodiments, the patients are dosed no more than twice a year. In some embodiments, the patients are dosed no more than once a year. In some embodiments, the subject receives the antibody or antibody conjugate via intravitreal injection.

The therapeutic proteins (e.g., both antibodies and antibody conjugates) described herein can be employed by expression of such polypeptides in vivo in a patient, i.e., gene therapy.

There are two major approaches to getting the nucleic acid (optionally contained in a vector) into the patient's cells: in vivo and ex vivo. For in vivo delivery the nucleic acid is injected directly into the patient, usually at the sites where the therapeutic protein is required, i.e., where biological activity of the therapeutic protein is needed. For ex vivo treatment, the patient's cells are removed, the nucleic acid is introduced into these isolated cells, and the modified cells are administered to the patient either directly or, for example, encapsulated within porous membranes that are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or transferred in vivo in the cells of the intended host. Techniques suitable for the transfer of nucleic acid into mammalian cells in vitro include the use of liposomes, electroporation, microinjection, transduction, cell fusion, DEAE-dextran, the calcium phosphate precipitation method, etc. Transduction involves the association of a replication-defective, recombinant viral (including retroviral) particle with a cellular receptor, followed by introduction of the nucleic acids contained by the particle into the cell. A commonly used vector for ex vivo delivery of the gene is a retrovirus.

In some embodiments, the in vivo nucleic acid transfer techniques include transfection with viral or non-viral vectors (such as adenovirus, lentivirus, Herpes simplex I virus, or adeno-associated virus (AAV)) and lipid-based systems (useful lipids for lipid-mediated transfer of the gene are, for example, DOTMA, DOPE, and DC-Chol; see, e.g., Tonkinison et al., Cancer Investigation, 14(1): 54-65 (1996)). In some embodiments the vectors for use in gene therapy are viruses, which include adenoviruses, AAV, lentiviruses, or retroviruses. A viral vector such as a retroviral vector includes at least one transcriptional promoter/enhancer or locus-defining element(s), or other elements that control gene expression by other means such as alternate splicing, nuclear RNA export, or post-translational modification of messenger. In addition, a viral vector such as a retroviral vector includes a nucleic acid molecule that, when transcribed in the presence of a gene encoding the therapeutic protein, is operably linked thereto and acts as a translation initiation sequence. Such vector constructs also include a packaging signal, long terminal repeats (LTRs) or portions thereof, and positive and negative strand primer binding sites appropriate to the virus used (if these are not already present in the viral vector). In addition, such vector typically includes a signal sequence for secretion of the PRO polypeptide from a host cell in which it is placed. In some embodiments, the signal sequence for this purpose is a mammalian signal sequence. In some embodiments, the signal is the native signal sequence for the therapeutic protein. Optionally, the vector construct may also include a signal that directs polyadenylation, as well as one or more restriction sites and a translation termination sequence. By way of example, such vectors will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

In some situations, it is desirable to provide the nucleic acid source with an agent that targets the target cells, such as an antibody specific for a cell-surface membrane protein or the target cell, a ligand for a receptor on the target cell, etc. Where liposomes are employed, proteins that bind to a cell-surface membrane protein associated with endocytosis may be used for targeting and/or to facilitate uptake, e.g., capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., J. Biol. Chem., 262: 4429-4432 (1987); and Wagner et al., Proc. Natl. Acad. Sci. USA, 87: 3410-3414(1990). For a review of the currently known gene marking and gene therapy protocols, see, Anderson et al., Science, 256: 808-813 (1992). See also WO 93/25673 and the references cited therein.

Suitable gene therapy and methods for making retroviral particles and structural proteins can be found in, e.g., U.S. Pat. No. 5,681,746.

In some embodiments, a method for treatment or prophylaxis of an ocular disease in a mammal is presented in which a nucleic acid molecule that encodes a therapeutic protein selected from the group consisting of an anti-VEGF-A antibody is administered. In some embodiments, the nucleic acid is set forth in FIG. 27.

In some embodiments, the heavy chain is that set forth in SEQ ID NO. 1 and the light chain is that set forth in SEQ ID NO. 2. In some embodiments, the nucleic acid molecule is administered via ex vivo gene therapy.

Therapeutic proteins can be incorporated into a pharmaceutical composition with a pharmaceutically acceptable excipient. Pharmaceutical compositions adapted for oral administration may be presented as discrete units such as capsules, as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions can be adapted for nasal administration wherein the excipient is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the excipient is a liquid, for administration as a nasal spray or as nasal drops, include aqueous or oil solutions of the active ingredient. Pharmaceutical compositions adapted for administration by inhalation include fine particle dusts or mists which may be generated by means of various types of metered dose pressurized aerosols, nebulizers or insufflators.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets. Pharmaceutical compositions can be substantially isotonic, implying an osmolality of about 250-400 mOsm/kg water.

The pharmaceutical compositions may contain preserving agents, solubilizing agents, stabilizing agents, wetting agents, emulsifiers, sweeteners, colorants, odorants, salts (substances may themselves be provided in the form of a pharmaceutically acceptable salt), buffers, coating agents or antioxidants. They may also contain therapeutically active agents in addition to the substance. The pharmaceutical compositions may be employed in combination with one or more pharmaceutically acceptable excipients. Such excipients may include, but are not limited to, saline, buffered saline (such as phosphate buffered saline), dextrose, liposomes, water, glycerol, ethanol and combinations thereof.

The antibodies and pharmaceutical compositions containing them may be administered in an effective regime for treating or prophylaxis of a patient's disease including, for instance, administration by oral, intravitreal, intravenous, subcutaneous, intramuscular, intraosseous, intranasal, topical, intraperitoneal, and intralesional administration. Parenteral infusions include intramuscular, intravenous, intraarterial, intraperitoneal, or subcutaneous administration or routes among others. In therapy or as a prophylactic, the active agent may be administered to an individual as an injectable composition, for example as a sterile aqueous dispersion In some embodiments the agent is isotonic or substantially isotonic.

For administration to mammals, and particularly humans, it is expected that the dosage of the active agent is from 0.01 mg/kg body weight, typically around 1 mg/kg. The physician can determine the actual dosage most suitable for an individual which depends on factors including the age, weight, sex and response of the individual, the disease or disorder being treated and the age and condition of the individual being treated. The above dosages are exemplary of the average case. There can, of course, be instances where higher or lower dosages are merited. In some embodiments, the dosage can be 0.5 to 20 mg/eye, e.g., 1, 2, 3, 4, 5, 6, 7, 8, 9, 10, 11, 12, 13, 14, 15, 16, 17, 18, or 19 mg.

This dosage may be repeated as often as appropriate (e.g., weekly, fortnightly, monthly, once every two months, quarterly, twice a year, yearly). If side effects develop the amount and/or frequency of the dosage can be reduced, in accordance with normal clinical practice. In one embodiment, the pharmaceutical composition may be administered once every one to thirty days. In one embodiment, the pharmaceutical composition may be administered twice every thirty days. In one embodiment, the pharmaceutical composition may be administered once a week.

The antibodies and pharmaceutical compositions can be employed alone or in conjunction with other compounds, such as therapeutic compounds or molecules, e.g. anti-inflammatory drugs, analgesics or antibiotics. Such administration with other compounds may be simultaneous, separate or sequential. The components may be prepared in the form of a kit which may comprise instructions as appropriate.

The antibodies and pharmaceutical compositions disclosed herein can be used for treatment or prophylaxis of disease, particularly the ocular diseases or conditions described herein.

So used, the conjugates are typically formulated for and administered by ocular, intraocular, and/or intravitreal injection, and/or juxtascleral injection, and/or subretinal injection and/or subtenon injection, and/or superchoroidal injection and/or subconjunctival and/or topical administration in the form of eye drops and/or ointment. Such antibodies and compositions can be delivered by a variety of methods, e.g. intravitreally as a device and/or a depot that allows for slow release of the compound into the vitreous, including those described in references such as Intraocular Drug Delivery, Jaffe, Ashton, and Pearson, editors, Taylor & Francis (March 2006). In one example, a device may be in the form of a minipump and/or a matrix and/or a passive diffusion system and/or encapsulated cells that release the compound for a prolonged period of time (Intraocular Drug Delivery, Jaffe, Ashton, and Pearson, editors, Taylor & Francis (March 2006).

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMD and CNV, is direct intravitreal injection. Intravitrial injections are usually repeated at intervals which depend on the patient's condition, and the properties and half-life of the drug delivered.

Therapeutic antibodies and related conjugates generally are placed into a container having a sterile access port, for example, an intravenous solution bag or vial having a stopper pierceable by a hypodermic injection needle. Such compositions may also be supplied in the form of pre-filled syringes.

A "stable" formulation is one in which the protein or protein conjugated to a polymer of other half-life extending moiety therein essentially retains its physical stability and/or chemical stability and/or biological activity upon storage. By "stable" is also meant a formulation which exhibits little or no signs of instability, including aggregation and/or deamidation. For example, the formulations provided may remain stable for at least two year, when stored as indicated at a temperature of 5-8° C.

Various analytical techniques for measuring protein stability are available in the art and are reviewed in Peptide and Protein Drug Delivery, 247-301 (Vincent Lee ed., New York, N.Y., 1991) and Jones, 1993 Adv. Drug Delivery Rev. 10: 29-90, for examples. Stability can be measured at a selected temperature for a selected time period. In some embodiments the storage of the formulations is stable for at least 6 months, 12 months, 12-18 months, or for 2 or more years.

A protein, such as an antibody or fragment thereof, "retains its physical stability" in a pharmaceutical formulation if it shows no signs of aggregation, precipitation, deamidation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity. Chemical stability can be assessed by detecting and quantifying chemically altered forms of the protein. Chemical alteration may involve size modification (e.g., clipping), which can be evaluated using size exclusion chromatography, SDS-PAGE and/or matrix-assisted laser desorption ionization/time-of-flight mass spectrometry (MALDI/TOF MS), for examples. Other types of chemical alteration include charge alteration (e.g., occurring as a result of deamidation), which can be evaluated by ion-exchange chromatography, for example. An antibody "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example.

A protein-polymer conjugate "retains its chemical stability" the chemical bond between the protein and the polymer is maintained intact, e.g., it is not hydrolyzed or otherwise disrupted. The protein part of the conjugate retains its chemical stability as described above.

By "isotonic" is meant that the formulation of interest has essentially the same osmotic pressure as human blood or the vitreous for intravitreal injections. Isotonic formulations will generally have an osmotic pressure from about 250 to 400 mOsm. Isotonicity can be measured using a vapor pressure or ice-freezing type osmometer, for example.

As used herein, "buffer" refers to a buffered solution that resists changes in pH by the action of its acid-base conjugate components. In some embodiments, the buffer has a pH from about 3.0 to about 8.0; for example from about 4.5 to 8; or about pH 6 to about 7.5; or about 6.0 to about 7.0, or about 6.5-7.0, or about pH 7.0 to about 7.5; or about 7.1 to about 7.4. A pH of any point in between the above ranges is also contemplated.

In some embodiments, "PBS" phosphate buffered saline, Tris based buffers and histidine based buffers are used.

In some embodiments, the PBS buffer is made up of at least $Na_2HPO_4$, $KH_2PO_4$ and NaCl adjusted so as to provide the appropriate pH. In some embodiments, the buffer may contain other pharmaceutical excipients such as KCl and other salts, detergents and/or preservatives so as to provide a stable storage solution.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

In some embodiments, formulations, to be safe for human use or for animal testing, should have sufficiently low levels of endotoxin. "Endotoxin" is lipopolysaccharide (LPS) derived from the cell membrane of Gram-negative bacteria. Endotoxin is composed of a hydrophilic polysaccharide moiety covalently linked to a hydrophobic lipid moiety (lipid A). Raetz C R, Ulevitch R J, Wright S D, Sibley C H, Ding A, Nathan C F. 1991. Gram-negative endotoxin: an extraordinary lipid with profound effects on eukaryotic signal transduction. FASEB J. 5(12):2652-2660. Lipid A is responsible for most of the biological activities of endotoxin, i.e., its toxicity. Endotoxins are shed in large amount upon bacterial cell death as well as during growth and division. They are highly heat-stable and are not destroyed under regular sterilizing conditions. Extreme treatments with heat or pH, e.g., 180-250° C. and over 0.1 M of acid or base must be used (Petsch D, Anspach F. 2000. Endotoxin removal from protein solutions. J Biotechnol. 76: 97-119). Such conditions of course would be highly detrimental to biological drugs.

In the biotech and pharmaceutical industries, it is possible to find endotoxin during both production processes and in final products. As bacteria can grow in nutrient poor media, including water, saline and buffers, endotoxins are prevalent unless precautions are taken. Endotoxin injection into an animal or human causes a wide variety of pathophysiological effects, including endotoxin shock, tissue injury and even death. Ogikubo Y, Ogikubo Y, Norimatsu M, Noda K, Takahashi J, Inotsume M, Tsuchiya M, Tamura Y. 2004. Evaluation of the bacterial endotoxin test for quantifications of endotoxin contamination of porcine vaccines. Biologics 32:88-93.

Pyrogenic reactions and shock are induced in mammals upon intravenous injection of endotoxin at low concentrations (1 ng/mL) (Fiske J M, Ross A, VanDerMeid R K, McMichael J C, Arumugham. 2001. Method for reducing endotoxin in *Moraxella catarrhalis* UspA2 protein preparations. J Chrom B. 753:269-278). The maximum level of endotoxin for intravenous applications of pharmaceutical and biologic product is set to 5 endotoxin units (EU) per kg of body weight per hour by all pharmacopoeias (Daneshiam M, Guenther A, Wendel A, Hartung T, Von Aulock S. 2006. In vitro pyrogen test for toxic or immunomodulatory drugs. J Immunol Method 313:169-175). EU is a measurement of the biological activity of an endotoxin. For example, 100 pg of the standard endotoxin EC-5 and 120 pg of endotoxin from *Escherichia coli* 0111:B4 have activity of 1 EU (Hirayama C, Sakata M. 2002. Chromatographic removal of endotoxin from protein solutions by polymer particles. J Chrom B 781:419-432). Meeting this threshold level has always been a challenge in biological research and pharmaceutical industry (Berthold W, Walter J. 1994. Protein Purification: Aspects of Processes for Pharmaceutical Products. Biologicals 22:135-150; Petsch D, Anspach F B. 2000. Endotoxin removal from protein solutions. J Biotech 76:97-119).

The presence of endotoxin in drugs to be delivered via intravitreal injection is of particular concern. Intravitreal injection of drug (penicillin) was first performed in 1945 by Rycroft. Rycroft B W. 1945. Penicillin and the control of deep intra-ocular infection. British J Ophthalmol 29 (2): 57-87. The vitreous is a chamber where high level of drug can be introduced and maintained for relatively long periods of time. The concentration of drug that can be achieved via intravitreal injection far exceeds what can be generated by topical administration or by systemic administration (e.g. intravenous).

One of the most dangerous complications potentially arising from intravitreal injections is endophthalmitis. Endophthalmitis falls into two classes: infectious and sterile.

Infectious endophthalmitis is generally cause by bacteria, fungi or parasites. The symptoms of infectious endophthalmitis include severe pain, loss of vision, and redness of the conjunctiva and the underlying episclera. Infectious endophthalmitis requires urgent diagnosis and treatment. Possible treatments include intravitreal injection of antibiotics and pars plana vitrectomy in some cases. Enucleation may be called for to remove a blind and painful eye. See, e.g., Christy N E, Sommer A. 1979. Antibiotic prophylaxis of postoperative endophthalmitis. Ann Ophthalmol 11 (8): 1261-1265.

Sterile endophthalmitis in contrast does not involve an infectious agent and can be defined as the acute intraocular inflammation of the vitreous cavity that resolves without the need of intravitreal antibiotics and/or vitreoretinal surgery. If a vitreous microbiological study has been done, it needs to be negative culture proven to sustain a diagnosis of sterile endophthalmitis. Marticorena J, Romano V, Gomez-Ulla F. 2012 "Sterile Endophthalmitis after Intravitreal Injections" Med Inflam. 928123.

It has been observed that intravitreal injection of biological drugs contaminated with endotoxin can result in sterile endophthalmitis. Marticorena, et al. Bevacizumab (Avastin) is approved by the Food and Drug Administration for the treatment of glioblastoma and of metastatic colorectal cancer, advanced nonsquamous non-small-cell lung cancer and metastatic kidney cancer. Bevacizumab is also widely used off label as a treatment for wet AMD. Bevacizumab comes from the manufacturer as a 100 mg/4 ml. This solution cannot be directly used for intravitreal injection and should be compounded by a pharmacist. Clusters of sterile endophthalmitis have been observed and are theorized to be cause by inadvertent contamination of bevacizumab by endotoxin by the compounding pharmacist.

Given the dire clinical results of intravitreal injection of endotoxin, the total amount of endotoxin that can be given to a patient via intravitreal dosing is highly limited. In some embodiments, a solution having an antibody or antibody-conjugate is provided having an endotoxin level that does not exceed 5.0 EU/ml. In some embodiments, the endotoxin level does not exceed 1.0 EU/ml. In some embodiments, the endotoxin level does not exceed 0.5 EU/ml. In some embodiments, the endotoxin level does not exceed 0.2 EU/ml. In some embodiments, the endotoxin level does not exceed 2, 1, 0.5, 0.2, 0.1, 0.09, 0.08, 0.07, 0.06, 0.05, 0.04, 0.03, 0.02 or 0.01 EU/ml.

Two commonly used FDA-approved tests for the presence of endotoxin are the rabbit pyrogen test and Limulus Amoebodyte Lysate (LAL) assay (Hoffman S, et al. 2005. International validation of novel pyrogen tests based on human monocytoid cells J. Immunol. Methods 298:161-173; Ding J L, Ho B A. 2001. New era in pyrogen testing. Biotech. 19:277-281). The rabbit pyrogen test was developed in the 1920s and involves monitoring the temperature rise in a rabbit injected with a test solution. However, use of the rabbit pyrogen test has greatly diminished over the years due to expense and long turnaround time. Much more common is the LAL test. LAL is derived from the blood of a horseshoe crab and clots upon exposure to endotoxin.

One of the simplest LAL assays is the LAL gel-clot assay. Essentially, the LAL clotting assay is combined with a serial dilution of the sample in question. Formation of the gel is proportional to the amount of endotoxin in the sample. Serial dilutions are prepared from the sample and each dilution assayed for its ability to form LAL gel. At some point a negative reaction is contained. The amount of endotoxin in the original sample can be estimated from the dilution assay.

Other LAL tests have also been developed, including the turbidimetric LAL assay (Ong K G, Lelan J M, Zeng K F, Barrett G, Aourob M, Grimes C A. 2006. A rapid highly-sensitive endotoxin detection system. Biosensors and Bioelectronics 21:2270-2274) and the chromogenic LAL assay (Haishima Y, Hasegawa C, Yagami T, Tsuchiya T, Matsuda R, Hayashi Y. 2003. Estimation of uncertainty in kinetic-colorimetric assay of bacterial endotoxins. J Pharm Biomed Analysis. 32:495-503). The turbidimetric and chromogenic assays are much more sensitive and quantitative than the simple gel-clot dilution assay.

In some embodiments a method of reducing the amount of endotoxin in a composition having an antibody disclosed herein is provided. The method having the steps of contacting the composition with an affinity chromatography resin that binds to the antibody; eluting the antibody from the affinity chromatography resin to form an affinity chromatography eluent having the antagonist; contacting the affinity chromatography eluent with an ion-exchange resin that binds the antibody; and eluting the antibody from the ion-exchange resin, wherein the antibody eluted from the ion-exchange resin is substantially free from endotoxin.

The above method for reducing the amount of endotoxin, or other method or process recited herein, can be performed in the order described in the steps above or it can optionally be performed by varying the order of the steps or even repeating one or more of the steps. In one embodiment, the method of reducing the amount of endotoxin in a composition is performed in the order of the described steps. In some embodiments, the affinity chromatography resin contacting, washing and eluting steps are repeated in the same order more than one time before contacting the affinity chromatography eluent with the ion exchange resin. The method can also include a filtering step using, for example, a 0.1 micron, 0.22 micron, or 0.44 micron filter, that can be performed on either one or more of the eluents removed after each resin binding step.

In certain instances, the steps of contacting the composition with affinity chromatography resin, washing and eluting the antibody from the affinity chromatography resin can be repeated more than one time before contacting the first eluent with an ion-exchange resin. In one embodiment, the affinity chromatography resin comprises a recombinant Protein A ("rProteinA") resin. One example of a suitable recombinant Protein A resin is rProteinA Sepharose FF® resin (Amersham, Piscataway, N.J.). In another embodiment, a suitable affinity chromatography resin would comprise a protein G chromatography resin. In other embodiments, a suitable affinity chromatography resin comprises a mixed Protein A/Protein G resin. In other embodiments, a suitable affinity chromatography resin comprises a hydrophobic charge induction resin that comprises a 4-mercaptoethylpyridine ligand such as a MEP HyperCel® resin (BioSepra, Cergy, Saint Christophe, France).

In some embodiments, the ion exchange resin comprises an anion-exchange resin. As will be known by the person skilled in the art, ion exchangers may be based on various materials with respect to the matrix as well as to the attached charged groups. For example, the following matrices may be used, in which the materials mentioned may be more or less cross-linked: MacroCap Q (GE Healthcare Biosciences, Piscataway, N.J.), agarose based (such as Sepharose CL-6B®, Sepharose Fast Flow® and Sepharose High Performance®), cellulose based (such as DEAE Sephacel®), dextran based (such as Sephadex®), silica based and synthetic polymer based. For the anion exchange resin, the charged groups, which are covalently attached to the matrix, may, for example, be diethylaminoethyl, quaternary aminoethyl, and/or quaternary ammonium. In some embodiments the anion-exchange resin comprises a quaternary amine group. An exemplarily anion-exchange resin that has a quaternary amine group for binding the anti-M-CSF antibody is a Q Sepharose® resin (Amersham, Piscataway, N.J.).

In other aspects, if the endotoxin levels are higher than desired after subjecting the composition to the aforementioned anion-exchange chromatography step, the composition may in the alternative be subjected to a cation exchange resin. In some embodiments, any endotoxin in the composition should have a differential binding to the ion-exchange resin than the protein in question to allow purification of the protein from the endotoxin. In this regard, endotoxin is negatively charged and will generally bind to an anion exchange resin. If both the protein and the endotoxin bind to the anion exchange resin, purification of one from the other may be effectuated by using a salt gradient to elute the two into different fractions. The relative binding of the protein to a particular resin may also be effected by changing the pH of the buffer relative to the pI of the protein. In some embodiments, cation-exchange chromatography is the sole ion-exchange chromatography employed.

In some embodiments, if the endotoxin levels are too high after the anion exchange resin, the composition may be further subjected to a second ion-exchange step, for example, by contacting the compositions with a cation exchange resin and followed by a wash step, then elution from the ion-exchange resin. In some embodiments, the cation exchange resin comprises a sulfonic group for binding. Exemplary cation exchange resins are SP Sepharose® resin FF (Amersham, Piscataway, N.J.) Poros XS (CEX) (Life Technology, Grand Island, N.Y.).

In some embodiments, after the solution of antibody protein is produced having the specified level of endotoxin, there are a number of steps prior to final formulation of the protein. In some embodiments, a half-life extending moiety is conjugated to the protein. The conjugate is then formulated into a final drug formulation which is injected into the patients. In some embodiments, the conjugate is again purified on an ion-exchange resin which can be a cation-exchange resin. In other embodiments, the protein is formulated. In all cases, normal laboratory procedures should be employed to prevent the introduction of endotoxin contaminants into the protein sample or into the protein-polymer conjugate.

EXAMPLES

Example 1

Route 1 Synthesis of OG1802

A first route for the synthesis of OG1802 is as follows. First, TFA/amine salt initiator (Compound L) having the structure shown in FIG. 1 was synthesized as follows.

Figure 2:
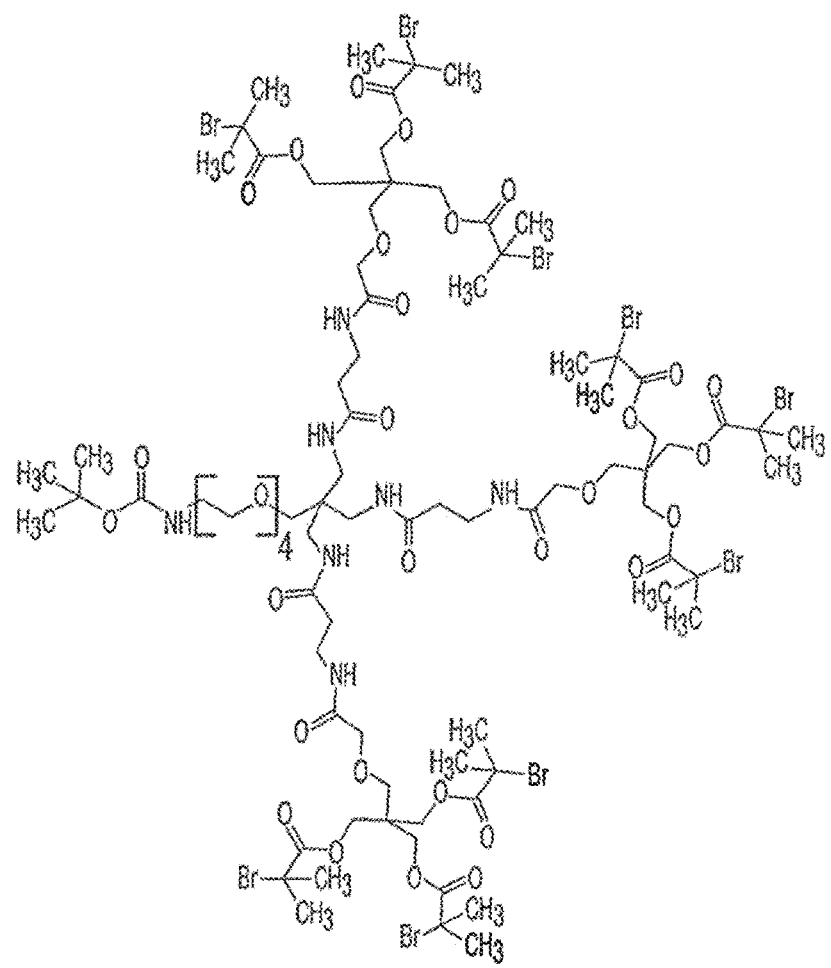
FIG. 2 shows Compound K.
Figure 4:
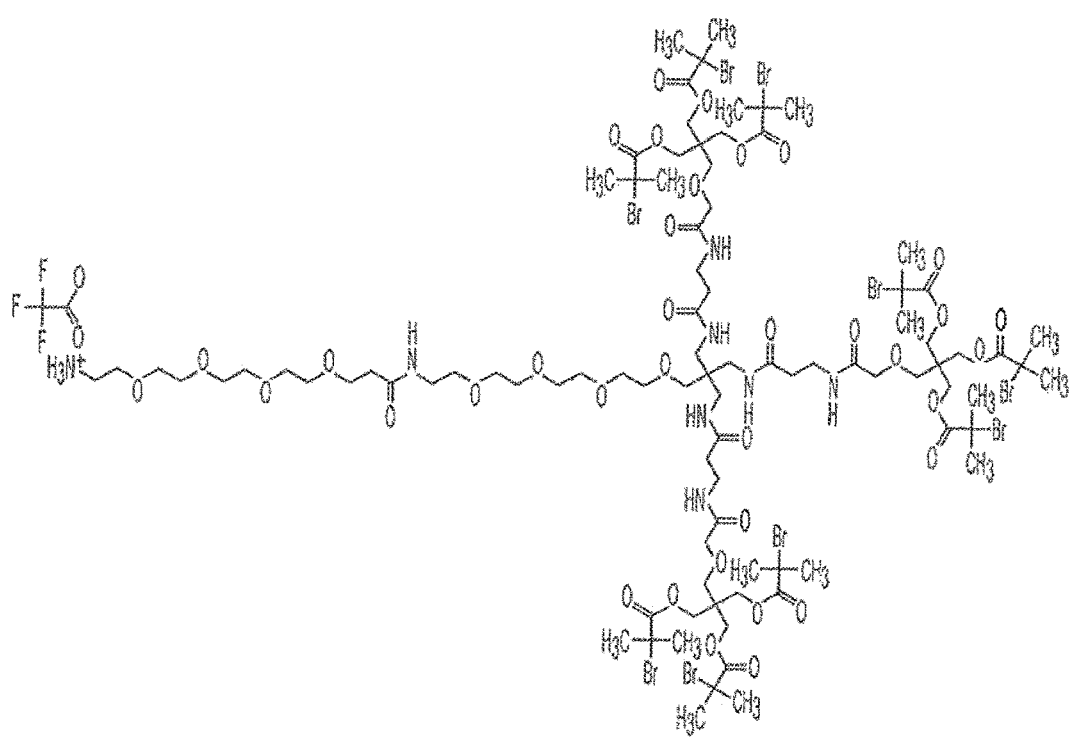
FIG. 4 shows OG1786.
Figure 5:
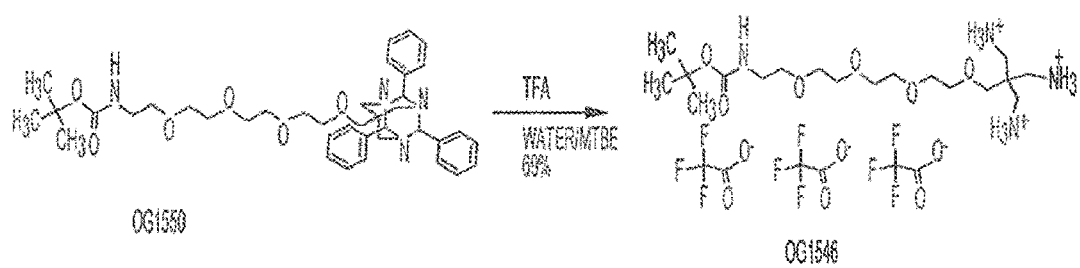
FIG. 5 shows the synthesis of OG1546 from OG1550.
Figure 6:
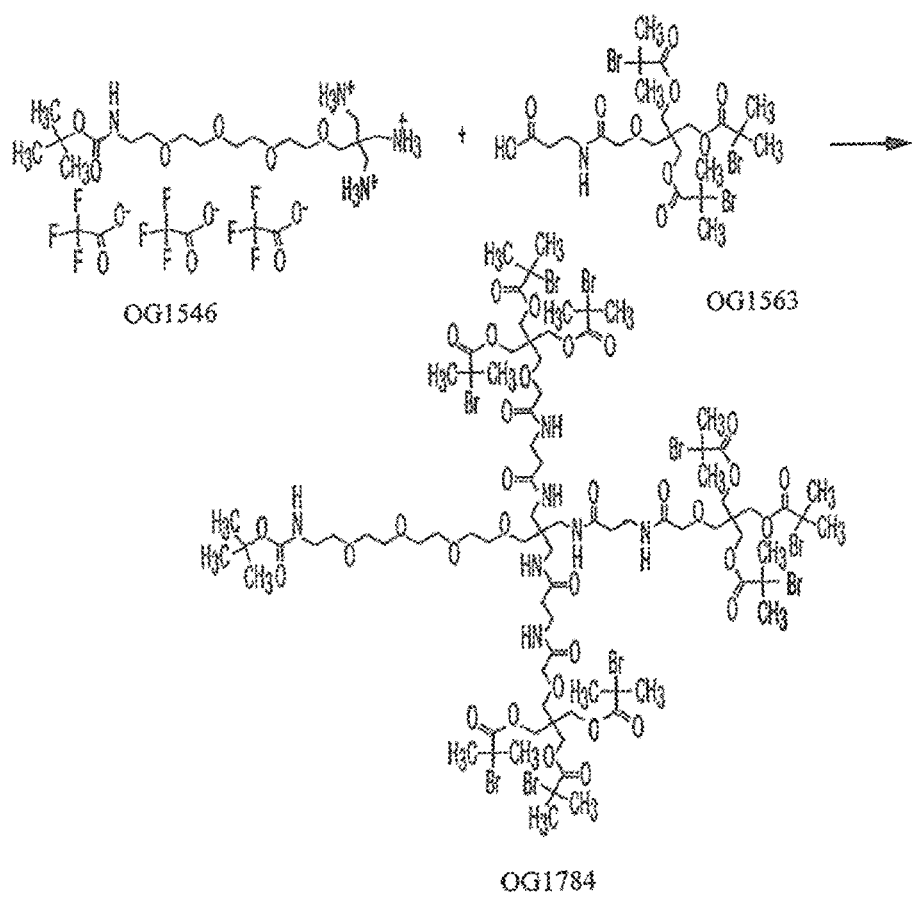
FIG. 6 shows the synthesis of OG1784 from OG1546 and OG1563.
Figure 8:
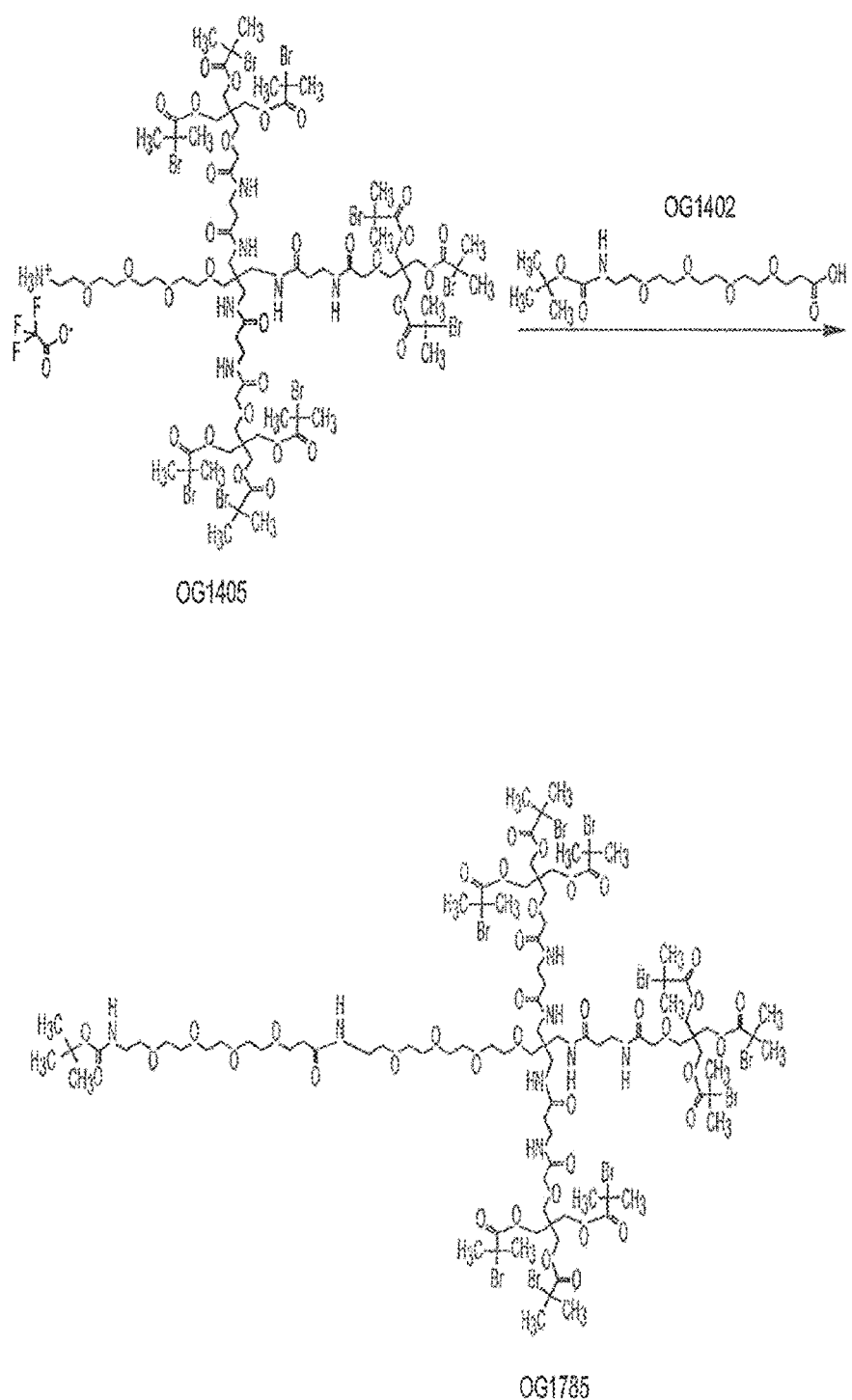
FIG. 8 shows the synthesis of OG1785 from OG1405.
Figure 9:
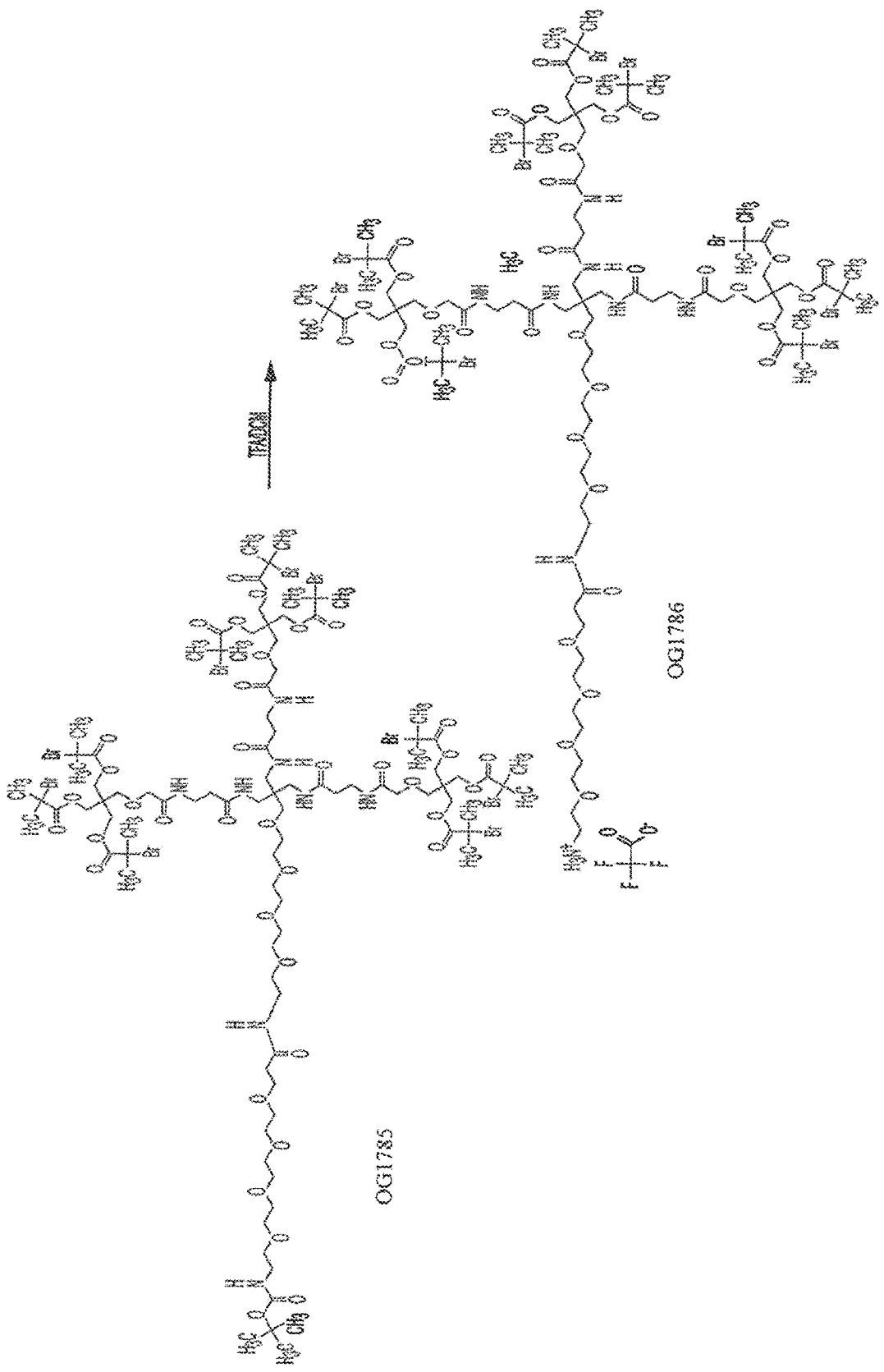
FIG. 9 shows the synthesis of OG1786 from OG1785.
Figure 10:
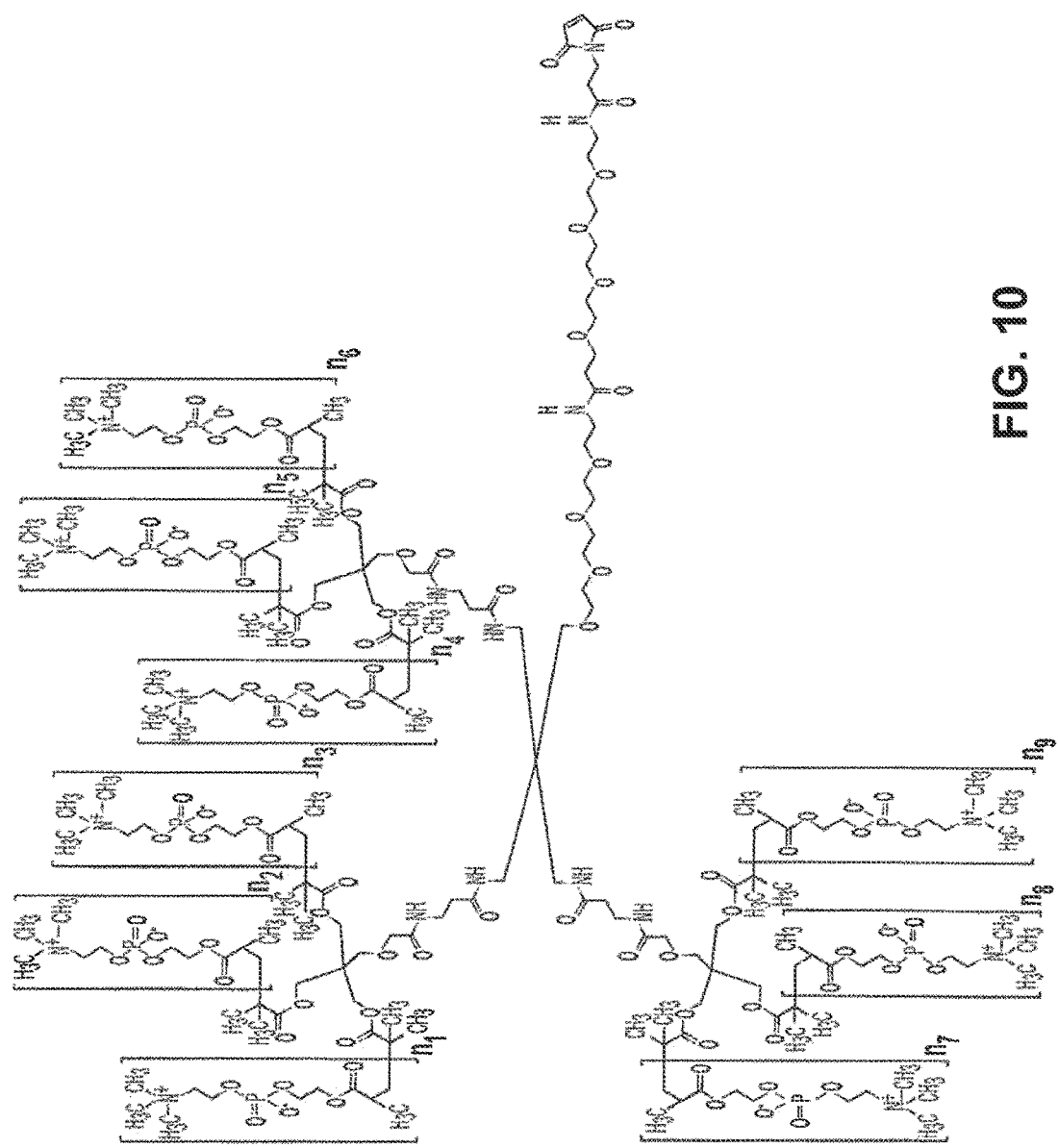
FIG. 10 shows OG1802.

First, Compound K, having the structure shown in FIG. 2 was synthesized as follows. Into a 200 mL round bottom flask under nitrogen was placed Compound J (OG1563) (1.9 g, 2.67 mmol, 3.3 equiv)

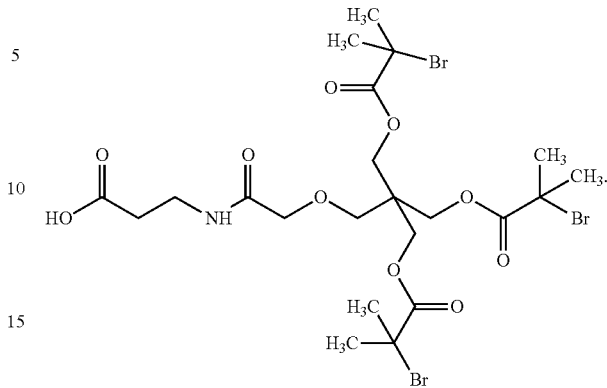

Figure 11:
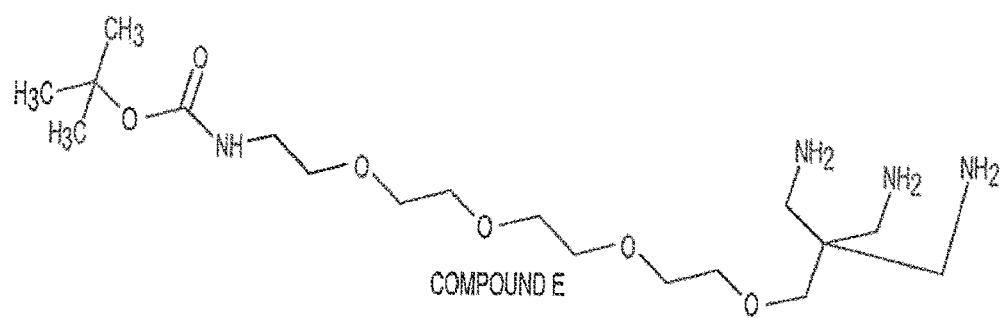
FIG. 11 shows Compound E.

COMPOUND J and Compound E (0.525 g, 0.81 mmol, 1.0 equiv) (see FIG. 11) followed by dimethylformamide (10 mL) then diisopropylethylamine (2.5 mL, 14.6 mmol, 18 equiv). The flask was cooled to 0° C. using an ice bath. To this was added propylphosphonic anhydride solution (50 wt. % in ethyl acetate, 2.5 mL, 4.04 mmol, 5 equiv) over ~6 minutes.

The reaction was warmed to room temperature and stirred for 15 minutes. The reaction was quenched by adding water (20 mL), saturated aqueous sodium bicarbonate (20 mL) and ethyl acetate (100 mL). The organic layer was separated and the aqueous layer extracted with ethyl acetate (75 mL). The combined organic layers were washed with saturated aqueous sodium bicarbonate (30 mL), 0.5 M aqueous citric acid (40 mL), water (25 mL), and saturated aqueous sodium chloride (40 mL), then dried (sodium sulfate), filtered and concentrated under vacuum. The residue which was used without further purification resulted in 2.0 g (0.80 mmol, 99%) of Compound K.

1H NMR (400 MHz DMSO-d6): δ=1.36 (s, 9H, OCCH3), 1.90 (s, 54H, CC(CH3)2Br), 2.31 (t, J=7.2 Hz, 6H, CCH2CH2NH), 2.98 (d, J=5.6 Hz, 6H, CCH2NH), 3.04 (q, J=6.0 Hz, 2H, OCH2CH2NH), 3.18 (s, 2H, OCH2C), 3.3-3.37 (m, 8H, CH2), 3.47-3.55 (m, 12H, CH2), 3.58 (s, 6H, OCH2C), 3.87 (s, 6H, O=CCH2O), 4.27 (s, 18H, CCH2OC=O), 6.74 (br t, 1H, CH2NHC=O), 7.69 (t, J=6.8 Hz, 3H, CH2NHC=O), 7.84 (t, J=6.0 Hz, 3H, CH2NHC=O).

LC-MS (ES, m/z): [(M+2H-boc)/2]+ Calcd for (C84H136Br9N7O33+2H-Boc)/2=1196.6; Found 1196.6.

Next Compound L (FIG. 1) was synthesized as follows: into a 100 mL round bottom under nitrogen was added Compound K (2.0 g, 0.8 mmol), dichloromethane (10 mL) followed by trifluoroacetic acid (5 mL). The reaction was stirred at room temperature for 30 minutes. The reaction was concentrated under a vacuum. The reaction was diluted using dichloromethane (10 mL) and concentrated under a vacuum. The residue was dissolved using acetonitrile (10 mL), filtered through a syringe filter (Acrodisc CR25, PN 4225T) and loaded onto a preparatory HPLC column and eluted with 60% acetonitrile in water (with 0.1% trifluoroacetic acid) up to 98% acetonitrile (with 0.1% trifluoroacetic acid). The tubes containing product were pooled, concentrated under vacuum, frozen and placed on a lyophilizer. This resulted in 990 mgs (0.4 mmol, 50% over 2 steps) Compound L as a white powder.

1H NMR (400 MHz DMSO-d6): δ=1.90 (s, 54H, CC(CH3)2Br), 2.31 (t, J=7.2 Hz, 6H, CCH2CH2NH), 2.97-3.0 (m, 8H, CCH2NH and OCH2CH2NH), 3.17 (s, 2H, O CH2C), 3.3 (q, 6H, CH2CH2NHC=O), 3.4-3.59 (m, 20H, CH2), 3.87 (s, 6H, O=CCH2O), 4.27 (s, 18H, CCH2OC=O), 7.69-7.84 (m, 9H, both CH2NHC=O and NH3+).

LC-MS (ES, m/z): [(M+2H)/2]+ Calcd for (C84H136Br9N7O33+2H)/2=1196.6; Found 1197.4.

Next, compound L was used as an initiator to synthesize MPC polymer. Initiator is typically prepared as a stock solution in DMF of about 100 mg/mL. The initiator and the ligand (2,2'-bipyridyl) were introduced into a Schlenk tube. The resultant solution was cooled to −78° C. using a dry ice/acetone mixture, and was degassed under vacuum for 10 min. The tube was refilled under Argon and the catalyst (CuBr unless otherwise indicated), kept under Argon, was introduced into the Schlenck tube (the Molar ratio of atom bromine on the initiator/catalyst (CuBr)/ligand was kept at 1/1/2). The solution became dark brown immediately. The Schlenk tube was sealed and immediately purged by applying a short cycle vacuum/Argon. A solution of HEMA-PC was prepared by mixing a defined quantity of monomer, prepared in a glovebox kept under nitrogen, with 200 proof degassed ethanol. The monomer solution was added drop wise into the Schlenk tube (via cannula) (and homogenized by light stirring). The temperature was maintained at −78° C. A thorough vacuum was applied to the reaction mixture for at least 10 to 15 min. until bubbling from the solution ceased. The tube was then refilled with Argon and warmed to room temperature. The solution was stirred, and as the polymerization proceeded, the solution became viscous. After 3 to 8 hours or just left overnight, the reaction was quenched by direct exposure to air in order to oxidize Cu (I) to Cu (II), the mixture became blue-green in color, and was passed through a silica column in order to remove the copper catalyst. The collected solution was concentrated by rotary evaporation and the resulting mixture was either precipitated with tetrahydrofuran or dialyzed against water followed by freeze drying to yield a free-flowing white powder. Table 1.1 below sets forth polymer data for polymer employing compound L as an initiator.

TABLE 1.1

| Theor. MW (kDa) | Polymer ID No. | Initiator | Mn(kDa) | Mp(kDa) | PDI |
|---|---|---|---|---|---|
| 500 | 130 | L | 490 | 530 | 1.1 |
| 750 | 150 | L | 645 | 750 | 1.1 |

Next, the maleimide Mal-PEG4-PFP ester was snapped on (as set forth in FIG. 29) to the 750 kDa polymer referred to above to provide OG1802. Into a 20 mL vial was placed Polymer R3707 (750 kDa polymer made using L as initiator, 515 mg) and dissolved using ethanol (4.0 mL) after stirring for 40 minutes. To this was added a 1% solution of 4-methylmorpholine in acetonitrile (22 uL). In a separate vial was dissolved Mal-PEG4-PFP (1.97 mg) in acetonitrile (1.0 mL) and this solution was added to the polymer solution over ~2 minute at room temperature and the resulting solution was stirred for overnight. The reaction was diluted with 0.1% aqueous trifluoroacetic acid (2 mL) (pH~5) followed by water (~12 mL), filtered through a syringe filter (Acrodisc Supor, PN 4612) and placed evenly into 3 Amicon centrifuge membrane dialysis tubes (30,000 mwco). The tubes were diluted and mixed with water (~5 mL each), placed into centrifuge (rpm 3200) for 25 minutes. The filtrate is removed for analysis while the retentate is diluted and mixed with water (~10 mL/tube). The centrifuge procedure repeated 5 more times, after which the retentate is removed and placed into a vial. The Amicon membrane tubes were rinsed with water (2×~2 mL each tube) and this combined with the retentate. The retentate solution was filtered through a syringe filter (Acrodisc Supor, PN 4612), frozen and placed on a lyophilizer. This resulted in 485 mgs as a white powder.

Example 2

Synthesis of Initiator OG1786

OG1786 is the nine-arm initiator for polymer synthesis used as a precursor in the synthesis of OG1802. Each arm is terminated with a 2-bromoisobutyrate which is capable of initiating polymerization under ATRP. OG1786 is a salt of trifluoro acetic acid (TFA) as shown in FIG. 30. OG1786 is prepared as follows. First, OG1550 is reacted with TFA (trifluoro acetic acid) to produce OG1546 as depicted in FIG. 31.

In a 1 L round bottom flask equipped with a magnetic stir bar and an addition funnel was added OG1550 (14.8 g), methyl tert-butyl ether (MTBE) (350 ml) and water (30 ml). The mixture was stirred to dissolve the OG1550, then cooled in an ice bath. To this mixture was added a solution of trifluoroacetic acid (4.9 ml) in water (90 ml) dropwise over 90 minutes. After addition is complete the mixture was stirred an additional 15 minutes then removed from the ice bath and allowed to warm to room temperature. The mixture was stirred (after removal from the ice bath) for a further 4-5 hours, until tlc showed ~5% starting material remaining, and the pH of the aqueous was between 3 and 4 (pH paper).

The mixture was partitioned. The MTBE layer was washed with water (30 ml). Combine aqueous layers then the aqueous extracted with MTBE (150 ml). This second MTBE phase was washed with water (30 ml). The combined aqueous layers were washed with a third portion of MTBE (100 ml). The third MBTE phase was washed with water (25 ml). The aqueous layers were again combined (~250 ml, pH~4, by pH paper).

The product was collected by lyophilization. 11.5 g white solid was obtained. This material is extremely hygroscopic, so best handled under nitrogen. The product was confirmed by LCMS.

The prepared OG1546 was then reacted with OG1563 to yield OG1784 (as depicted in FIG. 32).

In a 250 ml flask under nitrogen equipped with a stir bar was added OG1546 (hygroscopic, 9.0 g), followed by N,N-dimethylformamide (110 ml). The mixture was stirred at room temperature until all OG1546 dissolved (about 15 minutes), then OG1563 (29.9 g) was added, and the mixture stirred a further 3 minutes until the OG1563 had also been dissolved. The resulting solution was cooled in an ice bath, and N,N-diisopropylethylamine (37.6 ml) was added over 3 minutes, followed by propylphosphonic anhydride (T3P), 50% in ethyl acetate (34.5 ml) dropwise over 5 minutes (T3P addition is exothermic). After T3P addition was complete, the flask was removed from the cooling bath and allowed to reach room temperature. Samples were then taken at 5 minute intervals for LCMS analysis. The reaction showed very light yellow/tan color.

After 20 minutes the reaction was cooled again in an ice bath and 5 ml water added. The mixture was then removed from the cooling bath and a further 50 ml water portion added, followed by 50 ml 0.5 M citric acid then isopropylacetate (300 ml). The mixture was partitioned. The aqueous phase (~300 ml) was extracted with additional isopropyl acetate (150 ml). The aqueous phase was AQ1 for HPLC test. The combined organics were washed with aqueous citric acid (115 ml, 65 mM, which was the mixture of 15 ml of 0.5 M citric acid plus 100 ml water), and the aqueous phase was AQ2 (pH~3). The organic phase was washed with water/saturated sodium chloride (100 ml/25 ml), and the aqueous phase was AQ3 (pH~3). The organic phase was finally washed with saturated sodium chloride (100 ml), and the aqueous phase was AQ4. None of the AQ fractions contained any significant product (data not provided). The organic phase confirmed the product via LCMS. The product was dried over sodium sulfate (80 g), filtered and rinsed with isopropyl acetate (75 ml), and concentrated on a rotary evaporator to a tan oil (33.2 g). The crude was stored overnight under nitrogen.

The next day the crude was allowed to come to room temperature, then dissolved in acetonitrile/water (46 ml/12 ml) and filtered using an HPLC filter disk (Cole-Parmer PTFE 0.2 µm, product number 02915-20). The filtrate was split into three equal portions and purified in three runs.

The filtrate was loaded onto a RediSep Rf Gold C18 column (275 g, SN 69-2203-339, Lot #24126-611Y) equilibrated with 50% acetonitrile/water. The material was eluted at 100 ml/min using the following gradient (solvent A: water, solvent B: acetonitrile). All the relevant fractions were checked by HPLC. The fractions adjudged to be pure enough were pooled (from all three runs) and concentrated (bath temperature kept at about 20° C.) on rotovap, then partitioned between dichloromethane (100 ml) and water (5 ml)/saturated sodium chloride (25 ml). The aqueous was extracted twice more with dichloromethane (2×30 ml). The combined organics were dried over sodium sulfate (35 g), filtered, rinsed with DCM (30 ml), and concentrated. The product and purity were confirmed by LCMS methods. The isolated yield and the purity of the R5172 and R5228 lots are shown in Table 2.1.

TABLE 2.1

| OG1784 lot | R5172 | R5228 |
| --- | --- | --- |
| OG1546 used | 5.3 g | 9.0 g |
| OG1563 used | 17.6 g | 29.9 g |
| Isolated yield | 53% | 58% |
| Purity (a/a 210 nm) | 99.3% | 100.0% |

Next OG1405 was prepared from OG1784 as depicted in FIG. 33. In a 500 ml round bottom flask equipped with a magnetic stir bar was added OG1784 (20.9 g), followed by dichloromethane (50 ml) then trifluoroacetic acid (20 ml). The mixture was stirred at room temperature and HPLC analysis showed complete deprotection in 23 minutes. The mixture was concentrated on a rotary evaporator, redissolved in dichloromethane (25 ml) and re-concentrated, then redissolved in acetonitrile (25 ml) and re-concentrated. The product was confirmed by LCMS. The material from above (OG1405, 34.5 g, assume 21.0 g as quantitative yield) was used as a crude oil in the next step. No purification is needed.

Next, OG1405 was reacted with OG1402 to prepare OG1785 as set forth in FIG. 34. In a 500 ml flask under nitrogen equipped with a stir bar was placed OG1402 (5.5 g), followed by acetonitrile (70 ml), then N,N-diisopropylethylamine (26.3 ml) and T3P solution (see above) (7.9 ml). The solution was stirred at room temperature for 30 minutes, then cooled in an ice water bath and a solution of OG1405 (crude oil from above, 34.5 g) in acetonitrile (70 ml) added. The mixture was warmed to room temperature. After 20 minutes the reaction was cooled in an ice water bath and quenched with water (5 ml). The mixture was then concentrated under vacuum using a rotary evaporator to half volume. Samples were taken for LCMS.

More water (50 ml), followed by 0.5 M citric acid (75 ml) and isopropyl acetate (175 ml) was added. The mixture was partitioned in 5 minutes. The aqueous was extracted with additional isopropyl acetate (50 mL). The combined organics were washed with aqueous citric acid (0.13 M, 30 ml, consist of 10 ml of 0.5 M citric acid and 20 ml water). The organics were then washed with the mixture of saturated sodium chloride (25 ml) and water (25 ml), then finally washed with the saturated sodium chloride (25 ml). They were then dried over sodium sulfate (124 g), filtered and rinsed with isopropyl acetate (30 ml), and concentrated under rotary evaporator to a tan oil (27.3 g). Samples were taken for LCMS analysis.

The oil was dissolved in acetonitrile/water (3:1, 15 ml/5 ml), filtered through an HPLC filter disk (Cole-Parmer PTFE membrane 0.2 µm, product number 02915-20) and split into three equal portions, each of which were individually purified as follows.

Portions were loaded onto Redi-Sep Gold C18 column (275 g, SN-69-2203-339, Lot 241234-611W) equilibrated at 50% solvent B (acetonitrile)/50% solvent A (water). The material was then purified by reverse phase HPLC with a solvent A: water/solvent B: acetonitrile gradient. Appropriate fractions were pooled and partitioned between dichloromethane (150 ml) and water (5 ml)/saturated sodium chloride (25 ml). The aqueous was extracted twice with dichloromethane (2×50 ml). Combined organics were dried over sodium sulfate (60 g), filtered and rinsed with dichloromethane (40 ml) and concentrated. Structure and purity were confirmed by various analytics including LCMS: OG1785 was isolated as a foamy solid (R5329, 19.0 g, 83% yield, 95.1% purity (a/a 210 nm), stored under nitrogen at 4° C.

Next, the tert-butyloxycarbonyl protecting group on OG1785 was removed using trifluoroacetic acid (TFA) to produce OG1786 as depicted in FIG. 35.

Example 3

Synthesis of Polymer OG1801

Polymer OG1801 is made first from the initiator OG1786. OG1801 has an amine functionality, which is more stable (than maleimide) during polymer synthesis. To synthesize polymer OG1801, a modified version of ATRP is used wherein the copper species (Cu(I)) is generated in situ by adding metallic copper to Cu (II). Starting materials and reagents needed in the reaction are calculated based on batch input of the monomer (HEMA-PC) OG47, as well as the targeted molecular weight (MW).

Weighed 50 g monomer OG47 in glove box and added 200 mL of degassed EtOH to dissolve the monomer at room temperature; sampled for monomer concentration test. Weighed Cu (II), Bpy, Cu(0) in a 500 mL flask; purged with Argon, while adding monomer solution to the flask; sealed the flask with stopper and vacuumed for 25 min until no bubbles. The reaction changed color gradually from light green to dark green, then to light brown; weighed ~200 mg of initiator OG1786 in glove box, and dissolved in ~2000 uL of DMF under room temperature to make 100 mg/mL stock solution; sampled for initiator concentration and purity test; added the initiator solution to the flask under Argon. The reaction solution became dark brown and started thickening over time; sealed the system and let the reaction occur over 2 days.

OG1801 was then prepared for addition of the maleimide and catalyst (copper) was removed as follows: A prepacked RediSep® Rf normal phase silica column is used to remove the catalyst. The size of the column is chosen based on the copper amount in the reaction mixture. For instance, a 330 g column (Cat. #69-2203-330, Column size 330 g, CV=443 mL) was used for a 50 g batch of OG1801. Teflon tubing is used for all the connection as EtOH is the elute solvent.

After copper removal, all the fractions were transferred to a round bottom flask in batches, and evaporated the EtOH by rotary evaporator at 45-50° C. at reduced pressure to dryness. In this step, EtOH volume collected from condensation was monitored to make sure EtOH removal was >90%. The polymer was dissolved in 250 mL of WFI and filtered using a 0.2 um filter. It resulted in a clear to light yellow polymer solution at ~150 mg/mL. The solution could be stored at 2-8° C. up to 3 month before use.

Example 4

Synthesis of Polymer OG1802

Starting materials and reagents needed in the reaction are calculated based on batch input of OG1801. The linker is 3-maleimidopropionic acid, NHS ester. Added 30 ml of 0.5 M sodium phosphate (in WFI, pH 8) to 50 g polymer solution (~150 mg/mL). Let stir for 1 min; pH was 8.0 by pH paper. Weighed 204.8 mg of linker and dissolved in DMF 4.1 mL to make 50 mg/mL stock sln. Added linker solution dropwise 815 uL per minute to the polymer sln with strong stirring. Took 5 min to added 4095 uL of linker solution. Reacted at room temperature for 30 min. Quenched reaction with 20 mL of 5% acetic acid to achieve a final pH of 5. Filtered the solution using 1 L vacuum filter (0.2 um).

OG1802 (see FIG. 36) is then purified as follows: Milipore cross flow cassettes are used for polymer purification in aqueous system. Started with concentrating the polymer solution to 250 mL (~200 mg/mL). Added the fresh WFI from reservoir, and adjusted the flow rate of the fresh WFI feed to the same as the permeate (~2 mL/min). The UF/DF was set up at 2-8° C. overnight. Typically 2.5 L of WFI was used (10× volume ratio to the polymer solution). A sample of retente was collected for purity test. The targeted purity was >98%. Filtered the polymer solution by 0.2 μM 1 L filter bottle. The polymer solution could be stored at 2-8° C. for up to 3 month before conjugation.

Example 5

Alternative Phosphorylcholine Polymers

A HEA-PC polymer was synthesized as described below. HEA-PC (2-(acryloyloxy)ethyl-2-(trimethylammonium) ethyl phosphate), which is an acrylate as opposed to the methacrylate HEMA-PC described above, has the following structure:

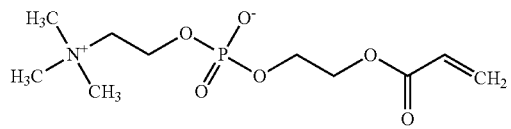

HEA-PC

HEA-PC was polymerized to the initiator shown in Example 1 as compound L.

TABLE 5.1

| Reactant | Name | Amount | MW |
| --- | --- | --- | --- |
| Initiator | Compound L (see above) | 1.65 mg | 2505.5 |
| Monomer | HEA-PC | 0.461 g | 281.24 |
| Catalyst | Cu (I) Bromide | 1.2 mg | 143.45 |
| Ligand | Tris [2-(dimethylamino)ethyl]amine (Me6TREN) | 2.73 mg | 230.39 |
| Solvent A | N,N-Dimethylformamide (DMF) | 21.85 μl | 73.09 |
| Solvent B | Water | 0.7 ml | 18.02 |
| Solvent C | Methanol | 0.7 ml | 32.04 |

Prepared a stock solution of initiator at 200 mg/mL by dissolving 2.2 mg of initiator in 11 μl of dry DMF and a 200 mg/ml solution of ligand by dissolving 4.6 mg of Me6TREN in 23 μL of dry DMF. Dispense 8.25 μl of the stock solution of initiator and 13.6 μl of the ligand into a tube. Degas at –78° C. for 5 mn then refill with Argon and add 1.2 mg of CuBr. Degas and refill with Argon. Add a stock solution of HEA-PC in methanol (weigh out 0.461 g of HEA-PC and dissolve it in 0.5 mL of methanol) to the solution inside the reactor at –78° C. Rinse the vial with 200 μl of methanol and add it inside the reactor at –78° C. and then 0.5 mL of distilled water then another 200 μl of water. Degas thoroughly until no bubbling is seen and all heterogeneity disappears (solid particulates dissolve or disappear). Refill with 4 psi of Argon and let the reaction to proceed at RT for an hour. The reaction was already viscous. The reaction was allowed to proceed for about one hour. A solution of bipyrindine in methanol (5 mg in 0.5 uL) was added. Another 2-3 ml of methanol was added and the catalyst was allowed to oxidize overnight at 4° C. Conversion determined by 1H NMR was estimated to be 94%.

The next day the polymer was dialyzed and subjected to SEC/MALS analysis using Shodex SB806M_HQ column (7.8×300 mm) in 1×PBS pH 7.4 at 1 ml/min, giving a PDI of 1.157, Mn of 723.5 kDa, Mp of 820.4 kDa and Mw of 837.2 kDa (before dialysis PDI is 1.12, Mn=695 kDa, Mp=778 kDa). Next a maleimide functionality was added to the polymer so that it could be conjugate to a protein.

Next, the maleimide Mal-PEG4-PFP (see Example 1 above) ester was snapped on to the HEA-PC polymer as shown in Example 1. The resulting maleimide functionalized HEA-PC polymer can then be conjugated to sulfhydryl groups as discussed herein for HEMA-PC polymers.

An acrylamide PC polymer was also made using the monomer 2-(acrylamyl)ethyl-2-(trimethylammonium)ethyl phosphate (Am-PC), having the following structure:

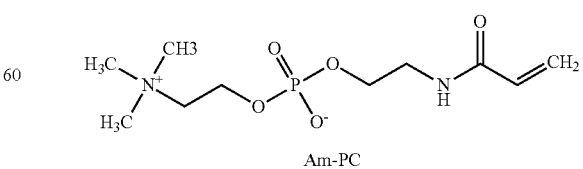

Am-PC

The Am-PC was used for polymerization employing a 3 arm initiator (a TFA salt) having the structure:

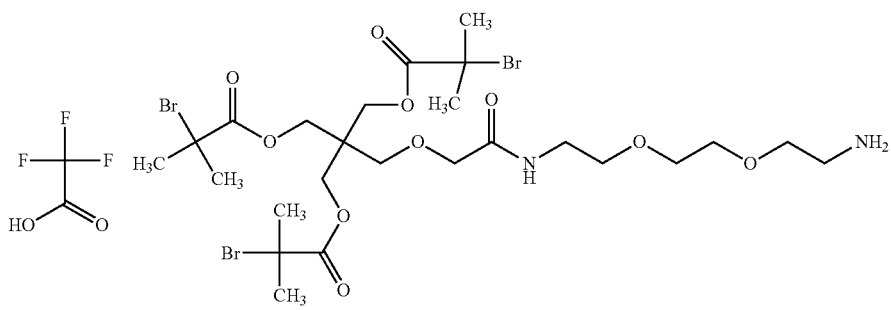

The synthesis of the Am-PC polymer was conducted as follows:

TABLE 5.2

| Reactant | Name/Identity | Amount | MW |
|---|---|---|---|
| Initiator | 3-arm initiator (see above) | 2.2 mg | 885.35 |
| Monomer | Am-PC | 0.5 g | 280.26 |
| Catalyst (I) | Copper (I) Bromide | 1 mg | 143.45 |
| Catalyst (II) | Copper (II) Bromide | 0.2 mg | 223.35 |
| Ligand | Tris[2-(dimethylamino)ethyl]amine (Me6TREN) | 3.94 mg | 230.39 |
| Solvent A | N,N-Dimethylformamide (DMF) | 31.7 μl | 73.09 |
| Solvent B | Water | 1 ml | 18.02 |
| Solvent C | Methanol | 1 ml | 32.04 |

A stock solution of ligand at 200 mg/mL was prepared by dissolving 9 mg of Me6TREN in 45 uL of dry DMF. Add 19.7 uL of the stock solution to a reaction vessel. Prepare a stock solution of initiator at 200 mg/mL by dissolving 6.5 mg of material in 32.5 uL of DMF. Add 11 uL of the initiator stock solution to the ligand from above. Degas for 5 mn. Add 1 mg of CuBr. Prepared a stock solution of $CuBr_2$ at 200 mg/mL by dissolving 4 mg $CuBr_2$ in 20 μL of DMF. Add 0.5 g of monomer (AmPC) to 1 mL of methanol (slow dissolution/viscous solution), followed by 1 uL of the stock solution of $CuBr_2$. Add the monomer solution dropwise to the reaction mixture above. Rinse with 1 mL of water. Degas the reaction mixture thoroughly (freeze-thaw). Let the reaction proceed for 24 hours.

Afterwards the Am-PC polymer may be dialyzed. The molecular weight of the above polymer was determined by SEC/MALS: Mn is 215 kDa, Mp: 250 kDa, PDI is 1.17. Conversion was estimated by 1H NMR to be 94%. A maleimide functionality can be added to the Am-PC polymer as discussed above for HEMA-PC and HEA-PC. Maleimide functionalized Am-PC polymer can be conjugated to a protein as described above.

Example 6

Reverse Ellman's Assay for Calculating Free Maleimide in a Compound

After addition of the maleimide functionality to polymer OG1801 to form OG1802 (see above), an Ellman's assay was used to determine the amount of functional maleimide (i.e. conjugatable) in a sample. Thiol converted Ellman's reagent (DTNB) to TNB– then to TNB2– in water at neutral and alkaline pH, which gave off a yellow color (measured at 412 nm). A standard curve was established with cysteine. Since the maleimide reacts with thiol, this assay actually measured the thiol (cysteine) left. The inhibition was calculated as the (original thiol—thiol left after maleimide polymer addition)/(original thiol) and is expressed as a percentage.

Reagents Employed in Assay: A standard curve was prepared using the cysteine from 62.5 μM to 2 μM. Polymer stock solutions were prepared by dissolving the powder in 1×PBS pH7.4 (reaction buffer) and mixing thoroughly. An equal molar of polymer and cysteine solutions were mixed and allowed to react at 27° C. for 30 minutes. The 150 μm of DTNB solution was added into the cysteine standards and polymer/cysteine reactions and the color was developed at 27° C. for 5 minutes. OD at 412 nm was read on the Spectramax plate reader and percent inhibition was calculated with the Softmax Pro software and the cysteine standard curve.

Example 7

Protein Sequence of Antibody (OG1950) Comprising an Anti-VEGF-A Antibody Heavy Chain with an L443C (EU Numbering, or 449C in SEQ ID NO: 1) Mutation and an Anti-VEGFA-Antibody Light Chain An anti-VEGF-A antibody with an L443C (EU numbering) mutation having the sequence set forth below in SEQ ID NO. 1 (FIG. 12) (heavy chain) was cloned. An anti-VEGF-A antibody light chain having the sequence set forth in SEQ ID NO. 2 (FIG. 13) below was cloned.

Example 8a

Purification and Decapping of OG1950

The OG1950 heavy and light chains may be cloned into expression plasmids and transfected into CHO cells. Cells can be grown up in appropriate media and harvested. OG1950 may be purified using techniques described above. The OG1950 cysteine at position 443 (L443C (EU numbering)) residue is typically "capped" or oxidized by chemicals in the cell culture media and is not available for conjugation. In this regard, purified OG1950 may be subjected to a decapping (i.e. reducing) procedure to remove the cap and enable the free (i.e. those not involved in Cys-Cys disulfide bonds) cysteine residue to be conjugated to the maleimide functionality of a polymer. Decapping may be done by mixing purified OG1950 protein with a 30× molar excess for 1 hour at 25° C. of the reducing agent TCEP (3,3',3"-Phosphanetriyltripropanoic acid). The reduction reaction with TCEP may be monitored by SDS-PAGE. Following denaturation, the OG1950 protein may be washed by UFdF using a Pellion XL Ultrafiltration Cassette with 20 mM Tris pH7.5, 150 mM NaCl, 0.5 mM TCEP buffer to remove the cap. The TCEP reagent may then be removed in the same UFdF setup with 20 mM Tris pH7.5, 150 mM NaCl. Reduced OG1950 may then be allowed to refold using air (ambient oxygen) which again is followed by SDS-PAGE as an assay Example 8b Purification and Decapping of OG1950

The OG1950 heavy and light chains may be cloned into expression plasmids and transfected into CHO cells. Cells can be grown up in appropriate media and harvested. OG1950 may be purified using techniques described above. The OG1950 cysteine at position 443 (L443C (EU numbering)) residue is typically "capped" or oxidized by chemicals in the cell culture media and is not available for conjugation. In this regard, purified OG1950 may be subjected to a decapping (i.e. reducing) procedure to remove the cap and enable the free (i.e. those not involved in Cys-Cys disulfide bonds) cysteine residue to be conjugated to the maleimide functionality of a polymer. Decapping may be done by mixing purified OG1950 protein with a 30× molar excess for 1 hour at 25° C. of the reducing agent TCEP (3,3',3"-Phosphanetriyltripropanoic acid). The reduction reaction with TCEP may be monitored by SDS-PAGE. Following reduction, the OG1950 protein can be washed by Ultrafiltration/Diafiltration (UF/DF) system using a Pellicon XL Ultrafiltration Cassette with 30 kDa MWCO membrane from Millipore with 20 mM Tris pH 7.5, 150 mM NaCl, 0.5 mM TCEP buffer to remove the cap and the excess TCEP. The residual TCEP reagent may then be removed in the same UF/DF setup with 20 mM Tris pH7.5, 150 mM NaCl. Reduced OG1950 can then be allowed to reoxidize using dHAA at ambient temperature for 1 hour followed by UF/DF for removal of dHAA to form decapped OG1950. The decapping status is monitored by SDS-PAGE assay.

Example 9

Conjugation of OG1950 to MPC Polymer

Decapped OG1950 may be conjugated to polymer OG1802. An excess of OG1802 is used (10-20 fold molar excess). Conjugation can be monitored by SDS-PAGE and driven to near completion. OG1950 conjugate may be purified via cation exchanger chromatography and buffer exchanged into the formulation buffer by UF/DF. Polymer-OG1950 conjugate may be purified chromatographically as described above.

Example 10

OG1950 SPR Binding Kinetics

Figure 21:
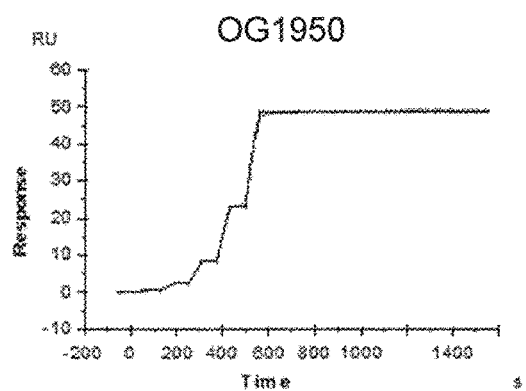
FIG. 21 depicts the OG1950 binding affinity to VEGF measured by BIAcore single cycle kinetics.

This Example illustrates binding of OG1950 to VEGF-165 in single cycle kinetics BIAcore™ experiment SPR interaction analysis of OG1950 to human VEGF-165 was performed on a BIAcore™ T200 system (GE Healthcare) equipped with a protein A chip (GE Healthcare). A single-cycle kinetics method was implemented. Antibody was captured at 25 μg/mL in HBS-EP+ buffer (0.01 M 4-(2-hydroxyethyl)-1-piperazineethanesulfonic acid, 0.15 μm sodium chloride, and 0.05% polysorbate 20) with a pulse of 25 s at a flow rate of 10 μl/min. Subsequently, recombinant human VEGF-165 (R&D Systems) was applied at various concentrations with a pulse of 60 s at a flow rate of 30 μl/min and a final dissociation time of 1000 s. The experiment was carried out at 25° C. The surface was regenerated with 10 mM glycine pH 1.7 for 1 min at a flow rate of 50 μL/min. Binding kinetics analysis was performed using the Biacore T200 evaluation software with responses globally fit to a 1:1 interaction. Results are summarized in Table 10.1 and FIG. 21.

TABLE 10.1

| BINDING KINETICS OF OG1950 TO VEGF-165 | | | |
|---|---|---|---|
| | ka (1/Ms) | kd (1/s) | KD(M) |
| OG1950 | 3.35E+05 | 6.77E−08 | 2.02E−13 |

OG1950 exhibits <1 pM KD in a 1:1 binding fit model (beyond instrument sensitivity).

Example 11

Conjugation and Purification of OG1953 Using Cation Exchanger Chromatography

OG1950 protein expression and protein preparation: OG1950 protein was expressed in mammalian GSCHOK1 expression system followed by purification using a Protein A affinity column. The purity of the Protein A column purified OG1950 was over 90% based on size exclusion chromatography and SDS-PAGE. The engineered specific cysteine residue of OG1950 was available for thiol conjugation to the OG1802 biopolymer. The thiol reacting chemical group of OG1802 was to react to form stable covalent linkage, which forms the OG1953 bioconjugate. To accomplish this, 1 mg of OG1950 was fully reduced with Tris-(2-Carboxyethyl)phosphine, Hydrochloride (TCEP) reducing agent followed by removal of TCEP via buffer exchange using a 30 KDa spin concentrator. The fully reduced OG1950 protein was then allowed to reoxidize to ensure all expected protein disulfide linkage was formed except the engineered cysteine residue (decap OG1950), which remained in reduced form for conjugation to the biopolymer via thiol specific conjugation chemistry.

Figure 19:
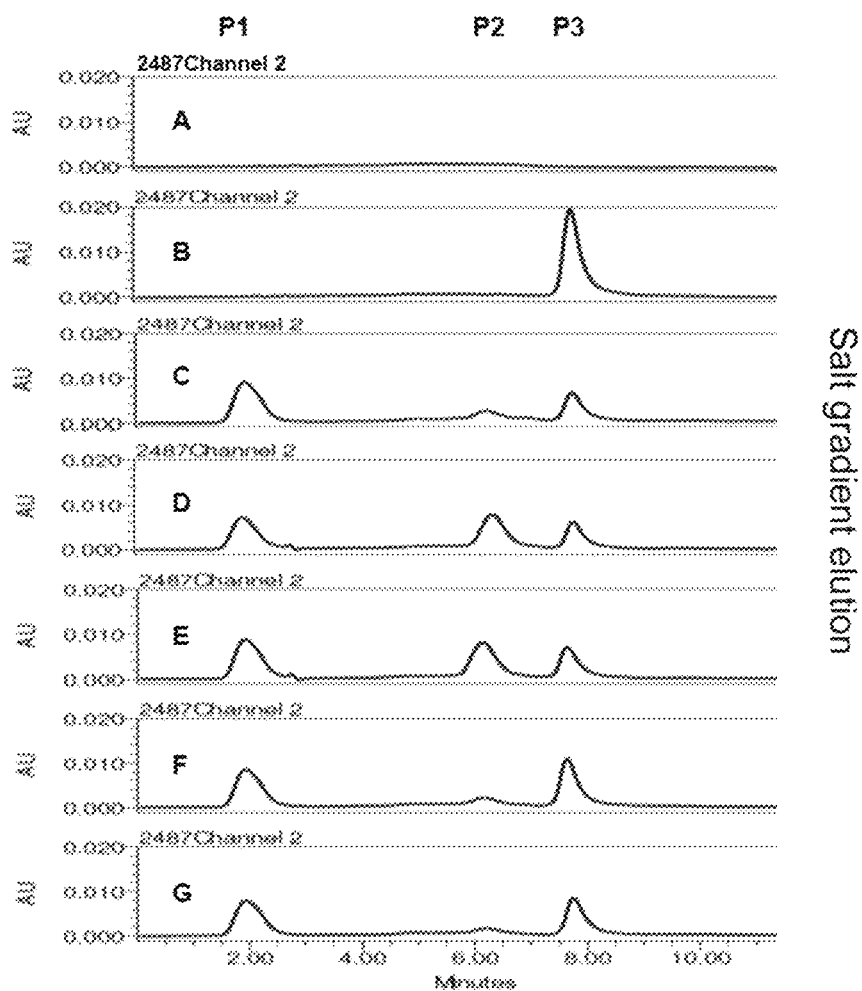
FIG. 19 depicts Ion Exchanger analysis (A280 absorbance) of reactions A through G.

Conjugation reaction: The conjugation reactions were performed by mixing 100 ug of decap OG1950 with 15× molar excess of OG1802 biopolymer with final protein concentration at 2 mg/mL in Tris buffer (20 mM Tris, 100 mM NaCl, pH 7.5). Various additives were evaluated in different conjugation reactions as shown in Table 11.1. in order to compare their impact on the conjugation efficiency. All reactions were setup in a fixed volume and incubated at 4° C. for 20 hours. Table 11.1 and FIG. 19 shows ion Exchanger analysis (A280 absorbance) and fractionation of the conjugation reactions A through G. Reaction A contained buffer only; reaction B contained OG1950 antibody only; reaction C contained OG1950 antibody+OG1802 polymer; reaction D contained OG1950 antibody+OG1802 polymer+sucrose; reaction E contained OG1950 antibody+OG1802 polymer+trehalose; reaction F contained OG1950 antibody+OG1802 polymer+glutamic acid; reaction G contained OG1950 antibody+OG1802 polymer+aspartic acid. Reactions B-G were started with 100 ug OG1950 protein input with a fixed total reaction volume. Upon reaction completion, equal volumes of B-G reactions were injected for IEX analysis. The conjugation efficiency comparison is shown in FIG. 19. Peak 1 (P1) represents the excess biopolymer (OG1802) that was not conjugated to the protein and unable to bind to the ion exchanger column and therefore eluted as unbound fraction in each reaction; Peak 2 (P2) represents the antibody polymer bioconjugate in each reaction; Peak 3 (P3) represents the free antibody that was not conjugated to the polymer in each reaction.

TABLE 11.1

| Samples | | (P2) OG1953 Conjugate (Au × Second) | (P3) OG1950 Protein (AU × Second) | Conjugation efficiency P2/[P3 of B] |
|---|---|---|---|---|
| A | Buffer blank injection | NA | NA | NA |
| B | OG1950 protein control | 0 | 410129 | NA |
| C | OG1950 + OG1802 biopolymer | 37334 | 125884 | 9% |
| D | C + Sucrose | 198064 | 110356 | 48% |
| E | C + Trehalose | 202682 | 139313 | 49% |
| F | C + Glutamic acid | 30401 | 220577 | 7% |
| G | C + Aspartic acid | 29054 | 175266 | 7% |

As can be seen from the results above, various excipients allowed for significantly higher conjugation efficiency. Without intending to be limited by theory, such excipients which assist in maintaining the solubility of the ingredients help the conjugation efficiency.

Cation exchanger analysis of the OG1953 conjugation reaction: Upon conjugation reaction completion, 5 ul of each reaction mixture was diluted 3 fold with a column equilibration buffer (20 mM sodium acetate pH 5.5) for cation exchanger chromatography (IEX) analysis and separation using a Shodex SP-825 HPLC column. IEX was performed under bind and elution mode where the reaction mixture was first diluted to lower the salt concentration so both conjugate and unreacted protein would bind to the column, followed by a salt gradient elution where increasing NaCl concentration resulted in elution of the conjugate (OG1953) and unconjugated free protein (OG1950) at different retention times due to the differential charge variation. IEX analysis results, as shown in FIG. 19 show that the OG1953 conjugate (peak P2) separated very well from the unreacted free polymer (OG1802) as shown in peak P1 and unreacted free protein (OG1950) as shown in P3.

Scale up purification of the OG1953 conjugate for activity analysis: Conjugation reactions D and E were pooled and further separated with the IEX where the conjugate Peak (P2) eluted fractions were collected and concentrated for activity analysis.

Example 12

Effect of Anti-VEGF Molecules on Biotin-VEGF Binding to VEGFR Using ELISA

The abilities of OG1950, OG1953 and other anti-VEGF molecules to inhibit binding of Biotin-VEGF-165 to VEGFR were tested on an ELISA assay. 96 well ELISA plates were coated with 1 ug/mL recombinant VEGF R1-Fc protein (R&D systems part #321-FL-050). Plates were Incubated o/n at RT. Plates were then washed and blocked with blocking buffer (1% BSA in 1×PBS, pH7.4) for >=90 min with gentle shaking. 3-fold dilution series of test samples were made. Starting from 400 nM samples were mixed with biotin-VEGF (R&D systems, part #custom06). The final concentration of biotin-VEGF was 4 ng/mL (100 pM). The top concentration of sample dilution series was 85 ug/mL. After dilutions were made, samples were incubated at RT for >=30 min and then washed 3×. After washing, 100 uL of the sample/biotin-VEGF mixture was transferred to each well. Plates were incubated for >=90 min at RT with gentle shaking. After incubation 100 µl of the 1:1500 diluted SA-HRP (R&D systems, part #A7906) was added to each well. Incubated plates were protected from light for approximately 20 min. Plates were then washed 3×. After washing 100 ul TMB substrate (R&D systems, part #DY998) was added. Plates were incubated and protected from light for approximately 30 min. Color development was monitored. Color development was stopped by adding 50 ul of stop solution. Plates were read at 450 nm. Results are shown in FIG. 20

These results show that the OG1953 antibody/conjugate reached a higher maximal inhibition of Biotin-VEGF binding to VEGFR when compared to OG1950 (the unconjugated antibody) as well as the commercially available VEGF inhibitors Lucentis®(ranibizumab) and Avastin®(bevacizumab). In a typical VEGF ligand VEGF receptor binding assay, addition of OG1953 results in inhibition 97-98% of VEGF ligand binding to the VEGF receptor. This is compared to adding OG1950, which results in inhibition of 75-87% of VEGF ligand/receptor binding and adding Lucentis®(ranibizumab) or Avastin®(bevacizumab), each of which only results in inhibition of 68-78% of VEGF ligand/receptor binding. Furthermore, previous studies have shown that adding either OG1950, Lucentis®(ranibizumab), or Avastin®(bevacizumab) at concentrations of 400 nM does not result in 100% inhibition of binding of the VEGF ligand to the VEGF receptor.

Figure 20:
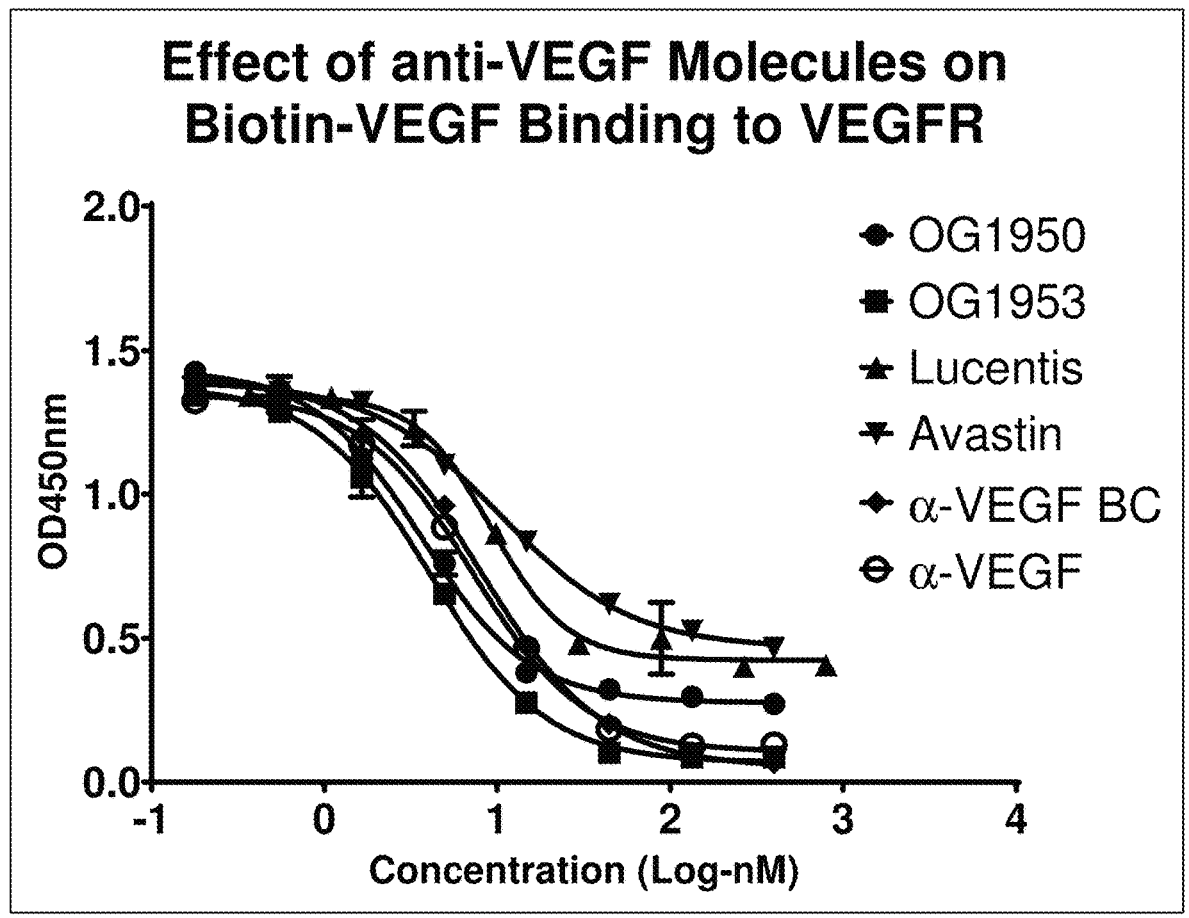
FIG. 20 depicts the effect of various anti-VEGF molecules on binding of biotin-VEGF to plate bound VEGFR ECD-Fc protein, and their IC50 values.

FIG. 20 also shows that the other antibody conjugate anti-VEGF Bio Conjugate (anti-VEGF BC) reached a higher maximal inhibition of binding of VEGF to the VEGF receptor when compared to the antibody alone (anti-VEGF). Together these results show that (i) the OG1953 antibody conjugate is more effective at inhibiting VEGF ligand binding to the VEGF receptor when compared to currently available VEGF inhibitors and (ii) conjugating VEGF antibodies at a site outside of the region of the active site can result increased inhibition of VEGF ligand binding to the VEGF receptor.

In some embodiments, provided herein are anti-VEGF antibody conjugates that display a superior (or at least equal) level of blocking ability, as compared to the anti-VEGF antibody alone.

Example 13

Method of Determining Binding of OG1950 to Fc Gamma Receptor I and IIIa

Binding kinetics experiments were performed at 25° C. using a BIAcore T200. An anti-his antibody was immobilized on a CM5 chip. Histidine-tagged FcγRI and FcγRIIIa at a concentration of 0.5 µg/mL prepared in HBS-EP buffer (0.01M HEPES pH7.4, 0.15M NaCl, 3 mM EDTA, 0.005% Tween-20) were injected independently for 60-s using a flow rate of 5 µL/min in the active flow cell only. Antibody candidate and Avastin®(bevacizumab), used as a positive control, were then injected over the reference and active flow cell using 60-s injections at 30 µL/mL, applying single-cycle kinetics method. Antibody concentrations in the range of 0.48 to 300 nM were used for FcγRI and 7.8 nM to 2000 nM for FcγRIIIa. Following each run, flow cells were regenerated with a 60 s injection of 10 mM glycine pH 1.7 using a flow-rate of 50 µL/mL. Data was double referenced, using subtraction of both reference flow cell and blank cycles. Analysis was performed using BIA evaluation software. Results are shown in FIGS. 22 and 23. Results show that OG1950 showed no significant binding to either Fc gamma receptor I and Ma in this assay.

Example 14

Method of Determining Binding of OG1950 to Human Complement Protein C1q

Figure 24:
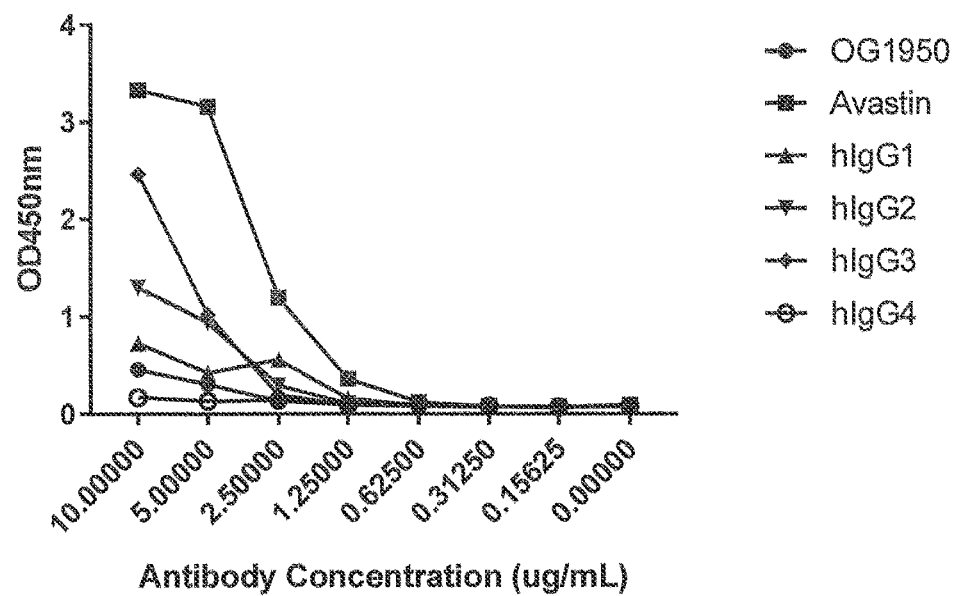
FIG. 24 depicts binding of QG 1950 to human complement protein C1q.

Complement engagement liabilities were assessed by C1q ELISA binding. The antibody panel was titrated 1:2 from a top concentration of 10 µg/mL in 1×PBS for overnight coating at 4 C. Plates were then blocked After a 2 hour blocking step in 1% BSA. Purified human C1q was then applied at 5 µg/mL in 1% BSA for 2 hours at room temperature followed by detection with HRP-conjugated anti-human C1q antibody and TMB development. Results are shown in FIG. 24. Results show that C1q has more binding affinity for Avastin®(bevacizumab) relative to OG1950 at antibody concentrations between 10 ug/mL and 0.625 ug/mL.

In some embodiments, OG1950 has less than 10% of the binding of that of Avastin. In some embodiments, OG1950 has less binding to C1q than Avastin®(bevacizumab).

Example 15

Effect of Anti-VEGF Agents to VEGF Stimulated HRMVEC Proliferation

Human retinal microvascular endothelial cell (HuRMVEC) proliferation assays were performed as follows: cells were maintained in CSC complete medium (cell systems, #4Zo-500) supplemented with 2% of CultureBoost (cell systems, #4CB-500) and 0.2% of Bac-off (cell systems, #4ZO-643), seeded in 96-well plates in assay medium (serum free medium (cell systems, #4Z3-500-S) with 5% FBS) at density of 10,000 cells per well. VEGF inhibitors were first added at the indicated concentrations to each well. Thirty minutes later, VEGF 165 (R&D systems, #293-VE-500/CF) was added to a final concentration of 1.3 nM. After 3 days, cells were incubated with WST-1 cell proliferation assay reagent and read at OD450 nM.

Figure 25:
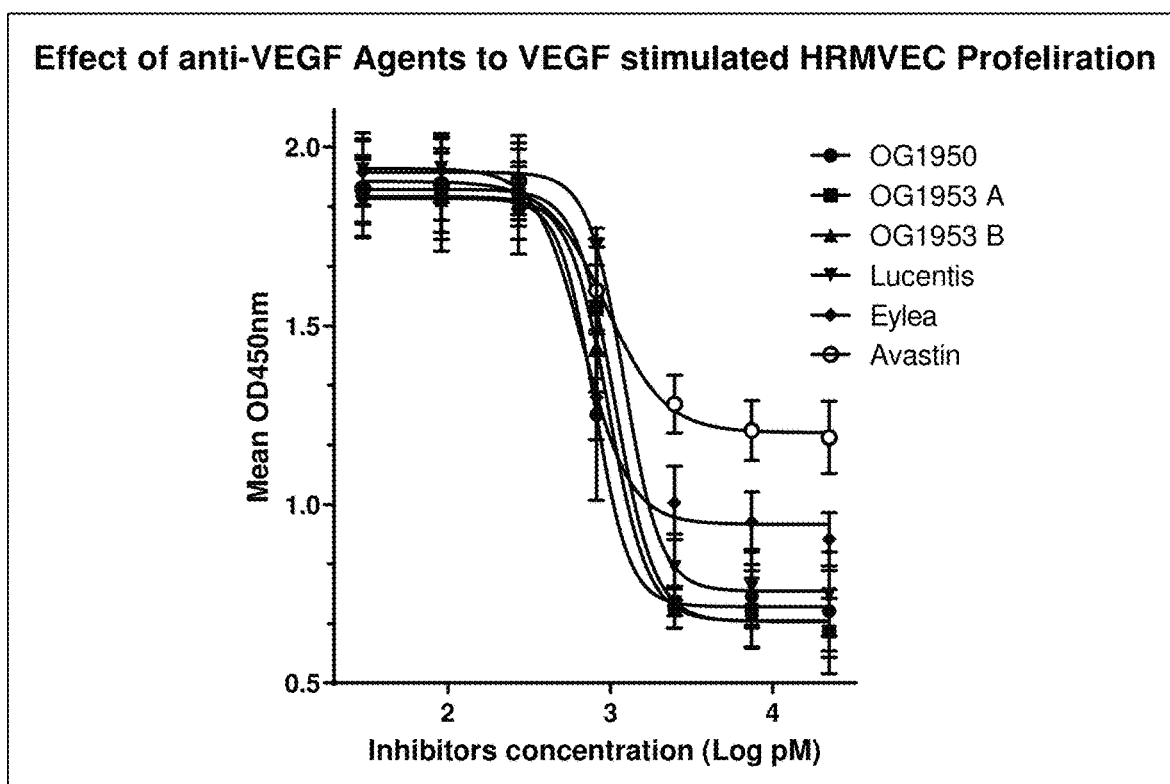
FIG. 25 depicts the results of a proliferation assay (including IC50 values).

Results demonstrated that two independent preps of OG1953 (OG1953A and OG1953B) both show potent inhibition to the HuRNVEC proliferation. Both maximal inhibition and IC50 of OG1953 is comparable to that of antibody alone OG1950 in this assay. Maximal inhibition of OG1953 is also significantly better than that of Avastin®(bevacizumab) and Eylea®(aflibercept). The results (including IC50 values and their comparison with Lucentis®(ranibizumab), Eylea®(aflibercept), and Avastin®(bevacizumab)) are shown in FIG. 25.

Example 16

Single Cycle Kinetics (SCK) of VEGF Binding to Anti-VEGF Agents Captured on a Protein A Chip at 25 Degrees Binding kinetics was performed at 25° C. using a BIAcore T200 on Avastin®(bevacizumab), OG1950 and OG1953. Briefly, anti-VEGF agents were captured on a Protein A chip (GE). 1 ug/ml OG1950 and Avastin®(bevacizumab) were flowed at 25 ul/min for 2 mins. 10 ug/ml OG1953 was flowed at 10 uls/min for 10 mins. VEGF (recombinant; R&D systems) was flowed over captured antibodies for 240 seconds contact time each at 0.56 nM, 1.67 nM, 5 nM, 15 nM, and 45 nM for single cycle kinetics, and dissociated for 30 minutes. Analysis was performed using BiaEvaluation software (GE). All sensorgrams were double reference subtracted and fit using a 1:1 Langmuir binding model. Off-rate of these anti-VEGF agents might be under-estimated in this experiment, due to the disassociation between anti-VEGF agents and Protein A capture.

Figure 26:
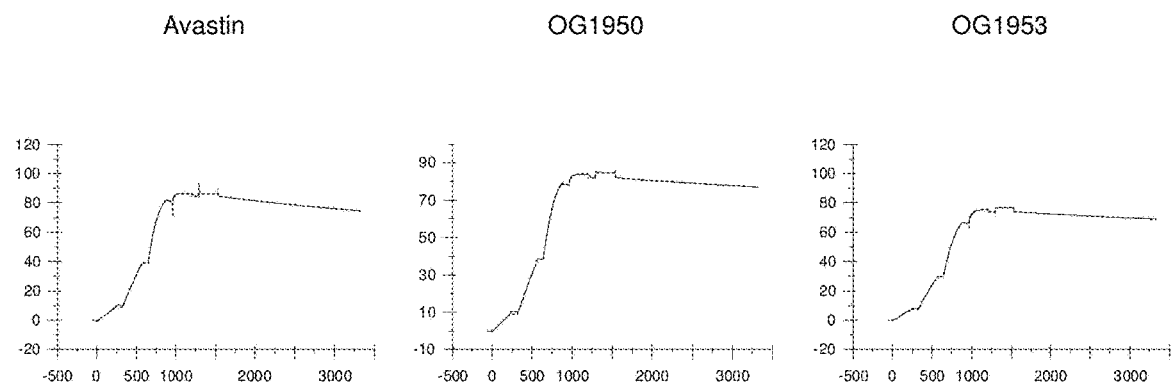
FIG. 26 depicts the results of single cycle kinetics of VEGF binding to anti-VEGF agents.

The results are presented in FIG. 26, including the calculated KD, ka, and kd values Example 17

Excipient Screening Experiment for Prevention of OG1802 Polymer Induced IgG1 Precipitation Using the standard conjugation reaction process setup, the OG1950 conjugation reaction mixture was found to be cloudy with precipitate immediately present upon mixing. Further investigation revealed the precipitate was the protein itself, which in turn resulted in poor conjugation efficiency observed via either SDS-PAGE or ion exchanger analysis as the protein was lost by precipitation instead of participating in the conjugation reaction.

Initial troubleshooting experiments performed revealed conditions that did not result in a clear reaction solution included (1) reduction of polymer molar excess ratio from over 10 to less than 5; (2) preadjusting the reaction solution pH to more acidic (e.g. pH 5) or basic (e.g. pH 8.5) from the standard neutral pH range (e.g. pH 6.5-7.5); (3) testing of other IgG1 protein samples with similar or different isoelectric point (pI) as compared to OG1950; (4) buffer exchanged the sample storage buffer into 1×PBS pH 7.4 or 20 mM Tris buffer pH 7.4, 100 mM NaCl; and (5) preadjusting the OG1802 solution with 20 mM Tris buffer pH 7.4.

Protein is known to carry net surface charge that helps protein solubility in aqueous solution. The amino acids are referred to as hydrophilic amino acids which include arginine, lysine, aspartic acid, and glutamic acid. At neutral pH 7 the side chains of these amino acids carry charges—positive for arginine and lysine, negative for aspartic acid, and glutamic acid. Altering the solution pH could modulate the intrinsic protein solubility which is therefore in one of the troubleshoot experiments mentioned above such as (2) this approach was applied. In theory, proteins solubility in aqueous solution differs depending on the level of hydrophobic or hydrophilic properties of the surface. Proteins with surfaces that have greater hydrophobic properties will readily precipitate. The addition of ions (e.g. NaCl or other salt) creates an electron shielding effect that nullifies some activity between water particles and the protein, reducing solubility as the proteins bind with each other and begin to aggregate. In the current situation, it was hypothesized that the biopolymer directly or indirectly modulates the protein surface charge and/or exposed surfaces in a manner that promotes the intermolecular hydrophobic interactions which results in protein precipitation.

Excipients that were determined to modulate protein solubility include the following categories (i) detergents including neutral detergent (e.g. 0.1-1% polysorbate20 or tween20) or charged detergent (e.g. 0.1-1% Sodium Dodecyl Sulfate (SDS)) (ii) sugars (e.g. 6% Trehalose or 6% sucrose) (iii) negatively charged amino acids (e.g. 0.03-1 mM glutamic acid or 0.03-1 mM aspartic acid) or positively charged amino acids (e.g. 1-100 mM lysine or arginine) (iv) chaotropic agents or denaturants (e.g. 1-100 mM urea, guanidine hydrochloride analog or 1-100 mM arginine) (v) polyethylene glycol (e.g. 0.03-1 mM PEG8000); and (vi) organic solvent (e.g. 20% ethanol).

In a further design of experiment (DOE) study, various excipients from each category mentioned above were selected based on their compatibility to the pharmaceutical manufacturing for human injectable use. In addition, extreme acidic pH at 4 and basic pH at 9 were also included in such evaluation. A standard IgG1 protein sample was selected for such evaluation which did not contain an engineered cysteine to minimize the potential interference of such unpaired cysteine residue complicating the precipitation observation. Table 17.1 depicted such matrix. The asterisk (*) code/rows are conditions that result in clear solution while the non-asterisk rows are the ones that result in various degree of cloudiness or precipitation.

TABLE 17.1

| code | Excipient | Reaction buffer |
| --- | --- | --- |
| 1 | OG1898_R5782_5xR7473 (control) | 20 mM Tris pH 7.4, 100 mM NaCl |
| 2* | 5 mg/mL_R5782_5xR7473_pH4 | sodium acetate |
| 3 | 5 mg/mL_R5782_5xR7473_pH9 | sodium carbonate |
| 4* | 5 mg/mL_R5782_5xR7473_1% Tween20 | Tris 20 mM NaCl |
| 5* | 5 mg/mL_R5782_5xR7473_0.1% Tween20 | Tris 20 mM NaCl |
| 6* | 5 mg/mL_R5782_5xR7473_1% SDS | Tris 20 mM NaCl |
| 7 | 5 mg/mL_R5782_5xR7473_0.1% SDS | Tris 20 mM NaCl |
| 8* | 5 mg/ml_R5782_5xR7473_6% Sucrose | Tris 20 mM NaCl |
| 9* | 5 mg/mL_R5782_5xR7473_6% Trehalose | Tris 20 mM NaCl |
| 10* | 5 mg/mL_R5782_5xR7473_0.03 mM Aspartic acid | Tris 20 mM NaCl |
| 11* | 5 mg/mL_R5782_5xR7473_1 mM Aspartic acid | Tris 20 mM NaCl |
| 12* | 5 mg/mL_R5782_5xR7473_0.03 mM Glutamic acid | Tris 20 mM NaCl |
| 13* | 5 mg/mL_R5782_5xR7473_1 mM Glutamic acid | Tris 20 mM NaCl |
| 14 | 5 mg/mL_R5782_5xR7473_1 mM Arginine | Tris 20 mM NaCl |
| 15* | 5 mg/mL_R5782_5xR7473_100 mM Arginine | Tris 20 mM NaCl |

TABLE 17.1-continued

| code | Excipient | Reaction buffer |
| --- | --- | --- |
| 16 | 5 mg/mL_R5782_5xR7473_1 mM Urea | Tris 20 mM NaCl |
| 17* | 5 mg/mL_R5782_5xR7473_100 mM Urea | Tris 20 mM NaCl |
| 18 | 5 mg/mL_R5782_5xR7473_0.03 mM PEG8000 | Tris 20 mM NaCl |
| 19 | 5 mg/mL_R5782_5xR7473_1 mM PEG8000 | Tris 20 mM NaCl |
| 20 | 5 mg/mL_R5782_5xR7473_20% EtOH | Tris 20 mM NaCl |
| 21 | 5 mg/mL_OG1931_R8399_5xR7473_CTL | Tris 20 mM NaCl |
| 22 | 5 mg/mL_OG1931_R8399_5xR7473_1 mM | Tris 20 mM NaCl |
| 23* | 5 mg/mL_OG1931_R8399_5xR7473_1 mM Arginine | Tris 20 mM NaCl |
| 24* | 8 mg/mL_OG1321_R7587_5xR7473_CTL | Tris 20 mM NaCl |
| 25 | 5 mg/mL_R5782_5xR7473_1 mM Lysine | Tris 20 mM NaCl |
| 26 | 5 mg/mL_R5782_5xR7473_100 mM Lysine | Tris 20 mM NaCl |

Figure 28:
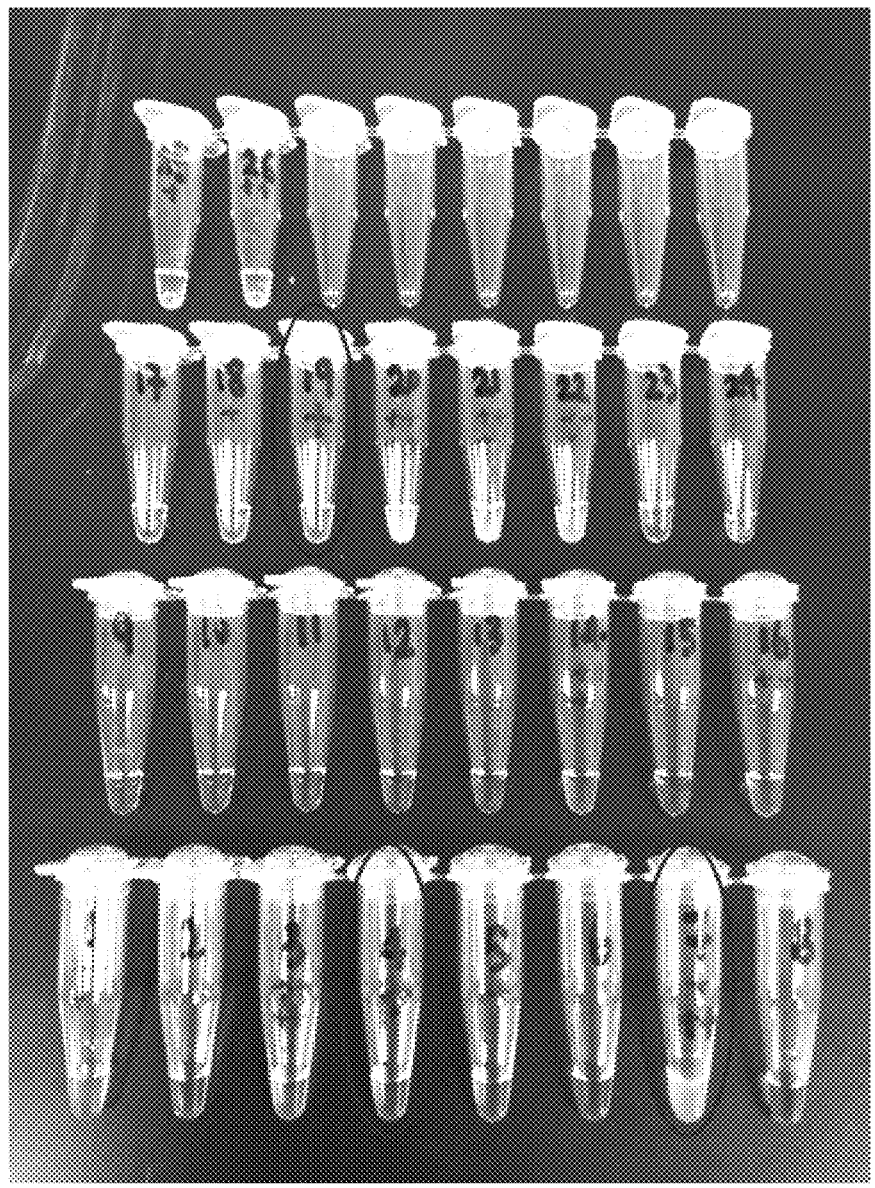
FIG. 28 depicts the screening results after incubation of various samples (of various excipients) in polymer solution (OG1802) for 20 hours at 2-8 degrees Centigrade.

The resulting precipitated solutions (or non-precipitated solutions) are shown in FIG. 28.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect disclosed herein can be used in combination with any other unless specifically indicated otherwise. Although some embodiments have been described in some detail by way of illustration and example for purposes of clarity and understanding, it will be apparent that certain changes and modifications may be practiced within the scope of the appended claims.

What is claimed is:

1. An antibody conjugate comprising:
   (1) an anti-VEGF-A antibody; and
   (2) a phosphorylcholine containing polymer, wherein the polymer is covalently bonded to the anti-VEGF-A antibody at a cysteine outside a variable region of the anti-VEGF-A antibody, and wherein said cysteine replaces a non-cysteine amino acid that occurs in a same position in a sequence, wherein the anti-VEGF-A antibody comprises a light chain and heavy chain, said heavy chain comprising an Fc region, wherein the cysteine is in the Fc region of the heavy chain, and wherein the anti-VEGF-A antibody heavy chain comprises $CDR_H1$: GYDFTHYGMN, $CDR_H2$: WINTYTGEPTYAADFKR, and $CDR_H3$: YPYYYGTSHWYFDV, and position 231 is T (via sequential counting as in SEQ ID NO: 1), and the anti-VEGF-A antibody light chain comprises $CDR_L1$: SASQDISNYLN (SEQ ID NO: 12), $CDR_L2$: FTSSLHS (SEQ ID NO: 13), and $CDR_L3$: QQYSTVPWT (SEQ ID NO: 14), and Kabat position 4 is L, wherein the antibody conjugate has the following structure:

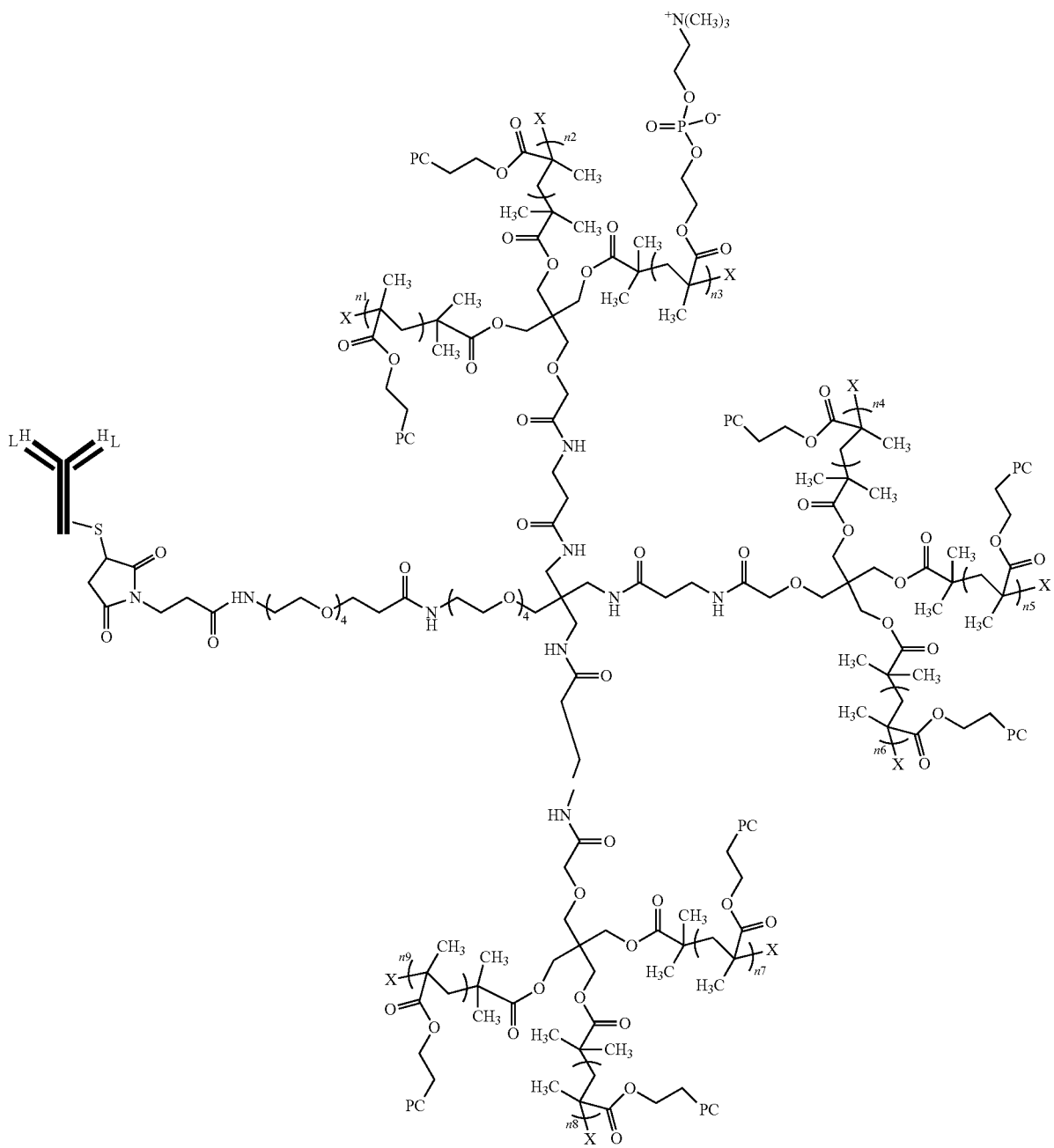

wherein X=a) OR where R=H, Methyl, ethyl, propyl, isopropyl, b) H, or c) a halide;

wherein:

each heavy chain of the anti-VEGF-A antibody is denoted by the letter H, and each light chain of the anti-VEGF-A antibody is denoted by the letter L;

the polymer is bonded to the anti-VEGF-A antibody through the sulfhydryl of a cysteine at position 449, as numbered in SEQ ID NO: 1, which bond is depicted on one of the heavy chains;

PC is

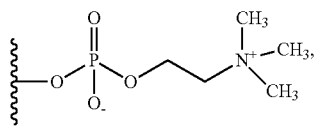

where the curvy line indicates the point of attachment to the rest of the polymer; and n1, n2, n3, n4, n5, n6, n7, n8 and n9 are the same or different such that the sum of n1, n2, n3, n4, n5, n6, n7, n8 and n9 is 2500 to 3000 plus or minus 15%.

2. An antibody conjugate comprising:

(1) an anti-VEGF-A antibody; and (2) a phosphorylcholine containing polymer, wherein the polymer is covalently bonded to the anti-VEGF-A antibody at a cysteine outside a variable region of the anti-VEGF-A antibody, and wherein said cysteine replaces a non-cysteine amino acid that occurs in a same position in a sequence, wherein the anti-VEGF-A antibody comprises a light chain and heavy chain, said heavy chain comprising an Fc region, wherein the cysteine is in the Fc region of the heavy chain, wherein the sequence of the heavy chain comprises SEQ ID NO: 1, and wherein the sequence of the light chain comprises SEQ ID NO: 2;

wherein the antibody conjugate has the following structure:

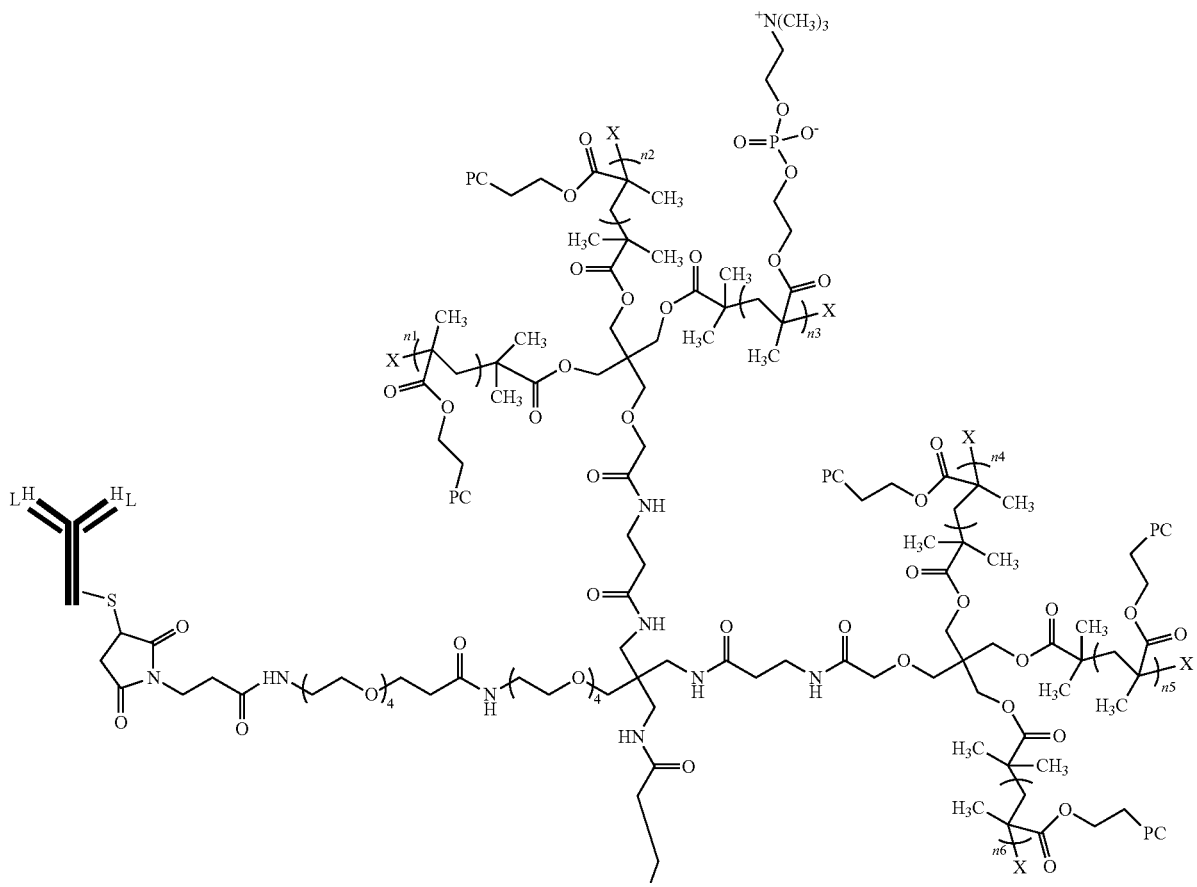

-continued

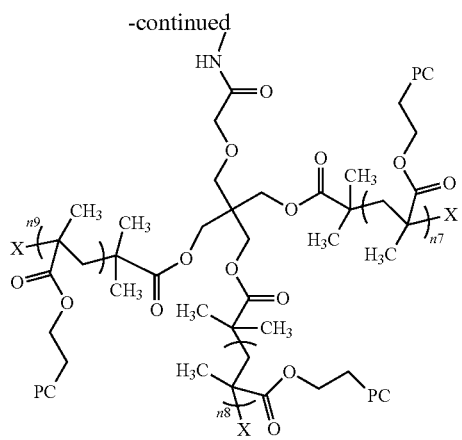

where X=a) OR where R=H, Methyl, ethyl, propyl, isopropyl, b) H, or c) a halide;
wherein:
each heavy chain of the anti-VEGF-A antibody is denoted by the letter H, and each light chain of the anti-VEGF-A antibody is denoted by the letter L;
the polymer is bonded to the anti-VEGF-A antibody through the sulfhydryl of a cysteine at position 449, as numbered in SEQ ID NO: 1, which bond is depicted on one of the heavy chains;
PC is

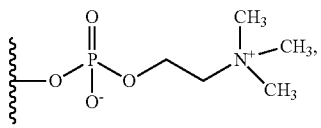 [SMILES: *OP(=O)([O-])OCC[N+](C)(C)C]

where the curvy line indicates the point of attachment to the rest of the polymer; and
n1, n2, n3, n4, n5, n6, n7, n8 and n9 are the same or different such that the sum of n1, n2, n3, n4, n5, n6, n7, n8 and n9 is 2500 to 3000 plus or minus 15%.

3. The antibody conjugate according to claim 1 comprising at least one of the following with reference to SEQ ID NO: 1: an alanine at position 240, an alanine at position 241 and an alanine at position 243.

4. The antibody conjugate according to claim 3 wherein the sequence of the anti-VEGF-A antibody heavy chain is SEQ ID NO: 1 and the sequence of the anti-VEGF-A antibody light chain is SEQ ID NO: 2.

5. The antibody conjugate according to claim 1 wherein the polymer has a molecular weight between about 300,000 and about 1,750,000 Da as measured by size exclusion chromatography—multi angle light scattering (hereinafter "SEC-MALS").

6. The antibody conjugate according to claim 1 wherein the polymer has a polydispersity index value (PDI) of less than about 1.5.

7. The antibody conjugate according to claim 2, wherein the polymer has a polydispersity index value (PDI) of less than about 1.5.

8. The antibody conjugate according to claim 2, wherein the antibody is conjugated to the polymer to form a bioconjugate, wherein the bioconjugate has a molecular weight between about 450,000 and 1,900,000 Daltons.

9. The antibody conjugate according to claim 2 comprising at least one of the following with reference to SEQ ID NO: 1: an alanine at position 240, an alanine at position 241 and an alanine at position 243.

10. The antibody conjugate according to claim 2, wherein the polymer has a molecular weight between about 300,000 and about 1,750,000 Da as measured by size exclusion chromatography-multi angle light scattering (hereinafter "SEC-MALS").

11. The antibody conjugate of according to claim 1, wherein the antibody is conjugated to the polymer to form a bioconjugate, wherein the bioconjugate has a molecular weight between about 450,000 and 1,900,000 Daltons.

12. The antibody conjugate of claim 1, wherein n1, n2, n3, n4, n5, n6, n7, n8 and n9 are independently integers from 2500 to 3000.

13. The antibody conjugate of claim 2, wherein n1, n2, n3, n4, n5, n6, n7, n8 and n9 are independently integers from 2500 to 3000.

14. The antibody conjugate of claim 1, wherein R is Br.

15. The antibody conjugate of claim 2, wherein R is Br.

* * * * *

UNITED STATES PATENT AND TRADEMARK OFFICE
CERTIFICATE OF CORRECTION

| | |
|---|---|
| PATENT NO. | : 11,066,465 B2 |
| APPLICATION NO. | : 15/394500 |
| DATED | : July 20, 2021 |
| INVENTOR(S) | : Daniel Victor Perlroth et al. |

It is certified that error appears in the above-identified patent and that said Letters Patent is hereby corrected as shown below:

On the Title Page

Column 2, Item (56), Line 1, under Other Publications, delete "al (Investigative" and insert --al., Investigative--.

On Page 2, Column 1, Item (56), Line 68, under U.S. Patent Documents, delete "7,374,767" and insert --7,374,757--.

On Page 8, Column 1, Item (56), Line 45, under Other Publications, delete "Verteporfln" and insert --Verteporfin--.

On Page 8, Column 1, Item (56), Line 52, under Other Publications, delete "healt" and insert --health--.

On Page 9, Column 1, Item (56), Line 22, under Other Publications, delete "Dedritic" and insert --Dendritic--.

On Page 9, Column 1, Item (56), Line 29, under Other Publications, delete ""Determinatino" and insert --"Determination--.

On Page 9, Column 1, Item (56), Line 41, under Other Publications, delete ""Pheriolic" and insert --"Phenolic--.

On Page 10, Column 1, Item (56), Line 44, under Other Publications, delete "Materialos" and insert --Materials--.

On Page 10, Column 1, Item (56), Line 50, under Other Publications, delete "Miltoarm" and insert --Miktoarm--.

Signed and Sealed this
Seventh Day of February, 2023

Katherine Kelly Vidal
*Director of the United States Patent and Trademark Office*

CERTIFICATE OF CORRECTION (continued)
U.S. Pat. No. 11,066,465 B2

On Page 10, Column 1, Item (56), Line 51, under Other Publications, delete "Methacdrylate,"" and insert --Methacrylate,"--.

On Page 10, Column 1, Item (56), Line 64, under Other Publications, delete "ramibizumab (reb)" and insert --ranibizumab (rbe)--.

On Page 10, Column 2, Item (56), Line 26, under Other Publications, delete "refoldin" and insert --refolding--.

On Page 11, Column 1, Item (56), Line 3, under Other Publications, delete "bispphosphonate" and insert --bisphosphonate--.

On Page 11, Column 1, Item (56), Line 31, under Other Publications, delete "Biomacromlecules," and insert --Biomacromolecules,--.

On Page 11, Column 2, Item (56), Line 19, under Other Publications, delete "Debaturation" and insert --Denaturation--.

On Page 11, Column 2, Item (56), Line 52, under Other Publications, delete "Phosphocrycholine" and insert --Phosphorylcholine--.

On Page 11, Column 2, Item (56), Lines 53-54, under Other Publications, delete "Campatability,"" and insert --Compatibility,"--.

On Page 11, Column 2, Item (56), Line 55, under Other Publications, delete "reterived" and insert --retrieved--.

On Page 11, Column 2, Item (56), Line 57, under Other Publications, delete "intersitial" and insert --interstitial--.

On Page 11, Column 2, Item (56), Line 63, under Other Publications, delete "Camtothecins:" and insert --Camptothecins:--.

On Page 12, Column 1, Item (56), Line 21, under Other Publications, delete "PhosphoachoLine" and insert --PhosphochoLine--.

On Page 12, Column 1, Item (56), Line 63, under Other Publications, delete "Internatnional" and insert --International--.

On Page 12, Column 2, Item (56), Line 11, under Other Publications, delete "Opion" and insert --Opinion--.

On Page 12, Column 2, Item (56), Line 11, under Other Publications, delete "in in" and insert --in--.

On Page 12, Column 2, Item (56), Line 50, under Other Publications, delete "Australain" and insert --Australian--.

On Page 13, Column 1, Item (56), Line 43, under Other Publications, delete "Equivilanet" and insert --Equivalent--.

On Page 13, Column 1, Item (56), Line 44, under Other Publications, delete "Bioscanvenger" and insert --Bioscavenger--.

On Page 13, Column 2, Item (56), Line 30, under Other Publications, delete "Toopgraphy," and insert --Topography,--.

On Page 13, Column 2, Item (56), Line 43, under Other Publications, delete "Effecotr" and insert --Effector--.

On Page 14, Column 1, Item (56), Line 31, under Other Publications, delete "Opthalmology" and insert --Ophthalmology--.

On Page 15, Column 1, Item (56), Line 43, under Other Publications, delete "indentification" and insert --identification--.

On Page 15, Column 2, Item (56), Line 30, under Other Publications, delete "Viuo"" and insert --Vivo"--.

On Page 16, Column 1, Item (56), Line 26, under Other Publications, delete "Retn" and insert --Retin--.

On Page 16, Column 2, Item (56), Lines 31-32, under Other Publications, delete "Opthalmology" and insert --Ophthalmology--.

In the Drawings

On Sheet 25 of 28, FIG. 25, Line 2 (Approx.), delete "Profeliration" and insert --Proliferation--.

In the Specification

In Column 10, Line 1, delete "the the" and insert --the--.

In Column 13, Lines 3-4, delete "hexaluorophosphate," and insert --hexafluorophosphate,--.

In Column 21, Lines 57-64, delete "conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996)." and insert the same on Column 21, Line 56, as the continuation of same paragraph.

In Column 24, Line 64, delete "(1991) and," and insert --(1991)), and--.

CERTIFICATE OF CORRECTION (continued)
U.S. Pat. No. 11,066,465 B2

In Column 24, Line 67, delete "5,565,332." and insert --5,565,332).--.

In Column 30, Line 19, delete "heterocyclalkyl" and insert --heterocycloalkyl--.

In Column 32, Line 51, delete "and or" and insert --and/or--.

In Column 33, Line 48, delete "trifluororacetic" and insert --trifluoroacetic--.

In Column 33, Line 51, delete "intiator" and insert --initiator--.

In Column 34, Line 6, delete "do/dc" and insert --dn/dc--.

In Column 34, Line 51, delete "Photodiole" and insert --Photodiode--.

In Column 34, Line 60, delete "Photodiole" and insert --Photodiode--.

In Column 35, Lines 7-8, delete "MW protein" and insert --MWprotein--.

In Column 36, Line 42, delete "inlight" and insert --in light--.

In Column 38, Line 28, delete "Fe" and insert --Fc--.

In Column 45, Line 59, delete "NO;" and insert --NO:--.

In Column 46, Line 24, delete "relatative" and insert --relative--.

In Column 47, Line 33, delete "G(VPGVG19-VPGV" and insert --G-(VPGVG)19-VPGV--.

In Column 47, Line 33, delete "Escheriachia" and insert --Escherichia--.

In Column 47, Line 52, delete "hydroxylethyl" and insert --hydroxyethyl--.

In Column 47, Line 53, delete "pullulane," and insert --pullulan,--.

In Column 47, Lines 59-60, delete "anyhydride," and insert --anhydride,--.

In Column 48, Line 16, delete "used" and insert --used.--.

In Column 50, Line 12, delete "thiolether" and insert --thioether--.

In Column 51, Line 48, delete "and and" and insert --and--.

In Column 52, Line 61, delete "hydroxylethyl" and insert --hydroxyethyl--.

In Column 52, Line 62, delete "pullulane," and insert --pullulan,--.

CERTIFICATE OF CORRECTION (continued)

In Column 53, Lines 1-2, delete "anyhydride," and insert --anhydride,--.

In Column 53, Line 19, delete "sites" and insert --sites.--.

In Column 53, Line 35 (Approx.), delete "with with" and insert --with--.

In Column 53, Line 58, delete "acqueous" and insert --aqueous--.

In Column 54, Line 42, delete "zwitterionc" and insert --zwitterionic--.

In Column 55, Lines 25-40, delete " 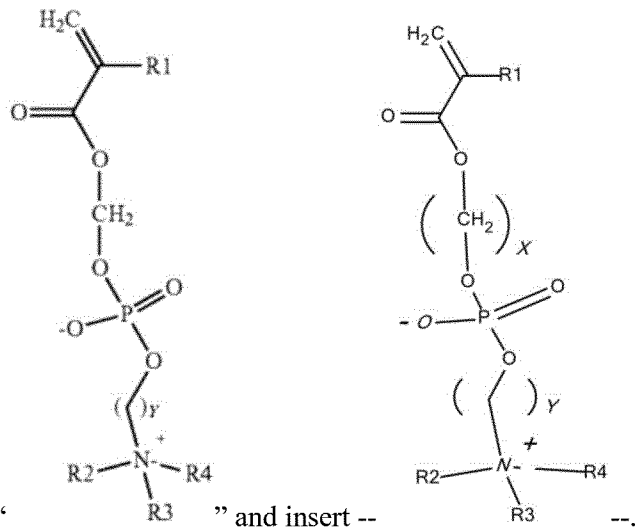 " and insert -- --.

In Column 56, Line 32, delete "(R⁷₂PO₄)," and insert --(R7₂PO₄),--.

In Column 56, Line 32, delete "hexaluorophosphate," and insert --hexafluorophosphate,--.

In Column 57, Line 2, delete "$R^1-R^2(-R3)_s$," and insert --R1-R2(-R3)$_s$--.

In Column 59, Line 60, delete "the an" and insert --the--.

In Column 61, Line 4, delete "pateints" and insert --patients--.

In Column 63, Line 44, delete "dispersion" and insert --dispersion.--.

In Column 64, Line 16 (Approx.), delete "superchoroidal" and insert --suprachoroidal--.

In Column 64, Line 30, delete "2006)." and insert --2006)).--.

In Column 64, Line 42, delete "Intravitrial" and insert --Intravitreal--.

In Column 67, Line 48-49, delete "Amoebodyte" and insert --Amebocyte--.

In Column 72, Lines 65-66, delete "isopropylacetate" and insert --isopropyl acetate--.

CERTIFICATE OF CORRECTION (continued)
U.S. Pat. No. 11,066,465 B2

In Column 74, Line 37 (Approx.), delete "210 nm)," and insert --210 nm)),--.

In Column 76, Line 35 (Approx.), delete "bipyrindine" and insert --bipyridine--.

In Column 76, Line 54 (Approx.), delete "(acrylamyl)" and insert --(acryloyl)--.

In Column 78, Line 67, delete "Pellion" and insert --Pellicon--.

In Column 79, Line 6, delete "assay" and insert --assay.--.

In Column 82, Line 13, delete "20" and insert --20.--.

In Column 83, Line 47, delete "HuRNVEC" and insert --HuRMVEC--.

In Column 86, Line 9 (Approx.), delete "1mM" and insert --1mM Aspartic acid--.

In the Claims

In Column 104, Claim 1, Line 4, delete "n6, n6," and insert --n6,--.

In Column 105, Claim 2, Line 42, delete "n6, n6," and insert --n6,--.

In Column 106, Claim 6, Line 24 (Approx.), delete "index value (PDI)" and insert --index (PDI) value--.

In Column 106, Claim 7, Line 26 (Approx.), delete "index value (PDI)" and insert --index (PDI) value--.

In Column 106, Claim 11, Line 41, delete "of according" and insert --according--.